US012642850B2

(12) United States Patent
Bathe et al.

(10) Patent No.: US 12,642,850 B2
(45) Date of Patent: *Jun. 2, 2026

(54) NUCLEIC ACID NANOSTRUCTURE PLATFORM FOR PROGRAMMING IMMUNE STIMULATION

(71) Applicant: Massachusetts Institute of Technology, Cambridge, MA (US)

(72) Inventors: Mark Bathe, Lincoln, MA (US); Remi Veneziano, Manassas, VA (US); Eike-Christian Wamhoff, Brookline, MA (US); Tyson Moyer, Boston, MA (US); Benjamin Joseph Read, Cambridge, MA (US); Rebecca Du, Cambridge, MA (US); Darrell Irvine, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 870 days.

This patent is subject to a terminal disclaimer.

(21) Appl. No.: 17/819,204

(22) Filed: Aug. 11, 2022

(65) Prior Publication Data

US 2023/0330219 A1 Oct. 19, 2023

Related U.S. Application Data

(63) Continuation-in-part of application No. 16/752,394, filed on Jan. 24, 2020, now Pat. No. 11,419,932.

(60) Provisional application No. 63/333,498, filed on Apr. 21, 2022, provisional application No. 62/796,472, filed on Jan. 24, 2019.

(51) Int. Cl.
| | |
|---|---|
| *A61K 39/00* | (2006.01) |
| *A61K 9/51* | (2006.01) |
| *A61K 39/12* | (2006.01) |
| *A61K 39/21* | (2006.01) |
| *A61K 39/385* | (2006.01) |
| *A61K 39/39* | (2006.01) |

(52) U.S. Cl.
CPC ............ *A61K 39/385* (2013.01); *A61K 39/21* (2013.01); *A61K 2039/55588* (2013.01); *A61K 2039/6025* (2013.01); *A61K 2039/6093* (2013.01); *A61K 2039/64* (2013.01)

(58) Field of Classification Search
CPC .......... A61K 2039/55555; A61K 2039/55561; A61K 39/39; A61K 2039/55588; A61K 39/12
See application file for complete search history.

(56) References Cited

U.S. PATENT DOCUMENTS

| | | | |
|---|---|---|---|
| 4,816,567 | A | 3/1989 | Cabilly |
| 5,356,802 | A | 10/1994 | Chandrasegaran |
| 5,436,150 | A | 7/1995 | Chandrasegaran |
| 5,487,994 | A | 1/1996 | Chandrasegaran |
| 5,624,821 | A | 4/1997 | Winter |
| 6,140,081 | A | 10/2000 | Barbas |
| 6,194,551 | B1 | 2/2001 | Idusogie |
| 6,453,242 | B1 | 9/2002 | Eisenberg |
| 6,534,261 | B1 | 3/2003 | Cox |
| 6,610,512 | B1 | 8/2003 | Barbas |
| 6,746,838 | B1 | 6/2004 | Choo |
| 6,866,997 | B1 | 3/2005 | Choo |
| 7,067,617 | B2 | 6/2006 | Barbas |
| 8,227,242 | B2 | 7/2012 | Bradbury |
| 8,501,923 | B2 | 8/2013 | Rothemund |
| 9,149,520 | B2 | 10/2015 | Walker |
| 9,579,396 | B2 | 2/2017 | Dwyer |
| 11,419,932 | B2 | 8/2022 | Bathe |
| 2002/0165356 | A1 | 11/2002 | Barbas |
| 2003/0215914 | A1 | 11/2003 | Houtzager |
| 2004/0180422 | A1 | 9/2004 | Hoet |
| 2004/0197892 | A1 | 10/2004 | Moore |

(Continued)

FOREIGN PATENT DOCUMENTS

| | | |
|---|---|---|
| CN | 106119269 | 11/2016 |
| KR | 101749230 | 6/2017 |

(Continued)

OTHER PUBLICATIONS

Michelotti, et al., "Beyond DNA origami: A look on the bright future of nucleic acid nanotechnology", Wiley Interdiscip Rev Nanomed Nanobiotechnol., 4(2): 139-152 (2012).

(Continued)

*Primary Examiner* — Barry A Chestnut

(74) *Attorney, Agent, or Firm* — PABST PATENT GROUP LLP

(57) ABSTRACT

Compositions containing a nucleic acid nanostructure having a desired geometric shape and immunostimulatory agent(s) bound to its surface are provided. The nanostructures can be, for example, in the form of a 6-helix bundle, or icosahedron, or a pentagonal bipyramid. The nanostructure design allows for control of the relative position and/or stoichiometry of the immunostimulatory agent(s) bound to its surface. The immunostimulatory agent(s) displayed on the nanostructure surface are arranged with the preferred number, spacing, and 3D organization to elicit a robust immune response. The displayed antigen can be a TLR agonist, such as a TLR9 agonist. The immunostimulatory compositions may thus be useful as immunogens, vaccines, adjuvants, and the like. Methods of inducing immune responses, and for targeted induction of TLR activation are also provided.

38 Claims, 27 Drawing Sheets

Specification includes a Sequence Listing.

(56) References Cited

U.S. PATENT DOCUMENTS

| | | | |
|---|---|---|---|
| 2005/0147962 A1 | 7/2005 | Wagstrom |
| 2005/0220814 A1 | 10/2005 | Dominowski |
| 2007/0117109 A1 | 5/2007 | Rothemund |
| 2007/0128728 A1 | 6/2007 | Bradbury |
| 2007/0154989 A1 | 7/2007 | Barbas |
| 2007/0213269 A1 | 9/2007 | Barbas |
| 2011/0206758 A1 | 8/2011 | Vandepapeliere |
| 2012/0251583 A1 | 10/2012 | Rothemund |
| 2014/0356384 A1 | 12/2014 | Hubbell |
| 2015/0017201 A1 | 1/2015 | Chang |
| 2019/0203242 A1 | 7/2019 | Praetorius |
| 2025/0387466 A1 | 12/2025 | Bathe et al. |

FOREIGN PATENT DOCUMENTS

| | | | |
|---|---|---|---|
| WO | 9633739 | | 10/1996 |
| WO | 9836772 | | 8/1998 |
| WO | 9853059 | | 11/1998 |
| WO | 9958572 | | 11/1999 |
| WO | 2000071694 | | 11/2000 |
| WO | 2003016496 | | 2/2003 |
| WO | 2007067818 | | 6/2007 |
| WO | 2013056122 | | 4/2013 |
| WO | 2013119676 | | 8/2013 |
| WO | 2013176772 | | 11/2013 |
| WO | 2014018423 | | 6/2014 |
| WO | WO2015187966 | * | 12/2015 |
| WO | 2017089567 | | 6/2017 |
| WO | 2017089570 | | 6/2017 |
| WO | 2017189870 | | 11/2017 |
| WO | 2017189914 | | 11/2017 |
| WO | 2020051507 | | 3/2020 |

OTHER PUBLICATIONS

Dietz, et al., " Folding DNA into twisted and curved nanoscale shapes", Science, 325(5941):725-730 (2009).

Castro, et al., "A primer to scaffolded DNA origami", Nat. Methods., 8(3):221-229 (2011).

Chandran, et al., "DNA origami: Folding DNA into Desired Shapes", 1-5, Fourth Warft Workshop on Brain Modeling and Supercomputing, (2009).

Douglas, et al., "Self-assembly of DNA into nanoscale three-dimensional shapes", Nature, 459:414-418 (2009A).

Douglas, et al., "Rapid prototyping of 3D DNA-origami shapes with caDNAno", Nucleic Acids Res., 37:5001-5006 (2009B).

Douglas, et al., "A logic-gated nanorobot for targeted transport of molecular payloads", Science, 335(6070):831-834 (2012).

Dunn, et al., "Guiding the folding pathway of DNA origami", Nature, 525(7567):82-86 (2015).

Fu, et al., "DNA double-crossover molecules", Biochemistry, 32(13):3211-3220 (1993).

Gradišar, et al., "Design of a single-chain polypeptide tetrahedron assembled from coiled-coil segments", Nat. Chem. Biol., 9(6):362-366 (2013).

Gu, et al., "Dynamic patterning programmed by DNA tiles captured on a DNA origami substrate", Nature Nanotechnology, 4(4):245-248 (2009).

Han, et al., "DNA origami with complex curvatures in three-dimensional space", Science, 332(6027):342-346 (2011).

Han, et al., "DNA gridiron nanostructures based on four-arm junctions", Science. 339(6126): 1412-1415 (2013).

He, et al., "On the Chirality of Self-Assembled DNA Octahedra", Angew. Chem., 122(4):760-763 (2010).

He, et al., "Hierarchical self-assembly of DNA into symmetric supramolecular polyhedra", Nature, 452(7184):198-201 (2008).

Irobalieva, et al., "Structural diversity of supercoiled DNA", Nat. Commun., 6(8440):1-10 (2015).

Jiang, et al., "DNA origami as a carrier for circumvention of drug resistance", Journal of the American Chemical Society, 134(32): 13396-13403 (2012).

Jones, et al., "Nanomaterials. Programmable materials and the nature of the DNA bond", Science, 347(6224):840; 1260901-1-12060901-11 (2015).

Kallenbach, et al., "An immobile nucleic acid junction constructed from oligonucleotides", Nature, 305:829-831 (1983).

Ke, et al. "Multilayer DNA Origami Packed on a Square Lattice", J. A. Chem. Soc., 131(43): 15903-15908 (2009).

Ke, et al., "Two design strategies for enhancement of multilayer-DNA-origami folding: underwinding for specific intercalator rescue and staple-break positioning", Chem. Sci., 3(8):2587-2597 (2012B).

Ko, et al., "Synergistic self-assembly of RNA and DNA molecules", Nature Chemistry, 2(12): 1050-1055 (2010).

Kuzyk, et al., "DNA-Based Self-Assembly of Chiral Plasmonic Nanostructures With Tailored Optical Response", Nature, 483(7389):311-314 (2012).

Li, et al., "Nucleic acid-based nanoengineering: novel structures for biomedical applications", Interface Focus, 1(5): 702-724 (2011).

Liu, et al., "Diamond family of nanoparticle superlattices", Science, 351(6273):582-586 (2016b).

Pan, et al., "Lattice-free prediction of three-dimensional structure of programmed DNA assemblies", Nature Communications., 5(5578): 1-7 (2014A).

Pandey, et al., "Algorithmic design of self-folding polyhedral", Proc. Natl. Acad. Sci. 108(50):19885-19890 (2011).

Peng, et al., "Bottom-up nanofabrication using DNA nanostructures", Chem Matter, 28(4):1012-1021 (2016).

Said, et al., "M1.3—a small scaffold for DNA origami", Nanoscale, 5(1):284-290 (2013).

Seeman, et al., "DNA nicks and nodes and nanotechnology", Nano Lett., 1(1):22-26 (2001).

Seeman, et al., "Design of immobile nucleic acid junctions", Biophys. J., 44(2):201-209 (1983).

Shaw, et al., "Purification of functionalized DNA origami nanostructures", ACS Nano, 9(5):4968-4975 (2015).

Shih, et al., "A 1.7-kilobase single-stranded DNA that folds into a nanoscale octahedron", Nature, 427(6975):618-621 (2004).

Sinclair, et al., "Generation of protein lattices by fusing proteins with matching rotational symmetry", Nat. Nanotechnol., 6(9):558-562 (2011).

Smola, et al., "Selective 2'-hydroxyl acylation analyzed by primer extension and mutational profiling (SHAPE-MaP) for direct, versatile and accurate RNA structure analysis", Nat Protoc., 10( 11):1643-1669 (2015).

Sobczak, et al., "Rapid folding of DNA into nanoscale shapes at constant temperature", Science, 338(6113):1458-1461 (2012).

Songsivilai, et al., "Bispecific antibody: a tool for diagnosis and treatment of disease", Clin. Exp. Immunol., 79(3):15-321 (1990).

Spink, et al., "Thermodynamics of forming a parallel DNA crossover", Biophysical Journal, 97(2):528-538 (2009).

Sun, et al., "Casting inorganic structures with DNA molds", Science, 346(6210): 1-24 (2014).

Tintore, et al., "DNA origami as a DNA repair nanosensor at the single-molecule level", Angew Chem Int Ed Engl., 52(30):7747-7750 (2013).

Ui-Tei, et al., "Sensitive assay of RNA interference in Drosophila and Chinese hamster cultured cells using firefly luciferase gene as target", FEBS Lett, 479(3):79-82 (2000).

Untergasser, et al., "Primer3—new capabilities and interfaces", Nucleic Acids Res. 40(15): e115-e115 (2012).

Wahlestedt, et al., "Potent and nontoxic antisense oligonucleotides containing locked nucleic acids", Proc. Natl Acad. Sci. USA, 97(10):5633-5638 (2000).

Wang, et al., "An atomic model of brome mosaic virus using direct electron detection and real-space optimization", Nature Communications, 5(4808):1-12 (2014).

Wang, "Double-stranded DNA homology produces a physical signature", PNAS, 107(28): 12547-12552 (2010).

Wei, et al., "Complex shapes self-assembled from single-stranded DNA tiles", Nature, 485(7400):623-626 (2012).

Wooddell, et al., "Use of asymmetric PCR to generate long primers and single-stranded DNA for incorporating cross-linking analogs into specific sites in a DNA probe", Genome Res. 6(9):886-892 (1996).

(56) References Cited

OTHER PUBLICATIONS

Yan, et al., "DNA-templated self-assembly of protein arrays and highly conductive nanowires", Science, 301(5641):1882-1884 (2003).

Yang, et al., "Self-assembly of DNA rings from scaffold-free DNA tiles," Nano Letters, 13(4):1862-1866 (2013).

Arizona State University, "Top-down design brings new DNA structures to life", retrieved from the internet: URL:https://phys.org/news/2016-05-top-down-dna-life.html :1-4 (2016).

Bai, et al., "Cryo-EM structure of a 3D DNA-origami object", Proc. Natl. Acad. Sci., 109(49): 20012-20017 (2012).

Bent, et al., "On non-intersecting Eulerian circuits", Discrete Appl. Math. 18(1):87-94 (1987).

Anonymous, et al., "M13mp18 (Cloning Vector)", New England BioLabs Catalog, http://international.neb.com/-/media/nebus/page-images/tools/dna-sequences-and-maps/m13mp18_map.pdf?la=en&hash+ABF432A1085CFA7CA7850D00B69ACBE654DFC580 (2002).

Benson, et al., "DNA rendering of polyhedral meshes at the nanoscale", Nature, 523(7561):441-444 (2015).

Benson, et al., "Computer-Aided Production of Scaffolded DNA Nanostructures from Flat Sheet Meshes", Angewandte Chemie, 55(31):8869-8872 (2016).

Brown, et al., "An easy-to-prepare mini-scaffold for DNA origami", Nanoscale, 7(4):16621-4 (2015).

Brudno, et al., "Recent progress toward the templated synthesis and directed evolution of sequence-defined synthetic polymers", Chem Biol., 16(3):265-276 (2009).

Chasteen, et al., "Eliminating helper phage from phage display", Nucleic Acids Res., 34(21)e145. 1-11 (2006).

Elbaz, et al., "Genetic encoding of DNA nanostructures and their self-assembly in living bacteria", Nat Commun, 7(11179 ): 1-11(2016).

Ennifar, et al., "Targeting the dimerization initiation site of HIV-1 RNA with aminoglyocosides: from crystal to cell", Nucleic Acids Research. ,34(8):2328-2339 (2006).

Faber, et al., "Structural Rearrangements of HIV-1 Tat-responsive RNA upon Binding of Neomycin B*", The Journal of Biological Chemistry, 275:20660-20666 (2000).

Fang, et al., "An unusual Toplogical Structure of the HIV-1 Rev Response Element" Cell, 155:594-605 (2013).

Fu, et al., "Controlled drug release by a nanorobot", Nature Biotechnology, 30(5):407-408 (2012).

Geary, et al., "RNA nanostructures. A single-stranded architecture for cotranscriptional folding of RNA nanostructures", Science, 345:799-804 (2014).

Gellman, "Foldamers: A Manifesto", Acc. Chem. Res., 31(4):173-180 (1998).

Han, et al., "Single-stranded DNA and RNA origami", Science, 358(6369):1-25 (2017).

Iinuma, et al., "Polyhedra Self-Assembled from DNA-Paint", Science, 344(6179): 65-69 (2014b).

Jones, et al., "Small-angle X-ray scattering-derived structure of the HIV-1 5' UTR reveals 3D tRNA mimicry", Proceedings of the National Academy of Sciences of the United States of America, 111:3395-3400 (2014).

Ke, et al., "DNA brick crystals with prescribed depths", Nat. Chem., 6(11):994-1002 (2014).

Ke, et al., "Three-dimensional structures self-assembled from DNA bricks", Science, 338(6111):1177-1183 (2012A).

Ke, et al., "Self-Assembled Water-Soluble Nucleic Acid Probe Tiles for Label-Free RNA Hybridization Assays", Science, 319(5860):180-183 (2008).

Kick, et al., "Efficient Production of Single-Stranded Phage DNA as Scaffolds for DNA Origami", Nano Lett, 15(7):4672-6 (2015).

Liedl, et al., "Self-assembly of 3D prestressed tensegrity structures from DNA", Nature Nanotechnology, 5:520-524 (2010).

Linko, et al., "Automated design of DNA origami", Nature Biotechnology, 34(8):826-827 (2016).

Liu, et al., "Crystalline two-dimensional DNA-origami arrays", Angew Chem Int. Ed, 50(1):264-7 (2011).

Lutz, et al., "Sequence-controlled Polymers", Science, 341(6146):628;1238149-1-1238149-8 (2013).

Marchi, et al., "Toward larger DNA origami", Nano Lett, 14(10):5740-7 (2014).

Martin, et al., "Magnesium-free self-assembly of multi-layer DNA objects", Nat. Commun., 3(1103):1-6 (2012).

Nickels, et al., "DNA origami structures directly assembled from intact bacteriophages", Small, 10(9): 1765-9 (2014).

Praetorius, et al., "Biotechnological mass production of DNA origami", Nature, 552(7683):84-7 (2017).

Rothemund, "Folding DNA to create nanoscale shapes and patterns", Nature, 440(7082):297-302 (2006a).

Rothemund, "Scaffolded DNA Origami: from Generalized Multicrossovers to Polygonal Networks", Nanotechnology: Science and Computation, 1-21 (2006b).

Rothemund, et al., "Algorithmic self-assembly of DNA Sierpinski triangles", PLoS Biol., 2(12)e424:2041-2053 (2004).

Santangelo, et al., "Nanostructured Probes for RNA Detection in Living Cells", Annals of Biomedical Engineering, 34(1):39-50 (2006).

Sharma, et al., "Control of self-assembly of DNA tubules through integration of gold nanoparticles", Science, 323(5910):112-6 (2009).

Specthrie, et al., "Construction of a microphage variant of filamentous bacteriophage", Mol. Biol., 228(3):720-724 (1992).

Staple, et al., "Solution structure and thermodynamic investigation of the HIV-1 frameshift inducing element", Journal of Molecular Biology, 349(5):1011-1023 (2005).

Stephenson, et al., "Three-Dimensional RNA Structure of the major HIV-1 Packaging Signal Region", Structure, 21(6):951-962 (2013).

Tomley, et al., "M13 Phage Growth and Single-Stranded DNA Preparation", Methods Mol. Biol., 58:359-362 (1996).

Torring, et al., "DNA origami: a quantum leap for self-assembly of complex structures," Chem. Soc. Rev., 40(12):5636-46 (2011).

Tumpane, et al., "Triplex addressability as a Basis for Functional DNA Nanostructures", Nano Lett., 7(12):3832-3839 (2007).

Veneziano, et al., "Enzymatic Synthesis of gene-length single-stranded DNA", bioRxiv, 6 pages (2017).

Vogel, et al., Hfq and its constellation of RNA, Nature Reviews Microbiology. 9(8):578-589 (2011).

Winfree, et al., "Design and self-assembly of two-dimensional DNA crystals", Nature, 394(6693):539-44 (1998).

Winter, et al., "Making antibodies by Phage Display Technology", Annu Rev Immunol., 12:433-455 (1994).

Woo, et al., "Programmable molecular recognition based on the geometry of DNA nanostructures", Nat. Chem., 3(8):620-7 (2011).

Wynn, et al., "HIV-1 drug discovery: targeting folded RNA structures with branched peptides", Organic & Biomolecular Chemistry, 13(21):5848-5858 (2015).

Xu, et al., "Design of 240,000 orthogonal 25mer DNA barcode probes", PNAS., 106(7):2289-2294 (2009).

Xuan, "Ultrasound-responsive block copolymer micelles based on a new amplification mechanism", Langmuir, 28(47):16463-16468 (2012).

Yazdi, et al., "A Rewritable, Random-Access DNA-Based Storage System", Scientific reports, 5(14138): 1-10 (2015).

Yim, et al., "The Essential Component in DNA-Based Information Storage System: Robust Error-Tolerating Module", Frontiers in bioengineering and biotechnology, 2(49):1-5 (2014).

Zhao, et al., ,,Organizing DNA origami tiles into larger structures using preformed scaffold frames, Nano Lett., 11(7):2997-3002 (2011).

Zuckermann, et al., "Efficient method for the preparation of peptoids [oligo(N-substituted glycines)] by submonomer solid-phase synthesis", J. Am. Chem. Soc., 114(26):10646-10647(1992).

Abbott, et al., "Precursor Frequency and Affinity Determine B Cell Competitive Fitness in Germinal Centers, Tested with Germline-Targeting HIV Vaccine Immunogens," Immunity, 48(1): 133-146 (2018).

Avalos, et al., "Monovalent engagement of the BCR activates ovalbumin-specific transnuclear B cells," J. Exp. Med., 211(2):365-379 (2014).

Barber, "STING: infection, inflammation, and cancer", Nat Rev Immunol., 15(12):760-770 (2015).

(56)         References Cited

OTHER PUBLICATIONS

Bachmann, et al., "The influence of antigen organization on B cell responsiveness," Science, 262(5138): 1448-1451 (1993).

Bachmann, et al.. "Vaccine delivery: a matter of size, geometry, kinetics and molecular patterns," Nat. Rev. Immunol., 10(11):787-796 (2010).

Batista, et al., "B cells acquire antigen from target cells after synapse formation," Nature, 411(6836):489-494 (2001).

Bennett, et al., "Multivalent Antigens for Promoting B and T Cell Activation. ACS Chem. Biol.," 10(8): 1817-1824 (2015).

Benson, et al., "Supplementary Material for DNA rendering of polyhedral meshes at the nanoscale", Nature, 523(7561):441-444 (2016).

Bhatia, et al., "Icosahedral DNA nanocapsules by modular assembly", Angew. Chem. Int. Ed., 48(23):4134-4137 (2009).

Bobbin, et al., "RNA interference approaches for treatment of HIV-1 infection", Genome Med., 7(50):1-16 (2015).

Brouwer, et al. "Enhancing and shaping the immunogenicity of native-like HIV-1 envelope trimers with a two-component protein nanoparticle," Nat. Commun., 10(4272):1-17 (2019).

Burnett, et al., "Germinal center antibody mutation trajectories are determined by rapid self/foreign discrimination," Science, 360(6385):223-226 (2018).

Burton, et al., "Broadly Neutralizing Antibodies Present New Prospects to Counter Highly Antigenically Diverse Viruses," Science, 337(6091):183-186 (2012).

Chattopadhyay, et al., "Nanoparticle Vaccines Adopting Virus-like Features for Enhanced Immune Potentiation", Nanotheranostics, 1(3): 244-260 (2017).

Cochran, et al., "Receptor Proximity, Not Intermolecular Orientation, Is Critical for Triggering T-cell Activation," J. Biol. Chem., 276(30):28068-28074 (2001).

Corti, et al., "Broadly Neutralizing Antiviral Antibodies," Annu. Rev. Immunol., 31:705-742 (2013).

Dahlman, et al., "Barcoded nanoparticles for high throughput in vivo dicovery of targeted therapeutics", Proc. Natl. Acad. Sci. USA, 114(8):2060-65 (2017).

Dintzis, et al., "Molecular determinants of immunogenicity: the immunon model of immune response," Proc. Natl. Acad. Sci. U. S. A., 73:3671-3675 (1976).

Earl, et al., "Catching HIV 'in the act' with 3D electron microscopy," Trends Microbiol, 21(8):397-404 (2013).

Ellis-Monaghan, et al., ., "DNA origami and the complexity of Eulerian circuits with turning costs", Nat. Comput., 14(3):491-503 (2015).

Fousteri, et al., "Subcutaneous insulin B:9-23/IFA immunisation induces Tregs that control late-stage prediabetes in NOD mice through IL-10 and IFNy" Diabetologia, 53:1958-1970 (2010).

Getts, et al., "Have we overestimated the benefit of human(ized) antibodies?", mAbs, 2(6):682-694 (2010).

Gold, et al., "Antigen receptor function in the context of the nanoscale organization of the B cell membrane," Annu. Rev. Immunol., 37:97-123 (2019).

Hartwell, et al., "Multivalent nanomaterials: learning from vaccines and progressing to antigen-specific immunotherapies," J Pharm Sci., 104(2):346-61 (2015).

Harwood, et al., "Early events in B cell activation," Annu. Rev. Immunol., 28:185-210 (2010).

Havenar-Daughton, et al. "The human naive B cell repertoire contains distinct subclasses for a germline-targeting HIV-1 vaccine immunogen," Sci. Transl. Med., 10(448): 1-29 (2018).

Havenar-Daughton, et al., "Rapid germinal center and antibody responses in non-human primates after a single nanoparticle vaccine immunization," Cell Rep., 29: 1756-1766 (2019).

IAVI Press Release, "IAVI Announces Clinical Trial of Next-Generation HIV Vaccine Candidate Designed to Induce Antibodies to Block HIV Infection," 6 pages, Oct. 8, 2018.

Iinuma et al., "Supplementary Material for Polyhedra self-assembled from tripods and Characterized with 3D DNA-Paint", Science, 344(6179):65-69 (2014a).

International Search Report for corresponding PCT application PCT/US2020/014957 mailed Jul. 17, 2020.

Ito, et al., Cancer Neoantigens: A Promising Source of Immunogens for Cancer Immunotherapy. J Clin Cell Immunol, 6:1-7 (2015).

Jardine, et al., "HIV-1 Vaccines. Priming a broadly neutralizing antibody response to HIV-1 using a germline-targeting immunogen," Science, 349(6244):156-61 (2015).

Jardine, et al., "Rational HIV Immunogen Design to Target Specific Germline B Cell Receptors", Science, 340:711-716 (2013).

Jardine, et al., "Supplementary Materials for Priming a broadly neutralizing antibody response to HIV-1 using a germline-targeting immunogen," Science, 349(6244):156-61 (2015).

Jardine, et al., "HIV-1 broadly neutralizing antibody precursor B cells revealed by germline-targeting immunogen", Science, 351(6280):1458-63 (2016).

Jun, et al., "Automated Sequence Design of 3D Polyhedral Wireframe DNA Origami with Honeycomb Edges", ACS Nano, 13(2):2083-2093 (2019).

Keane, et al., ., "Structure of the HIV-1 RNA packaging signal", Science, 348(6237):917-921 (2015).

Kim, et al., "Monovalent ligation of the B cell receptor induces receptor activation but fails to promote antigen presentation," PNAS, 103(9):3327-3332 (2006).

Kläsener, et al., "B cell activation involves nanoscale receptor reorganizations and inside-out signaling by Syk," Elife, 3(e02069):1-17 (2014).

Klein, et al., "Few and Far between: How HIV May Be Evading Antibody Avidity", PLOS Pathog., 6(5)e1000908:1-6 (2010).

Kouskoff, et al., "Antigens Varying in Affinity for the B Cell Receptor Induce Differential B Lymphocyte Responses," Journal of Experimental Medicine, 188(8):1453-64 (1998).

Krishnan, et al., ., "Designer nucleic acids to probe and program the cell", Trends in Cell Biology, 22(12):624-633 (2012).

Lee, et al., "The nanoscale spatial organization of B-cell receptors on immunoglobulin M- and G-expressing human B-cells," Mol. Biol. Cell, 28:511-523 (2017).

Li, et al., "Broad HIV-1 neutralization mediated by CD4-binding site antibodies," Nat. Med., 13(9):1032-1034 (2007).

Liao, et al., "Co-evolution of a broadly neutralizing HIV-1 antibody and founder virus," Nature, 496(7446):469-476 (2013).

Liu, et al., "Antigen affinity discrimination is an intrinsic function of the B cell receptor," J. Exp. Med., 207:1095-1111 (2010).

Liu, et al., "Antigen receptor nanoclusters: small units with big functions. Trends Immunol.," 37(10):680-689 (2016a).

Marcandalli, et al. "Induction of potent neutralizing antibody responses by a designed protein nanoparticle vaccine for respiratory syncytial virus,"Cell, 176(6): 1420-1431 (2019).

Marras, et al., "Programmable motion of DNA origami mechanisms," Proc. Natl Acad. Sci. USA, 112(3):713-718 (2015).

Minguet, et al., "Low-valency, but not monovalent, antigens trigger the B-cell antigen receptor (BCR)", Int. Immunol., 22(3):205-212 (2010).

Morelli, et al., "ISCOMATRIX: a novel adjuvant for use in prophylactic and therapeutic vaccines against infectious diseases", J Med Microbiol., 61:935-43 (2012).

Mukherjee, et al. "Monovalent and multivalent ligation of the B cell receptor exhibit differential dependence upon Syk and Src family kinases," Sci. Signal., 6(256)ra1: 1-27 (2013).

Nafisi, et al., "Construction of a novel phagemid to produce custom DNA origami scaffolds", Synthetic Biology, 3(1)ysy015:1-8 (2018).

Natkanski, et al., "B Cells Use Mechanical Energy to Discriminate Antigen Affinities," Science, 340(6140): 1-12 (2013).

Okholm, et al., "Quantification of cellular uptake of DNA nanostructures by qPCR", Methods, 67(2):193-7 (2014).

Olson, et al., "New Structure Sheds Light on Selective HIV-1 Genomic RNA Packaging", Viruses, 7(8):4826-4835 (2015).

Pan, et al., "Structure-based model for light-harvesting properties of nucleic acid nanostructures", Nucleic Acids Research, 42(4):2159-2170 (2014B).

Plesa, et al., "Multiplexed Gene Synthesis in Emulsions for Exploring Protein Functional Lanscapes", Science, 359(6373):343-347 (2018).

(56) References Cited

OTHER PUBLICATIONS

Puffer, et al., "Activating B cell signaling with defined multivalent ligands," ACS Chem. Biol., 2:252-262 (2007).

Rouskin, et al., "Genome-wide probing of RNA structure reveals active unfolding of mRNA structures in vivo", Nature, 505(7485):701-705 (2014).

Sacca, et al., "Orthogonal Protein Decoration of DNA Origami", Angew Chem Int Ed Engl., 49(49):9378-83 (2010).

Saunders, et al. "Targeted selection of HIV-specific antibody mutations by engineering B cell maturation," Science 366(6470): 1-42 (2019).

Scharenberg, et al. "Calcium signalling and cell-fate choice in B cells," Nat. Rev. Immunol., 7(10):778-789 (2007).

Schumaker, et al., "Neoantigens in cancer immunotherapy", Science, 348(6230):69-74 (2015).

Shaw, et al. "Binding to nanopatterned antigens is dominated by the spatial tolerance of antibodies," Nat. Nanotechnol., 14(2):184-190 (2019).

Shaw, et al., "Spatial control of membrane receptor function using ligand nanocalipers," Nat Methods, 11(8):841-6 (2014).

Shepherd, "Bioproduction of pure, kilobase-scale single-stranded DNA" Sci. Rep. 9(6121):1-9 (2019a).

Shepherd, et al., "Bioproduction of single-stranded DNA from isogenic miniphage", bioRxiv, 521443:1-18 (2019b).

Siegfried, et al., "RNA motif discovery by SHAPE and mutational profiling (SHAPE-MaP)", Nature Methods, 11(9):959-965 (2014).

Sil, et al., "Trivalent ligands with rigid dna spacers reveal structural requirements for ige receptor signaling in rbl mast cells," ACS Chem. Biol., 2(10):674-84 (2007).

Simek, et al., "Human Immunodeficiency Virus Type 1 Elite Neutralizers: Individuals with Broad and Potent Neutralizing Activity Identified by Using a High-Throughput Neutralization Assay together with an Analytical Selection Algorithm," J. Virol., 83(14):7337-7348 (2009).

Sok, et al. "Priming HIV-1 broadly neutralizing antibody precursors in human Ig loci transgenic mice," Science, 353:1557-1560 (2016).

Spillane, et al., "B cell antigen extraction is regulated by physical properties of antigen-presenting cells," J Cell Biol., 216(1): 217-230 (2016).

Stamatatos, et al. "Germline-targeting immunogens," Immunol. Rev., 275(1):203-216 (2017).

Steichen, et al. "A generalized HIV vaccine design strategy for priming of broadly neutralizing antibody responses," Science, 366(6470): 1-21 (2019).

Steichen, et al. "HIV vaccine design to target germline precursors of glycan-dependent broadly neutralizing antibodies," Immunity, 45(3):483-496 (2016).

Stone, et al. "Protein sorting by lipid phase-like domains supports emergent signaling function in B lymphocyte plasma membranes," eLife, 6(e19891):1-33 (2017).

Sun, et al., "ISCOMs and ISCOMATRIX™", Vaccine, 27(33): 4388-4401 (2009).

Tokatlian, et al., "Enhancing Humoral Responses Against HIV Envelope Trimers via Nanoparticle Delivery with Stabilized Synthetic Liposomes", Scientific Reports, 8(1)16527:1-13 (2018).

Tolar, et al. "The constant region of the membrane immunoglobulin mediates B cell-receptor clustering and signaling in response to membrane antigens," Immunity 30(1): 44-55 (2009).

Tolar, et al., "Cytoskeletal control of B cell responses to antigens", Nat. Rev. Immunol., 17(10):621-634 (2017).

Tolar, et al., "Immunological Synapse", Curr Top Microbiol Immunol., 340:155-169 (2010).

Ubaidurrahman, et al., ., "A Novel DNA Computing Based Encryption and Decryption Algorithm", Procedia Comput Sci., 46:463-475 (2015).

Veneziano, et al. "In vitro synthesis of gene-length single-stranded DNA," Sci. Rep. 8(1)6548:1-7 (2018).

Veneziano, et al., "Designer nanoscale DNA assemblies programmed from the top down", Science, 352(6293):1534 (2016).

Veneziano, et al., "Supplementary Material for Designer nanoscale DNA assemblies programmed from the top down," Science, 352(6293):1534 (2016).

Veneziano, et al., "Probing the Role of HIV Antigen Nanoscale Organization on B-Cell Activation with DNA Origami," Biophysical Journal, 116(3):578a-578a (2019).

Villar, et al. "Reconstituted B cell receptor signaling reveals carbohydrate-dependent mode of activation," Sci. Rep., 6(36298):1-11 (2016).

Wamhoff, et al. "Programming structured DNA assemblies to probe biophysical processes," Annu. Rev. Biophys. 48, 395-419 (2019).

Watts, et al., ., "Architecture and secondary structure of an entire HIV-1 RNA genome", Nature, 460(7256):711-716 (2009).

Weaver, et al. "In vitro reconstitution of B cell receptor-antigen interactions to evaluate potential vaccine candidates," Nat. Protoc. 11, 193-213 (2016).

Wilkinson, et al., "Selective 2'-hydroxyl acylation analyzed by primer extension (SHAPE): quantitative RNA structure analysis at single nucleotide resolution", Nature Protocols, 1(3)1610-1616 (2006).

Wilson, et al., Inflammasome-dependent and -independent IL-18 production mediates immunity to the ISCOMATRIX adjuvant, Journal of Immunology, 192(7):3259-68 (2014).

Wong, et al., "Organic Data Memory Using the DNA Approach", Communications of the ACM., 46:95-98 (2003).

Wu, et al., "Rational design of envelope identifies broadly neutralizing human monoclonal antibodies to HIV-1", Science, 329(5993):856-861 (2010).

Yang, et al., "Oligomeric organization of the B-cell antigen receptor on resting cells", Nature, 467(7314):465-469 (2010).

Zhang, et al., "Complex wireframe DNA origami nanostructures with multi-arm junction vertices", Nat. Nanotechnol. 10(9):779-784 (2015).

Zhirnov, et al., "Nucleic acid memory", Nat Mater., 15(4):366-70 (2016).

Zhu, et al., "Distribution and three-dimensional structure of AIDS virus envelope spikes", Nature, 441(7095):847-852 (2006).

Veneziano, et al., "Structured DNA Nanoparticles for Spatially Controlled Antigen Presentation," Supplement 1, 112(3):591A-592A, (2017).

Veneziano, et al., "Structured DNA Nanoparticles for Spatially Controlled Antigen Presentation," Poster 591a, Wednesday, Feb. 15, 2017, Biophysical Society, 61st Annual Meeting, New Orleans Louisiana (2017).

Chen, et al., "Regulation and function of the cGAS-STING pathway of cytosolic DNA sensing" Nature Immunology, 17 (10), 1142-1149 (2016).

Civril et al., "Structural mechanism of cytosolic DNA sensing by cGAS" Nature, 498 (7454), 332-337 (2013).

Hong, et al., "Toll-Like Receptor-Mediated Recognition of Nucleic Acid Nanoparticles (NANPs) in Human Primary Blood Cells" Molecules, 24 (6), 1094 (2019).

Hong, et al., "Researchers report unraveling the immune recognition of nucleic acid nanoparticles"Nano Letters, 18 (7), 4309-4321 (2018).

Irvine, et al., "Synthetic Nanoparticles for Vaccines and Immunotherapy"Chemical Reviews, 115(19), 11109-11146 (2015).

Jin, et al., "Modular delivery of CpG-incorporated lipid-DNA nanoparticles for spleen DC activation" Biomaterials, 115, 81-89 (2017).

Jun, et al., "Rapid prototyping of arbitrary 2D and 3D wireframe DNA origami" Nucleic Acids Research, 49 (18), 10265-10274 (2021).

Knappe, et al., "In Situ Covalent Functionalization of DNA Origami Virus-Like Particles"ACS Nano, 15 (9), 14316-14322 (2021).

Leleux, et al., "Biophysical Attributes of CpG Presentation Control TLR9 Signaling to Differentially Polarize Systemic Immune Responses" Cell Reports, 18 (3), 700-710 (2017).

Schlee & Hartmann, "Discriminating self from non-self in nucleic acid sensing" Nature Reviews Immunology, 16 (9), 566-580 (2016).

Paludan, et al., "Activation and Regulation of DNA-Driven Immune Responses" Microbiology and Molecular Biology Reviews, 79 (2), 225-241 (2015).

(56) References Cited

OTHER PUBLICATIONS

Paludan & Bowie, "Immune sensing of DNA" Immunity, 38 (5), 870-880 (2013).

Surana, et al., "Designing DNA nanodevices for compatibility with the immune system of higher organisms" Nature Nanotechnology, 10 (9), 741-747 (2015).

Zhou, et al., "Structure of the Human cGAS-DNA Complex Reveals Enhanced Control of Immune Surveillance" Cell, 174 (2), 300-311. e11 (2018).

Ito, et al., "Cancer Neoantigens: A Promising Source of Immunogens for Cancer Immunotherapy",. J Clin Cell Immunol, 6:322 (2015).

Bonham, et al., "A promiscuous lipid-binding protein diversifies the subcellular sites of Toll-like Receptor signal transduction" Cell, 156 (4), 705-716 (2014).

Chen, et al., "Effects of particle size on toll-like receptor 9-mediated cytokine profiles" Biomaterials, 32 (6), 1731-1737 (2011).

Luchner, et al., "TLR Agonists as Vaccine Adjuvants Targeting Cancer and Infectious Diseases" Pharmaceutics, 13 (2), 142 (2021).

Vollmer, et al., "Characterization of three CpG oligodeoxynucleotide classes with distinct immunostimulatory activities"., Journal of Immunology, 34 (1), 251-262 (2004).

Braasch, et al., "Locked nucleic acid (LNA): Fine-tuning the recognition of DNA and RNA", Chem. Biol., 8(1):1-7 (2001).

Kurreck, et al., "Design of antisense oligonucleotides stabilized by locked nucleic acids", Nucleic Acids Res., 30(9):1911-1918 (2002).

Ponnuswamy, et al., "Oligolysine-based coating protects DNA nanostructures from low-salt denaturation and nuclease degradation" Nat. Commun., 8:15654 (2017).

Kiviaho et al., "Cationic polymers for DNA origami coating—examining their binding efficiency and tuning the enzymatic reaction rates"., Nanoscale, 8: 11674-11680 (2015).

Tuite, et al., "Effects of minor and major groove-binding drugs and intercalators on the DNA association of minor groove-binding proteins RecA and deoxyribonuclease I detected by flow linear dichroism"Eur J Biochem, 243(1):482-492 (1997).

Morita, et al., "Genetic regulation of the RUNX transcription factor family has antitumor effects" J Clin Invest, 127(7):2815-2828 (2017).

Gregoriadis and Ryman, "Liposomes as carriers of enzymes or drugs: a new approach to the treatment of storage diseases", Biochem J, 124:58P (1971).

Gregoriadis, et al., "Improving the therapeutic efficacy of peptides and proteins: a role for polysialic acids", Int J Pharm, 300:125-30 (2005).

Immmordino, et al., "Stealth liposomes: review of the basic science, rationale, and clinical applications, existing and potential" Int J Nanomedicine, 1(3):297-315 (2006).

Paszko et al., "Immunoliposomes"Curr Med Chem., 19(31):5239-77 (2012).

Kelly, et al., "Targeted Liposomal Drug Delivery to Monocytes and Macrophages" Journal of Drug Delivery, vol. 2011 (2011).

Croy and Kwon, "Polymeric micells for drug delivery", Curr. Pharm. Design, 12:4669-4684 (2006).

Pohar, et al., "Minimal Sequence Requirements for Oligodeoxyribonucleotides Activating Human TLR9" The Journal of Immunology, 194 (8), 3901-3908 (2015).

* cited by examiner

DNA nanoparticles for antigen presentation eOD-GT8 60-mer               DNA-NPs/eOD-GT8 10-mer Design of DNA-NP antigen conjugates Stoichiometry          Distance          1D to 3D 1D                                3D eOD-PB84-10        eOD-PB84-40 eOD monomer
eOD-60mer
PB84
eOD-PB84-10
eOD-PB84-40

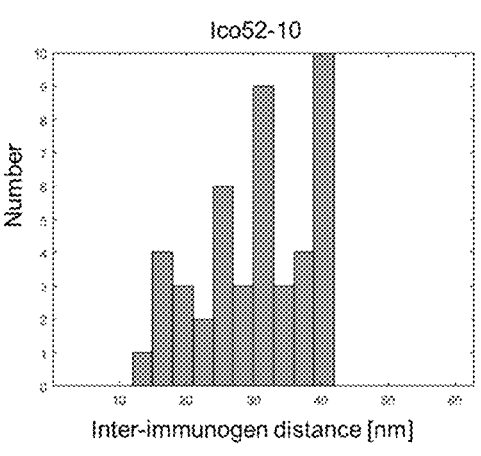
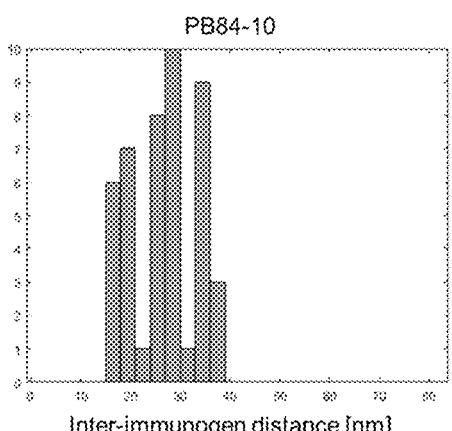
FIG. 6G
FIG. 6H
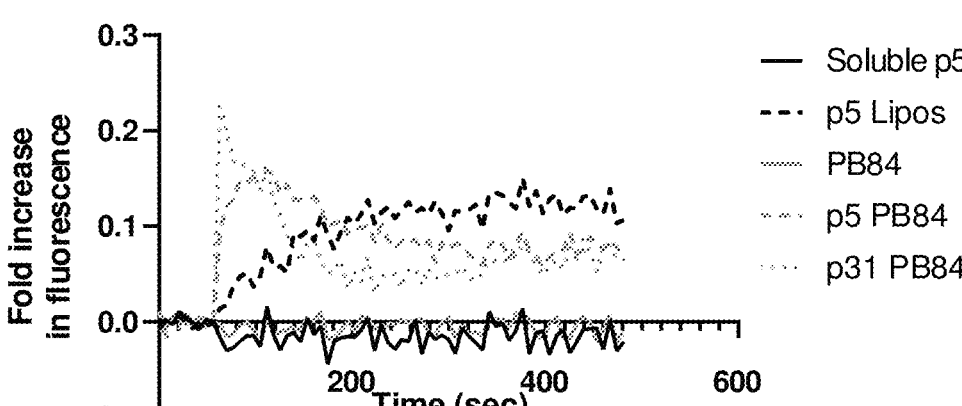
FIG. 7A
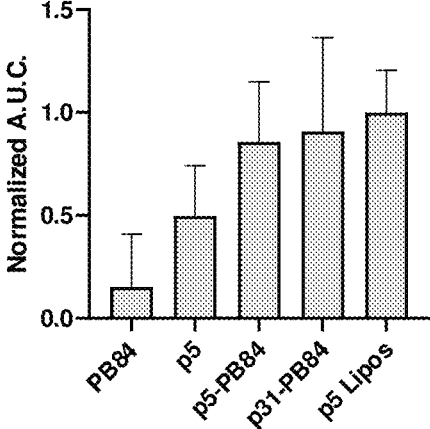
FIG. 7B

| Construct | Coverage (%) |
|-----------|--------------|
| PB84 | -0.17 ± -0.07 |
| PB84 10oh | 10.58 ± 0.44 |
| PB84 20oh | 20.67 ± 1.00 |
| PB84 40oh | 46.49 ± 2.18 |

NUCLEIC ACID NANOSTRUCTURE PLATFORM FOR PROGRAMMING IMMUNE STIMULATION

CROSS-REFERENCE TO RELATED APPLICATIONS

This application is a continuation-in-part (CIP) of U.S. application Ser. No. 16/752,394 filed Jan. 24, 2020, which claims the benefit of and priority to U.S. Provisional Application No. 62/796,472 filed Jan. 24, 2019. This application also claims the benefit of and priority to U.S. Provisional Application No. 63/333,498 filed Apr. 21, 2022. U.S. application Ser. No. 16/752,394, U.S. Provisional Application No. 62/796,472 and U.S. Provisional Application No. 63/333,498 are hereby incorporated by reference in their entireties.

STATEMENT REGARDING FEDERALLY SPONSORED RESEARCH

This invention was made with government support under AI162307, MH112694, EB026008 awarded by the National Institutes of Health and under N00014-17-1-2609, N00014-21-1-4013 awarded by the Office of Naval Research. The government has certain rights in the invention.

REFERENCE TO SEQUENCE LISTING

The Sequence Listing submitted as an xml file named "MIT_20929_H_CIP.xml", created on Jan. 20, 2023, and having a size of 458,182 bytes is hereby incorporated by reference pursuant to 37 C.F.R. § 1.834(c)(1).

FIELD OF THE INVENTION

The present invention generally relates to immunostimulatory compositions, and in particular, the use of nucleic acid nanostructures having a specified geometric shape, for example a shape that mimics a natural macromolecular assembly, as a platform for the user-defined, programmable display of immunostimulatory molecules.

BACKGROUND OF THE INVENTION

Peptide- and protein-based vaccines form the major class of vaccination strategies globally. Inactivated or otherwise attenuated antigenic particles are typically used in vaccine formulations to display protein or peptide antigens to stimulate and train the immune response. Adjuvants including small molecules and nucleic acids are often co-formulated in these nanoparticles to further stimulate immune activation.

The field of nucleic acid nanotechnology has over the past several decades developed technologies enabling the fabrication of programmable DNA-based assemblies of prescribed size, geometry, rigidity, and chemical Composition (Jun, et al., Nucleic Acids Research, 49 (18), 10265-10274 (2021), Pettersen, et al., Journal of Computational Chemistry, 25 (13), 1605-1612 (2004), Benson, et al., Angewandte Chemie International Edition, 55 (31), 8869-8872 (2016), Jun, et al., ACS Nano (2019), Benson, et al., Nature, 523 (7561), 441-444 (2016), Dietz, et al., Science, 325 (5941), 725-730 (2009), Castro, et al., Nature Methods, 8 (3), 221-229 (2011), Douglas, et al., Nucleic Acids Research, 37 (15), 5001-5006 (2009), Veneziano, et al., Science, 352 (6293), 1534-1534 (2016)). These nanomaterials now represent a toolbox for the design and fabrication of nanodevices capable of interacting with diverse cellular environments (Veneziano, et al., Nature Nanotechnology, 15 (8), 716-723 (2020), Lee, et al., Nature Nanotechnology, 7 (6), 389-393 (2012)). One approach to designing nucleic acid nanostructures on the 10-100 nm scale is the concept of DNA origami, wherein programmed regions of a long, single-stranded DNA scaffold that are far apart in sequence space are brought into spatial proximity through the hybridization of small, single-stranded DNA staples. Scalable scaffold production strategies using M13 bacteriophage engineering and bioproduction have also now provide control over scaffold sequence composition and length, expanding the accessible design space for such wireframe nucleic acid nanoparticles (NANPs).

The ability to chemically functionalize NANPs also permits the attachment of therapeutic nucleic acid (TNA) cargo such as siRNA and miRNA, as well as small molecules, aptamers, peptides, and proteins with nanometer level spatial control for active targeting or immune cell stimulation (Veneziano, et al., Nature Nanotechnology, 15 (8), 716-723 (2020), Douglas, et al., Science, 335 (6070), 831-834 (2012), Knappe, et al., ACS Nano, 15 (9), 14316-14322 (2021)) and enhances the potential of NANPs to interface with biological systems in vitro and in vivo (Liu, et al., Nano Letters, 12 (8), 4254-4259 (2012), Irvine, et al., Chemical Reviews, 115 (19), 11109-11146 (2015)). However, the ability to selectively and controllably modulate specific immunostimulatory pathways in vivo using DNA based NANPs has only been examined to a limited extent (Hong, et al., Molecules, 24 (6), 1094 (2019), Surana, et al., Nature Nanotechnology, 10 (9), 741-747 (2015), Hong, et al., Nano Letters, 18 (7), 4309-4321 (2018), Schüller, et al., ACS Nano, 5 (12), 9696-9702 (2011)).

The innate immune system contains several pattern recognition receptors (PRRs) that are responsible for recognizing evolutionarily conserved pathogen-associated or damage-associated molecular patterns (PAMPs or DAMPs). Once activated, these PRRs invoke innate immune recognition while simultaneously activating the adaptive immune response (Schlee & Hartmann, Nature Reviews Immunology, 16 (9), 566-580 (2016), Paludan, Microbiology and Molecular Biology Reviews, 79 (2), 225-241 (2015)). Binding of PRRs to their corresponding ligand triggers activation of downstream signaling pathways, ultimately resulting in the production of Type I interferons (IFNs) and other proinflammatory cytokines that are essential for initiation of a host of immune functions (Paludan & Bowie, Immunity, 38 (5), 870-880 (2013), Wu & Chen, Annual Review of Immunology, 32 (1), 461-488 (2014)). Cyclic GMP-AMP synthase (cGAS) is one such PRR that responds to cytosolic double-stranded DNA (dsDNA) from both endogenous sources such as certain forms of cell death as well as exogenous DNA from pathogens (Li, et al., Immunity, 39 (6), 1019-1031 (2013), Chen, et al., Nature Immunology, 17 (10), 1142-1149 (2016)) in a sequence-independent but length-dependent manner (Sun, et al., Science, 339 (6121), 786-791 (2013), Zhou, et al., Cell, 174 (2), 300-311.ell (2018), Civril, et al., Nature, 498 (7454), 332-337 (2013), Andreeva, et al., Nature, 549 (7672), 394-398 (2017)).

Toll-like Receptors (TLRs) can also stimulate innate immune signaling through activation. Cancer vaccine nanodevices containing unmethylated cytosine-phosphate-guanine dinucleotides (CpGs) within loops of ssDNA were hybridized within an antigen-displaying DNA origami tube to enable TLR9 activation following pH-triggered conformational change of DNA locks (Comberlato, et al., Nano Letters (2022)). This study followed earlier work that placed CpG oligos onto immune inert DNA origami tubes to induce CpG-dependent cytokine production and immune cell activation (Schuller, et al., *ACS Nano,* 5 (12), 9696-9702 (2011)), as well as work demonstrating that small self-assembled DNA tetrahedra functionalized with multivalent CpG motifs could induce enhanced secretion of inflammatory cytokines via activation of the TLR9 pathway (Li, et al., *ACS Nano,* 5 (11), 8783-8789 (2011)). It was also shown that fixed CpG dimer pairs at distances of 7 nm or 38 nm on a 2D nano-disk showed that the 7 nm dimer pair, which matched the distance between binding sites in the TLR9 dimer, induced increased immune activation, demonstrating the important of inter-ligand distance (Leleux, et al., *Cell Reports,* 18 (3), 700-710 (2017)).

However, while these studies evaluated changes in overall cytokine or surface marker expression levels induced by NANP delivery, there has not yet been an investigation of the relative contributions of individual pathways in NANP-induced innate immune responses, nor has there been a systematic evaluation of the impacts of specific NANP properties on innate immune activation. Previous studies using alternative nanotechnologies to DNA-based materials have also demonstrated that incorporating CpGs into nanostructures can influence the resulting immune response (Leleux, et al., *Cell Reports,* 18 (3), 700-710 (2017), Jin, et al., *Biomaterials,* 115, 81-89 (2017)). However, those studies were limited by the inability to precisely control ligand presentation and stoichiometry.

It is an object of the invention to provide alternative and/or improved immunogenic compositions containing immuno-modulatory agents and vaccine formulations formed therewith, and methods of use thereof.

It is also an object of the invention to provide a platform generally applicable to the controlled organization and preferred display of any immuno-modulatory agents for eliciting or otherwise manipulating an immune response.

It is another object of the invention to provide nanoscale structures that enable the user-defined display and organization of immuno-modulatory agents to provide tunable control of the intensity of immune-pathway activation and methods of use thereof.

It is a further object of the invention to provide methods of displaying TLR agonists in a preferred form for use in stimulation of TLR responses in a selective and user-defined manner in vivo.

It is a further object of the invention to provide methods of inducing an immune response or protective immunity or immune tolerance in a subject, and methods of treating subjects having, or at risk of having, a disease or condition.

SUMMARY OF THE INVENTION

It has been established that nucleic acid nanostructures including one or more immunostimulatory agents can be designed to illicit user-defined modulation of immune responses in a subject. Elements including the structure of an immunostimulatory agent, the number of copies of the immunostimulatory agent, the spacing of copies of the immunostimulatory agent (i.e., distance between two copies of immunostimulatory agent), the location of the immunostimulatory agent on a nanostructure, the rigidity/flexibility of the immunostimulatory agent; the dimensionality of the immunostimulatory agent, the topology of the nanostructure, the ultra-structural organization of the nanostructure, and the geometric shape of the nanostructure can affect the magnitude of the immune response that can be induced by the antigen when presented to immune cells by the nanostructure. Nanostructures can be designed and created that vary one or more of these elements in systematic or non-systematic ways, and the most effective immunogen can be selected. Thus, antigen-bound nucleic acid nanostructures with improved immunogenicity are provided.

For example, nucleic acid nanostructures having at least two copies of an immunostimulatory agent are provided. Typically, the number of copies of the immunostimulatory agent, the distance between adjacent copies of the immunostimulatory agent, the location of the immunostimulatory agent on the nanostructure, the rigidity/flexibility of the immunostimulatory agent, the dimensionality of the immunostimulatory agent, the topology of the nanostructure, the ultra-structural organization of the nanostructure, the geometric shape of the nanostructure, or a combination thereof improves, initiates or otherwise controls an immune response induced by the immunostimulatory agent relative to a control nucleic acid nanostructure having at least one copy of the same immunostimulatory agent. In some embodiments, the disclosed nucleic acid nanostructure improves an immune response induced by the immunostimulatory agent relative to a control nucleic acid nanostructure having multiple copies of distinct immunostimulatory agent on the same nanostructure.

In some embodiments, the nanostructure has 2 to 100, or 3 to 75, or 4 to 60, or 5 to 50, or 5 to 25, or 5 to 10 inclusive copies of an immunostimulatory agent per nanostructure, for example, 5, 6, 7, 8, 9, or 10 copies per nanostructure. The distance between adjacent copies of immunostimulatory agent can be in the range of, for example, 1 nm to 150 nm, or 10 nm to 80 nm, or 15 nm to 50 nm, or 25 nm to 30 nm inclusive. The geometric shape of the nanostructure can be selected from, for example a helix bundle, cuboidal structure, icosahedral structure, tetrahedral structure, cuboctahedral structure, octahedral structure, pentagonal bipyramidal structure and hexahedral structure. In particular exemplary embodiments, the geometric shape is a polyhedron such as an icosahedron, pentagonal bipyramid, or a 6-helix bundle. The nucleic acid of the nanostructure can be, for example, DNA.

The immunostimulatory agent can be covalently or non-covalently bound to the nanostructure. For example, the immunostimulatory agent can be indirectly or directly bound to the nanostructure via outwardly facing nucleic acid overhangs extending from the 3' and/or 5' ends of selected staple strands. In particular embodiments, the nucleic acid overhangs hybridize to a complementary target RNA, DNA or PNA sequence covalently linked to the immunostimulatory agent, by, for example, maleimide-thiol coupling.

In some embodiments, the nanostructure includes 2, 3, 4, 5, or more structurally different immunostimulatory agents. The immunostimulatory agent(s) can be or include, for example, peptides, proteins, nucleic acids, lipids, and/or polysaccharides. In preferred embodiments, the immunostimulatory agent(s) is a peptide or protein immunostimulatory agent(s). The immunostimulatory agent(s) can be antigens associated with one or more diseases or conditions including, but not limited to, infectious diseases, autoimmune diseases, and cancer.

In some embodiments, the immunostimulatory agent is an HIV immunogen. For example, a nucleic acid nanostructure having a defined geometric shape and one or more copies of an immune-stimulatory agent that can induce an immune response against human immunodeficiency virus (HIV) are provided. In some embodiments, the immunostimulatory agent is an antigen that binds to a broadly neutralizing antibody. For example, in some embodiments, the immunostimulatory agent is an antigen, such as an HIV gp120 epitope, for example, an epitope that encompasses binding site of gp120. In some embodiments, the binding site is a CD4 binding site. Exemplary immunostimulatory agents include eOD-GT6, eOD-GT8, and variants thereof. In another example, the epitope can encompass or mimic the trimer interface of gp120. In particular embodiments, the nanostructure includes 2 to 20, or 5 to 10 copies of the immunostimulatory agent inclusive. Adjacent immunostimulatory agents can be separated by an inter-immunostimulatory agent distance of, for example, 5 nm to 80 nm inclusive, and preferably at least 28 nm. The nanostructure can be a helix bundle, cuboidal structure, icosahedral structure, tetrahedral structure, cuboctahedral structure, octahedral structure, pentagonal bipyramidal structure or hexahedral structure.

In particular embodiments, an immunogen for inducing an immune response against HIV includes an icosahedron-shaped DNA nanostructure including, for example, 5-60, 5-50, 5-40, 5-30, 5-20, or 5-10, copies of eOD-GT8 antigen, wherein each copy of the antigen agent is linked to the nanostructure by a single stranded peptide nucleic acid conjugated directly to the antigen and hybridized to a complementary sequence at the 3' single stranded overhang of a staple strand of the nanostructure, and wherein each copy of the antigen agent is spaced from the other copies of antigen by at least 5 nm, 10 nm, 15 nm, 20 nm, 25 nm, 28 nm, or 30 nm and optionally not more than 100 nm.

In some embodiments, the immunostimulatory agent is a peptide antigen derived from the H-2K$^k$ MHC class I molecule. For example, a nucleic acid nanostructure having a defined geometric shape and one or more copies of an antigen than can induce a response from B cell specific to the H-2K$^k$ MHC class I molecule are provided. In some embodiments, the antigens have been previously defined and are known to have varying affinity B cell receptors from NOD.D2(B10)-Tg(Igh2$^k$3-83)1Nemz/Dvs mice (Kouskoff, et al, *Journal of Experimental Medicine,* 188(8):1453-64, 1998).

In particular embodiments, the immunostimulatory agent is the p31 peptide, which has a high affinity for NOD.D2 (B10)-Tg(Igh2$^k$3-83)1Nemz/Dvs B cell receptors, or the p5 peptide, which has an intermediate affinity for NOD.D2 (B10)-Tg(Igh2$^k$3-83)1Nemz/Dvs B cell receptors, placed on a pentagonal bipyramidal structure.

Any of the nanostructures can further include one or more moieties incorporated in and/or linked to the nanostructure. Such moieties include, for example, adjuvants, targeting molecules, therapeutic agents, stabilizing agents, passivating agents, etc.

Cationic polymers and minor groove binders (as monomers, oligomers or polymers) may be used to coat the DNA nanoparticles for stabilization from endonuclease degradation. In particular, minor groove binders may act as tethers for covalent modifications of nucleic acids, for example to develop cross-linking strategies for DNA nanoparticles. These approaches can be combined, e.g. using brush or block copolymers, with PEGylation to further improve stabilization and passivation.

Pharmaceutical compositions and immunogenic compositions including the nucleic acid nanostructure are also provided. The composition can include, for example, a pharmaceutically acceptable carrier, diluent, preservative, excipient, or combination thereof. The nucleic acid nanostructure can be present in an effective amount to induce an immune response in a subject in need thereof, with or without the aid of an adjuvant. In some embodiments, the immunostimulatory agent is, or includes an adjuvant. The composition can also be free from adjuvant. The adjuvant can form part of the nanostructure or can be independent therefrom or otherwise unlinked or unbound thereto. The adjuvant can be in an effective amount to enhance the immune response relative to administration of the nucleic acid nanostructure alone.

Methods of using immunostimulatory agent-bound nucleic acid nanostructures are also provided. The methods can include, for example, administering to a subject in need thereof an effective amount of an immunostimulatory agent-bound nanostructure to induce or enhance an immune response, induce or enhance protective immunity against an infectious agent, disease, or condition, treat or prevent a disease or condition, induce or enhance the production of neutralizing antibodies or inhibitory antibodies, or a combination thereof in a subject in need thereof. The methods can further include administering the subject one or more additional agents, such as adjuvants, one or more therapeutic agents, or a combination thereof. The adjuvant and/or therapeutic agent can be in the same or a different composition from the immunostimulatory agent-bound nanostructure. The adjuvant and/or therapeutic agent can be administered at the same or a different time from the antigen. In some embodiments, the subject is a mammal such as a human.

In particular embodiments, the methods include treating HIV in a subject in need thereof by administering the subject an effective amount of an antigen-bound nanostructure to induce an immune response against HIV in the subject.

Methods of vaccination are also provided. The methods typically include administering to a subject an effective amount of an immunostimulatory agent-bound nanostructure to induce an immune response in the subject. In more specific embodiments, the vaccination is against HIV and the immunostimulatory agent is an antigen such as eOD-GT8.

Methods of selecting nucleic acid nanostructures are also provided. The methods can include, for example, assaying the ability of two or more structurally different immunostimulatory agent-bound nucleic acid nanostructures to induce an immune response, wherein the two or more structurally different nucleic acid nanostructures differ by (i) the structure of the antigen(s);
(ii) the copy number of the immunostimulatory agent(s);
(iii) spacing of the immunostimulatory agent(s);
(iv) location of the immunostimulatory agent(s) on the nanostructure;
(v) rigidity/flexibility of the immunostimulatory agent(s);
(vi) dimensionality of the immunostimulatory agent(s);
(vii) topology of the nanostructure;
(viii) ultra-structural organization of the nanostructure;
(ix) geometric shape of the nanostructure; or
(x) a combination thereof.

For example, in some embodiments, the two or more structurally different nucleic acid nanostructures differ by (ii) and the copy number of immunostimulatory agent on each nanostructure is independently selected from 2 to 60 copies per nanostructure. In some embodiments, the two or more structurally different nucleic acid nanostructures differ by (iii) and the inter-agent distance between adjacent immunostimulatory agents on each nanostructure is independently selected from 3 nm to 80 nm. In some embodiments, the two or more structurally different nucleic acid nanostructures differ by (ix), and the geometric shape of each nanostructure is independently selected from helix bundles, cuboidal structures, icosahedral structures, tetrahedral structures, cuboctahedral structures, octahedral structures, bipyramidal structures, and hexahedral structures.

BRIEF DESCRIPTION OF THE DRAWINGS

In FIGS. 4A-4D, raw fluorescence of cells loaded with Fluo-4 calcium probe normalized by division by unstimulated levels and then subtraction of buffer-only control curves are shown. In FIGS. 4E-4F, data is normalized to the condition showing maximum activation.

FIGS. 6G and 6H are bar graphs showing a comparison of inter-immunogen distances for icosahedral (FIG. 6G) and pentagonal bipyramidal (FIG. 6H) DNA nanostructures bearing 10 copies of eOD-GT8.

FIG. 7A is a line graph and FIG. 7B is a bar graph, each showing quantification of B cell (primary mouse 3-83 splenocyte) activation upon exposure to pentagonal bipyramid DNA NPs modified with 3-83 peptide antigens p5 or p31 at 1 nM peptide. Raw fluorescence of cells loaded with Fluo-4 calcium probe normalized by unstimulated levels, buffer-only control curves (FIG. 7A) and areas under the curves normalized to the maximum in repeat (FIG. 7B) are shown.

FIG. 8A is a schematic illustrating folding of the two types of DNA-NPs; (i) an icosahedron with 42 base pairs per edge (ICO42); and (ii) a pentagonal bipyramid with 84 base pairs per edge (PB84). The schematic demonstrates an overview of the thermal annealing of scaffold and staple strands to form ICO42 with a 15 nm edge/35 nm diameter and PB84 with a 28 nm edge/50 nm diameter, respectively. The unmodified and, modified forms of nanostructure including antigen (CpG dinucleotide motif; •) conjugated to the structure via single-stranded DNA (ssDNA) overhangs in the staple strands are shown. FIG. 8B is a schematic illustrating various designs in the distribution, density and spacing of CpG motifs presented at the surface of DNA nucleic acid nanostructure particles (DNA-NANP), showing variation in the Inter-CpG distance and CpG copy number in overhang sequences. The overhang sequence including CpG motifs (TCGTCGTTTTGTCGTTTGTCGTT (SEQ ID NO:489)), as well as a phosphorothioated version (SEQ ID NO:490) are depicted, and a non-immunogenic control overhang sequence (TTTGATACTGCCAT-AGAAGGCAAC (SEQ ID NO:491)) is also shown. The schematic indicates that overhangs can be designed to be orientated such that they face inwards or outwards with respect to the nanostructure itself.

OH groups, respectively. Data plotted are the average of three technical replicates of each sample.

Figure 14A:
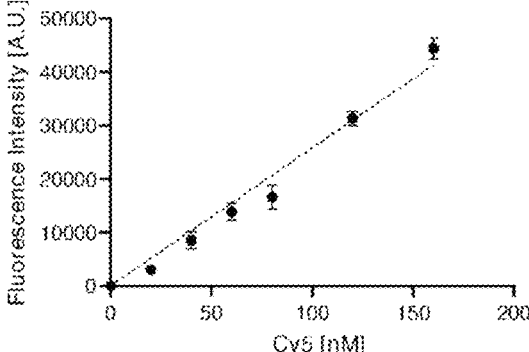
Figures 14B, 15:
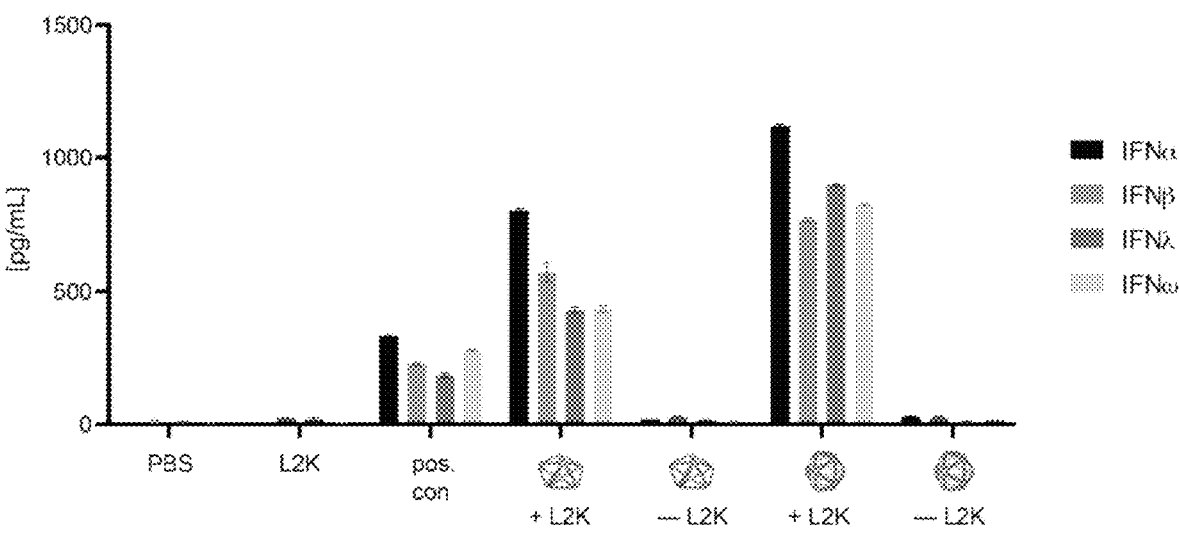

FIGS. 14A-14B depict quantification of CpG overhang coverage on PB84 constructs using fluorimetry. FIG. 14A is an exemplary standard curve of fluorescence intensity [10,000 to 50,000 A.U.] over Cy5 (0-200 nm), acquired by measuring serial dilutions of Cy5-CpG duplexes. Three independent serial dilutions were performed, and data were measured in triplicate. FIG. 14B shows quantification of CpG overhang coverage on PB84 variants. Error propagation calculations were used to determine the coverage error. All samples were measured in triplicate.

FIG. 15 is a bar graph of IFN production induced by NANPs in the presence and absence of lipofectamine complexation, showing amount (pg/ml) of each of IFNα, IFNλ, IFNβ, and IFNω induced by PBS (negative control), lipofectamine (L2K), ODN2006 as a positive control (pos. con.), and each of PB84 and ICO42 complexed with (+) or without (−) lipofectamine, respectively. Each bar represents the mean response and standard error of the mean (n=3).

Figure 16A:
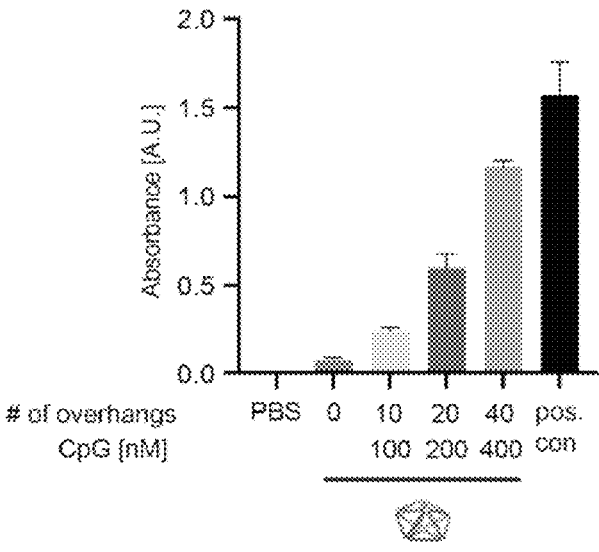
Figure 16B:
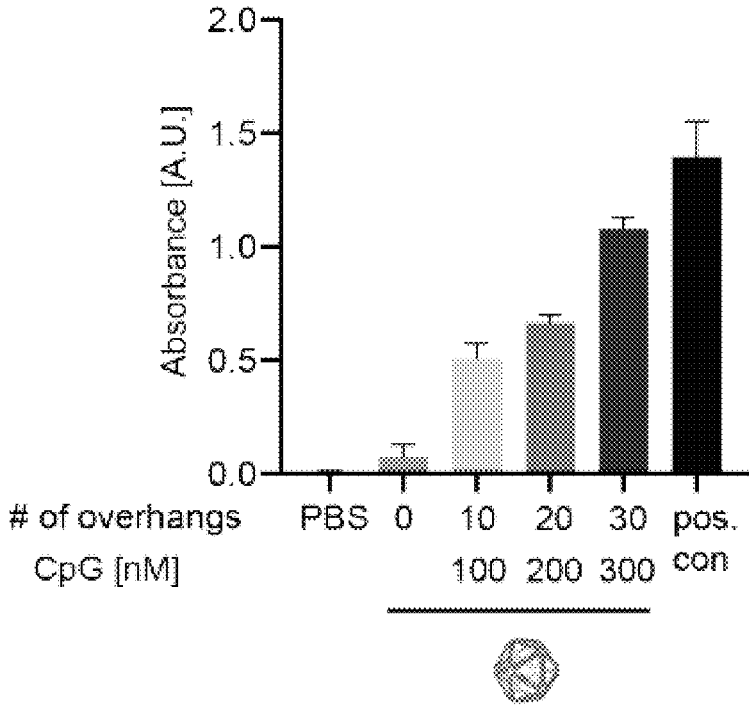

FIGS. 16A-16B are bar graphs showing magnitude of TLR9 activation (Absorbance, 0-2.0 A.U.) for each of variants of PB84 (FIG. 16A), and ICO42 (FIG. 16B), with different numbers of CpG overhangs (0-40/0-30), respectively, and different concentrations of CpG (100, 200, 400 nM/100, 200, 300 nM), respectively; PBS is a negative control; ODN2006 is a positive control (pos. con.). Data show the average absorbance of samples in triplicate with standard error, where n=3 biologically independent assays.

Figure 17:
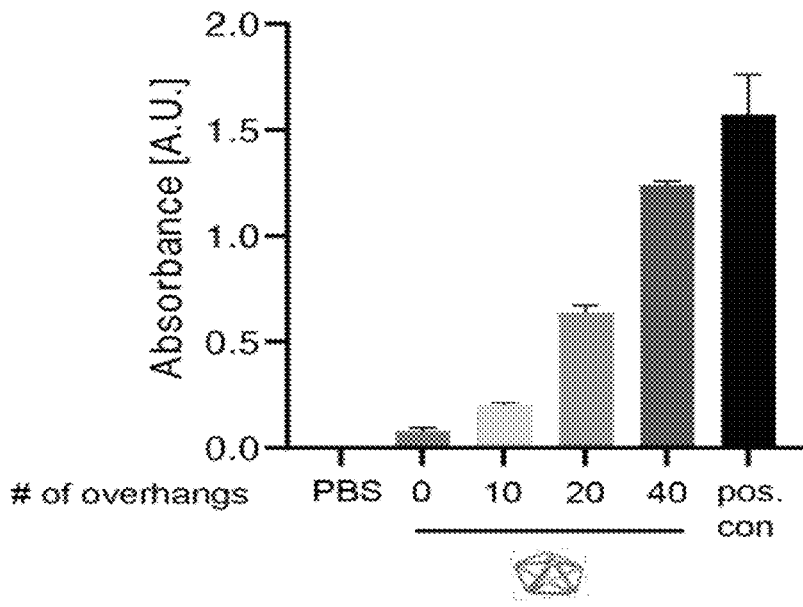

FIG. 17 is a bar graph of IFN production (Absorbance, 0-2.0 A.U.) induced by TLR activation by PB84 NANPs having CpG motifs within staple strand overhangs facing either inwards or outwards directions, for each of 0-40 total CpG motif overhangs. PBS is a negative control; ODN2006 is a positive control (pos. con.).

Figure 18:
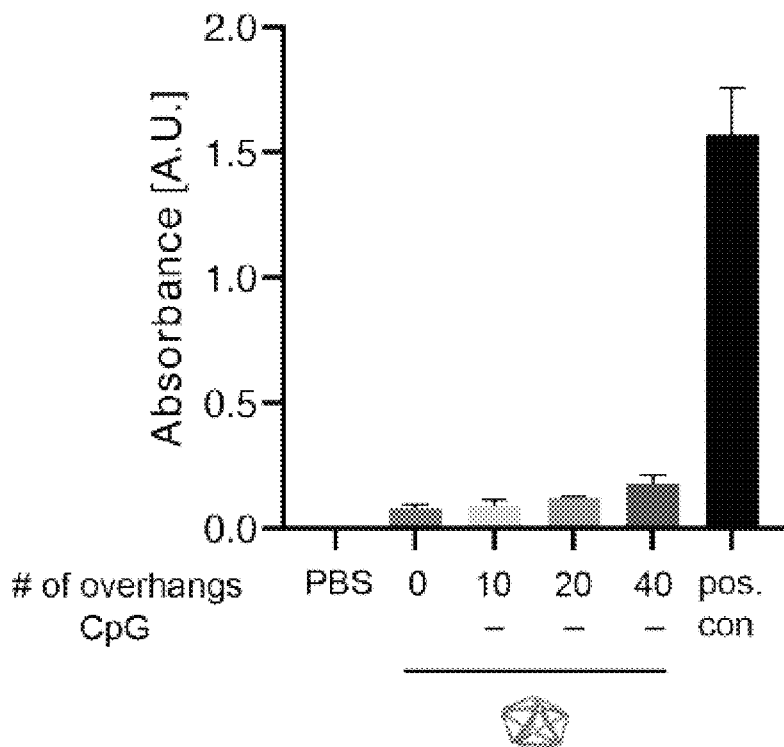

FIG. 18 is a bar graph of IFN production (Absorbance, 0-2.0 A.U.) induced by PB84 NANPs having no CpG motifs within staple strand overhangs, for each of 0-40 total CpG motif overhangs. PBS is a negative control; ODN2006 is a positive control (pos. con.).

Figure 19:
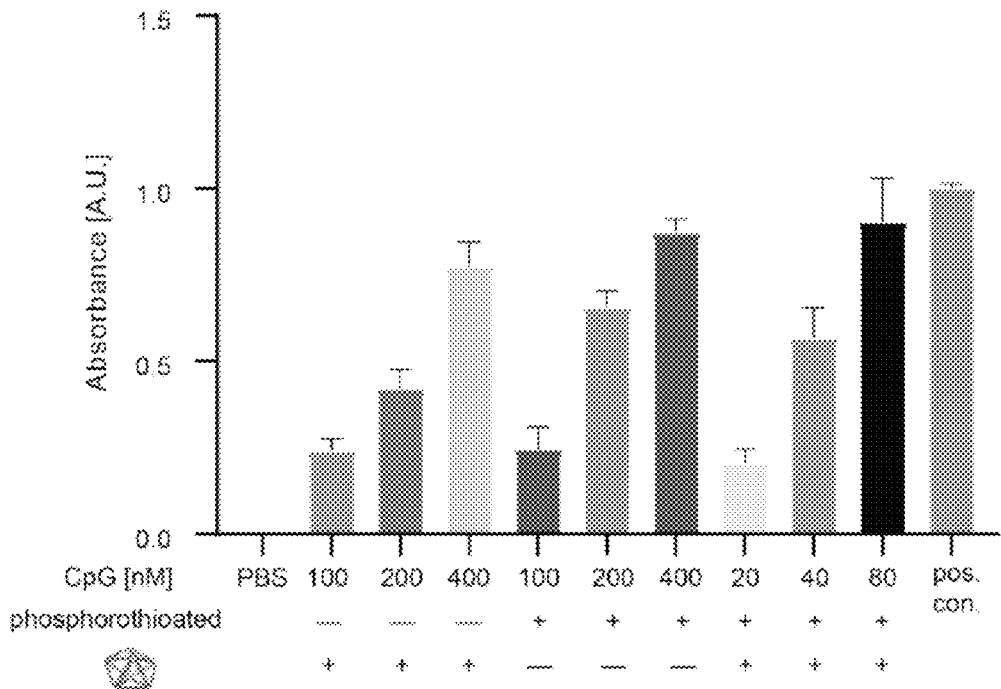

FIG. 19 is a bar graph of the effect of attachment to NANPs and phosphorothioate stabilization on the ability of CpG overhangs to activate TLR9IFN production, showing Absorbance, (0-1.5 A.U.) induced by 20, 40, 80, 100, 200, or 400 nanomolar CpG motifs within staple strand overhangs, for each of 0-40 total CpG motif overhangs, in the presence (+) or absence (−) of phosphorothioation, and the presence (+) or absence (−) of PB84 NANPs, respectively. PBS is a negative control; ODN2006 is a positive control (pos. con.).

Figure 20A:
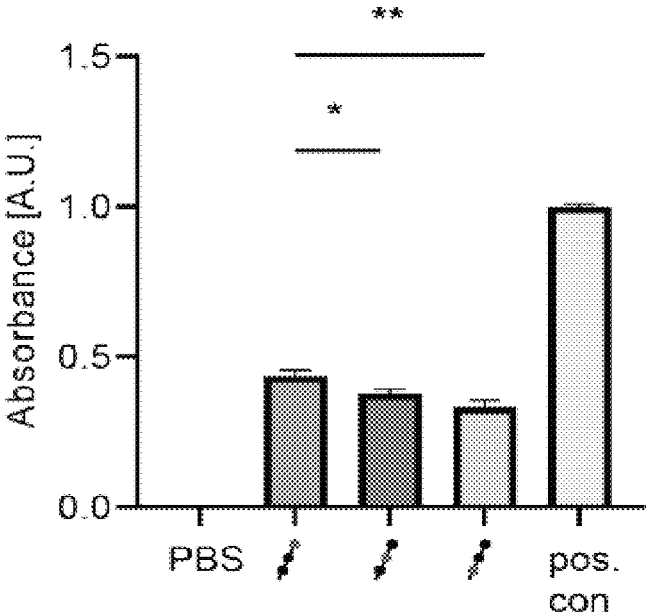
Figure 20B:
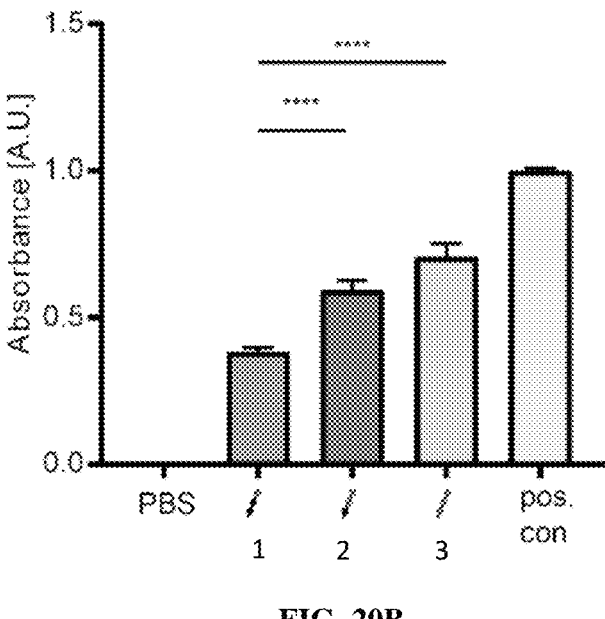

FIGS. 20A-20B are bar graphs of assays to demonstrate how the location and number of CpG motifs within ssDNA overhangs affects the strength of TLR9 activation, showing magnitude of TLR9 activation (Absorbance, 0-1.5 A.U.) for each of overhangs including a CpG motif at the furthest, mid-point, and closest part of the overhang relative to the pint of attachment to the nanostructure, respectively (FIG. 20A), and with different numbers of CpG motifs (1, 2, or 3) within overhangs, respectively (FIG. 20B). The total concentration of overhangs is kept constant in each sample; PBS is a negative control; ODN2006 is a positive control (pos. con.). Data show the average absorbance of samples in triplicate with standard error, where n=3 biologically independent assays. P values are from a one-sided analysis of variance (ANOVA) with correction for multiple comparisons (*: $P \leq 0.05$; : $P \leq 0.01$, *: $P \leq 0.001$, ****: $P \leq 0.0001$). All unlabeled pair-wise comparisons are not significant.

DETAILED DESCRIPTION OF THE INVENTION

I. Definitions

The terms "nucleic acid molecule," "nucleic acid sequence," "nucleic acid fragment," "oligonucleotide" and "polynucleotide" are used interchangeably and are intended to include, but not limited to, a polymeric form of nucleotides that can have various lengths, either deoxyribonucleotides (DNA) or ribonucleotides (RNA), or analogs or modified nucleotides thereof, including, but not limited to locked nucleic acids (LNA) and peptide nucleic acids (PNA). An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Oligonucleotides may optionally include one or more non-standard nucleotide(s), nucleotide analog(s) and/or modified nucleotides.

In some cases, nucleotide sequences are provided using character representations recommended by the International Union of Pure and Applied Chemistry (IUPAC) or a subset thereof. IUPAC nucleotide codes used herein include, A=Adenine, C=Cytosine, G=Guanine, T=Thymine, U=Uracil, R=A or G, Y=C or T, S=G or C, W=A or T, K=G or T, M=A or C, B=C or G or T, D=A or G or T, H=A or C or T, V=A or C or G, N=any base, "." or "-"=gap. In some embodiments the set of characters is (A, C, G, T, U) for adenosine, cytidine, guanosine, thymidine, and uridine respectively. In some embodiments the set of characters is (A, C, G, T, U, I, X, Ψ) for adenosine, cytidine, guanosine, thymidine, uridine, inosine, uridine, xanthosine, pseudouridine respectively. In some embodiments the set of characters is (A, C, G, T, U, I, X, Ψ, R, Y, N) for adenosine, cytidine, guanosine, thymidine, uridine, inosine, uridine, xanthosine, pseudouridine, unspecified purine, unspecified pyrimidine, and unspecified nucleotide respectively.

The terms "staple strands" or "helper strands" are used interchangeably. When used in the context of a nucleic acid nanostructure object, "Staple strands" or "helper strands" refer to oligonucleotides that work as glue to hold the scaffold nucleic acid in its three-dimensional geometry. Additional nucleotides can be added to the staple strand at either 5' end or 3' end, and those are referred to as "staple overhangs". Staple overhangs can be functionalized to have desired properties such as a specific sequence to hybridize to a target nucleic acid sequence, or a targeting element. Target nucleic acid sequences used to mask staple overhangs during the functionalization process are herein referred to as "guard strands". In some instances, the staple overhang is biotinylated for capturing the DNA nanostructure on a streptavidin-coated bead. In some instances, the staple overhang can be also modified with chemical moieties. Non-limiting examples include CLICK-chemistry groups (e.g., azide group, alkyne group, DIBO/DBCO), amine groups, and thiol groups. In some instances, some bases located inside the oligonucleotide can be modified using base analogs (e.g., 2-Aminopurine, Locked Nucleic Acids, such as those modified with an extra bridge connecting the 2' oxygen and 4' carbon) to serve as linker to attach functional moieties (e.g., lipids, proteins). Alternatively, DNA-binding proteins or guide RNAs can be used to attach secondary molecules to the DNA scaffold.

The terms "scaffolded origami", "origami", "nucleic acid nanoparticle", "nucleic acid nanostructure", "nanostructure", "nucleic acid assembly" are used interchangeably. They can be one or more short single strands of nucleic acids (staple strands) (e.g., DNA) that fold a long, single strand of polynucleotide (scaffold strand) into desired shapes on the order of about 10 nm to a micron. or more. Wireframe scaffolded DNA origami may use edges having 2, 4, 6, or more duplexes crosslinked in parallel to endow rigidity to the nanoparticle (Jun et al., *ACS Nano,* 2019, 10.1021/acsnano.8b08671; Veneziano et al., *Science,* 352(6293): 1534 (2016)). Single-stranded DNA scaffold may be produced from M13 or using a helper plasmid as shown by Shepherd, et al., *bioRxiv* 521443 (2019), doi: https://doi.org/10.1101/521443 and Praetorius et al., *Nature,* 552:84-87 (2017). Alternatively, single-stranded synthetic nucleic acid can fold into an origami object without helper strands, for example, using parallel or paranemic crossover motifs. Alternatively, purely staple strands can form nucleic acid memory blocks of finite extent. The scaffolded origami or origami can be composed of deoxyribonucleotides (DNA) or ribonucleotides (RNA), or analogs or modified nucleotides thereof, including, but not limited to locked nucleic acids (LNA) and peptide nucleic acids (PNA). A scaffold or origami composed of DNA can be referred to as, for example a scaffolded DNA origami or DNA origami, etc. It will be appreciated that where compositions, methods, and systems herein are discussed or exemplified with DNA (e.g., DNA origami), other nucleic acid molecules can be substituted.

The term "polyhedron" refers to a three-dimensional solid figure in which each side is a flat surface. These flat surfaces are polygons and are joined at their edges.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

The terms "epitope" or "antigenic determinant" refer to a site on an antigen to which B and/or T cells respond. In the context of a polypeptide, B-cell epitopes can be formed both from contiguous amino acids or noncontiguous amino acids juxtaposed by tertiary or quarternary folding of a protein. Epitopes formed from contiguous amino acids are typically retained on exposure to denaturing solvents whereas epitopes formed by tertiary or quarternary folding are typically lost on treatment with denaturing solvents. An epitope typically includes at least 3, and more usually, at least 5 or 8-10, amino acids, in a unique spatial conformation. Methods of determining spatial conformation of epitopes include, for example, X-ray crystallography and multi-dimensional nuclear magnetic resonance spectroscopy.

The term "immunostimulatory agent" refers to any agent that stimulates, up-regulates, induces, enhances or otherwise activates one or more physiological pathways associated with the active, passive, innate or adaptive immune response in a subject. Exemplary immunostimulatory agents include antigens, adjuvants, and agonists/ligands for Toll Like Receptor (TLR), T Cell Receptor (TCR), B Cell Receptor (BCR), cytokines, etc.

The term "antigen" as used herein is defined as a molecule capable of being recognized or bound by an antibody, B-cell receptor or T-cell receptor. An "immunogen" is an antigen that is additionally capable of provoking an immune response against itself (e.g., upon administration to a mammal, optionally in conjunction with an adjuvant). This immune response can involve either antibody production, or the activation of specific immunologically-competent cells, or both. Any macromolecule, including virtually all proteins or peptides as well as lipids and oligo- and polysaccharides, can serve as an antigen or immunogen. Furthermore, antigens/immunogens can be derived from recombinant or genomic DNA. Any DNA that includes a nucleotide sequences or a partial nucleotide sequence encoding a protein or peptide that elicits an immune response therefore encodes an "immunogen" as that term is used herein. An antigen/immunogen need not be encoded solely by a full-length nucleotide sequence of a gene. An antigen/immunogen need not be encoded by a "gene" at all. An antigen/immunogen can be generated, synthesized, or can be derived from a biological sample. Such a biological sample can include, but is not limited to a tissue sample, a tumor sample, a cell or a biological fluid.

The term "small molecule," as used herein, generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

As used herein, the term "carrier" refers to an organic or inorganic ingredient, natural or synthetic, with which the active ingredient is combined to facilitate the application.

As used herein, the term "pharmaceutically acceptable" describes a material that is not biologically or otherwise undesirable. The term refers to those compounds, materials, compositions, and/or dosage forms which are, within the scope of sound medical judgment, suitable for use in contact with the tissues, organs, and/or bodily fluids of a subject without excessive toxicity, irritation, allergic response, or other problems or complications commensurate with a reasonable benefit/risk ratio. Such materials can be administered to a subject along with the selected compound without causing any undesirable biological effects or interacting in a deleterious manner with any of the other components of the pharmaceutical composition in which it is contained.

As used herein, the term "pharmaceutically-acceptable carrier" means one or more compatible solid or liquid fillers, dilutants or encapsulating substances which are suitable for administration to a human or other vertebrate animal.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

"Treatment" or "treating" means to administer a composition to a subject or a system with an undesired condition (e.g., an infectious disease, cancer). The condition can include one or more symptoms of a disease, pathological state, or disorder. Treatment includes medical management of a subject with the intent to cure, ameliorate, stabilize, or prevent a disease, pathological condition, or disorder. This includes active treatment, that is, treatment directed specifically toward the improvement of a disease, pathological state, or disorder, and also includes causal treatment, that is, treatment directed toward removal of the cause of the associated disease, pathological state, or disorder. In addition, this term includes palliative treatment, that is, treatment designed for the relief of symptoms rather than the curing of the disease, pathological state, or disorder; preventative treatment, that is, treatment directed to minimizing or partially or completely inhibiting the development of the associated disease, pathological state, or disorder; and supportive treatment, that is, treatment employed to supplement another specific therapy directed toward the improvement of the associated disease, pathological state, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

As used herein, the terms "effective amount" or "therapeutically effective amount" are used interchangeably and mean a quantity sufficient to alleviate or ameliorate one or more symptoms of a disorder, disease, or condition being treated, to induce or enhance an immune response, or to otherwise provide a desired pharmacologic and/or physiologic effect. Such amelioration only requires a reduction or alteration, not necessarily elimination. The precise quantity will vary according to a variety of factors such as subject-dependent variables (e.g., age, immune system health, weight, etc.), the disease or disorder being treated, the disease stage, as well as the route of administration, and the pharmacokinetics and pharmacodynamics of the agent being administered.

Recitation of ranges of values herein are merely intended to serve as a shorthand method of referring individually to each separate value falling within the range, unless otherwise indicated herein, and each separate value is incorporated into the specification as if it were individually recited herein.

II. Compositions

Peptide- and protein-based vaccines form the major class of vaccination strategies globally. Inactivated viral particles or other passivated protein nanoparticles can be used in vaccine formulations to display protein or peptide antigens to stimulate and train the immune response. Adjuvants including small molecules and nucleic acids are often co-formulated with these antigens to further stimulate immune activation.

Disclosed herein is a highly versatile class of viral-like nanoparticle formed of structured nucleic acid structures displaying immunostimulatory agents. One or more immunostimulatory agents of interest can be displayed in varying copy numbers with precise control over inter-antigen spacing, number, and spatial organization in 1, 2, and 3 dimensions.

Protein/peptide-conjugation strategies based on peptide nucleic acids are provided and can be used to adapt the platform for display of any number of immunostimulatory agent, such as antigens, adjuvants, or combinations thereof. The nucleic acid sequence of the underlying viral-like nanostructure scaffold can be controlled fully together with adjuvant display of small molecules or targeting ligands including sugars. Chemical modifications to the DNA nanoparticle including 3' and 5' PEGylation and incorporation of phosphorothioates may be used to stabilize and passivate nanostructures for in vivo administration. Additionally, or alternatively, 3' and/or 5' terminal ends of staples may be ligated to stabilize the nanoparticle from exonuclease degradation. Cationic polymers and minor groove binders (as monomers, oligomers or polymers) may be used to coat the DNA nanoparticles for stabilization from endonuclease degradation. In particular, minor groove binders may act as tethers for covalent modifications of nucleic acids, for example to develop cross-linking strategies for DNA nanoparticles. These approaches can be combined, e.g. using brush or block copolymers, with PEGylation to further improve stabilization and passivation.

For example, HIV presents distinct barriers against the formation of prophylactic immune responses due to antigenic diversity of viral proteins as well as the similarity of the virus to self-epitopes (Burton, et al., *Science,* 337(6091): 183-186 (2012); Burnett, et al., *Science,* 360(6385):223-226 (2018)). The HIV gp120 CD4 binding site protein has emerged as an attractive target for the induction of broadly neutralizing antibodies against HIV. Env spike proteins are sparsely distributed on the viral surface, possibly allowing HIV to evade host immune responses (Zhu, et al., *Nature,* 441(7095):847-852 (2006); Klein, J S. and Bjorkman, P J., *PLOS Pathog.,* 6(5):e1000908 (2010)). Consistent with this observation, germline-targeting CD4 binding-site immunogens assembled into protein nanoparticles have allowed for highly multivalent (e.g., 60mer) antigen presentation to B cells. It is thought that such high degree of multimerization of immunogens on nanoparticles elicits enhanced adaptive immune responses (Jardine, et al., *Science,* 349(6244):156-161 (2015), Abbott, et al., *Immunity,* 48(1):133-146.e6 (2018)). However, it was previously unknown how the structural features of nanoparticle-antigen presentation (such as for example, antigen number, inter-antigen distance, 3D organization) affect B cell responses.

In the Examples described below, eOD-GT8 antigens were displayed on DNA origami, systematically varying antigen number, inter-antigen distances, and 3D organization. The Examples show that eOD dimers templated by DNA origami elicited robust B cell responses at inter-antigen distances greater than 28 nm. These results indicate that sparse distributions of viral spikes on HIV and other viruses do not inhibit B cell receptor signaling responses, and support non-local models for B cell receptor activation mechanisms.

Hence, the distances between antigenic sites are important determinants of B cell receptor activation and cellular response. In contrast to a model where tight clustering of antigen sites yields greater B cell activation due to spatially-dependent cooperative effects between B cell receptor immunoglobulin signaling subunits, the Examples show that extended antigen placement led to equivalent, and in some cases superior, B cell receptor activation. Both linear and clustered antigen presentation yielded similar cellular responses when the inter-antigen distance was greater than ~15 nm threshold, indicating that the average distances between antigenic sites does not drive observed differences between the constructs.

Although compositions and methods of use for treatment of HIV are expressly provided and exemplified in the experiments below, the illustrated principles are believed to extend to wide-ranging compositions and methods of immune modulation by varying, for example, the antigen(s) and/or nanostructure(s) and in some cases further varying the valance and spatial organization of the antigen(s). Unlike biologically produced vaccine particles, fully synthetic production of the entire platform offers strict quality control over the formulation. The platform can be utilized in immune stimulation as well as immune tolerance using proteins, peptides, and small molecule adjuvants. Targeting molecules can be used to direct the compositions to desired tissues or cells. Methods of using the compositions for treating infectious diseases, auto-immune diseases, as well as in cancer immunotherapies are also provided.

The Examples below also investigate 3D wireframe DNA origami on the TLR9 and cGAS-STING pathways using reporter cells and primary immune cells, which indicate that wireframe DNA origami induce a cGAS-STING dependent immune response, but are minimally TLR9 activating, despite the presence of numerous CpG dinucleotides within the scaffold and staples. However, displaying CpG-containing oligos from wireframe DNA origami results in robust TLR9 pathway activation and enhancement of the downstream immune response, which is substantiated by an increase in Type I and Type III IFN production in peripheral blood mononuclear cells. Results also show the impacts of CpG copy number, inter-CpG spacing, and spatial patterning on the strength of TLR9 activation, and find that signaling intensity is correlated with CpG valency and density of clustering. These results illustrate that properties of immunostimulatory wireframe DNA origami can be programmed to modulate immune pathway activation controllably, offering an improved understanding of how nanoscale organization of immunostimulatory oligos influences their interactions with the innate immune system, and highlighting design parameters that may prove useful for downstream biological applications.

The disclosed compositions typically include one or more immunostimulatory agents such as antigens or adjuvants bound or linked to, incorporated into (e.g., bound to surfaces of, encapsulated in), or otherwise associated with, nucleic acid nanostructures. The antigens, adjuvants, and other immunostimulatory agents are typically displayed on the nanostructure surface and can be arranged for their most preferred presentation (e.g., preferred valency, preferred spacing, preferred rigidity/flexibility, preferred dimensionality, etc.) for eliciting an immune response.

Exemplary immunostimulatory agents such as antigens and adjuvants and nanostructures are each discussed in more detail below.

A. Immunostimulatory Agents

Nanostructures including one or more immunostimulatory agents are provided. Exemplary immunostimulatory agents are capable of activating, stimulating, inducing or otherwise actuating one or more pathways associated with one or more of the active, passive, adaptive or innate immune systems in a subject are provided. In some embodiments, the immunostimulatory agent is an antigen or an adjuvant. In some embodiments, the immunostimulatory agent is a ligand for a cell-bound receptor, such as a Toll like receptor. Examples of immunostimulatory agents are discussed below and elsewhere herein.

1. Antigens

In some forms, the immunostimulatory agent is an antigen. Antigens are compounds that are specifically bound by antibodies or T lymphocyte antigen receptors. They stimulate production of or are recognized by antibodies. Sometimes antigens are part of the host itself in an autoimmune disease. An immunogen is an antigen (or adduct) that is able to trigger a humoral or cell-mediated immune response. It first initiates an innate immune response, which then causes the activation of the adaptive immune response. An antigen binds the highly variable immunoreceptor products (B cell receptor or T cell receptor) once these have been generated. Immunogens are those antigens, termed immunogenic, capable of inducing an immune response. Thus, an immunogen is necessarily an antigen, but an antigen may not necessarily be an immunogen. For brevity, the disclosed nanostructure-based compositions are typically referred to as having an antigen conjugated or bound thereto or otherwise associate therewith. However, unless specifically indicated otherwise, any of the antigens can also be an immunogenic (i.e., an immunogen). Thus, all the disclosure of compositions and methods of use related to antigen bound nanostructures is also expressly provided with respect to immunogen bound nanostructures unless indicated to the contrary.

As discussed in more detail below, in some embodiments, antigens are selected or designed for immune stimulation or immune tolerance, of B-cells and/or T-cells, with or without the context of an MHC complex. In some embodiments, the antigen-bound nanostructures mimic dendritic cell presentation of antigenic peptides. Such embodiments may include MHC complex presentation of antigen(s) incorporated into the nanostructure.

The nucleic acid nanostructures act as scaffolds for one or more copies of one or more antigens. The nanostructures can be used to capture and/or restrain the antigen in a fixed and known orientation, for example, in preferred antigen presentation for eliciting an immune response. For example, organizations (e.g., 1D, 2D, 3D) of viral proteins can be used to stimulate the immune system by presenting these proteins in geometries that mimic the one or more naturally occurring antigens, or in geometries designed to elicit a robust immune response.

The nucleic acid nanostructures allow for control of the relative position, number, flexibility or rigidity, and/or dimensionality of the antigen that it contains (e.g., bound to its surface).

It is believed there is virtually no limit to the number of copies of antigen, or number of different (types of) antigens, beyond any structural limitations of the nanostructure itself, which can also be increased in size and complexity to accommodate increasing numbers of antigen. For example, the nanostructure can be functionalized with any integer number of antigens from 1 to 1000, or any specific range of there between. A nanostructure can include, e.g., between about 1 and 100, or 2 and 60, or 3 and 50, or 4 and 25, or 5 and 10 antigen molecules. A nanostructure can have 2, 3, 4, 5, 6, 7, 8, 9, 10, 11, 12, 13, 14, 15, 16, 17, 18, 19, 20, 25, 30, 35, 40, 45, 50, 55, 60, etc. antigens. In particular embodiments, a nanostructure has 5-10 antigen molecules (e.g., 5, 6, 7, 8, 9, or 10 copies). Large structures, e.g., microstructures, may include hundreds of antigens.

The Examples below show that B cell responses increase with increasing copies of antigen (eOD-GT8) through between about 5 and about 10 copies of antigen, but increasing the number to 30 or 60 on an icosahedral nanostructure did not further improve the response. Thus, in some embodiments, the number of copies of an antigen is between 1 and 40, 1 and 30, preferably, between 5 and 30, or between 5 and 10, inclusive, particularly where the nanostructure is icosahedral.

The Examples also show, the pentagonal bipyramid efficiently activated B cell in vitro. At 5 nM immunogen concentration, activation levels saturate for both 10 and 40 copies of immunogen and are comparable to or higher than the eOD-GT8-60mer protein nanoparticle reference. At lower immunogen concentrations, the activation level for 10 copies of immunogen is decreased, while the 40 copy DNA nanostructure activates B cells comparably to the eOD-GT8-60mer protein nanoparticle. Thus, in some embodiments, the number of copies of an antigen is between 1 and 50, 1 and 40, preferably, between 10 and 50, or between 10 and 40, inclusive, particularly where the antigen(s) are on a pentagonal bipyramidal structure.

As used herein, "adjacent antigen" can refer to the antigen or antigens in closest proximity to a reference antigen. In particular embodiments, the adjacent antigen must be on the same face of the nanostructure. In some embodiments, there will be two or more adjacent antigens to a single reference antigen. Each adjacent antigen can independently be another copy or copies of the reference antigen or a structurally different antigen or antigens from the reference antigen. Thus, in some embodiments, all of the adjacent antigens are structurally the same as the reference antigen, all of the adjacent antigens are structurally different from the reference antigen, or the adjacent antigens are a combination of being structurally the same and structurally different from the reference antigen. Antigens may be covalently or non-covalently attached to the nanostructure, and they may be cleavable by proteases or other enzymes or undergo triggered dissociation in response to environmental cues such as pH, etc. They and/or the nanoparticle may also be shielded from the immune system by encapsulating polymers or other materials for shielding and targeting purposes prior to antigen exposure at physiological sites of interest such as the injection site or within lymph nodes.

The inter-antigen distance between any two adjacent antigens can be any integer number from 1 nm to 500 nm, or any specific range there between. For example, in some embodiments, the distance between two adjacent antigens, also referred to herein as inter-antigen distance and the space between two antigens, is in the range of 1 nm to 150 nm, or 10 nm to 100 nm, or 15 nm to 80 nm, or 28 nm to 80 nm, or 10 nm to 80 nm, or 15 nm to 50 nm, or 25 nm to 30 nm. The Examples below show that B cell responses decreased when inter-antigen distance (eOD-GT8) was less than 28 nm when presented on a 6HB dimer, or 15 nm when presented on a polyhedron. Thus, preferably, the distance between two adjacent antigens is at least 15 nm, or at least 28 nm. The Examples did not illustrate a decrease in B cell responses when the distance increased beyond 80 nm, a distance well beyond the size where two separate immunoglobulin Igα/β pairs could be interacting. However, in some embodiments, the inter-antigen distance does not exceed the distance where two separate immunoglobulin Igα/β pairs could be interacting.

In some specific embodiments, the distance between adjacent antigens is 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 100, 150, 200, 25, 300, 400, or 500 nm.

The distance between adjacent antigens may vary based on other parameters, such as, the shape of the nanostructure being used. For example, in some embodiments, when the nanostructure is a 6HB, the distance between adjacent antigens can be 28 nm or more (e.g., 28, 29, 30, 35, 40, 45, 50, 55, 60, 65, 70, 75 nm, or more). In some embodiments, when the nanostructure is a polyhedron, such as an icosahedron for example, the distance between adjacent antigens (e.g., on the same face of the nanostructure) are 15 nm or more (e.g., 15, 16, 17, 18, 19, 20, 21, 22, 23, 24, 25, 26, 27, 28, 29, 30, 35, 40, 45, 50, 55, 60, 65, 70, 75 nm, or more).

Antigen location and orientation can also be varied. For example, antigen placement can be linear, or clustered. Inter-antigen distance between adjacent antigens can be equidistant or non-equidistant. Inter-antigen distance can be equidistant in 2, 3, 4, 5 or more directions. The Examples show that for larger inter-antigen distances (e.g. 15 nm or greater), clustering on both linear and planar structures leads to an equivalent cellular response. However, when inter-antigen distances are smaller (e.g., less than 14 nm), linear placement of antigen yields a greater response than a clustered planar placement of antigen. In both cases, further decreases can cause a relative reduction in immune response.

The antigen can be covalently or non-covalently bound to the nanostructure. In some embodiments, the antigen is directly or indirectly bound to the nanostructure via outwardly facing nucleic acid overhangs extending from the 3' and/or 5' ends of selected staple strands. The exemplary embodiments below feature 3' overhangs. The nucleic acid overhangs can include one or more sequences that is complementary to a target RNA, DNA or PNA sequence. In some embodiments, the nucleic acid overhangs hybridize to the complementary target RNA, DNA or PNA sequence which can be covalently linked to the antigen. Such covalent linkage can be formed by maleimide-thiol coupling. Some exemplary non-covalent interactions for attachment or incorporation include intercalation, biotin-streptavidin interaction, or hybridization between complementary nucleotide sequences. In situ template CLICK chemistry can also be used to covalently attach the antigen to the nucleic acid nanoparticle following a non-covalent, hybridization reaction that templates the antigen by binding it to the nanoparticle through PNA:DNA or other nucleic acid hybridization reaction. In a preferred embodiment, copper-assisted alkyne-azide CLICK chemistry or other catalyst-dependent bioconjugate techniques are used for the implementation of this approach by the addition of the catalyst after removal of excess antigen to maintain overhang sequence-specific addressability of the DNA nanoparticle.

Antigens can be or can include, for example, proteins, nucleic acids, lipids, and oligo- or polysaccharides as well as the corresponding cooligo- and polymers. Exemplary antigens include B cell antigens and T cell antigens. B cell antigens can be peptides, proteins, oligo- and polysaccharides, lipids, nucleic acids, small molecules (alone or with a hapten) or combinations thereof. T cell antigens are typically proteins or peptides. The antigen can be derived from a virus, bacterium, parasite, plant, protozoan, fungus, tissue or transformed cell such as a cancer or leukemic cell and immunogenic component thereof, e.g., cell wall components or molecular components thereof. The antigens can be allergens or environmental antigens or tumor antigens. The antigen can be associated with one or more diseases or conditions such as infectious diseases, autoimmune diseases, and cancer.

Suitable antigens are known in the art and are available from commercial, government and scientific sources. The antigens can be purified or partially purified polypeptides derived from tumors or viral or bacterial sources. The antigens can be recombinant polypeptides produced by expressing DNA encoding the polypeptide antigen in a heterologous expression system. Antigens can be provided as single antigens or can be provided in combination. Antigens can also be provided as complex mixtures of polypeptides or nucleic acids.

In some embodiments, the antigen is a viral antigen. A viral antigen can be isolated from any virus. In an exemplary embodiment, the antigen is a natural viral capsid structure. In some embodiments, the antigen is a bacterial antigen. Bacterial antigens can originate from any bacteria. In some embodiments the antigen is a parasite antigen. In some embodiments, the antigen is an allergen or environmental antigen. Exemplary allergens and environmental antigens, include but are not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. In some embodiments, the antigen is a self-antigen such as in immune tolerance applications for auto-immune or related disorders such as Multiple Sclerosis. In some embodiments, the antigen is a tumor antigen. Exemplary tumor antigens include a tumor-associated or tumor-specific antigen.

In some embodiments, the antigen is a peptide derived from the H-2K$^k$ MHC class I molecule. For example, a nucleic acid nanostructure having a defined geometric shape and one or more copies of an antigen than can induce a response from B cell specific to the H-2K$^k$ MHC class I molecule are provided. In some embodiments, the antigens have been previously defined and are known to have varying affinity B cell receptors from NOD.D2(B10)-Tg(Igh2$^k$3-83) 1Nemz/Dvs mice (Kouskoff, et al, *Journal of Experimental Medicine*, 188(8):1453-64, 1998).

In particular embodiments, the antigen is the p31 peptide, which has a high affinity for NOD.D2(B10)-Tg(Igh2$^k$3-83) 1Nemz/Dvs B cell receptors, or the p5 peptide, which has an intermediate affinity for NOD.D2(B10)-Tg(Igh2$^k$3-83) 1Nemz/Dvs B cell receptors, placed on, for example, a pentagonal bipyramidal structure.

i. Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens can be derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomegalovirus, Epstein-Barr, rotavirus, rhinovirus, adenovirus, coxsackieviruses, equine encephalitis, Japanese encephalitis, yellow fever, Rift Valley fever, and lymphocytic choriomeningitis.

In some preferred embodiments, the antigen is an HIV antigen. The antigen may bind to a broadly neutralizing antibody. The antigen can be, for example, an HIV gp120 epitope of an HIV envelope trimer. In particular embodiments, the antigen is an HIV epitope that encompasses a binding site of gp120. In some embodiments, the binding site is a CD4 binding site. Exemplary antigens include, but are not limited to, eOD-GT6, eOD-GT8, p5, p31, and/or variants thereof.

ii. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus,* Hemophilus influenza type B (HIB), *Hyphomicrobium, Legionella, Leptospirosis, Listeria,* Meningococcus A, B and C, *Methanobacterium, Micrococcus, Mycobacterium, Mycoplasma, Myxococcus, Neisseria, Nitrobacter, Oscillatoria,* Prochloron, *Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.* iii. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.* These include Sporozoan antigens, Plasmodian antigens, such as all or part of a Circumsporozoite protein, a Sporozoite surface protein, a liver stage antigen, an apical membrane associated protein, or a Merozoite surface protein.

iv. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including e.g., grasses of the genera *Lolium, Phleum, Poa, Cynodon,*

*Dactylis, Holcus, Phalaris, Secale,* and Sorghum, the orders of Asterales and Urticales including i.a. herbs of the genera *Ambrosia, Artemisia,* and *Parietaria.* Other allergen antigens that may be used include allergens from house dust mites of the genus *Dermatophagoides* and *Euroglyphus,* storage mite e.g. Lepidoglyphus, Glycyphagus and Tyrophagus, those from cockroaches, midges and fleas e.g. Blatella, *Periplaneta, Chironomus* and Ctenocepphalides, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.* v. Cancer Antigens

A cancer antigen is an antigen that is typically expressed preferentially by cancer cells (i.e., it is expressed at higher levels in cancer cells than on non-cancer cells; cancer-associated antigen) and in some instances it is expressed solely by cancer cells (cancer-specific antigen). The cancer antigen may be expressed within a cancer cell or on the surface of the cancer cell. The cancer antigen can be MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A 11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2.

vi. Neoantigens

In some embodiments the antigen is a neoantigen or a patient-specific antigen. Recent technological improvements have made it possible to identify the immune response to patient-specific neoantigens that arise as a consequence of tumor-specific mutations, and emerging data indicate that recognition of such neoantigens is a major factor in the activity of clinical immunotherapies (Schumacher and Schreidber, *Science,* 348(6230):69-74 (2015). Neoantigen load provides an avenue to selectively enhance T cell reactivity against this class of antigens.

Traditionally, cancer vaccines have targeted tumor-associated antigens (TAAs) which can be expressed not only on tumor cells but in the normal tissues (Ito, et al., *Cancer Neoantigens: A Promising Source of Immunogens for Cancer Immunotherapy. J Clin Cell Immunol,* 6:322 (2015) doi:10.4172/2155-9899.1000322). TAAs include cancer-testis antigens and differentiation antigens, and even though self-antigens have the benefit of being useful for diverse patients, expanded T cells with the high-affinity TCR (T-cell receptor) needed to overcome the central and peripheral tolerance of the host, which would impair anti-tumor T-cell activities and increase risks of autoimmune reactions.

Thus, in some embodiments, the antigen is recognized as "non-self" by the host immune system, and preferably can bypass central tolerance in the thymus. Examples include pathogen-associated antigens, mutated growth factor receptor, mutated K-ras, or idiotype-derived antigens. Somatic mutations in tumor genes, which usually accumulate tens to hundreds of fold during neoplastic transformation, could occur in protein-coding regions. Whether missense or frameshift, every mutation has the potential to generate tumor-specific antigens. These mutant antigens can be referred to as "cancer neoantigens" Ito, et al., *Cancer Neoantigens: A Promising Source of Immunogens for Cancer Immunotherapy. J Clin Cell Immunol*, 6:322 (2015) doi:10.4172/2155-9899.1000322. Neoantigen-based cancer vaccines have the potential to induce more robust and specific anti-tumor T-cell responses compared with conventional shared-antigen-targeted vaccines. Recent developments in genomics and bioinformatics, including massively parallel sequencing (MPS) and epitope prediction algorithms, have provided a major breakthrough in identifying and selecting neoantigens.

vii. Tolerogenic Antigens

The antigen can be a tolerogenic antigen. Exemplary antigens are known in the art. See, for example, U.S. Published Application No. 2014/0356384.

In some cases, the tolerogenic antigen is derived from a therapeutic agent protein to which tolerance is desired. Examples are protein drugs in their wild type, e.g., human factor VIII or factor IX, to which patients did not establish central tolerance because they were deficient in those proteins; or nonhuman protein drugs, used in a human. Other examples are protein drugs that are glycosylated in nonhuman forms due to production, or engineered protein drugs, e.g., having non-native sequences that can provoke an unwanted immune response. Examples of tolerogenic antigens that are engineered therapeutic proteins not naturally found in humans including human proteins with engineered mutations, e.g., mutations to improve pharmacological characteristics. Examples of tolerogenic antigens that have nonhuman glycosylation include proteins produced in yeast or insect cells.

Tolerogenic antigens can be from proteins that are administered to humans that are deficient in the protein. Deficient means that the patient receiving the protein does not naturally produce enough of the protein. Moreover, the proteins can be proteins for which a patient is genetically deficient. Such proteins include, for example, antithrombin-III, protein C, factor VIII, factor IX, growth hormone, somatotropin, insulin, pramlintide acetate, mecasermin (IGF-1), β-gluco cerebrosidase, alglucosidase-.alpha., laronidase (α-L-iduronidase), idursuphase (iduronate-2-sulphatase), galsulphase, agalsidase-.beta. (α-galactosidase), α-1 proteinase inhibitor, and albumin.

The tolerogenic antigen can be from therapeutic antibodies and antibody-like molecules, including antibody fragments and fusion proteins with antibodies and antibody fragments. These include nonhuman (such as mouse) antibodies, chimeric antibodies, and humanized antibodies. Immune responses to even humanized antibodies have been observed in humans (Getts D R, Getts M T, McCarthy D P, Chastain E M L, & Miller S D (2010), mAbs, 2(6):682-694).

The tolerogenic antigen can be from proteins that are nonhuman. Examples of such proteins include CRISPR-associated proteins, adenosine deaminase, pancreatic lipase, pancreatic amylase, lactase, botulinum toxin type A, botulinum toxin type B, collagenase, hyaluronidase, papain, L-Asparaginase, rasburicase, lepirudin, streptokinase, anistreplase (anisoylated plasminogen streptokinase activator complex), antithymocyte globulin, crotalidae polyvalent immune Fab, digoxin immune serum Fab, L-arginase, and L-methionase.

Tolerogenic antigens include those from human allograft transplantation antigens. Examples of these antigens are the subunits of the various MHC class I and MHC class II haplotype proteins, and single-amino-acid polymorphisms on minor blood group antigens including RhCE, Kell, Kidd, Duffy and Ss.

The tolerogenic antigen can be a self-antigen against which a patient has developed an autoimmune response or may develop an autoimmune response. Examples are pro-insulin (diabetes), collagens (rheumatoid arthritis), myelin basic protein (multiple sclerosis). For instance, Type 1 diabetes mellitus (T1D) is an autoimmune disease whereby T cells that recognize islet proteins have broken free of immune regulation and signal the immune system to destroy pancreatic tissue. Numerous protein antigens that are targets of such diabetogenic T cells have been discovered, including insulin, GAD65, chromogranin-A, among others. In the treatment or prevention of T1D, it would be useful to induce antigen-specific immune tolerance towards defined diabetogenic antigens to functionally inactivate or delete the diabetogenic T cell clones.

Tolerance and/or delay of onset or progression of autoimmune diseases may be achieved for various of the many proteins that are human autoimmune proteins, a term referring to various autoimmune diseases wherein the protein or proteins causing the disease are known or can be established by routine testing. In some embodiments, a patient is tested to identify an autoimmune protein and an antigen is created for use in a molecular fusion to create immunotolerance to the protein.

Embodiments can include an antigen, or choosing an antigen from or derived from, one or more of the following proteins. In type 1 diabetes mellitus, several main antigens have been identified: insulin, proinsulin, preproinsulin, glutamic acid decarboxylase-65 (GAD-65), GAD-67, insulinoma-associated protein 2 (IA-2), and insulinoma-associated protein 2.beta. (IA-213); other antigens include ICA69, ICA12 (SOX-13), carboxypeptidase H, Imogen 38, GLIMA 38, chromogranin-A, FISP-60, caboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor. In Addison's disease, main antigens include 21-hydroxylase, 17α-hydroxylase, and P450 side chain cleavage enzyme (P450scc); other antigens include ACTH receptor, P450c21 and P450c17. In premature ovarian failure, main antigens include FSH receptor and .alpha.-enolase. In auto-immune hypophysitis, or pituitary autoimmune disease, main antigens include pituitary gland-specific protein factor (PGSF) 1a and 2; another antigen is type 2 iodothyronine deiodinase. In multiple sclerosis, main antigens include myelin basic protein, myelin oligodendrocyte glycoprotein and proteolipid protein. In rheumatoid arthritis, a main antigen is collagen II. In immunogastritis, a main antigen is H+, K+-ATPase. In pernicious angemis, a main antigen is intrinsic factor. In celiac disease, main antigens are tissue transglutaminase and gliadin. In vitiligo, a main antigen is tyrosinase, and tyrosinase related protein 1 and 2. In myasthenia gravis, a main antigen is acetylcholine receptor. In pemphigus vulgaris and variants, main antigens are desmoglein 3, 1 and 4; other antigens include pemphaxin, desmocollins, plakoglobin, perplakin, desmoplakins, and acetylcholine receptor. In bullous pemphigoid, main antigens include BP180 and BP230; other antigens include plectin and laminin 5. In dermatitis herpetiformis Duhring, main antigens include endomysium and tissue transglutaminase. In epidermolysis bullosa acquisita, a main antigen is collagen VII. In systemic sclerosis, main antigens include matrix metalloproteinase 1 and 3, the collagen-specific molecular chaperone heat-shock protein 47, fibrillin-1, and PDGF receptor; other antigens include Scl-70, U1 RNP, Th/To, Ku, Jol, NAG-2, centromere proteins, topoisomerase I, nucleolar proteins, RNA polymerase I, II and III, PM-Slc, fibrillarin, and B23. In mixed connective tissue disease, a main antigen is U1snRNP. In Sjogren's syndrome, the main antigens are nuclear antigens SS-A and SS-B; other antigens include fodrin, poly(ADP-ribose) polymerase and topoisomerase. In systemic lupus erythematosus, main antigens include nuclear proteins including SS-A, high mobility group box 1 (HMGB1), nucleosomes, histone proteins and double-stranded DNA. In Goodpasture's syndrome, main antigens include glomerular basement membrane proteins including collagen IV. In rheumatic heart disease, a main antigen is cardiac myosin. Other autoantigens revealed in autoimmune polyglandular syndrome type 1 include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega. In some cases, the tolerogenic antigen is a foreign antigen against which a patient has developed an unwanted immune response. Examples are food antigens. Some embodiments include testing a patient to identify foreign antigen and creating a molecular fusion that includes the antigen and treating the patient to develop immunotolerance to the antigen or food. Examples of such foods and/or antigens are provided. Examples are from peanut: conarachin (Ara h 1), allergen II (Ara h 2), *arachis* agglutinin, conglutin (Ara h 6); from apple: 31 kda major allergen/disease resistance protein homolog (Mal d 2), lipid transfer protein precursor (Mal d 3), major allergen Mal d 1.03D (Mal d 1); from milk: .alpha.-lactalbumin (ALA), lactotransferrin; from kiwi: actinidin (Act c 1, Act d 1), phytocystatin, thaumatin-like protein (Act d 2), kiwellin (Act d 5); from mustard: 2S albumin (Sin a 1), 11 S globulin (Sin a 2), lipid transfer protein (Sin a 3), profilin (Sin a 4); from celery: profilin (Api g 4), high molecular weight glycoprotein (Api g 5); from shrimp: Pen a 1 allergen (Pen a 1), allergen Pen m 2 (Pen in 2), tropomyosin fast isoform; from wheat and/or other cereals: high molecular weight glutenin, low molecular weight glutenin, alpha- and gamma-gliadin, hordein, secalin, avenin; from strawberry: major strawberry allergy Fra a 1-E (Fra a 1), from banana: profilin (Mus xp 1). Many protein drugs that are used in human and veterinary medicine induce immune responses, which create risks for the patient and limits the efficacy of the drug. This can occur with human proteins that have been engineered, with human proteins used in patients with congenital deficiencies in production of that protein, and with nonhuman proteins. It would be advantageous to tolerize a recipient to these protein drugs prior to initial administration, and it would be advantageous to tolerize a recipient to these protein drugs after initial administration and development of immune response. In patients with autoimmunity, the self-antigen(s) to which autoimmunity is developed are known. In these cases, it would be advantageous to tolerize subjects at risk prior to development of autoimmunity, and it would be advantageous to tolerize subjects at the time of or after development of biomolecular indicators of incipient autoimmunity. For example, in Type 1 diabetes mellitus, immunological indicators of autoimmunity are present before broad destruction of beta cells in the pancreas and onset of clinical disease involved in glucose homeostasis. It would be advantageous to tolerize a subject after detection of these immunological indicators prior to onset of clinical disease 2. Immunostimulatory Receptor Agonists In some embodiments, the immunostimulatory agent is a ligand or binding partner for an immunostimulatory receptor. Ligands that bind to receptors to induce activation of one or more physiological pathways through the immunostimulatory receptor are termed immunostimulatory receptor agonists. Therefore, in some embodiments, the immunostimulatory agent is an immunostimulatory receptor agonist. Exemplary immunostimulatory receptors include those associated with activation of the innate immune system.

The innate immune system contains several pattern recognition receptors (PRRs) that are responsible for recognizing evolutionarily conserved pathogen-associated or damage-associated molecular patterns (PAMPs or DAMPs). Once activated, these PRRs invoke innate immune recognition while simultaneously activating the adaptive immune response (Schlee & Hartmann, *Nature Reviews Immunology,* 16 (9), 566-580 (2016), Paludan, *Microbiology and Molecular Biology Reviews,* 79 (2), 225-241 (2015)). Binding of PRRs to their corresponding ligand triggers activation of downstream signaling pathways, ultimately resulting in the production of Type I interferons (IFNs) and other proinflammatory cytokines that are essential for initiation of a host of immune functions (Paludan & Bowie, *Immunity,* 38 (5), 870-880 (2013), Wu & Chen, *Annual Review of Immunology,* 32 (1), 461-488 (2014)).

Although ligands and binding partners for immunostimulatory receptors are a particularly preferred example of an immunostimulatory agent, and examples are provided in the sections that follow, other adjuvants, including, but not limited to the examples mentioned further below, can also be used.

i. Cyclic GMP-AMP Synthase (cGAS) Agonists

In some embodiments, the immunostimulatory agent is a ligand or binding partner for pattern recognition receptor (PRR). An exemplary PRR is Cyclic GMP-AMP synthase (cGAS).

Cyclic GMP-AMP synthase (cGAS) is a PRR that responds to cytosolic double-stranded DNA (dsDNA) from both endogenous sources such as certain forms of cell death as well as exogenous DNA from pathogens 28-30 in a sequence-independent but length-dependent manner 30-33. The cGAS enzyme recognizes foreign, intracellular double-stranded DNA and catalyzes the formation of the second messenger cyclic GMP-AMP which initiates a cascade ultimately activating transcription of Type I interferon genes. Human mutations in the cGAS pathway are associated with the neurodevelopmental disorder, Aicardi-Goutières syndrome, and overactivation of cGAS has been linked to Systemic Lupus Erythematosus. Activation of cGAS occurs more efficiently with long DNA. This preference is an intrinsic property of cGAS. Therefore, in some forms, the immunostimulatory agent is a ligand or binding partner for cGAS.

An exemplary ligand or binding partner for cGAS is a long, double stranded DNA. As described in the examples, DNA wireframe DNA NANP edges are composed of duplex DNA that, if these NANPs are internalized into the cytosol of cells that express the cGAS-STING pathway, trigger cGAS binding and downstream immune activation. In some forms, the nucleic acid nanoparticle itself is, or has the potential to become, a ligand that can trigger cGAS binding and downstream immune activation. For example, in some forms, the nanostructure scaffold sequence, once fully or partially unfolded, can form a duplex structure that triggers cGAS binding and immune activation. In some embodiments, the nanostructure scaffold is designed to specifically form a hairpin structure, for other double-stranded DNA configurations within the cytosol of a cell, amenable to trigger cGAS binding and induce immune activation. In other embodiments, the nanostructure has bound to it one or more nucleic acids that trigger GAS binding and induce immune activation.

ii. Toll-Like Receptor Agonists

In some embodiments, the immunostimulatory agent is a ligand or binding partner for a Toll Like Receptor (TLR). Ligands that bind to TLRs and induce activation of one or more physiological pathways through the TLR are termed TLR agonists. Therefore, in some embodiments, the immunostimulatory agent is a TLR agonist.

Toll-like Receptors (TLRs) are a family of transmembrane PRRs that sense and respond to a wide variety of ligands, including nucleic acids. TLRs are composed of an N-terminal PAMP-binding ectodomain, a transmembrane domain and a C-terminal Toll IL-1 receptor domain (TIR) and are subdivided into two groups according to whether they localize at the cell surface membrane or within the endosomal membrane (Kawai & Akira, *Nature Immunology*, 11 (5), 373-384 (2010), Kawasaki & Kawai, *Frontiers in Immunology*, 5 (2014)). The TIR domain mediates the recruitment of adapter molecules such as myeloid differentiation factor-88 (MyD88), TIR-associated protein (TIRAP), Toll receptor-associated-activator of interferon (TRIF) and/ or Toll-receptor-associated molecule (TRAM). While most TLRs are expressed on the cell surface, TLR3, 7, 8 and 9 are found within endosomes, where they are activated following capture and internalization of pathogens or their products. The endosomal TLR subfamily, which consists of TLR3, TLR7/8, and TLR9, is involved in nucleic acid recognition, and while TLR3 and TLR7/8 recognize dsRNA and ssRNA, respectively, TLR9 responds to single-stranded DNA (ssDNA) containing unmethylated cytosine-phosphate-guanine dinucleotides (CpGs)36-38.

Toll-like receptor signaling pathway activation results in transcription of type I IFN genes and proinflammatory cytokine genes such as TNF-$\alpha$, IL-1 and IL-6. The cytokine induction pattern is determined by the type of TLR-activated cell. Stimulation of human TLR7, for instance, induces IFN-$\alpha$ from plasmacytoid dendritic cells (pDCs) important for innate antiviral immunity and the development of adaptive immunity, whereas it induces IL-12 from myeloid dendritic cells (mDCs), associated with the induction of a Th1 response. It has also been suggested that, at least for murine TLR4, relative activation of its two distinct downstream signaling pathways affects the therapeutic index of the agonist. Despite differences in the induced cytokine pattern defined by dendritic cell (DC) subset, TLR agonist and signaling adaptors, TLR activation generally results in activation and phenotypic maturation of all DCs.

Exemplary TLR agonists include BCG (TLR 2, 4 or 9); Poly I:C, Poly ICLC (TLR 3); MPL (TLR4); LPS (TLR4); Imiquimod (TLR7); 852A (TLR7); Resiquimod (TLR7, 8); VTX-2337 (TLR8) and CpG ODN (TLR9). Therefore, in some embodiments, the immunostimulatory agent is one or more TLR agonist selected from BCG; Poly I:C, Poly ICLC; MPL; LPS; Imiquimod; 852A; Resiquimod; VTX-2337 and CpG ODN.

In some embodiments, one or more TLR agonist are present within the staple strands, or the scaffold sequence, or both the staple and scaffold sequence of a nanostructure. When a TLR agonist is present within one or more staple strands, the TLR agonist can be present in a single-stranded nucleic acid overhang appended to the staple, so that the TLR agonist is present at a distance to the nanostructure itself. In some embodiments, the amount of TLR agonists present on the surface of a nanostructure is proportional to the level of activation of TLR that occurs upon recognition of the TLR agonists by TLR receptors in a cell. For example, the number of distinct TLR agonists on a nanostructure can be from 1 to 10,000, for example, from 1 to 100, from 1 to 50, from 1 to 40, from 1 to 30, from 1 to 20, or from 1 to 10, or less than 10. Typically, the density of TLR agonists on any given face of a nanostructure can be varied according to the scale of TLR activation, and scale of immune response that is desired. Therefore, the density, total number, distance from one another and distance from the nanostructure itself can all be varied according to the desired design characteristics of the nanostructure. In some embodiments, the concentration of the TLR agonists is from 1 to 1,000 nM, for example, from 1 to 400 nM, from 1 to 300 nM, from 1 to 200 nM, from 1 to 100 nM, from 1 to 80 nM, from 1 to 60 nM, from 1 to 40 nM, from 1 to 20 nm, from 1 to 10 nM, or less than 10 nM. In some embodiments, the TLR agonist(s) is present within the inner volume of the nanostructure. In other embodiments, the TLR agonist(s) is present on the outer surface of the nanostructure. In further embodiments, one or more TLR agonists are present on both the outer surface of the nanostructure and within the inner volume of the nanostructure. When TLR agonists are present within a ssDNA overhang appended to a staple strand attached to the nanostructure, the number of TLR agonists within a single overhang can be from 1 to 100, for example, from 1 to 90, from 1 to 80, from 1 to 70, from 1 to 60, from 1 to 50, from 1 to 40, from 1 to 30, from 1 to 20, from 1 to 10, or less than 10 TLR agonists per staple strand, such as 9, 8, 7, 6, 5, 4, 3, 2, or 1 TLR agonist per staple strand. In some embodiments, the distance of a TLR agonist within a staple strand from a point of attachment to the body of the nanostructure is from 0.1 to 100 nm, e.g. 10, 9, 8, 7, 6, 5, 4, 3, 2, or 1 nm, or less than 1 n, such as 0.9, 0.8, 0.7, 0.6, 0.5, 0.4, 0.3, 0.2, or 0.1 nm from the point of attachment to the body of the nano-structure. TLR agonists can be present on one or more than one face of a nanostructure. For example, in some embodiments, one or more TLR agonists are attached to a single face of a nanostructure. In other embodiments, one or more TLR agonists are attached to all faces of a nanostructure. In some embodiments, TLR agonists are attached to 20, 15, 10, 9, 8, 7, 6, 5, 4, 3, or 2 faces of a nanostructure. In some forms, TLR agonists are present within or are attached to from 1% to 10%, 20%, 30%, 40%, 50%, 60%, 70%, 80% 90% or more than 90%, such as 95%, 99% or 100% of the staples attached to a nanostructure. In some forms, TLR agonists are present in from 1 to 10%, 20%, 30%, 40%, 50%, 60%, 70%, 80% 90% or more than 90%, such as 95%, 99% or 100% of the staples associated with edges, or vertices, or both the edges and vertices of a nanostructure.

a. Toll-Like Receptor 9 Agonists

In some embodiments, the immunostimulatory agent is a ligand or binding partner for a Toll Like Receptor 9 (TLR9). Ligands that bind to TLR9 to induce activation of one or more physiological pathways through the TLR9 are termed TLR9 agonists. Therefore, in some embodiments, the immunostimulatory agent is a TLR9 agonist.

Each of the monomers within the TLR9 homodimer undergoes a conformational change upon binding to a CpG-containing ssDNA oligo, enabling the formation of a 2:2 TLR9 monomer:CpG oligo complex in which each monomer interacts with both CpGs (Latz, et al., *Nature Immunology*, 8 (7), 772-779 (2007), Ohto, et al., *Immunity*, 48 (4), 649-658.e4 (2018)). Activated TLR9 homodimer formation brings the two C-terminal TIR domains into close proximity, allowing for assembly of TIR-containing adaptor proteins (TIRAP) and MyD88 adaptor proteins into the myddosome, successful formation of which is critical for initiation of the downstream signaling cascade and production of Type I IFNs and pro-inflammatory cytokines (Latz, et al., *Nature Immunology*, 8 (7), 772-779 (2007), Deguine & Barton, *F1000Prime Reports* 6 (2014), Marongiu, et al., *Journal of Leukocyte Biology*, 106 (1), 147-160 (2019), Bonham, et al., *Cell*, 156 (4), 705-716 (2014)). Thus, the presence of CpG dinucleotides within the scaffold and staples of DNA-based NANPs may elicit TLR9 signaling and enable innate immune activation. Indeed, the therapeutic potential of the immune cascade triggered by TLR9 activation has prompted investigations into the optimization of CpG motifs, which are CpG dinucleotides placed within a particular sequence context that enhances their TLR9 activation efficacy, as well as into the application of TLR9 agonist as anti-cancer drugs, vaccine adjuvants, and combination therapies, a few of which, such as MGN-1703 and SD-101, are in ongoing clinical development (Krieg, *Oncogene,* 27 (2), 161-167 (2008), Chen, et al., *Biomaterials,* 32 (6), 1731-1737 (2011), Luchner, et al., *Pharmaceutics,* 13 (2), 142 (2021), Pohar, et al., *The Journal of Immunology,* 194 (8), 3901-3908 (2015), Vollmer, et al., *Journal of Immunology,* 34 (1), 251-262 (2004)).

Unmethylated Cytosine-Guanine Dinucleotide Oligodeoxynucleotide

An exemplary TLR9 agonist immunostimulatory agent is an unmethylated cytosine-guanine dinucleotide (CpG) oligodeoxynucleotide motif. Therefore, in some embodiments, the immunostimulatory agent is a CpG motif.

CpG oligodeoxynucleotides (or CpG ODN) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants. CpG motifs are considered pathogen-associated molecular patterns (PAMPs) due to their abundance in microbial genomes but their rarity in vertebrate genomes. The CpG PAMP is recognized by the pattern recognition receptor (PRR) Toll-Like Receptor 9

(TLR9), which is constitutively expressed only in B cells and plasmacytoid dendritic cells (pDCs) in humans and other higher primates.

The frequency of the cytidine-guanosine (CG) dinucleotide is strongly underrepresented in the human genome, and ~80% of the cytidine in the CG dinucleotide is methylated, which establishes the recognition of DNA-comprising CpG motifs as the structural pattern for the innate immune response. Synthetic ssDNA fragments, oligodeoxyribonucleotides (ODNs) containing stimulatory CpG motifs, also initiate immune signaling in a TLR9-MyD88-dependent fashion, leading to the activation of transcription factors NF-κB and IRF7 and, consequently, the secretion of cytokines and chemokines by B cells, plasmacytoid dendritic cells (pDCs), NK cells, and macrophages that express TLR9. Membrane receptors-mannose receptor 1, Ig-like receptor KIR3DL2, multilectin receptor DEC-205, and scavenger receptor CXCL16—enhance internalization and define the route of endocytosis of ODNs.

Several types of CpG ODNs, each with a distinct sequence, secondary structure, and specificity for TLR9 activation, are potent activators of Th1-type cytokines:

The B-class CpG ODNs (alias K-type) with the CG motif and a phosphorothioate (PTO) backbone are strong stimulators of B cell proliferation as well as the secretion of IL-6, IL-10, and IL-12 through NF-κB signaling.

A-class ODNs (alias D-type), which are poor stimulators of B cells, contain a palindromic sequence at the center of the ODN and poly-G motif, which can form quadruplexes at each end. These ODNs activate NK cells, and in pDCs, A-class ODNs induce secretion of type I IFNs (IFN-α/β), TNF-α, IL-12, and IFN-γ-IP10.

C-class ODNs are chimeras of A- and B-class ODNs with one or two CGT motifs at the 5' end and a CG-rich palindromic sequence at the 3' end of the ODN. This class of CpG ODNs possesses the immune-stimulatory properties of the A- and B-class ODNs and induces proliferation of B cells and the production of low amounts of IFN-α from pDCs.

A-, C-, and P-class CpG ODNs form intra- and intermolecular duplexes. These multi-ODN structures are suggested to take a different route of endocytosis and, therefore, induce the synthesis of type I IFNs. In addition to unmethylated CpG motifs within the ODN, other factors determine the immune response of TLR9-expressing cells. The position, number, and accessibility of CpG motifs, the nucleotides adjacent to the CG dinucleotide, and the secondary structures of the ODNs influence agonist potency for TLR9 activation. Moreover, CpG ODNs show sequence-species specificity for the activation of TLR9. GACGTT has been proposed as the optimal TLR9 recognition hexamer for mice, whereas GTCGTT is optimal for humans and other vertebrate species.

The naturally occurring agonist of TLR9 is ssDNA with a phosphodiester (PD) backbone. To prevent degradation of ODNs by deoxyribonucleases, synthetic ODNs typically consist of a partial or complete PTO backbone. Some important differences are noted in terms of TLR9 activation between ODNs based on a PD backbone and those based on a PTO backbone. A base-free PD-deoxyribose homopolymer is a very weak TLR9 agonist, whereas the base-free PTO homopolymer does not activate TLR9 but instead competitively inhibits TLR9 activation in the presence of B-class ODN, which is not the case for the PD homopolymer. The best activation of TLR9 is achieved with ODNs with CG dinucleotide motifs separated with a spacer of at least six nucleotides, which corresponds to a distance of ~40-50 Å and is probably the distance between the binding sites on the TLR9 ECD dimer. In addition, the tail at the 3' end of ODN that is ≥10 nt long probably serves as an initial nonspecific binding of ssDNA to TLR9 through a negative phosphate backbone and a positive interface on TLR9 (Pohar et al., J Immunol Apr. 15, 2015, 194 (8) 3901-3908). The minimal ODNs defined by the sequence $TCG[T]_{6-10}CG[T]_{9-19}$ have a total length of >21 nt. These minimal ODNs induce production of TNF-α in human PBMCs. Therefore, in some embodiments, nucleic acid sequences containing CpG motifs for activation of TLR9 include two CpG motifs. In some embodiments, the nucleic acid sequences containing 2 or more CpG motifs include a stretch of at least six nucleotides separating each of the CpG motifs from each of the other CpG motifs. In some embodiments, the nucleic acid sequences containing 2 or more CpG motifs include a distance of ~40-50 Å separating each of the CpG motifs from each of the other CpG motifs. In some embodiments, CpG motifs for activation of TLR9 are present in nucleic acid sequences having a minimum length of 21 nucleotides, such as 21, 22, 23, 24, 25, 26, 27, 28, 29 or 30 nucleotides, or more than 30 nucleotides.

In some embodiments, CpG ODN are present within the staple strands, or the scaffold sequence, or both the staple and scaffold sequence of a nanostructure. When a CpG motif is present within one or more staple strands, the CpG can be present in a single-stranded nucleic acid overhang appended to the staple, so that the CpG motif is present at a distance to the nanostructure itself. In some embodiments, the amount of CpG motifs present on the surface of a nanostructure is proportional to the level of activation of TLR9 that occurs upon recognition of the CpG motifs by TLR9 receptors in a cell. For example, the location and number of CpG motifs can be from 1 to 10,000, for example, from 1 to 100, from 1 to 50, from 1 to 40, from 1 to 30, from 1 to 20, or from 1 to 10, or less than 10. The density of CpG motifs on any given face of a nanostructure can be varied according to the scale of TLR9 activation, and scale of immune response that is desired. Therefore, the density, total number, distance from one another and distance from the nanostructure itself can all be varied according to the desired design characteristics of the nanostructure. In some embodiments, the concentration of the CpG motifs is from 1 to 1,000 nM, for example, from 1 to 400 nM, from 1 to 300 nM, from 1 to 200 nM, from 1 to 100 nM, from 1 to 80 nM, from 1 to 60 nM, from 1 to 40 nM, from 1 to 20 nm, from 1 to 10 nM, or less than 10 nM. In some embodiments, the CpG motif(s) is present within the inner volume of the nanostructure. In some embodiments, the CpG motif(s) is present on the outer surface of the nanostructure. In further embodiments, one or more CpG motifs are present on both the outer surface of the nanostructure and within the inner volume of the nanostructure. When CpG motifs are present within a ssDNA overhang appended to a staple strand attached to the nanostructure, the number of CpG motifs within a single overhang can be from 1 to 100, for example, from 1 to 90, from 1 to 80, from 1 to 70, from 1 to 60, from 1 to 50, from 1 to 40, from 1 to 30, from 1 to 20, from 1 to 10, or less than 10 CpG motifs per staple strand, such as 9, 8, 7, 6, 5, 4, 3, 2, or 1 CpG motif per staple strand. The distance of a CpG motif within a staple strand from a point of attachment to the body of the nanostructure can vary from 0.1 to 100 nm, e.g., 10, 9, 8, 7, 6, 5, 4, 3, 2, or 1 nm, or 0.9, 0.8, 0.7, 0.6, 0.5, 0.4, 0.3, 0.2, or 0.1 nm from the point of attachment to the body of the nanostructure. CpG motifs can be present on one or more than one face of a nanostructure. For example, in some embodiments, one or more CpG motifs are attached to a single face of a nanostructure. In other embodiments, one or more CpG motifs are attached to all faces of a nanostructure. In some embodiments, CpG motifs are attached to 10, 9, 8, 7, 6, 5, 4, 3, or 2 faces of a nanostructure. In some forms, CpG motifs are present in from 1% to 10%, 20%, 30%, 40%, 50%, 60%, 70%, 80% 90% or more than 90%, such as 95%, 99% or 100% of the staples attached to a nanostructure. In some forms, CpG motifs are present in from 1 to 10%, 20%, 30%, 40%, 50%, 60%, 70%, 80% 90% or more than 90%, such as 95%, 99% or 100% of the staples associated with edges of a nanostructure.

B. Nucleic Acid Nanostructures

The disclosed nucleic acid nanostructures can be formed from any nucleic acid. In preferred embodiments, the nanostructure is formed of DNA. The basic technique for creating nucleic acid nanostructures of various shapes (also referred to herein as nucleic acid or DNA origami) typically involves folding a long single stranded polynucleotide, referred to as a "scaffold strand," into a desired shape or structure using a number of small "staple strands" as glue to hold the scaffold in place. Several variants of geometries can be used for construction of nucleic acid nanostructures. For example, in some embodiments, nucleic acid nanostructure from purely shorter single stranded staples can be assembled, or nucleic acid nanostructure including purely a single stranded scaffold folded onto itself, any of which can take on diverse geometries/architectures including wireframe or bricklike objects.

The nanostructure is typically in the range of less than 0.5 nm up to 1,000 nm, inclusive or exclusive. In some embodiments, the nanostructure is between 1 nm and 1,000 nm inclusive or exclusive, or range of two integers there between, or any specific integer or fraction of an integer (e.g., to the nearly tenth), there between. The size can be the size of the structure with or without antigen, and/or with or without other elements discussed in more detail elsewhere herein. For example, in some embodiments, the size or range of sizes of the nanostructure is determined before antigen and/or other elements are added thereto (i.e., a naked nanostructure). In other embodiments, the size or range of sizes of the size or range of sizes of the nanostructure is determined after antigen and/or other elements are added thereto.

Nucleic acid nanostructures are nucleic acid assemblies of any arbitrary geometric shapes. Nucleic acid nanostructures can be of two-dimensional shapes, for example plates, or any other 2-D shape of arbitrary sizes and shapes. In some embodiments, the nucleic acid nanostructures are simple DX-tiles, with two DNA duplexes connected by staples. DNA double crossover (DX) motifs are examples of small tiles (~4 nm×~16 nm) that have been programmed to produce 2D crystals (Winfree E et al., *Nature*. 394:539-544 (1998)); often, these tiles contain pattern-forming features when more than a single tile constitutes the crystallographic repeat. In some embodiments, nucleic acid nanostructures are 2-D crystalline arrays by parallel double helical domains with sticky ends on each connection site (Winfree E et al., *Nature*. 6; 394(6693):539-44 (1998)). In other embodiments, nucleic acid nanostructures are 2-D crystalline arrays by parallel double helical domains, held together by crossovers (Rothemund P W K et al., *PLoS Biol.* 2:2041-2053 (2004)). In some embodiments, nucleic acid nanostructures are 2-D crystalline arrays by an origami tile whose helix axes propagate in orthogonal directions (Yan H et al., *Science.*301:1882-1884 (2003)).

In some embodiments, nucleic acid nanostructures are three-dimensional wireframe nucleic acid assemblies of a uniform polyhedron that has regular polygons as faces and is isogonal. In some embodiments, nucleic acid nanostructures are wireframe nucleic acid assemblies of an irregular polyhedron that has unequal polygons as faces. In some embodiments, nucleic acid nanostructures are wireframe nucleic acid assemblies of a convex polyhedron. In some further embodiments, nucleic acid nanostructures are wireframe nucleic acid assemblies of a concave polyhedron. In some further embodiments, nucleic acid nanostructures are brick-like square or honeycomb lattices of nucleic acid duplexes in cubes, rods, ribbons or other rectilinear geometries. The corrugated ends of these structures are used to form complementary shapes that can self-assemble via non-specific base-stacking.

Some exemplary superstructures of nucleic acid nanostructures include Platonic, Archimedean, Johnson, Catalan, and other polyhedral. In some embodiments, Platonic polyhedron are with multiple faces, for example, 4 face (tetrahedron), 6 faces (cube or hexahedron), 8 faces (octahedron), 10 faces (decahedron), 12 faces (dodecahedron), 20 faces (icosahedron). In some embodiments, nucleic acid nanostructures are toroidal polyhedra and other geometries with holes. In some embodiments, nucleic acid nanostructures are wireframe nucleic acid assemblies of any arbitrary geometric shapes. In some embodiments, nucleic acid nanostructures are wireframe nucleic acid assemblies of non-spherical topologies. Some exemplary topologies include nested cube, nested octahedron, torus, and double torus. In some embodiments, nucleic acid nanostructures are in the form of a bundle or lattice of nucleic acid duplexes (e.g., a 6-helix bundle or a 4-helix bundle or other bundle cross-section with arbitrary number of duplexes on either a square or honeycomb lattice, where the honeycomb lattice may be filled or hollow).

In particular embodiments, the nanostructure of the disclosed compositions can be in the form of a 6-helix bundle. In some embodiments, the nanostructure is shaped as a polyhedron, for example, an icosahedron. In some embodiments, the nanostructure is shaped as a decahedron, such as a pentagonal bipyramid. In some embodiments, the nanostructure is a 6-helix bundle or a polyhedron such as an icosahedron, or a decahedron, such as a pentagonal bipyramid, with HIV antigen, such as eOD-GT6 or eOD-GT8 bound, or another antigen such as p5 or p31, attached thereto.

1. Nucleic Acid Scaffold Sequences

Nucleic acids for use in the described nanostructures can be synthetic or natural nucleic acids. In some embodiments, the nucleic acid sequences are not naturally occurring nucleic acid sequences. In some embodiments, the nucleic acid sequences are artificial or otherwise user defined nucleic acid sequences. Nucleic acid sequences that are artificial or otherwise user defined are typically non-naturally occurring nucleic acid sequences and can also be referred to as synthetic nucleic acid sequences.

In some embodiments, the nucleic acid nanostructures are not the genomic nucleic acid of a virus. In some embodiments, the nucleic acid nanostructures are virus-like particles.

Numerous other sources of nucleic acid samples are known or can be developed and any can be used with the described nanostructures, compositions and methods. In some embodiments, nucleic acids used in the described methods are naturally occurring nucleic acids. Examples of suitable nucleic acid samples for use with in the described methods include DNA including genomic DNA samples, RNA samples, cDNA samples, nucleic acid libraries (including cDNA and genomic libraries), whole cell samples, environmental samples, culture samples, tissue samples, bodily fluids, and biopsy samples.

Nucleic acid fragments are segments of larger nucleic molecules. Nucleic acid fragments generally refer to nucleic acid molecules that have been cleaved. A nucleic acid sample that has been incubated with a nucleic acid cleaving reagent is referred to as a digested sample. A nucleic acid sample that has been digested using a restriction enzyme is referred to as a digested sample. In certain embodiments, the nucleic acid sample is a fragment or part of genomic DNA, such as human genomic DNA. Human genomic DNA is available from multiple commercial sources (e.g., Coriell #NA23248). Therefore, nucleic acid samples can be genomic DNA, such as human genomic DNA, or any digested or cleaved sample thereof. Generally, an amount of nucleic acids between 375 bp and 1,000,000 bp is used per nucleic acid nanostructure.

Although only a single nucleic acid strand is typically used as a scaffold sequence for folding the nanostructures, the reverse complement of the nucleic acid strand is used as an alternative for all applications.

M13 is a common source of scaffold strand with native protein-coding sequence and approximately 7k bases. Sequence-controlled scaffold strands may also be produced using helper plasmids (Shepherd, et al., *bioRxiv* 521443 (2019), doi: https://doi.org/10.1101/521443 and Praetorius et al., *Nature*, 552:84-87 (2017), Chasteen, et al., *Nature*, 34(21):e145 (2006)) or using a hybrid synthetic-enzymatic approach (Plesa, et al., *Science*, 359(6373):343-347 (2018), DOI: 10.1126/science.aao5167), or purely enzymatic approach (Veneziano, et al., *Scientific Reports*, 8, Article number: 6548 (2018)).

2. Staple Strands

The number of staple strands will depend upon the size of the scaffold strand and the complexity of the shape or structure to be formed. For example, for relatively short scaffold strands (e.g., about 50 to 1,500 bases in length) and/or simple structures, the number of staple strands are small (e.g., about 5, 10, 50 or more). For longer scaffold strands (e.g., greater than 1,500 bases) and/or more complex structures, the number of staple strands are several hundred to thousands (e.g., 50, 100, 300, 600, 1,000 or more helper strands).

Typically, staple strands include between 10 and 600 nucleotides, for example, 14-600 nucleotides.

Using a DNA nanostructure for illustration, in scaffolded DNA origami, a long single-stranded DNA can be associated with complementary short single-stranded oligonucleotides that bring two distant sequence-space parts of the long strand together to fold into a defined shape. A robust computational-experimental approach can be used to generate DNA-based wireframe polyhedral structures of arbitrary scaffold sequence, symmetry and size (Jun et al., *ACS Nano*, 2019, 10.1021/acsnano.8b08671). Staple strands are typically provided in a folding buffer. The staple strands are typically added to the single-stranded scaffold sequence in molar excess, in combination with appropriate salts and detergents. Staple strands may be produced using liquid state synthesis or more commonly solid-state synthesis, or alternatively biologically using phage (Praetorius et al., *Nature*, 552:84-87 (2017)).

3. Purification Tags

In addition to nucleic acid overhangs, other purification tags can be incorporated into the overhang nucleic acid sequence in any nucleic acid nanostructures for purification. In some embodiments, the overhang contains one or more purification tags. In some embodiments, the overhang contains purification tags for affinity purification. In some embodiments, the overhang contains one or more sites for conjugation to a nucleic acid, or non-nucleic acid molecule. For example, the overhang tag can be conjugated to a protein, or non-protein molecule, for example, to enable affinity-binding of the nucleic acid nanostructures. Exemplary proteins for conjugating to overhang tags include biotin and antibodies, or antigen-binding fragments of antibodies. Purification of antibody-tagged nucleic acid nanostructures can be achieved, for example, via interactions with antigens, and or protein A, G, A/G or L.

Further exemplary affinity tags are peptides, nucleic acids, lipids, or mono-, oligo- and polysaccharides. For example, if an overhang contains monosaccharides such as mannose molecules, then mannose-binding lectin can be used for selectively retrieving mannose-containing nucleic acid nanostructures, and vice versa. Other overhang tags allow further interaction with other affinity tags, for example, any specific interaction with magnetic particles allows purification by magnetic interactions.

4. Nucleic Acid Overhang Tag

In some embodiments, the overhang sequences are between 4 and 60 nucleotides, depending on user preference and downstream purification techniques. In preferred embodiments, the overhang sequences are between 4 and 25 nucleotides. In some embodiments, the overhang sequences contain 4, 5, 6, 7, 8, 9, 10, 11, 12, 13, 14, 15, 16, 17, 18, 19, 20, 21, 22, 23, 24, 25, 30, 35, 40, 45, 50 nucleotides in length.

In some embodiments, these overhang tag sequences are placed on the 5' end of any of the staples used to generate a wireframe nucleic acid. In other embodiments, these overhang tag sequences are placed on the 3' end of any of the staples used to generate a wireframe nucleic acid. Staples or scaffold may also contain sequences that act as barcodes for qPCR-based or sequencing-based determination of cellular or tissue or organ localization and copy number (Okholm, et al., *Methods*, 67(2):193-7 (2014) doi:10.1016/j.ymeth.2014.01.013, Dahlman, et al., *Proc Natl Acad Sci USA*, 114(8):2060-65 (2017), doi: 10.1073/pnas.1620874114).

5. Additional Functional Elements i. Agents

In some embodiments, nucleic acid nanostructures are modified by covalent or non-covalent association with a therapeutic agent, a toxic agent, a prophylactic agent, a diagnostic agent, or other agent, particularly protein- or nucleic acid-based therapeutic, functional nucleic acid, prophylactic, or diagnostic agents. For example, one or more therapeutic, prophylactic, or diagnostic agents can be associated with the exterior of the nucleic acid nanoparticle, or packaged within the interior space of the nucleic acid nanoparticle, according to the design of the particle and location of the capture tag or site of interaction with the therapeutic or prophylactic or diagnostic agent.

Exemplary agents that can be used include proteins, peptides, carbohydrates, nucleic acid molecules, polymers, small molecules, and combinations thereof. In some embodiments, the nucleic acid nanoparticles are used for the presentation and/or delivery of a peptide, drug, dye, antibody, or antigen-binding fragment of an antibody.

Therapeutic agents can include anti-cancer, anti-inflammatories, or more specific drugs for inhibition of the disease or disorder to be treated. These may be administered in combination.

Suitable genetic therapeutics include anti-sense DNA and RNA as well as DNA coding for proteins, mRNA, miRNA, piRNA and siRNA. In some embodiments, the nucleic acid that forms the nanoparticles include one or more therapeutic, prophylactic, diagnostic, or toxic agents.

a. Gene Editing Molecules

In certain embodiments, the nucleic acid nanostructures are functionalized to include gene editing moieties, or to include components capable of binding to gene editing moieties. Exemplary gene-editing moieties that can be included within or bound to nucleic acid nanoparticles are CRISPR RNAs (e.g., single-guide- or CRISPR-RNAs (sg- or crRNA)) for the gene editing through the CRISPR/Cas system, Cas protein or nucleic acids encoding a Cas protein, encoding TAL effector proteins, or zinc-finger proteins, or constructs encoding them, and triplex forming oligonucleotides.

b. mRNA

In some embodiments, nucleic acid nanostructures are modified by covalent or non-covalent association with an RNA that encodes one or more polypeptides, such as a protein. Therefore, in some embodiments, nucleic acid nanostructures are modified to include one or more messenger RNA molecules (mRNA). The messenger RNA can encode any protein or polypeptide. For example, in some embodiments, nucleic acid nanostructures are modified to include one or more mRNAs, each encoding one or more proteins. In an exemplary embodiment, the mRNA encodes a fluorescent protein or fluorophore. Exemplary fluorescent proteins include mCherry, mPlum, mRaspberry, mStrawberry, tdTomato, GFP, EBFP, Azurite, T-Sapphire, Emerald, Topaz, Venus, mOrange, AsRed2, and J-Red. In some embodiments, nucleic acid nanostructures are modified to include one or more messenger RNA molecules an RNA that encodes one or more polypeptides, such as a protein that is an antigen.

In some embodiments, functionalized nucleic acid nanostructures include one or more single-strand overhang or scaffold DNA sequences that are complementary to the loop region of an RNA, such as an mRNA. In one exemplary case, a tetrahedron (but could be any other object that can be designed from the procedure) can be functionalized with 3 (or 1 or 2 or more than 3) single-strand overhang DNA sequences that are complementary to the loop region of an RNA, for example an mRNA, for example an mRNA expressing a protein.

c. Functional Nucleic Acids

In some embodiments, the nucleic acid nanostructures include one or more functional nucleic acids. Functional nucleic acids that inhibit the transcription, translation or function of a target gene are described.

Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the target polypeptide itself. Functional nucleic acids are often designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place. Therefore, the compositions can include one or more functional nucleic acids designed to reduce expression or function of a target protein.

Methods of making and using vectors for in vivo expression of the described functional nucleic acids such as antisense oligonucleotides, siRNA, shRNA, miRNA, EGSs, ribozymes, and aptamers are known in the art.

In some embodiments, the functional nucleic acids, for example siRNA, are designed for targeted knock-down of immune cells based on antigen-recognition and uptake. Exemplary strategies for utilizing siRNA and other therapies in the treatment and prevention of HIV are discussed in Bobbin, et al., Genome Med., 7(1):50 (2015) doi: 10.1186/s13073-015-0174-y, any of which can be used in combination with the disclosed compositions and methods.

ii. Targeting Elements

Targeting elements can be added to the staple strands of the DNA nanostructures, to enhance targeting of the nanostructures to one or more cells, tissues or to mediate specific binding to a protein, lipid, oligo- or polysaccharide, nucleic acid, etc. For example, for use as biosensors, additional nucleotide sequences are included as overhang sequences on the staple strands.

Exemplary targeting elements include proteins, peptides, nucleic acids, lipids, mono-, oligo- and polysaccharides or their synthetic analogs that bind to one or more targets associated with an organ, tissue, cell, or extracellular matrix, or specific type of tumor or infected cell. Typically, the targeting moieties exploit the surface-markers specific to a group of cells to be targeted. The degree of specificity with which the nucleic acid nanostructures are targeted can be modulated through the selection of a targeting molecule with the appropriate affinity and specificity. For example, antibodies, or antigen-binding fragments thereof are very specific.

Additional functional groups can be introduced on the staple strand for example by incorporating biotinylated nucleotides into the staple strand. Any streptavidin-coated targeting molecules are therefore introduced via biotin-streptavidin interaction. In other embodiments, non-naturally occurring nucleotides are included for desired functional groups for further modification. Exemplary functional groups include targeting elements, immunomodulatory elements, chemical groups, biological macromolecules, and combinations thereof.

In some embodiments, nanostructures include one or more sequences of nucleic acids that act as capture tags, or "bait" sequences to specifically bind one or more targeted molecules.

6. Modifications to Nucleotides

In some embodiments, the nucleotides of the scaffolded nucleic acid (e.g., nucleic acid nanostructure) and/or additional functional element sequences are modified. In some embodiments, the nucleotides of the encapsulated nucleic acid sequences are modified. In some embodiments, the nucleotides of the DNA staple sequences are modified. In some embodiments, the nucleotides of the DNA tag sequences are modified for further diversification of addresses associated with nucleic acid nanostructures.

Examples of modified nucleotides that may be used include, but are not limited to, diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and (acp3)w, 2,6-diaminopurine.

Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amino-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS). Nucleic acid molecules may also contain azido-modified groups, such as N6-(6-azido) hexyl-dATP or alkyne- and DBCO-modified groups, such as C8-alkyne-dCTP and 5-DBCO-PEG$_4$-dCTP for either copper-assisted or strain-promoted azide-based CLICK chemistry.

Locked nucleic acid (LNA) is a family of conformationally locked nucleotide analogues which, amongst other benefits, imposes truly unprecedented affinity and very high nuclease resistance to DNA and RNA oligonucleotides (Wahlestedt C, et al., *Proc. Natl Acad. Sci. USA,* 975633-56380 (2000); Braasch, D A, et al., *Chem. Biol.* 81-7 (2001); Kurreck J, et al., *Nucleic Acids Res.* 301911-1918 (2002)). In some embodiments, the scaffolded DNAs include synthetic RNA-like high affinity nucleotide analogues, such as locked nucleic acids. In some embodiments, the staple strands are synthetic locked nucleic acids.

Peptide nucleic acid (PNA) is a nucleic acid analog in which the sugar phosphate backbone of natural nucleic acid has been replaced by a synthetic peptide backbone usually formed from N-(2-amino-ethyl)-glycine units, resulting in an achiral and uncharged mimic (Nielsen P E et al., *Science* 254,1497-1500 (1991)). It is chemically stable and resistant to hydrolytic (enzymatic) cleavage. In some embodiments, the scaffolded DNAs are PNAs. In some embodiments, the staple strands are PNAs.

In some embodiments, a combination of PNAs, DNAs, and/or LNAs is used for the nucleic acids encoding the format of information. In other embodiments, a combination of PNAs, DNAs, and/or LNAs is used for the staple strands, overhang sequences, or any nucleic acid component of the disclosed compositions.

7. Terminal Modifications to Staple Strands

In some embodiments, some or all of the staple strands include one or more terminal modifications to the 3'end, 5' end, or both the 3' and 5' ends.

For example, terminal PEG modifications to the 3'end, 5' end, or both the 3' and 5' ends of staples can improve stability against exonucleases and/or passivate the nucleic acid nanostructures, for example against unspecific cellular uptake. In particular examples, dendritic or high-molecular weight PEG modifications provide steric hindrance and thus display improved stabilization and passivation properties (see, e.g., Bujold, et al., *Chem. Sci.,* 5: 2449-2455 (2014)). The terminal modifications can be designed to be cleavable (see, e.g., Govan, et al., *Bioconjugate Chem.,* 22(10): 2136-2142 (2011)).

In some embodiments, staple strands are modified at the 5' end with phosphate groups to enable ligation of nick positions by for example, but not limited to, T4 ligase to confer stability against exonucleases and simultaneously generate topologically interlocked nucleic acid nanostructures that cannot be unfolded without breakage of covalent bonds, thereby providing physicochemical stability (see, e.g., Conway, et al., *Chem. Commun.,* 49: 1172-1174 (2013)).

In some embodiments, staple strands are modified at the 3' end, 5' end, or both the 3' and 5' ends with functional groups to permit covalent functionalization with antigens and other agents. In some embodiments, staple strands are modified at the 5' end with a DBCO or TEG-DBCO group that allows conjugation to azide-modified antigens and other agents by strain-promoted CLICK chemistry at quantitative yields on the assembled nucleic acid nanostructure. Other common bioconjugate techniques are applicable, including, but not limited to, amide chemistry and thiol-maleimide CLICK chemistry.

In some embodiments, staple strands are terminally modified with functional groups to implement in situ templated CLICK chemistry-based functionalization of assembled nucleic acid nanostructures. For example, staple overhangs hybridize to a complementary nucleic acid sequence on an antigen (or other agents) and excess antigen is subsequently purified away. The nucleic acid sequence itself is terminally modified with an azido or alkyne group and gets conjugated to the staple terminus (correspondingly bearing an alkyne or azido group) at the nick position adjacent to the staple overhang via copper-assisted CLICK chemistry. This example combines covalent functionalization strategies with sequence-based addressability of the nucleic acid nanostructure. Analogously, other catalyst-dependent bioconjugate techniques are also applicable.

8. Coating Agents for Nucleic Acid Nanostructures

In some embodiments, the nucleic acid nanostructures are coated with agents to convey stabilization against endo- and/or exonucleases, passivation, or a combination thereof. Coating agents can be, for example, naturally occurring or synthetic cationic oligomers or polymers or cooligomers or -polymers containing PEG moieties. In a preferred embodiment, the nucleic acid nanostructures are coated with oligolysine conjugated to a PEG moiety. Preferably, this coating agent includes or consists of 10 lysine units conjugated terminally to a linear PEG moiety, preferably with a molecular weight of approximately 5000 Da (see, e.g., Ponnuswamy, et al., *Nat. Commun.,* 8:15654 (2017)).

Other coating strategies include the use of poly(2-dimethylaminoethyl methacrylate (PDMAEMA) and PEG copolymers thereof in, for example, molecular weight range between 5000 Da to 20000 Da (see, e.g., Kiviaho, et al., *Nanoscale,* 8:11674-11680) as well as linear polyethyleneimine (PEI), for example, in a molecular weight range between 5000 Da and 10000 Da (see, e.g., Ahmadi, et al., *Nanoscale,* 10:7494-7504 (2018)). Chitosan represents an example of a naturally occurring cationic polymer and, in a molecular weight range between 4000 Da and 6000 Da with deacetylation of more than 90%, can be used to coat nucleic acid nanostructures (see, e.g., Ahmadi, et al., *Nanoscale,* 10:7494-7504 (2018)).

In some embodiments, coating agents can be minor groove binders that convey stability against endonucleases as well as passivation. Three distinct classes of minor groove binders that represent suitable coating agents with varying sequence specificity and pharmacological profiles are: bisamidines, polyamides and bisbenzimidazoles. Bisamidines, such as DAPI and others derived therefrom or designed de novo, can provide general protection from endonucleases with relatively low levels of sequence specificity (see, e.g., Tuite, et al., *Eur J Biochem,* 243(1):482-492 (1997). Polyamides, such as Distamycin and Netropsin and others derived therefrom or designed de novo, display higher levels of sequence specificity. In particular, the sequence specificity and avidity of pyrrole-imidazole polyamides can be rationally designed and cocktails of different polyamides can be used to provide general protection of nucleic acid nanostructures from endonucleases (see, e.g., Kawamoto, et al., *Bioorg Med Chem,* 26(8):1393-1411 (2018)). In a preferred embodiment, pyrrole-imidazole polyamides demonstrated to be non-toxic are used (see, e.g., Dickinson, et al., *Proc Natl Acad Sci USA,* 95(22):12890-5 (1998)). Bisbenzimidazoles, such as Hoechst dyes and others derived therefrom or designed de novo, represent an alternative class of minor groove binders that can convey stabilization against endonucleases. In a preferred embodiment, bifunctional minor groove binders enable the passivation of nucleic acid nanostructures via conjugation to a PEG moiety, preferably with a molecular weight of approximately 5000 Da. In another preferred embodiment, bifunctional minor groove binders can be covalently tethered to nucleic acid nanostructures via the installment of alkylating agents to improve long-term stabilization (see, e.g., Oyoshi, et al., *J Am Chem Soc,* 125(16):4752-4 (2003) and Morita, et al., *J Clin Invest,* 127(7):2815-2828 (2017)).

III. Design and Preparation of Nucleic Acid Nanostructures

Systems and methods for the automated, step-wise design of a nucleic acid nanostructure having arbitrary geometries are known in the art.

Scaffolded deoxyribonucleic acid (DNA) origami folds a long single-stranded DNA (ssDNA; "scaffold") into a user-defined shape by slowly annealing the scaffold in the presence of shorter oligonucleotides ("staples") containing segments or regions of complementary sequences to the scaffold that bring sequences that are far apart in sequence space to nearby locations in Euclidian space. These interactions and geometries are stabilized by specific Watson-Crick base pairing in the presence of salt that uses immobile Holliday junctions ("crossovers") to constrain neighboring duplexes physically in space. Crossovers are generally engineered to occur between two parallel DNA duplexes at positions closest or nearest between the two or more helices of the DNA within a 1D, 2D, or 3D structure. Scaffolded DNA origami was initiated by William Shih using a combination of parallel and anti-parallel crossovers (Shih, et al., *Nature,* 427(6975):618-21 (2004)) and subsequently Paul Rothemund using solely anti-parallel crossovers that has become the most ubiquitous form of scaffolded DNA origami (Rothemund, P W, *Nature,* 440, 297-302 (2006)), where Rothemund used M13 genomic ssDNA as the scaffold, and the technique has been further modified and generalized by numerous laboratories (Sharma, J et al.,

*Science,* 323, 112-116 (2009); Dietz, H. et al., *Science,* 325, 725-730 (2009); Douglas, S. M. et al., *Nature,* 459, 414-418. (2009); Brown, S et al., *Nanoscale,* 7, 16621-16624 (2015); Marchi, A. N. et al., *Nano Lett,* 14, 5740-5747 (2014)) using M13 or Phage lambda DNA.

Additional, top-down design of scaffolded DNA origami nanostructures have been demonstrated to automatically generate the scaffold routing and complementary ssDNA staple strands to self-assemble under appropriate folding conditions into user-defined geometries of 1D, 2D, or 3D shapes (Veneziano, R et al., *Science,* 352, 1534 (2016); Benson, E et al., *Nature,* 523, 441-444 (2015); Douglas, S. M. et al., *Nucleic Acids Res,* 37, 5001-5006 (2009), Jun et al., *ACS Nano,* 2019, 10.1021/acsnano.8b08671), and was the subject of work demonstrating generality of sequence design for scaffold DNA (see, for example, US20030215914A1, US20050147962A1, WO2017089567A1, WO2017089570A1, and CN106119269A).

One tile-based method allowed for generation of 2D wireframe objects (Yan, H et al., *Science,* 301, 1882-1884 (2003)) that was subsequently implemented experimentally using M13-based scaffolded DNA origami to a include diversity of 2D and closed 3D shapes (Zhang, et al., *Nat Nanotechnol.,* 10(9):779-84 (2015)). This latter scaffolded DNA origami approach was subsequently generalized and fully automated for 3D shapes by Veneziano et al., (Veneziano, et al., *Science,* 352(6293):1534 (2016)) for DX-based polyhedral origami and by Jun et al., *ACS Nano,* 2019, 10.1021/acsnano.8b08671 for honeycomb and other polyhedral DNA origami.

Non-scaffolded DNA origami is an alternative approach that uses purely short strands of synthetic single-stranded DNA to self-assemble via thermally annealed folding large-scale arrays of structured DNA via a process known as 'tile-based' assembly (Yan, H et al., *Science,* 301, 1882-1884 (2003); Winfree, E et al., *Nature,* 394, 539-544 (1998); Ke, Y et al., *Science,* 338, 1177-1183 (2012); Ke, Y et al., *Nat Chem,* 6, 994-1002 (2014)). In vivo production of top-down designed nanoparticles has long been one goal of the field, with recent promising successes in RNA and DNA (Elbaz, J et al., *Nat Commun,* 7, 11179 (2016); Geary, C et al., *Science,* 345, 799-804 (2014); Nickels, P. C. et al., *Small,* 10, 1765-1769 (2014); Han, et al., *Science,* 358(6369) (2017)).

Historically, scaffolded DNA origami has largely relied on the natural M13 phage genomic single-stranded DNA as the scaffold (Rothemund, P W, *Nature,* 440, 297-302 (2006)). This is because it is natively single stranded and easy to produce in the bacteria *E. coli,* and therefore is available at low cost in large quantities. Efforts to increase production of M13 phage DNA have shown success, obtaining up to 410 mg of ssDNA from 1 liter of *E. coli* growth (Kick, B et al., *Nano Lett,* 15, 4672-4676 (2015)).

Additional composition and methods for making DNA origami structures are discussed in, for example, Dietz H et al (Dietz H et al., *Science,* 325, 725-730 (2009)), Liu et al (Liu et al., *Angew. Chem. Int. Ed.,* 50, pp. 264-267 (2011)), Zhao et al (Zhao et al., *Nano Lett.,* 11, pp. 2997-3002 (2011)), Woo et al (Woo et al., *Nat. Chem.* 3, pp. 620-627 (2011)), Torrirg et al (Torring et al, *Chem. Soc. Rev.* 40, pp. 5636-5646 (2011), Shepherd, et al, (Shepherd, et al., *bioRxiv* 21443 (2019)), doi: https://doi.org/10.1101/521443) and Praetorius et al (Praetorius et al., *Nature,* 552:84-87 (2017)).

Typically, creating a nucleic acid nanostructure includes one or more of the steps of (a) designing the nanostructure; (b) assembling, and optionally labeling, the nanostructure; (c) purifying the assembled nanostructure; (d) conjugating antigen to the nanostructure; and (e) determining or verifying the structure of the nanostructure, each of which is discussed in more detail below.

A. Design of Nucleic Acid Nanostructures

The nucleic acid nanostructure has a defined shape and size. Typically, one or more dimensions of the nanostructure are determined by the target sequence. The methods include designing nanostructures including the target nucleic acid sequence.

The starting point for the design process can be the selection of a target or desired shape. An exemplary method for designing a nucleic acid nanostructure having a desired polyhedral form includes selecting a desired 3D polyhedral or 2D polygon form as a target structure; providing geometric parameters and physical dimensions of the a target structure for a selected 3D polyhedral or 2D polygon form; identifying the route of a single-stranded nucleic acid scaffold that traces throughout the entire target structure; and generating the sequences of the single-stranded nucleic acid scaffold and/or the nucleic acid sequence of staple strands that combine to form a nucleic acid nanostructure having the desired shape. DNA nanostructures having the desired shape are produced by folding a long single stranded polynucleotide, referred to as a "scaffold strand", into a desired shape or structure using a number of small "staple strands" as glue to hold the scaffold in place.

Any arbitrary geometric shape that can be rendered as a "wireframe" model can be selected as input for the design of nucleic acid assemblies. Target structures can be selected based upon one or more design criteria, or can be selected randomly. In some embodiments, structures are selected based on existing 'natural' 3-dimensional organizations (e.g., virus capsids, antigens, toxins, etc.). Therefore, in some embodiments, target shapes are designed for use directly or as part of a system to mediate one or more biological or other responses which are dependent upon, or otherwise influenced by 3D geometric spatial properties. For example, in some embodiments, all or part of a nanostructure is designed to include architectural features known to elicit or control one or more biological functions. In some embodiments, structures are designed to fulfill the 3D geometric spatial requirements to induce, prevent, stimulate, activate, reduce or otherwise control one or more biological functions. Typically, the desired shape defines a specific geometric form that will constrain the other physical parameters, such as the absolute size of the particle. For example, the minimum size of nucleic acid nanostructures designed according to the described methods will depend upon the degree of complexity of the desired shape.

Nucleic acid nanostructures can be geometrically simple, or geometrically complex, such as polyhedral three-dimensional structures of arbitrary geometry. Target structures can be any solid in two dimensions. Therefore, target structures can be a grid or mesh or wireframe topologically similar to a 2D surface or plane. The grid or mesh can be composed of regular or irregular geometries that can be tessellated over a surface. Exemplary target structures include triangular lattices, square lattices, pentagonal lattices, or lattices of more than 5 sides. 2D structures can be designed to have varied length and thickness in each dimension. In some embodiments, the edges of 2D nanostructures include a single nucleic acid helix. In other embodiments, the edges of 2D nanostructures include two or more nucleic acid helices. For example, in some embodiments, each edge of the 2D nanostructure includes 2 helices, 4 helices, 6 helices, 7 or 8 helices, or more than 8 helices on cubic or honeycomb lattices, up to 100 helices per edge, although theoretically unlimited in number.

Target structures can also be any solid in three dimensions that can be rendered with flat polygonal faces, straight edges and sharp corners or vertices. Exemplary basic target structures include cuboidal structures, icosahedral structures, tetrahedral structures, cuboctahedral structures, octahedral structures, decahedral, and hexahedral structures. In some embodiments, the target structure is a convex polyhedron, or a concave polyhedron. For example, in some embodiments, a nucleic acid nanostructure is shaped as a uniform polyhedron that has regular polygons as faces and is isogonal. In other embodiments, a nucleic acid nanostructure is shaped as an irregular polyhedron that has unequal polygons as faces. In further embodiments, the target structure is a truncated polyhedral structure, such as truncated cuboctahedron.

In some embodiments, the target structure is a nucleic acid assembly that has a non-spherical geometry. Therefore, in some embodiments, the target structure has a geometry with "holes". Exemplary non-spherical geometries include toroidal polyhedra and nested shapes. Exemplary toroidal polyhedra include a torus and double torus. Exemplary topologies of nested shapes include nested cube and nested octahedron. In other embodiments, target structures can be a combination of one or more of the same or different polyhedral forms, linked by a common contiguous edge.

Any method for the manipulation, assortment or shaping of nucleic acids can be used to produce the nanostructures. Typically, the methods include methods for "shaping" or otherwise changing the conformation of nucleic acid, such as methods for DNA origami.

In some embodiments, nucleic acid nanostructures are designed using methods that determine the single-stranded oligonucleotide staple sequences that can be combined with the target sequence to form a complete three-dimensional nucleic acid nanostructure of a desired form and size. Therefore, in some embodiments, the methods include the automated custom design of nucleic acid nanostructure corresponding to a target nucleic acid sequence. For example, in some embodiments, a robust computational approach is used to generate DNA-based wireframe polyhedral structures of arbitrary scaffold sequence, symmetry and size. In particular embodiments, design of a nanostructure corresponding to the target nucleic acid sequence, includes providing information as geometric parameters corresponding to the desired form and dimensions of the nanostructure, which are used to generate the sequences of oligonucleotide "staples" that can hybridize to the target nucleic acid "scaffold" sequence to form the desired shape. Typically, the target nucleic acid is routed throughout the Eulerian circuit of the network defined by the wire-frame geometry of the nanostructure.

A step-wise, top-down approach has been proven for generating DNA nanostructure origami objects of any regular or irregular wireframe polyhedron, with edges composed of a multiple of two number of helices (i.e., 2, 4, 6, etc.) and with edge lengths a multiple of 10.5 rounded down to the closest integer. Exemplary methods for the top-down design of nucleic acid nanostructures of arbitrary geometry are described in Venziano et al, *Science,* 352:6293 (2016), Jun et al., *ACS Nano,* 2019, 10.1021/acsnano.8b08671, WO2017089567A1, and WO2017089570A1, the contents of which are incorporated by reference in their entireties.

In other embodiments, the sequence of the nanostructure is designed manually, or using alternative computational sequence design procedures. Exemplary design strategies that can be incorporated into the methods for making and using NMOs include single-stranded tile-based DNA origami (Ke Y, et al., Science 2012); brick-like DNA origami, for example, including a single-stranded scaffold with helper strands (Rothemund, et al., and Douglas, et al.); and purely single-stranded DNA that folds onto itself in PX-origami, for example, using paranemic crossovers.

Alternative structured NMOs include bricks, bricks with holes or cavities, assembled using DNA duplexes packed on square or honeycomb lattices (Douglas et al., *Nature* 459, 414-418 (2009); Ke Y et al., Science 338: 1177 (2012)). Paranemic-crossover (PX)-origami in which the nanostructure is formed by folding a single long scaffold strand onto itself can alternatively be used, provided bait sequences are still included in a site-specific manner. Further diversity can be introduced such as using different edge types, including 6-, 8-, 10, or 12-helix bundle. Further topology such as ring structure is also useable for example a 6-helix bundle ring.

B. Assembly of Nucleic Acid Nanostructures

The single-stranded nucleic acid scaffold and the corresponding staple sequences are assembled into a nanostructure having the desired shape and size. In some embodiments, assembly is carried out by hybridization of the staples to the scaffold sequence. In other embodiments, nanostructures include only single-stranded DNA oligos. In further embodiments, the nanostructures include a single-stranded DNA molecule folded onto itself. Therefore, in some embodiments, the NMOs are assembled by DNA origami annealing reactions.

Typically, annealing can be carried out according to the specific parameters of the staple and/or scaffold sequences. For example, the oligonucleotide staples are mixed in the appropriate quantities in an appropriate reaction volume. In preferred embodiments, the staple strand mixes are added in an amount effective to maximize the yield and correct assembly of the nanostructure. For example, in some embodiments, the staple strand mixes are added in molar excess of the scaffold strand. In an exemplary embodiment, the staple strand mixes are added at a 10-20× molar excess of the scaffold strand. In some embodiments, the synthesized oligonucleotides staples with and without tag overhangs are mixed with the scaffold strand and annealed by slowly lowering the temperature (annealing) over the course of 1 to 48 hours. In some embodiments, in particular at high numbers of tag overhangs per nucleic acid nanostructure, tag overhangs can be masked with guard strands to avoid aggregation and inter-nanostructure insertion of tag overhangs. This process allows the staple strands to guide the folding of the scaffold into the final nanostructure.

Material usage for assembly can be minimized and assembly hastened by use of microfluidic automated assembly devices. For example, in certain embodiments, the oligonucleotide staples are added in one inlet, the scaffold can be added in a second inlet, with the solution being mixed using methods known in the art, and the mix traveling through an annealing chamber, wherein the temperature steadily decreases over time or distance. The output port then contains the assembled nanostructure for further purification or storage. Similar strategies can be used based on digital droplet-based microfluidics on surfaces to mix and anneal solutions, and applied to purely single-stranded oligo-based nanostructures or single-stranded scaffold origami in the absence of helper strands. Overhang sequences for hybridization of antigen-oligo conjugates or for covalent attachment of antigen-click/other chemical groups may be incorporated either using solid-state or liquid-state synthesized oligos, or using bacterially produced oligos for large-scale, low-cost production (Praetorius et a, *Nature,* 552:84-87 (2017)).

C. Purification of Nucleic Acid Nanostructures

The methods include purification of the assembled nanostructures. Purification separates assembled structures from the substrates and buffers required during the assembly process. Typically, purification is carried out according to the physical characteristics of nanostructures, for example, the use of filters and/or chromatographic processes (FPLC, etc.) is carried out according to the size and shape of the nanostructures.

In an exemplary embodiment, nanostructures are purified using filtration, such as by centrifugal filtration, or gravity filtration, or by diffusion such as through dialysis. In some embodiments, filtration is carried out using, e.g., an Amicon Ultra-0.5 ml (or larger scales) centrifugal filter (MWCO 100 kDa). In some embodiments, for example, those for which antigen functionalization is not compatible with Amicon filters, Pluronic F-127-passivated Spin-X UF-0.5 ml (or larger scales) centrifugal filters can be used (MWCO 100 kDa).

In some embodiments, nanostructures are purified after assembly, after antigen conjugation, or both.

D. Pairing with Immunostimulatory Agents

Immunostimulatory agents, such as antigens, adjuvants, and other agents can be covalently or non-covalently bound to, or otherwise associated with the nanostructure. The association can before, during or after nanostructure assembly.

In some embodiments, the immunostimulatory agent is directly or indirectly bound to the nanostructure via outwardly facing nucleic acid overhangs extending from the 3' and/or 5' ends of selected staple strands. The nucleic acid overhangs can include one or more sequences that is complementary to a target RNA, DNA or PNA sequence covalently linked to the immunostimulatory agent. Such covalent linkage may be formed by, for example, maleimide-thiol coupling. Additionally, or alternatively, the nucleic acid overhangs can include one or more sequences that is complementary to part of all of target RNA, DNA or PNA sequence that is or includes the immunostimulatory agent, e.g., a nucleic acid adjuvant such as a TLR9 ligand. In some embodiments, the immunostimulatory agent is a single stranded nucleic acid that is complementary in part or in total to a nucleic acid overhang of the nanostructure, or a double stranded nucleic acid with a single stranded segment, optionally an overhang, that is complementary in part or in total to a nucleic acid overhang of the nanostructure. When the immunostimulatory agent-nucleic acid is mixed together with nucleic acid overhangs having a complementary sequence, the nucleic acid sequence of the immunostimulatory agent-nucleic acid conjugate can non-covalently hybridize with the nucleic acid overhang.

Other interactions for attachment or incorporation of immunostimulatory agent include, but are not limited to, intercalation, minor groove interactions, biotin-streptavidin interaction, and chemical linkers (e.g., using Click-chemistry groups).

In a particular embodiment illustrated below, an immunostimulatory agent is conjugated to peptide nucleic acid oligomers, which then hybridize with stable strand overhangs on the nucleic acid nanostructure. For example, PNA peptide containing a maleimide formed by, for example, solid phase synthesis, can be dissolved in an aqueous solution and reacted with N-terminal cysteine of an immunostimulatory agent, such as a peptide antigen. Nucleic acid nanostructures can be mixed with the PNA-immunostimulatory agent conjugates, typically molar excess of PNA-immunostimulatory agent conjugates, which hybridize with overhangs on nucleic acid nanostructures.

Alternatively, dCas9 with guide sequence may be used to target specific nucleic acid sequences in the origami particle, or DNA-binding peptides or proteins such as bZIPs or deactivated TALENs or nanobodies that may be sequence-specific or not, or other orthogonal protein decoration of DNA origami (Sacca, et al., *Angew Chem Int Ed Engl.,* 49(49):9378-83 (2010). Doi: 10.1002/anie.201005931), minor groove binders, or polycationic oligomers and polymers that non-covalently condense onto the nucleic acid nanostructure. In all cases, the nucleic acid binding component may constitute the antigen, or template the antigen through covalent or non-covalent interactions.

In some embodiments, the immunostimulatory agent is linked to the nanostructure indirectly and further includes a linker that alters the rigidity or flexibility of the antigen relative to the nanostructure, as above.

Suitable linkers include, but are not limited to, oligonucleotides (e.g., a string of nucleic acids such as single or double stranded DNA, RNA, PNA, or others including those described elsewhere herein), polymers including but not limited to poly(ethylene glycol), polyacrylamide, polyacrylic acid; a string of amino acids (i.e., peptide linker), dextran, or combinations thereof, as listed above.

In some embodiments, the linker is or includes engineered nucleic acid (e.g., DNA)-binding proteins such as those listed above, including inactive endo- or exonucleases, that bind the DNA duplex in specific orientations and positions may be engineered to bear antigenic domains that are subsequently rigidly presented by the nanostructure due to its linking domain.

Linkers can be of any suitable length. Typically, the length is suitable for antigen to induce an immune response. Lengths in the range of 0.6 nm to 52 nm were tested below (see, e.g., Table 3). In some embodiments, the length of the linker is between 0.5 nm and 500 nm, 0.5 nm and 250 nm, 0.5 and 100 nm, 0.5 nm and 75 nm, 0.6 nm and 52 nm, inclusive, or an specific integer length or range of lengths there between, or a specific length exemplified in Table 3. In some embodiments, the linker itself does or does contribute to or otherwise induce an immune response.

The Examples below show that rigid presentation of immunostimulatory agents, such as antigens, is preferred over flexible presentation, whereas flexibility of immunostimulatory agents, such as TLR agonists, is preferred over rigid presentation. Thus, in some embodiments, there is no linker, or only a minimal linker, to facilitate attachment of the antigen to the nanostructure, while encouraging rigid presentation of the antigen on the surface of the structure. In some embodiments, the linker is a rigid linker. In other embodiments, flexibility is preferred. In some embodiments, the linker is a flexible linker.

E. Validation of Nucleic Acid Nanostructures

Methods for designing nucleic acid nanostructures of a desired shape and size can include steps for validation of the resulting nucleic acid structure based on the output sequences. For example, in some embodiments, the methods also include the step of predicting the 3-dimensional coordinates of the nucleic acids within the nucleic acid nanostructure, based on the output of the system used for positioning scaffold and staple sequences. When structural information for a nucleic acid nanostructure is predicted, the predicted information can be used to validate the nucleic acid nanostructure. Typically, validation of the resulting nucleic acid structure includes (1) calculating the positions of each base pair in the structural model; (2) determining the positions of each base pair in the nucleic acid nanostructure; and (3) comparing the calculated structural data obtained for the model with that experimentally determined (i.e., observed) for the nanostructure.

Validation can also include, for example, electron microscopic observation of the structures formed.

IV. Formulations

A. Pharmaceutical Compositions

Pharmaceutical compositions containing nucleic acid nanostructures and one or more immunostimulatory agents in combination with a pharmaceutically acceptable carrier, diluent, preservative, excipient, or combination thereof are provided. In some embodiments, the pharmaceutical compositions also contain one or more agents or moieties, such as targeting agent(s) or coating agent(s) for example. Pharmaceutical compositions disclosed herein include any combination and sub-combination of the aforementioned compositions including nucleic acid nanostructures, immunostimulatory agents, and optionally moieties (e.g., targeting agents, coating agent(s), etc.), gene editing molecules, siRNAs, and linear or circular mRNAs, which may also form the scaffold sequence of the nanostructure, in combination with a pharmaceutically acceptable carrier, diluent, preservative, excipient, or combination thereof.

The pharmaceutical compositions disclosed herein can be used in immunogenic compositions and as vaccines or components of vaccines. Typically, immunogenic compositions disclosed herein include a nucleic acid nanostructure, and immunostimulatory agents, such as an antigen, an adjuvant, or a combination thereof. Immunogenic compositions may also include a coating agent. When administered to a subject in combination, the immunostimulatory agents (e.g., adjuvant and/or antigen) can be administered in separate pharmaceutical compositions, or they can be administered together in the same pharmaceutical composition. When present in the same pharmaceutical composition, or administered in combination, an adjuvant and an antigen can be referred to as a vaccine.

Pharmaceutical compositions can be for administration by parenteral (intramuscular, intraperitoneal, intravenous (IV), intradermal, or subcutaneous injection), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. In certain embodiments, the compositions are administered locally, for example by injection directly into a site to be treated. Typically, local injection causes an increased localized concentration of the compositions which is greater than that which can be achieved by systemic administration.

In some embodiments, the pharmaceutical compositions are injected or otherwise administered directly to one or more tumors. Most typically, the pharmaceutical compositions are administered by intramuscular, intradermal, subcutaneous, or intravenous injection or infusion, or by intranasal delivery.

In some embodiments, the pharmaceutical compositions are delivered by catheter or syringe. Other means of delivering such compositions include using infusion pumps (for example, from Alza Corporation, Palo Alto, Calif.) or incorporating the pharmaceutical compositions into polymeric implants (see, for example, P. Johnson and J. G. Lloyd-Jones, eds., Drug Delivery Systems (Chichester, England: Ellis Horwood Ltd., 1987), which can affect a sustained release of the composition to the immediate area of the implant.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired effect, on the route of administration, and on the duration of the treatment desired.

An exemplary dosage range for immunostimulatory agents, such as antigen and/or adjuvant components of a vaccine are about 10 µg to about 500 µg of antigen, and about 10 µg to about 1000 µg of adjuvant for in vivo application. In some embodiments, the dosage range of the immunostimulatory agent, such as an antigen is between about 10 ng and about 500 µg, or about 10 ng 100 µg.

Immunostimulatory agents dosages, such as adjuvant dosages, can also be determined based on activity or units. For example, in some embodiments, the unit dosage of an adjuvant is between about 1 U and about 10 U, or between about 2 U and about 7 U, or between about 2.5 U and about 5 U.

1. Formulations for Parenteral Administration

In a preferred embodiment, the pharmaceutical compositions are administered in an aqueous solution, by parenteral injection. The formulation can be in the form of a suspension or emulsion. In general, pharmaceutical compositions are provided including an effective amount of the nanostructure and immunostimulatory agent and optionally including additional moieties (e.g., targeting agent, coating agent(s), etc.), pharmaceutically acceptable diluents, preservatives, solubilizers, emulsifiers, adjuvants, and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate.

The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical and Mucosal Administration

The disclosed pharmaceutical compositions can be applied topically. Topical administration can include application to the lungs (pulmonary), nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

3. Delivery Vehicles

Any of the disclosure compositions can be formulated in a delivery vehicle. Exemplary delivery vehicles include those that enhance delivery of the nanostructures across cell membrane such as the plasma membrane. Exemplary delivery vehicles include, but are not limited to, lipid-based delivery vehicles such as liposome or micelle. Liposomes are spherical vesicles composed of concentric phospholipid bilayers separated by aqueous compartments. Liposomes can adhere to and form a molecular film on cellular surfaces. Structurally, liposomes are lipid vesicles composed of concentric phospholipid bilayers which enclose an aqueous interior (Gregoriadis, et al., *Int. J. Pharm.,* 300, 125-30 2005; Gregoriadis and Ryman, Biochem. J., 124, 58P (1971)). Hydrophobic compounds associate with the lipid phase, while hydrophilic compounds associate with the aqueous phase.

Liposomes and micelles can be formed from one or more lipids, which can be neutral, anionic, or cationic at physiologic pH. Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including, but limited to, 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-α-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids. In some embodiments, the liposomes contain a phosphaditylcholine (PC) head group, and optionally sphingomyelin. In some embodiments, the liposomes contain DPPC. In a further embodiment, the liposomes contain a neutral lipid, such as 1,2-dioleoylphosphatidylcholine (DOPC).

In certain embodiments, the liposomes are generated from a single type of phospholipid. In some embodiments, the phospholipid has a phosphaditylcholine head group, and, can be, for example, sphingomyelin. The liposomes may include a sphingomyelin metabolite. Sphingomyelin metabolites used to formulate the liposomes include, without limitation, ceramide, sphingosine, or sphingosine 1-phosphate. The concentration of the sphingomyelin metabolites included in the lipids used to formulate the liposomes can range from about 0.1 mol % to about 10 mol %, or from about 2.0 mol % to about 5.0 mol %, or can be in a concentration of about 1.0 mol %.

Suitable cationic lipids in the liposomes include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanaminium trifluoro-acetate (DOSPA), β-alanyl cholesterol, cetyl trimethyl ammonium bromide (CTAB), diC$_{14}$-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N, N, N', N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

The lipids may be formed from a combination of more than one lipid, for example, a charged lipid may be combined with a lipid that is non-ionic or uncharged at physiological pH. Non-ionic lipids include, but are not limited to, cholesterol and DOPE (1,2-dioleolylglyceryl phosphatidylethanolamine). The molar ratio of a first phospholipid, such as sphingomyelin, to second lipid can range from about 5:1 to about 1:1 or 3:1 to about 1:1, or from about 1.5:1 to about 1:1, or the molar ratio is about 1:1.

In some embodiments, liposomes or micelles include phospholipids, cholesterols and nitrogen-containing lipids. Examples include phospholipids, including natural phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, and lysolecithin, as well as hydrogenated products thereof obtained in a standard manner. It is also possible to use synthetic phospholipids such as dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, eleostearoylphosphatidylethanolamine as well as homo-poly{N'—[N-(2-aminoethyl)-2-aminoethyl]aspartamide} P[Asp(DET)] and block-cationer poly(ethyleneglycol) (PEG)-b-P[Asp(DET)].

In some embodiments, the liposomes are long circulating liposomes or stealth liposomes such as those reviewed in Immordino, et al, *Int J Nanomedicine,* 1(3):297-315 (2006)), which is specifically incorporated by reference herein in its entirety. For example, liposomes have been developed with surfaces modified with a variety of molecules including glycolipids and sialic acid. Long-circulating liposomes can include, for example, synthetic polymer poly-(ethylene glycol) (PEG) in liposome composition. The PEG on the surface of the liposomal carrier can extend blood-circulation time while reducing mononuclear phagocyte system uptake (stealth liposomes) and serve as an anchor for the targeting moiety.

Antibodies and antibody fragments are widely employed for targeting moieties for liposomes due to the high specificity for their target antigens. Referred to immunoliposomes, methods of generated targeted liposomes by coupling of antibodies to the liposomal surface are known in the art. Such techniques include, but are not limited to, conventional coupling and maleimide based techniques. See also, Paszko and Senge, Curr Med Chem., 19(31):5239-77 (2012), Kelly, et al., *Journal of Drug Delivery,* Volume 2011 (2011), Article ID 727241, 11 pages.

The micelles can be polymer micelles, for example, those composed of amphiphilic di- or tri-block copolymers made of solvophilic and solvophobic blocks (see, e.g., Croy and Kwon, *Curr Pharm Des.,* 12(36):4669-84 (2006)).

B. Immunogenic Compositions

The nanostructures disclosed herein can be used in immunogenic compositions or as components in vaccines. Typically, an immunogenic composition includes one or more immunostimulatory agent(s), such as adjuvant, an antigen, or a combination thereof. The combination of an adjuvant and an antigen can be referred to as a vaccine. When administered to a subject in combination, the adjuvant and antigen can be administered in separate pharmaceutical compositions, or they can be administered together in the same pharmaceutical composition. As described herein, the nanostructure can be engineered to present or otherwise contain antigen, and thus the antigen-nanostructure composition can serve as the antigen component of an immunogenic composition or vaccine formulation. Additionally, or alternatively, the nanostructure can include an adjuvant. Thus, in some embodiments, the nanostructure includes both an antigen and an adjuvant. Two or more different nanostructures can be utilized each presenting one or more different antigens, one or more different adjuvants, or combinations thereof.

Specific DNA sequences can be included as adjuvants, with the 3D patterning in geometry and size controlled in an arbitrary manner scaffolded by the nucleic acid nanostructure.

In some embodiments, the nanostructure does not include an adjuvant. In some embodiments, the nanostructure includes an adjuvant that is used alone or in combination with an antigen that may or may not be linked to a nanostructure. Thus, in some embodiments, an adjuvant can be administered together (e.g., in the same pharmaceutical composition) or separately (e.g., in a different pharmaceutical composition) from a nanostructure containing the antigen. In some embodiments, an antigen can be administered together (e.g., in the same pharmaceutical composition) or separately (e.g., in a different pharmaceutical composition) from a nanostructure containing an adjuvant.

C. Adjuvants

Immunostimulatory agents include immunologic adjuvants. Adjuvants stimulate the immune system's response to a target antigen, but do not provide immunity themselves. Adjuvants can act in various ways in presenting an antigen to the immune system. Adjuvants can act as a depot for the antigen, presenting the antigen over a longer period of time, thus maximizing the immune response before the body clears the antigen. Examples of depot type adjuvants are oil emulsions. An adjuvant can also act as an irritant, which engages and amplifies the body's immune response.

The adjuvant may be without limitation alum (e.g., aluminum hydroxide, aluminum phosphate); saponins purified from the bark of the *Q. saponaria* tree such as Quil A (a mixture of more than 25 different saponin molecules), or subcombinations or individual molecules thereof such as QS21 (a glycolipid that elutes in the $21^{st}$ peak with HPLC fractionation; Antigenics, Inc., Worcester, Mass.); poly[di (carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

Adjuvants may be TLR ligands, such as those discussed above. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor.

Immunostimulatory complexes called ISCOMs are particulate antigen delivery systems having antigen, cholesterol, phospholipid and saponin (Quil A or other saponin) with potent immunostimulatory activity. ISCOMATRIX® is a particulate adjuvant having cholesterol, phospholipids and saponins (Quil A) but without containing antigen. See, e.g., U.S. Pat. No. 9,149,520, Sun, et al., Volume 27, Issue 33, 16 Jul. 2009, Pages 4388-4401, and Morelli, et al., *J Med Microbiol.* 2012 July; 61(Pt 7):935-43. Doi: 10.1099/jmm.0.040857-0. Epub 2012 March 22. This adjuvant has principally the same structure as ISCOMs, consisting of perforated cage-like particles of approximately 40 nm in diameter. The antigens can be formulated with ISCOMATRIX® to produce vaccines capable of antigen presentation and immunostimulants similar to ISCOMs-type formulations, but with a wider range of applicability, since its use is not limited to hydrophobic membrane proteins. Modifications of ISCOMs formulations and ISCOMATRIX® have also been developed to achieve a better association of some antigens, such as described in WO 98/36772.

ISCOMs and ISCOMATRIX® combine the advantages of a particulate delivery system with the in situ presence of an adjuvant (Quil A) and consequently have been found to be more immunogenic than other colloidal systems such as liposomes and protein micelles. Formulations of ISCOMs and ISCOMATRIX® retained the adjuvant activity of the Quil A, while increasing its stability, reducing its hemolytic activity, and producing less toxicity. They also generate a similar immune response to the one obtained by immunizing with simple mixtures of antigen and saponin, but allow for the use of substantially smaller amounts of antigen. Several ISCOMs-type vaccine formulations or containing ISCOMATRIX® have been approved for veterinary use, for example against equine influenza virus.

Other liposomal systems mainly composed of saponins from *Q. saponaria* and sterols (primarily cholesterol) have been described, one of which is referred to as ASO1B. See, e.g., WO 96/33739, being also formulated as emulsions such as described in US 2005/0220814. See, also, U.S. Published Application No. 2011/0206758.

Iscomatrix-like adjuvants such as ISCOMATRIX® are thought to function via canonical inflammasome activation and subsequent release of pro-inflammatory cytokines such as IL-18 and IL-1β (Wilson, et al., *Journal of immunology.* 2014; 192(7):3259-68. Doi: 10.4049/jimmunol.1302011. PubMed PMID: 24610009). This mechanism is thought to be mediated at least in-part by endosomal degradation and the release of NRLP3-activating cathepsin proteases into the cytosol.

V. Methods

Disclosed are various methods of using the provided compositions. For example, the compositions may be administered as an immunostimulatory agent. In some embodiments, the nanostructure is administered as part of a vaccine and/or as part of a method of treatment. For example, the disclosed compositions can be administered in an effective amount to induce, increase, or enhance an immune response. Immune response typically refers to responses that induce, increase, or perpetuate the activation or efficiency of innate and/or adaptive immunity. The compositions can also be used to promote tolerance, e.g., to an allergen or autoimmune antigen, rather than immunity.

The composition can be delivered parenterally (e.g., by subcutaneous, intradermal, or intramuscular injection) through the lymphatics, or by systemic administration through the circulatory system (e.g., by intravenous injection or infusion). In some embodiments, different compositions are administered in the same manner or route. In other embodiments, different compositions are administered in two or more different manners or routes.

The compositions can be delivered non-systemically. In some embodiments, at least the immunostimulatory agent-containing nanostructure alone or in combination with one or more additional agent is delivered locally, for example, by subcutaneous injection. In some embodiments, the composition is administered at a site adjacent to or leading to one or more lymph nodes which are close to the site in need of an immune response (i.e., close to a tumor or site of infection). The composition can be injected into the muscle. In some embodiments, the composition is administered in multiple doses at various locations throughout the body. The composition can also be administered directly to a site in need of an immune response (e.g., a tumor or site of infection).

A. Methods of Inducing an Immune Response, Immunity, and/or Antibody Production

Methods of inducing an immune response in a subject (e.g., a human) by administering to the subject a therapeutically effective amount of the disclosed compositions are provided. The immune response can be induced, increased, or enhanced by the composition compared to a control (e.g., absence of the composition or presence of another composition).

In some embodiments, the antigen-bound nanostructure functions as MHC with peptides to mimic dendritic cell presentation to T-cells for their activation and/or is subject to cleavage of antigen (e.g., neoantigenic peptides) by proteases to release them site-specifically, preferably in a prescribed stoichiometric amount; alone or in combination with inducing or enhancing immune cell activation through DNA duplex internalization and activation of e.g., STING/RIG, in, for example, a tumor microenvironment.

In some embodiments, the disclosed antigen-bound nanostructures increase a B cell response, for example increasing antigen binding to B cell receptors, increased antigen internalization by B cells, increased calcium release, increased pSyk phosphorylation, or a combination thereof. In some embodiments, B cell proliferation and/or differentiation is increased.

In some embodiments, a disclosed composition is administered to a subject in need thereof in an effective amount to increase an antigen-specific antibody response (e.g., IgG, IgG2a, IgG1, or a combination thereof), increase a response in germinal centers (e.g., increase the frequency of germinal center B cells, increase frequencies and/or activation T follicular helper (Tfh) cells, increase B cell presence or residence in dark zone of germinal center or a combination thereof), increase plasmablast frequency, increase inflammatory cytokine expression (e.g., IL-6, IFN-γ, IFN-α, IL-1β, TNF-α, CXCL10 (IP-10), or a combination thereof), or a combination thereof.

In some embodiments, the administration of the composition alternatively or additionally induces an improved B-memory cell response in subjects administered the composition compared to a control. An improved B-memory cell response is intended to mean an increased frequency of peripheral blood B lymphocytes capable of differentiation into antibody-secreting plasma cells upon antigen encounter.

In some embodiments, the administration of the composition alternatively or additionally induces activation of an immune response through triggering of the cGAS-STING pathway in subjects administered the composition compared to a control. For example, in some embodiments, the administration of the composition alternatively or additionally induces cGAS binding within the cell cytosol. In some embodiments, the administration of the composition alternatively or additionally induces cGAS binding within the cell cytosol. In some embodiments, the administration of the composition alternatively or additionally induces IFN production associated with triggering of the cGAS-STING pathway.

In some embodiments, the administration of the composition alternatively or additionally induces activation of an immune response through activation of TLRs in subjects administered the composition compared to a control. For example, in some embodiments, the administration of the composition alternatively or additionally induces TLR activation. In some embodiments, the administration of the composition alternatively or additionally induces IFN production associated with TLR activation.

The experiments below show that immunostimulatory wireframe structures can be programmed to modulate immune pathway activation controllably, to, for example, TLR9 activation, cGAS-STING immune responses, or a combination thereof. Thus, for example, in some embodiments, the immunostimulatory agent, such as double stranded nucleic acid (e.g., DNA) and/or CpG motif(s) form part of the wireframe. Such embodiments may be free from immunostimulatory agent(s) hybridized to a staple strand overhangs. These embodiments may favor cGAS-STING immune responses optionally with limited or free from TLR9 activation. In embodiments wherein TLR9 activation is desired, the nanostructure typically include display of one or more immunostimulatory agent outside the wireframe structure, e.g., hybridized to a staple strand overhangs or otherwise covalently or non-covalently attached to the wireframe.

The compositions can induce an improved effector cell response such as a CD4 or CD8 T-cell immune response, against at least one of the component antigen(s) or antigenic compositions compared to the effector cell response obtained under control conditions (e.g., absence of the composition or presence of another composition). The term "improved effector cell response" refers to a higher effector cell response such as a CD8 or CD4 response obtained in a human patient after administration of a disclosed composition than that obtained under control conditions. The improved effector cell response can be assessed by measuring, for example, the number of cells producing any of the following cytokines: (1) cells producing at least two different cytokines (CD40L, IL-2, IFN-gamma, TNF-alpha); (2) cells producing at least CD40L and another cytokine (IL-2, TNF-alpha, IFN-gamma); (3) cells producing at least IL-2 and another cytokine (CD40L, TNF-alpha, IFN-gamma); (4) cells producing at least IFN-gamma and another cytokine (IL-2, TNF-alpha, CD40L); (5) cells producing at least TNF-alpha and another cytokine (IL-2, CD40L, IFN-gamma); and (6) cell producing at least IFN-gamma.

The disclosed pharmaceutical compositions can be used, for example, to induce an immune response, when administering the immunostimulatory component alone or alternative compositions that are available (such as vaccines) is ineffectual. In some embodiments, the disclosed compositions may reduce the dosage of an immunostimulatory agent (e.g., antigen, adjuvant, or both) required to induce, increase, or enhance an immune response; or reduce the time needed for the immune system to respond following administration.

The described compositions may be administered as part of prophylactic vaccines or immunogenic compositions which confer resistance in a subject to subsequent exposure to infectious agents, or as part of therapeutic vaccines, which can be used to initiate or enhance a subject's immune response to a pre-existing antigen, such as a viral antigen in a subject infected with a virus or with cancer.

The desired outcome of a prophylactic or therapeutic immune response may vary according to the disease or condition to be treated, or according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

The disclosed compositions may be used in methods of inducing protective immunity against an infectious agent, disease, or condition by administering to a subject (e.g., a human) a therapeutically effective amount of the compositions. "Protective immunity" or "protective immune response" refers to immunity or eliciting an immune response against an infectious agent, which is exhibited by a subject (e.g., a human), that prevents or ameliorates an infection or reduces at least one symptom thereof.

Another disclosed method provides for inducing the production of neutralizing antibodies or inhibitory antibodies in a subject (e.g., a human) by administering any of the disclosed compositions to the subject. In some embodiments, a disclosed composition is administered to a subject in need thereof in an effective amount to increase an antigen-specific antibody response (e.g., IgA, IgD, IgE, IgM, IgG, IgG2a, IgG1, or a combination thereof).

The antibody response is important for preventing many viral infections and may also contribute to resolution of infection. When a vertebrate (e.g., a human) is infected with a virus, antibodies are produced against many epitopes on multiple virus proteins. A subset of these antibodies can block virus infection by a process called neutralization. Antibodies can neutralize viral infectivity in a number of ways. They may interfere with virion binding to receptors (blocking viral attachment), block uptake into cells (e.g., blocking endocytosis), prevent uncoating of the genomes in endosomes, or cause aggregation of virus particles. Many enveloped viruses are lysed when antiviral antibodies and serum complement disrupt membranes.

B. Methods of Inducing Tolerance

The compositions and methods disclosed herein may also be used to promote tolerance. Tolerogenic therapy aims to induce immune tolerance where there is pathological or undesirable activation of the normal immune response. Such embodiments may also include co-administration of an immunosuppressive agent (e.g., rapamycin).

Tolerogenic vaccines deliver antigens with the purpose of suppressing immune responses (e.g., induce or increase a suppressive immune response) and promoting robust long-term antigen-specific immune tolerance. For example, Incomplete Freund's Adjuvant (IFA) mixed with antigenic peptides stimulates Treg proliferation (and/or accumulation) and IFA/Insulin peptide prevents type I diabetes onset in susceptible mice, though this approach is ineffective in reversing early onset type I diabetes (see, e.g., Fousteri, et al., *Diabetologia,* 53:1958-1970 (2010)).

The compositions and methods disclosed herein are also useful for controlling the immune response to an antigen. For example, in some embodiments, the compositions are used as part of a tolerizing vaccine.

An exemplary composition typically contains nucleic acid nanostructure with an antigen or a nucleic acid encoding an antigen, and an adjuvant. The antigen, for example, a self-antigen, depends on the disease to be treated, and can be determined by one of skill in the art. Exemplary self-antigens and other tolerizing antigens are discussed in more detail above. Adjuvant and antigen can be administered in an amount effective to, for example, to increase immunosuppression.

C. Methods of Treatment

Also provided are methods of treating a subject (e.g., a human) having or at risk of having a disease or condition by administering to the subject a therapeutically effective amount of the disclosed compositions.

1. Infectious Diseases

The compositions are useful for treating acute or chronic infectious diseases. Thus, the compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the composition can be administered topically to treat viral skin diseases such as herpes lesions or shingles, or genital warts. The composition can also be administered to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Histoplasma, Hyphomicrobium, Legionella, Leishmania, Leptsirosis, Listeria,* Meningococcus A, B and C, *Methanobacterium, Micrococcus, Myobacterium, Mycoplasma, Myxococcus, Neisseria, Nitrobacter, Oscillatoria,* Prochloron, *Proteus, Pseudomonas, Phodospirillum, Rick-*

*ettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni.*

In some embodiments, the type of disease to be treated or prevented is a chronic infectious disease caused by a bacterium, virus, protozoan, helminth, or other microbial pathogen that enters intracellularly. In particular embodiments, infections to be treated are chronic infections caused by a hepatitis virus, a human immunodeficiency virus (HIV), a human T-lymphotrophic virus (HTLV), a herpes virus, an Epstein-Barr virus, or a human papilloma virus.

2. Cancer

The disclosed compositions are useful for treating cancer by, for example, stimulating or enhancing an immune response in host against the cancer. The types of cancer that may be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The compositions can be administered as an immunogenic composition or as part of vaccine, such as prophylactic vaccines, or therapeutic vaccines, which can be used to initiate or enhance a subject's immune response to a pre-existing antigen, such as a tumor antigen in a subject with cancer.

The desired outcome of a prophylactic or therapeutic immune response may vary according to the disease, according to principles well known in the art. Similarly, immune responses against cancer, may alleviate symptoms, or may be one facet in an overall therapeutic intervention against a disease. For example, administration of the composition may reduce tumor size, or slow tumor growth compared to a control. The stimulation of an immune response against a cancer may be coupled with surgical, chemotherapeutic, radiologic, hormonal and other immunologic approaches in order to affect treatment. In some embodiments, the nanostructure itself or an additional active agent administered in combination therewith induces or enhances STING/RIG pathway activation (Baber, *Nat Rev Immunol.,* 15(12):760-770 (2015)).

3. Inflammatory and Autoimmune Disorders

The compositions (e.g., those that increase tolerance) disclosed herein can be used to inhibit immune-mediated tissue destruction for example in a setting of inflammatory responses, autoimmune and allergic diseases, and transplant rejection.

In certain embodiments, the disclosed compositions are used to treat an inflammatory response or autoimmune disorder in a subject. For example, the disclosed methods can be used to prophylactically or therapeutically inhibit, reduce, alleviate, or permanently reverse one or more symptoms of an inflammatory response or autoimmune disorder. An inflammatory response or autoimmune disorder can be inhibited or reduced in a subject by administering to the subject an effective amount of a composition in vivo, or cells modulated by the composition ex vivo.

Representative inflammatory responses and autoimmune diseases that can be inhibited or treated include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments, the disclosed compositions and methods for inducing or perpetuating a suppressive immune response can be used prophylactically or therapeutically to suppress allergies and/or asthma and/or inflammation. Allergies and/or asthma and/or inflammation can be suppressed, inhibited or reduced in a subject by administering to the subject an effective amount of a composition that promotes an immune suppressive immune response or tolerance as described above.

4. Transplant Rejection

In some embodiments, the disclosed compositions and methods can be used prophylactically or therapeutically to reduce or inhibit graft rejection or graft verse host disease. Transplant rejection occurs when a transplanted organ or tissue is not accepted by the body of the transplant recipient. Typically, rejection occurs because the immune system of the recipient attacks the transplanted organ or tissue. The disclosed methods can be used to promote immune tolerance of the transplant or graft by the receipt by administering to the subject an effective amount of a composition in vivo, or cells modulated by the composition ex vivo.

The transplanted material can be cells, tissues, organs, limbs, digits or a portion of the body, for example the human body. The transplants are typically allogenic or xenogenic. The disclosed compositions are administered to a subject in an effective amount to reduce or inhibit transplant rejection. The compositions can be administered systemically or locally by any acceptable route of administration. In some embodiments, the compositions are administered to a site of transplantation prior to, at the time of, or following transplantation. In one embodiment, compositions are administered to a site of transplantation parenterally, such as by subcutaneous injection.

In other embodiments, the compositions are administered directly to cells, tissue or organ to be transplanted ex vivo. In one embodiment, the transplant material is contacted with the compositions prior to transplantation, after transplantation, or both.

In other embodiments, the compositions are administered to immune tissues or organs, such as lymph nodes or the spleen.

The transplant material can also be treated with enzymes or other materials that remove cell surface proteins, carbohydrates, or lipids that are known or suspected of being involved with immune responses such as transplant rejection.

5. Graft-Versus-Host Disease (GVHD)

The disclosed compositions and methods can be used to treat graft-versus-host disease (GVHD) by administering an effective amount of the composition to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

D. Combination Therapies

In some embodiments, the compositions are administered in further combination with one or more additional therapeutic agents. The agents can be administered in the same or separate pharmaceutical composition from the nanostructure, antigen, adjuvant, or combinations thereof.

In some embodiments, the compositions are administered in combination with a conventional therapeutic agent used for treatment of the disease or condition being treated. Conventional therapeutics agents are known in the art and can be determined by one of skill in the art based on the disease or disorder to be treated. For example, if the disease or condition is cancer, the compositions can be co-administered with a chemotherapeutic drug; or if the disease or condition is a bacterial infection, the compositions can be co-administered with an antibiotic. When administered as a cancer vaccine, the disclosed compositions may be administered in combination with a checkpoint inhibitor (PD1, CTLA4, TIM3, etc.).

E. Treatment Regimens

The disclosed compositions can be administered as a vaccine that includes a first ("prime") and optionally one or more ("boost") administrations. Thus in some embodiments, the composition is administered 2, 3, 4, or more times, for example, 1, 2, 3, 4, 5, 6, 7, 8, 9, 10, 11, 12, 13, 14, or 15 days, weeks, months, or years apart. Dosage regimens or cycles of the compositions and/or additional therapeutic agents can be completely or partially overlapping, or can be sequential.

F. Methods of Determining the Valency and Spatial Organization of Effective Presentation of Immunostimulatory Agent Also disclosed are methods of determining the most preferred valance and spatial organization of antigen presentation on nanostructure to, for example, induce an immune response.

An exemplary method of selecting a nucleic acid nanostructure can include assaying the ability of two or more structurally different antigen-bound nucleic acid nanostructure to induce an immune response, wherein the two or more structurally different nucleic acid nanostructures differ by (i) the structure of the antigen(s); (ii) the copy number of the antigen(s); (iii) spacing of the antigen(s); (iv) location of the antigen(s) on the nanostructure; (v) rigidity/flexibility of the antigen(s); (vi) dimensionality of the antigen(s); (vii) topology of the nanostructure; (viii) ultra-structural organization of the nanostructure; (ix) geometric shape of the nanostructure; or (x) a combination thereof.

For example, in some embodiments, the two or more structurally different nucleic acid nanostructures differ by (ii) and the copy number of antigen on each nanostructure is independently selected from 2 to 60 copies inclusive per nanostructure.

In some embodiment, the two or more structurally different nucleic acid nanostructures differ by (iii) and wherein the inter-antigen distance between adjacent antigens on each nanostructure is independently selected from between 3 nm to 80 nm inclusive.

In some embodiments, the two or more structurally different nucleic acid nanostructures differ by (ix), and the geometric shape of each nanostructure is independently selected from helix bundles, cuboidal structures, icosahedral structures, tetrahedral structures, cuboctahedral structures, octahedral structures, decahedral structures, and hexahedral structures.

Such methods can also include additional steps such as preparing the two or more nucleic acid nanostructure having a desired geometric shape, where the nanostructure is designed to allow for control of the relative position and/or stoichiometry of the antigen; covalently or non-covalently conjugating antigen to the surface of the nanostructure, wherein each of the two or more nanostructures vary by one or more of the structure of the antigen(s), the copy number of the antigen(s), spacing of the antigen(s), location of the antigen(s) on the nanostructure, rigidity/flexibility of the antigen(s), dimensionality of the antigen(s), topology of the nanostructure, ultra-structural organization of the nanostructure, and/or geometric shape of the nanostructure.

In some embodiments, one or more antigen-bound nanostructures having the highest or most desirable immune response is selected for use as an antigen in method of immunization or treatment such as those disclosed herein.

Any one or more of the factors (i)-(ix) can be varied systematically or non-systematically. In some embodiments, 2, 5, 10, 25, 50, 100, or more different antigen-bound nanostructures are tested.

In some embodiments, where two or more nanostructures induce the same or similar immune responses, the nanostructure that is the simplest to make, the nanostructure that is the least expensive to make, or a combination thereof is selected for use as an antigen in a method of immunization or treatment such as those disclosed herein.

The disclosed compositions and methods can be further understood through the following numbered paragraphs.

1. A nucleic acid nanostructure including a defined geometric shape and two or more copies of an antigen bound to the surface of the nanostructure,
   wherein the number of copies of the antigen, the distance between adjacent copies of the antigen, the location of the antigen on the nanostructure, the rigidity/flexibility of the antigen, the dimensionality of the antigen, the topology of the nanostructure, the ultra-structural organization of the nanostructure, the geometric shape of the nanostructure, or a combination thereof improves an immune response induced by the antigen relative to a control nucleic acid nanostructure including at least one copy of the same antigen.

2. The nanostructure of paragraph 1, wherein the number of copies of the antigen is 2 to 100, or 3 to 75, or 4 to 60, or 5 to 50, or 10 to 50, or 5 to 25, or 5 to 10 inclusive.

3. The nanostructure of paragraph 2, wherein the number of copies of the antigen is 5, 6, 7, 8, 9, or 10.

4. The nanostructure of any one of paragraphs 1-3, wherein the distance between adjacent copies of the antigen is 1 nm to 150 nm, or 10 nm to 80 nm, or 15 nm to 50 nm, or 25 nm to 30 nm inclusive.

5. The nanostructure of any one of paragraphs 1-4, wherein the geometric shape is selected from the group including a helix bundle, cuboidal structure, icosahedral structure, tetrahedral structure, cuboctahedral structure, octahedral structure, and hexahedral structure.

6. The nanostructure of any one of paragraphs 1-4, wherein the geometric shape is a polyhedron or a 6-helix bundle.

7. The nanostructure of paragraph 6, wherein the geometric shape is a polyhedron, and wherein the polyhedron is an icosahedron.

8. The nanostructure of any one of paragraphs 1-7, wherein the copies of the antigen are covalently or non-covalently bound to the nanostructure.

9. The nanostructure of any one of paragraphs 1-8, wherein the antigen is indirectly or directly bound to the nanostructure via outwardly facing nucleic acid overhangs extending from the 3' or 5' ends of selected staple strands of the nanostructure.

10. The nanostructure of any one of paragraphs 1-9, wherein the nucleic acid is DNA.

11. The nanostructure of paragraph 10, wherein the nucleic acid overhangs hybridize to the complementary target RNA, DNA or PNA covalently linked to the antigen.

12. The nanostructure of paragraph 11, wherein the covalent linkage is formed by maleimide-thiol coupling.

13. The nanostructure of any one of paragraphs 1-12, including two or more structurally different antigens.

14. The nanostructure of paragraphs 1-13, wherein the antigen(s) is associated with one or more diseases or conditions selected from infectious diseases, autoimmune diseases, and cancer.

15. The nanostructure of any one of paragraphs 1-14, wherein the antigen is an HIV immunogen.

16. The nanostructure of any one of paragraphs 1-15, wherein the antigen binds to a broadly neutralizing antibody.

17. The nanostructure of paragraph 16, wherein the antigen is an HIV gp120 epitope.

18. The nanostructure of paragraph 17, wherein the epitope encompasses the CD4 binding site of gp120.

19. The nanostructure of paragraphs 1-18, wherein the antigen is selected from eOD-GT6, eOD-GT8, or variants thereof.

20. The nanostructure of any one of paragraphs 1-19 further including one or more moieties incorporated in and/or linked to the nanostructure.

21. The nanostructure of paragraph 20, wherein one or more of the moieties is an adjuvant.

22. The nanostructure of paragraph 20 or 21, wherein one or more of the moieties is a targeting molecule.

23. The nanostructure of any one of paragraphs 20-22, wherein one or more of the moieties is a therapeutic agent.

24. The nanostructure of any one of paragraphs 1-23, wherein the nanostructure is coated with a coating agent.

25. The nanostructure of paragraph 24, wherein the coating agent is a naturally occurring or synthetic cationic oligomer or polymer or cooligomer, optionally including or including PEG moieties.

26. The nanostructure of paragraphs 24 or 25 wherein the coating agent includes or consists of (a) 10 lysine units optionally conjugated terminally to a linear PEG moiety, optionally wherein the PEG has a molecular weight of approximately 5000 Da; (b) poly(2-dimethylaminoethyl methacrylate (PDMAEMA) or a PEG copolymer thereof optionally having a molecular weight range between 5000 Da to 20000 Da; (c) linear polyethyleneimine (PEI), optionally, in a molecular weight range between 5000 Da and 10000 Da; (iv) chitosan optionally a molecular weight range between 4000 Da and 6000 Da optionally with deacetylation of more than 90%.

27. The nanostructure of paragraphs 24 or 25, wherein the coating agent includes or consists of a minor groove binder.

28. The nanostructure of paragraph 27, wherein the minor groove binder increases stabilization, optionally wherein the stabilization includes protecting the protection for endonuclease.

29. The nanostructure of paragraphs 27 and 28, wherein the minor groove binder is selected from bisamidines, polyamides, bisbenzimidazoles and combinations thereof.

30. The nanostructure of any one of paragraphs 1-29, wherein the nanostructure is an icosahedron including 5 to 50 copies of the antigen, and wherein the copies of the antigen are spaced 10 nm to 40 nm inclusive apart.

31. The nanostructure of any one of paragraphs 1-29, wherein the nanostructure is an a pentagonal bipryamidal structure including 10 to 40 copies of the antigen, and wherein the copies of the antigen are spaced 10 nm to 40 nm inclusive apart.

32. A pharmaceutical composition including the nucleic acid nanostructure of any one of paragraphs 1-31 and a pharmaceutically acceptable carrier, diluent, preservative, excipient, or combination thereof.

33. The pharmaceutical composition of paragraph 32, further including a coating agent.

34. The pharmaceutical composition of paragraph 33, wherein the coating agent is the same or different from the coating agent of any one of paragraphs 26-29.

35. The pharmaceutical composition of any one of paragraphs 32-34, wherein the nucleic acid nanostructure is present in an effective amount to induce an immune response in a subject in need thereof, with or without the aid of an adjuvant.

36. The pharmaceutical composition of paragraph 35, further including an adjuvant in an effective amount to enhance the immune response relative to administration of the nucleic acid nanostructure alone.

37. A method of inducing an immune response in a subject including administering to the subject an effective amount of the nucleic acid nanostructure of any one of paragraphs 1-31 or the pharmaceutical composition of any one of paragraphs 32-36 alone or in combination with an adjuvant.

38. A method of vaccinating or otherwise inducing protective immunity against an infectious agent, disease, or condition including administering to the subject an effective amount of the nucleic acid nanostructure of any one of paragraphs 1-31 or the pharmaceutical composition of any one of paragraphs 32-36 alone or in combination with an adjuvant.

39. A method of treating a subject having or at risk of having a disease or condition including administering to the subject an effective amount of the nucleic acid nanostructure of any one of paragraphs 1-31 or the pharmaceutical composition of any one of paragraphs 32-36 alone or in combination with an adjuvant.

40. A method of inducing the production of neutralizing antibodies or inhibitory antibodies in a subject including administering to the subject an effective amount of the nucleic acid nanostructure of any one of paragraphs 1-31 or the pharmaceutical composition of any one of paragraphs 32-36 alone or in combination with an adjuvant.

41. The method of any one of paragraphs 37-38, wherein the subject is a human.

42. A method of selecting a nucleic acid nanostructure including assaying the ability of two or more structurally different antigen-bound nucleic acid nanostructure to induce an immune response, wherein the two or more structurally different nucleic acid nanostructures differ by (i) the structure of the antigen(s);

(ii) the copy number of the antigen(s);

(iii) spacing of the antigen(s);

(iv) location of the antigen(s) on the nanostructure;

(v) rigidity/flexibility of the antigen(s);

(vi) dimensionality of the antigen(s);

(vii) topology of the nanostructure;

(viii) ultra-structural organization of the nanostructure;

(ix) geometric shape of the nanostructure; or (x) a combination thereof.

43. The method of paragraph 42, wherein the two or more structurally different nucleic acid nanostructures differ by (ix), and wherein the geometric shape of each nanostructure is independently selected from helix bundles, cuboidal structures, icosahedral structures, tetrahedral structures, cuboctahedral structures, octahedral structures, and hexahedral structures.

44. The method of paragraphs 32 or 43, wherein the two or more structurally different nucleic acid nanostructures differ by (ii) and wherein the copy number of antigen on each nanostructure is independently selected from 2 to 60 copies per nanostructure.

45. The method of any one of paragraphs 42-44, wherein the two or more structurally different nucleic acid nanostructures differ by (iii) and wherein the inter-antigen distance between adjacent antigens on each nanostructure is independently selected from 3 nm to 80 nm.

46. A nucleic acid nanostructure including a defined geometric shape and one or more copies of an antigen that can induce an immune response against human immunodeficiency virus (HIV).

47. The nanostructure of paragraph 46, wherein the antigen binds to a broadly neutralizing antibody.

48. The nanostructure of paragraph 47, wherein the antigen is an HIV gp120 epitope.

49. The nanostructure of paragraph 48, wherein the epitope encompasses the CD4 binding site of gp120.

50. The nanostructure of any of paragraphs 46-49, wherein the antigen is selected from eOD-GT6, eOD-GT8, or variants thereof.

51. A nucleic acid nanostructure including a defined geometric shape and one or more copies of an antigen derived from a H-2K$^k$ MHC class I molecule.

52. The nucleic acid nanostructure of paragraph 51, wherein the antigen is a p31 peptide or a p5 peptide.

53. The nanostructure of any one of paragraphs 46-52 including 2 to 50 or 10 to 50, or 10 to 40, or 2 to 20 or 5 to 10 copies of the antigen inclusive.

54. The nanostructure of paragraph 53 including 5 to 10 copies of the antigen inclusive.

55. The nanostructure of paragraphs 53 or 54 wherein adjacent antigens are separated by an inter-antigen distance of 5 nm to 80 nm inclusive.

56. The nanostructure of paragraph 55, wherein adjacent antigens are separated by an inter-antigen distance of at least 28 nm.

57. The nanostructure of any one of paragraphs 46-56, wherein the geometric shape is a helix bundle, cuboidal structure, icosahedral structure, decahedron structure, tetrahedral structure, cuboctahedral structure, octahedral structure, or hexahedral structure.

58. The nanostructure of any one of paragraphs 46-57, wherein the geometric shape is a polyhedron or a 6-helix bundle.

59. The nanostructure of paragraph 58, wherein the geometric shape is a polyhedron, and wherein the polyhedron is an icosahedron.

60. The nanostructure of any one of paragraphs 46-57, wherein the genometric shape is a pentagonal bipyramid.

61. An immunogen for inducing an immune response against HIV including icosahedron-shaped DNA nanostructure including 5-50 copies or 10-50 or 5-10 copies of eOD-GT8 antigen, wherein each copy of the antigen is linked to the nanostructure by a single stranded peptide nucleic acid conjugated directly to the antigen and hybridized to a complementary sequence at the 3' single stranded overhang of a staple strand of the nanostructure, and wherein each copy of the antigen is spaced from the other copies of antigen by at least 5 nm, 10 nm, 15 nm, 20 nm, 25 nm, 28 nm, or 30 nm and optionally not more than 100 nm.

62. An immunogen for inducing an immune response again HIV including pentagonal bipyramid-shaped DNA nanostructure including 10-50 copies or 10-40 copies inclusive of eOD-GT8 antigen, wherein each copy of the antigen is linked to the nanostructure by a single stranded peptide nucleic acid conjugated directly to the antigen and hybridized to a complementary sequence at the 3' single stranded overhang of a staple strand of the nanostructure, and wherein each copy of the antigen is spaced from the other copies of antigen by at least 5 nm, 10 nm, 15 nm, 20 nm, 25 nm, 28 nm, or 30 nm and optionally not more than 100 nm.

63. The nanostructure of any one of paragraphs 46-60 or the immunogen of paragraphs 61 or 62 wherein the nanostructure or immunogen is coated with a coating agent.

64. The nanostructure or immunogen of paragraph 63, wherein the coating agent is a naturally occurring or synthetic cationic oligomer or polymer or cooligomer, optionally including or including PEG moieties.

65. The nanostructure or immunogen of paragraphs 63 or 64, wherein the coating agent includes or consists of (a) 10 lysine units optionally conjugated terminally to a linear PEG moiety, optionally wherein the PEG has a molecular weight of approximately 5000 Da; (b) poly (2-dimethylaminoethyl methacrylate (PDMAEMA) or a PEG copolymer thereof optionally having a molecular weight range between 5000 Da to 20000 Da; (c) linear polyethyleneimine (PEI), optionally, in a molecular weight range between 5000 Da and 10000 Da; (iv) chitosan optionally a molecular weight range between 4000 Da and 6000 Da optionally with deacetylation of more than 90%.

66. The nanostructure or immunogen of paragraphs 63 or 64, wherein the coating agent includes or consists of a minor groove binder.

67. The nanostructure or immunogen of paragraph 66, wherein the minor groove binder increases stabilization, optionally wherein the stabilization includes protecting the protection for endonuclease.

68. The nanostructure or immunogen of paragraphs 66 and 67, wherein the minor groove binder is selected from bisamidines, polyamides, bisbenzimidazoles and combinations thereof.

69. A pharmaceutical composition including the nanostructure or immunogen of any one of paragraphs 46-68, a pharmaceutically acceptable carrier, and optionally an adjuvant.

70. The pharmaceutical composition of paragraph 69 further including a coating agent.

71. The pharmaceutical composition of paragraph 70, wherein the coating agent is coating agent of any one of paragraphs 63-68.

72. A method of treating a subject in need thereof including administering to the subject an effective amount of the pharmaceutical composition of any one of paragraphs 69-71 to induce an immune response in the subject.

73. The method of paragraph 72, wherein the subject has HIV, the antigen is eOD-GT8, and the immune response is again HIV.

74. A method of vaccinating a subject against HIV including administering the subject an effective amount of the pharmaceutical composition of any one of paragraphs 69-71 to induce an immune response against eOD-GT8.

75. A method of inducing an immune response in a subject including administering to the subject an effective amount of the pharmaceutical composition of paragraph 32.

76. The method of paragraph 75, further including administering to the subject an adjuvant.

77. A nucleic acid nanostructure including
(i) nucleic acids folded into a defined three-dimensional geometric shape; and
(ii) one, two, or more copies of an immunostimulatory agent,
wherein the number of copies of the immunostimulatory agent, the distance between adjacent copies of the immunostimulatory agent, the location of the immunostimulatory agent on the nanostructure, the rigidity/flexibility of the immunostimulatory agent, the dimensionality of the immunostimulatory agent, the topology of the nanostructure, the ultra-structural organization of the nanostructure, the geometric shape of the nanostructure, or a combination thereof improves an immune response induced by the immunostimulatory agent relative to a control having an equal amount of the same immunostimulatory agent, wherein the control includes the same nucleic acid nanostructure including a single copy of the immunostimulatory agent.

78. The nanostructure of paragraph 77, wherein the nanostructure includes a single stranded nucleic acid scaffold sequence and one or more single stranded nucleic acid staple strands that hybridize to the scaffold sequence to form the three-dimensional nanostructure having a defined geometric shape.

79. The nanostructure of paragraph 77 or 78, wherein the number of copies of the immunostimulatory agent is 2 to 1,000, or 2 to 100, or 3 to 75, or 4 to 60, or 5 to 50, or 10 to 50, or 5 to 25, or 5 to 10, inclusive.

80. The nanostructure of any one of paragraphs 77-79, wherein the number of copies of the immunostimulatory agent is 2, 3, 4, 5, 6, 7, 8, 9, or 10.

81. The nanostructure of any one of paragraphs 77-80, wherein the distance between adjacent copies of the immunostimulatory agent is from 1 to 100 Angstroms, or 1 to 40 Angstroms, or from 1 nm to 150 nm, or 10 nm to 80 nm, or 15 nm to 50 nm, or 25 nm to 30 nm, inclusive.

82. The nanostructure of any one of paragraphs 77-81, wherein the geometric shape is selected from the group including a helix bundle, cuboidal structure, icosahedral structure, tetrahedral structure, cuboctahedral structure, octahedral structure, and hexahedral structure.

83. The nanostructure of any one of paragraphs 77-82, wherein the geometric shape is a polyhedron or a 6-helix bundle.

84. The nanostructure of any one of paragraphs 77-83, wherein the geometric shape is a polyhedron, and wherein the polyhedron is an icosahedron.

85. The nanostructure of any one of paragraphs 77-84, wherein the copies of the immunostimulatory agent are covalently or non-covalently bound to the nanostructure.

86. The nanostructure of any one of paragraphs 77-85, wherein the copies of the immunostimulatory agent are indirectly or directly associated with the nanostructure via nucleic acid overhangs extending from the 3' or 5' ends of one or more selected staple strands of the nanostructure.

87. The nanostructure of paragraph 86, wherein the nucleic acid overhangs hybridize to complementary target RNA, DNA or PNA covalently linked to, or incorporating the immunostimulatory agent.

88. The nanostructure of any one of paragraphs 85-87, wherein the covalent linkage is formed by maleimidethiol coupling.

89. The nanostructure of any one of paragraphs 77-88, including two or more structurally different immunostimulatory agent.

90. The nanostructure of any one of paragraphs 77-89, wherein one or more of the immunostimulatory agent(s) is selected from an antigen, an adjuvant, a TLR agonist and a cGAS ligand.

91. The nanostructure of paragraph 90, wherein the TLR agonist is selected from the group including BCG; Poly I:C, Poly ICLC; MPL; LPS; Imiquimod; 852A; Resiquimod; VTX-2337 and an immunostimulatory CpG motif.

92. The nanostructure of any one of paragraphs 77-90, wherein the immunostimulatory agent(s) is a TLR9 agonist.

93. The nanostructure of any one of paragraphs 78-90, wherein the immunostimulatory agent includes an immunostimulatory CpG motif that is capable of binding to a TLR.

94. The nanostructure of paragraph 93, wherein the immunostimulatory CpG motif is located within a single stranded nucleic acid overhang associated with a staple strand within the nanostructure.

95. The nanostructure of paragraph 94, wherein the nanostructure includes a total of from 1 to 1,000 CpG motifs, inclusive.

96. The nanostructure of paragraph 94 or 95, including from 2 to 100, from 2 to 50, from 1 to 30, from 1 to 20, from 1 to 10 immunostimulatory CpG motifs, inclusive, or less than 10 immunostimulatory CpG motifs.

97. The nanostructure of any one of paragraphs 94 to 96, including 10, or more than 10 immunostimulatory CpG motifs.

98. The nanostructure of any one of paragraphs 94 to 97, including between 1 and 10 immunostimulatory CpG motifs within at least one staple strand.

99. The nanostructure of any one of paragraphs 94 to 98, including 1, 2 or 3 immunostimulatory CpG motifs within at least one staple strand.

100. The nanostructure of any one of paragraphs 94-99, wherein the two or more copies of immunostimulatory CpG motifs are separated by a distance of at least 40 angstroms.

101. The nanostructure of any one of paragraphs 77-100, further including a targeting molecule.

102. The nanostructure of paragraph 101, wherein the targeting molecule directs the nanostructure to the cell cytosol.

103. The nanostructure of any one of paragraphs 77-102, further including a therapeutic agent.

104. The nanostructure of any one of paragraphs 77-103, wherein the nanostructure is coated with a coating agent.

105. The nanostructure of paragraph 104, wherein the coating agent is a naturally occurring or synthetic cationic oligomer or polymer or co-oligomer, optionally including or including PEG moieties.

106. The nanostructure of any one of paragraphs 104 or 105, wherein the coating agent includes or consists of (a) 10 lysine units optionally conjugated terminally to a linear PEG moiety, optionally wherein the PEG has a molecular weight of approximately 5000 Da; (b) poly (2-dimethylaminoethyl methacrylate (PDMAEMA) or a PEG copolymer thereof optionally having a molecular weight range between 5000 Da to 20000 Da; (c) linear polyethyleneimine (PEI), optionally, in a molecular weight range between 5000 Da and 10000 Da; (d) chitosan optionally having a molecular weight range between 4000 Da and 6000 Da optionally with deacetylation of more than 90%.

107. The nanostructure of paragraph 104, wherein the coating agent includes or consists of a minor groove binder.

108. The nanostructure of paragraph 107, wherein the minor groove binder increases stabilization, optionally wherein the stabilization includes protecting the protection for endonuclease.

109. A nucleic acid nanostructure including (i) a pentagonal bipyramid with 84 base pairs per edge, or an icosahedron with 42 base pairs per edge; and (ii) two or more copies of single stranded DNA including an immunostimulatory CpG motif bound to the surface of the nanostructure, wherein the number of copies of the immunostimulatory CpG motif, the distance between adjacent copies of the immunostimulatory CpG motifs, the location of the immunostimulatory CpG motifs on the nanostructure, the rigidity/flexibility of the single stranded DNA including a immunostimulatory CpG motif, the dimensionality of the immunostimulatory CpG motifs, the topology of the nanostructure, the ultra-structural organization of the nanostructure, the geometric shape of the nanostructure, or a combination thereof improves an immune response induced by the immunostimulatory CpG motifs relative to a control, wherein the control includes the same nucleic acid nanostructure including a single copy of the immunostimulatory CpG, wherein the nanostructure includes a single stranded nucleic acid scaffold sequence and one or more single stranded nucleic acid staple strands that hybridize to the scaffold sequence to form the three dimensional nanostructure having a defined geometric shape, and wherein the two or more copies of single stranded DNA including an immunostimulatory CpG motif are located within one or more single stranded nucleic acid overhang extending from the 3' or 5' end of one or more selected staple strand of the nanostructure.

110. The nanostructure of any one of paragraph 109, including at least 10 immunostimulatory CpG motifs.

111. The nanostructure of any one of paragraphs 84-110, wherein one or more of the single stranded nucleic acid overhang extending from the 3' or 5' end of one or more selected staple strands of the nanostructure face inwards towards the center of the nanostructure.

112. The nanostructure of any one of paragraphs 84-111, wherein one or more of the single stranded nucleic acid overhang extending from the 3' or 5' end of one or more selected staple strands of the nanostructure face outwards away from the nanostructure.

113. The nanostructure of any one of paragraphs 77-112, including a nucleic acid scaffold sequence of SEQ ID NO:5.

114. The nanostructure of any one of paragraphs 84-113, including a nucleic staple sequence from any one of Tables 4-14.

115. The nanostructure of paragraph 113, wherein the nanostructure includes a pentagonal bipyramid with 84 base pairs per edge, including one or more staple sequence from any one or more of Tables 5, 6, or 8.

116. The nanostructure of paragraph 115, including 20, 30, or 40 immunostimulatory CpG motifs.

117. The nanostructure of paragraph 113, wherein the nanostructure includes a icosahedron with 42 base pairs per edge, including one or more staple sequence from any one or more of Tables 10, 11, or 13.

118. The nanostructure of paragraph 117, including 10, 20, or 30 immunostimulatory CpG motifs.

119. A liposomal composition, including the nanostructure of any one of paragraphs 1-31, wherein the nanostructure is encapsulated within the liposome.

120. A liposomal composition, including the nanostructure of any one of paragraphs 77-118, wherein the nanostructure is encapsulated within the liposome.

121. A pharmaceutical composition including the nucleic acid nanostructure of any one of paragraphs 77-118, or the liposomal composition of paragraph 83 in an effective amount to induce an immune response in a subject in need thereof, with or without the aid of an adjuvant and/or antigen, and a pharmaceutically acceptable carrier, diluent, preservative, excipient, or combination thereof.

122. The pharmaceutical composition of paragraph 121, further including an adjuvant and/or antigen.

123. A method of inducing or enhancing an immune response in a subject including administering to the subject an effective amount of the pharmaceutical composition of paragraph 121 or 122.

124. A method of inducing a TLR9 response in a subject, including administering to the subject an effective amount of the pharmaceutical composition paragraph 121 or 122, or a pharmaceutical composition including a effective amount of nucleic acid nanoparticle include one or more CpG motifs, a double stranded nucleic acid structure optionally but preferable including double stranded edges and/or corner, or a combination thereof.

125. The method of paragraph 124, wherein the method does not include administering an antigen to the subject.

126. A nucleic acid nanostructure including a defined geometric shape and one, two or more copies of an adjuvant bound to the surface of the nanostructure, wherein the number of copies of the adjuvant, the distance between adjacent copies of the adjuvant, the location of the adjuvant on the nanostructure, the rigidity/flexibility of the adjuvant, the dimensionality of the adjuvant, the topology of the nanostructure, the ultra-structural organization of the nanostructure, the geometric shape of the nanostructure, or a combination thereof improves an immune response induced by the adjuvant relative to a control nucleic acid nanostructure including at least one copy of the same adjuvant.

127. The nanostructure of paragraph 126, wherein the number of copies of the adjuvant is 2 to 100, or 3 to 75, or 4 to 60, or 5 to 50, or 10 to 50, or 5 to 25, or 5 to 10 inclusive.

128. The nanostructure of paragraph 127, wherein the number of copies of the adjuvant is 5, 6, 7, 8, 9, or 10.

129. The nanostructure of paragraph 126, wherein the distance between adjacent copies of the adjuvant is 1 nm to 150 nm, or 10 nm to 80 nm, or 15 nm to 50 nm, or 25 nm to 30 nm inclusive.

130. The nanostructure of paragraph 126, wherein the geometric shape is selected from the group including a helix bundle, cuboidal structure, icosahedral structure, tetrahedral structure, cuboctahedral structure, octahedral structure, and hexahedral structure.

131. The nanostructure of paragraph 126, wherein the geometric shape is a polyhedron or a 6-helix bundle.

132. The nanostructure of paragraph 126, wherein the geometric shape is a polyhedron, and wherein the polyhedron is an icosahedron.

133. The nanostructure of paragraph 126, wherein the copies of the adjuvant are covalently or non-covalently bound to the nanostructure.

134. The nanostructure of paragraph 126, wherein the adjuvant is indirectly or directly bound to the nanostructure via outwardly facing nucleic acid overhangs extending from the 3' or 5' ends of selected staple strands of the nanostructure.

135. The nanostructure of paragraph 126, wherein the nucleic acid is DNA.

136. The nanostructure of paragraph 134, wherein the nucleic acid overhangs hybridize to the complementary target RNA, DNA or PNA covalently linked to the adjuvant.

137. The nanostructure of paragraph 135, wherein the covalent linkage is formed by maleimide-thiol coupling.

138. The nanostructure of paragraph 126, including two or more structurally different adjuvants.

139. The nanostructure of paragraph 126, wherein the adjuvant(s) is a TLR ligand.

140. The nanostructure of paragraph 139, wherein the adjuvant is a TLR9 ligand.

141. The nanostructure of paragraph 140, wherein the adjuvant is an oligonucleotide.

142. The nanostructure of paragraph 141, wherein the oligonucleotide includes CpG.

143. The nanostructure of paragraph 142, wherein the oligonucleotide is synthetic.

144. The nanostructure of paragraph 143, wherein oligonucleotide or a segment thereof hybridizes to an overhang of a stable strand of the nanostructure.

145. The nanostructure of paragraph 126, further including one or more moieties incorporated in and/or linked to the nanostructure.

146. The nanostructure of paragraph 145, wherein one or more of the moieties is an antigen.

147. The nanostructure of paragraph 145, wherein one or more of the moieties is a targeting molecule.

148. The nanostructure of paragraph 145, wherein one or more of the moieties is a therapeutic agent.

149. The nanostructure of paragraph 126, wherein the nanostructure is coated with a coating agent.

150. The nanostructure of paragraph 149, wherein the coating agent is a naturally occurring or synthetic cationic oligomer or polymer or cooligomer, optionally including or including PEG moieties.

151. The nanostructure of paragraph 149 wherein the coating agent includes or consists of (a) 10 lysine units optionally conjugated terminally to a linear PEG moiety, optionally wherein the PEG has a molecular weight of approximately 5000 Da; (b) poly(2-dimethylamino-ethyl methacrylate (PDMAEMA) or a PEG copolymer thereof optionally having a molecular weight range between 5000 Da to 20000 Da; (c) linear polyethyl-eneimine (PEI), optionally, in a molecular weight range between 5000 Da and 10000 Da; (iv) chitosan optionally a molecular weight range between 4000 Da and 6000 Da optionally with deacetylation of more than 90%.

152. The nanostructure of paragraph 149, wherein the coating agent includes or consists of a minor groove binder.

153. The nanostructure of paragraph 152, wherein the minor groove binder increases stabilization, optionally wherein the stabilization includes protecting the protection for endonuclease.

154. The nanostructure of paragraph 153, wherein the minor groove binder is selected from bisamidines, polyamides, bisbenzimidazoles and combinations thereof.

155. The nanostructure of paragraph 126, wherein the nanostructure is an icosahedron including 5 to 50 copies of the adjuvant, and wherein the copies of the adjuvant are spaced 10 nm to 40 nm inclusive apart.

156. The nanostructure of paragraph 126, wherein the nanostructure is a pentagonal bipyramidal structure including 10 to 40 copies of the adjuvant, and wherein the copies of the adjuvant are spaced 10 nm to 40 nm inclusive apart.

157. A pharmaceutical composition including the nucleic acid nanostructure of paragraph 126 in an effective amount to induce an immune response in a subject in need thereof, with or without the aid of an antigen, and a pharmaceutically acceptable carrier, diluent, preservative, excipient, or combination thereof.

158. The pharmaceutical composition of paragraph 157, further including an adjuvant.

159. A method of inducing an immune response in a subject including administering to the subject an effective amount of the pharmaceutical composition of paragraph 157.

160. The method of paragraph 159, further including administering the subject an antigen.

161. A method of selecting a nucleic acid nanostructure including assaying the ability of two or more structurally different adjuvant-bound nucleic acid nanostructure to induce an immune response, wherein the two or more structurally different nucleic acid nanostructures differ by (i) the structure of the adjuvant(s);

(ii) the copy number of the adjuvant(s);

(iii) spacing of the adjuvant(s);

(iv) location of the adjuvant(s) on the nanostructure;

(v) rigidity/flexibility of the adjuvant(s);

(vi) dimensionality of the adjuvant(s);

(vii) topology of the nanostructure;

(viii) ultra-structural organization of the nanostructure;

(ix) geometric shape of the nanostructure; or (x) a combination thereof.

162. The method of paragraph 161, wherein the two or more structurally different nucleic acid nanostructures differ by (ix), and wherein the geometric shape of each nanostructure is independently selected from helix bundles, cuboidal structures, icosahedral structures, tetrahedral structures, cuboctahedral structures, octahedral structures, and hexahedral structures.

163. The method of paragraph 162, wherein the two or more structurally different nucleic acid nanostructures differ by (ii) and wherein the copy number of adjuvant on each nanostructure is independently selected from 2 to 60 copies per nanostructure.

164. The method of paragraph 162, wherein the two or more structurally different nucleic acid nanostructures differ by (iii) and wherein the inter-adjuvant distance between adjacent adjuvants on each nanostructure is independently selected from 3 nm to 80 nm.

165. A method of inducing an innate immune response in a subject, including administering to the subject an effective amount of a nucleic acid nanoparticle including one or more immunostimulatory agents.

166. The method of paragraphs 165 wherein the immunostimulatory agent include one or more CpG motifs, a double stranded nucleic acid structure suitable for stimulating an innate immune response optionally but preferable including double stranded edges and/or corner, or a combination thereof.

167. The method of paragraphs 165 and 166, wherein the nanostructure includes a wireframe structure and the immunostimulatory agent forms part of the wireframe sequence (e.g., scaffold alone or in combination with staples).

168. The method of paragraph 165 wherein the nanostructure is free from immunostimulatory agents extending from the wireframe by hybridization to staple strand overhangs.

169. The method of paragraph 165, wherein the nanostructure includes immunostimulatory agent(s) extending from the wireframe by hybridization to staple strand overhangs, optionally wherein the immunostimulatory agent is single or double stranded oligonucleotide(s), optionally, but preferably including one or more CpG motifs.

170. The method of any one of paragraphs 165-169, wherein the innate immune response includes TLR9 activation, a cGAS-STING-dependent immune response, or a combination thereof.

171. The method of paragraph 170, including TLR9 activation wherein the nanostructure includes immunostimulatory agent(s) extending from the wireframe by hybridization to staple strand overhangs, optionally wherein the immunostimulatory agent is single or double stranded oligonucleotide(s), optionally, but preferably including one or more CpG motifs.

172. The method of paragraph 170, including a cGAS-STING-dependent immune response, wherein the nanostructure is free from immunostimulatory agent(s) extending from the wireframe by hybridization to staple strand overhangs.

173. The method of paragraph 172, wherein the immunostimulatory agent forms part of the wireframe sequence (e.g., scaffold alone or in combination with staples), optionally wherein the immunostimulatory agent is single or double stranded oligonucleotide(s), optionally, but preferably including one or more CpG motifs.

174. The method of any one of paragraphs 165-173, wherein the method is free from administration of antigen to the subject.

U.S. Ser. No. 62/796,472, U.S. Ser. No. 16/752,394, published as U.S. Published Application No. 2020/0237903, and PCT/US2020/014957, published as WO 2020/154595 are each specifically incorporated by reference herein in their entireties.

EXAMPLES

Example 1: DNA Nanoparticles can Efficiently Organize and Present Antigens

Figure 1A:
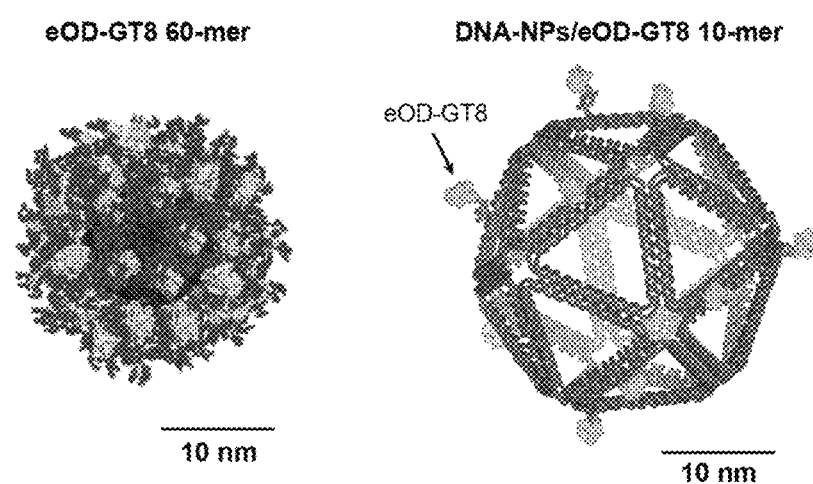
FIG. 1A is a schematic showing an eOD-GT8 60-mer nanoparticle (left) and an icosahedral DNA-NP (right) designed to assemble the eOD-GT8 antigen in a controlled manner.
Figure 1B:
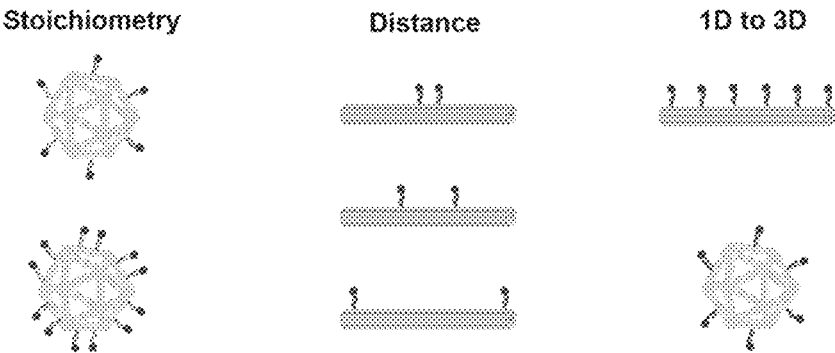
FIG. 1B is a schematic illustrating how an icosahedron and 6-helix bundle structures were used to explore the stoichiometry, inter-antigen distance, and dimensionality of eOD-GT8 antigen presentation.
Figure 1C:
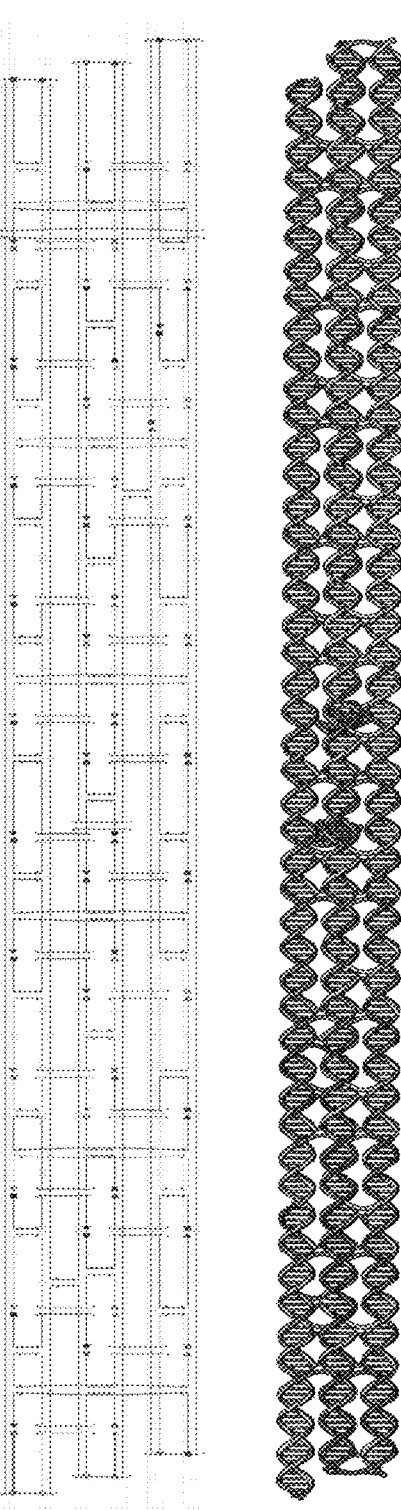
FIG. 1C is a Cadnano design illustration of a DNA 6 helix bundle (6HB) structure side-by-side with a corresponding model generated with CanDo.

The ultra-structural parameters of displayed antigen that drive efficient B cell responses were evaluated in a DNA nanostructure model. Previously, eOD-GT8 and eOD-GT6 displayed in a self-assembled 60-mer protein nanoparticle elicited robust B cell activation both in vitro against VRCO1+B cells and in engineered mouse models (Jardine, et al., *Science*, 349(6244):156-161 (2015), Jardine, et al., *Science*, 340(6133):711-6 (2013), Jardine, et al., *Science*, 351(6280):1458-63 (2016)). Here, in order to determine which features (namely the stoichiometry, inter-antigen distances, substrate flexibility, and ultra-structural organization) of eOD-GT8 60-mer drive efficient B cell responses, a viral-like icosahedral DNA nanoparticle (DNA-NP; Veneziano, et al., *Science*, 352(6293):1534 (2016)) of size and shape similar to the eOD-GT8 60-mer was designed and assembled (FIG. 1A). eOD-GT8 was displayed on engineered DNA origami nanoparticles (Venziano, et al., *Science*, 352(6293):1534 (2016))), which allow for site specific and stoichiometric control over antigen conjugation through base pairing between engineered single stranded DNA (ssDNA) overhangs on the DNA nanoparticle and complementary peptide nucleic acid (PNA) strands site-specifically conjugated to eOD monomers. Using icosahedral DNA-NPs as well as rigid 6-helical DNA rods (6HB) (FIG. 1C), flexible ssDNA, and polyethylene glycol (PEG) polymer templates, the number of eOD-GT8 antigens per particle, the distance between these antigens, the topology or dimensionality of antigen presentation, and the flexibility of the scaffold used for presentation of the antigens were varied (FIG. 1B).

Methods and Materials

Chemicals and Kits

Magnesium chloride, TRIS acetate EDTA (TAE) buffer, TRIS-base, sodium chloride, Phosphate Buffer Saline, and Amicon ultra 0.5 centrifugal filter were provided by Sigma-Aldrich. Nuclease free water was provided by Integrated DNA Technologies (IDT). The DNTPs mix, the DNA ladder (Quick-Load® Purple 2-Log DNA ladder 0.1-10 kb) were provided by New England Biolabs (NEB), The polymerase enzyme (Accustart Taq DNA polymerase HiFi) was provided by Quanta Biosciences. Low melt agarose was purchased from IBI Scientific and agarose by Seakem. G-capsule for electroelution was provided by G-Biosciences and Freeze 'N Squeeze DNA gel extraction columns by Bio-rad. The Zymoclean Gel DNA recovery kit was purchased from Zymo Research. The SybrSafe DNA staining reagent was provided by ThermoFisher.

Oligonucleotides and DNA Templates

All oligonucleotides used for asymmetric PCR (aPCR) amplification of template and for folding of the various DNA nanostructures were purchased from IDT. The circular plasmid DNA scaffold M13mp18 used for amplification of the short scaffold with aPCR was provided by NEB (#N4040S).

Antigens and Cell Lines

The eOD antigen with an N-terminal cysteine was produced in HEK cells, and purified by affinity chromatography using a Nickel affinity column. The protein was then further purified by size exclusion chromatography using a Superdex 75 10/300 column (GE Healthcare). Ramos B cells expressing VRC01 germline B cell receptor were provided by Daniel Lingwood (Ragon Institute).

ssDNA Scaffold Synthesis

The ssDNA scaffolds used to fold the DNA 6 helix bundle (6-HB) and the DNA icosahedron were produced using a previously described method of asymmetric PCR (Venziano, et al., *Science*, 352(6293):1534 (2016), Veneziano, et al., *Sci. Rep.*, 8(1):6548 (2018)). Briefly, two specific primers sets were used to amplify the ssDNA fragments (Table 1) with Quanta Accustart HiFi DNA polymerase. The aPCR mix was prepared in a final volume of 50 μL with the specific polymerase buffer complemented with 2 mM of Magnesium chloride, 200 μM of dNTPs, 1 μM of forward primer, 20 nM of reverse primer, 25 ng of M13mp18 template and 1 unit of Quanta Accustart HiFi polymerase. The amplification program used is the following: 94° C., 1 min for the initial denaturation; followed by 35 cycles of 94° C., 20 sec; 56° C., 30 sec; 68° C., 1 min per kb to amplify. Following amplification the aPCR mix were run on a 1% low melt agarose gel prestained with SybrSafe and the ssDNA product was extracted using the Zymoclean gel DNA recovery kit. Purified ssDNA concentration was measured using NanoDrop 2000.

TABLE 1

| List of primers used for amplification of the DNA nanostructures | | |
| --- | --- | --- |
| Structure | 5'-primer (forward) | 3'-primer (reverse) |
| 6-HB | CCCTTTAGGGTTCCGATTTA (SEQ ID NO: 1) | GCTGAAAAGGTGGCATCAAT (SEQ ID NO: 3) |
| Icosahedron | TCTTTGCCTTGCCTGTATGA (SEQ ID NO: 2) | GCTAACGAGCGTCTTTCCA (SEQ ID NO: 4) |

DNA Origami Nanostructure Folding

The DNA nanoparticles (Icosahedron and 6-HB) with or without overhangs were assembled in a one-pot reaction annealing as described previously (Venziano, et al., *Science,* 352(6293):1534 (2016). Briefly, 20-40 nM of scaffold was mixed with an excess of the correct staple strand mix (molar ratio of 10x) in buffer TAE-MgCl2 (40 mM Tris, 20 mM acetic acid, 2 mM EDTA, 16 mM MgCl2, pH 8.0) in a final reaction volume of 50 uL and annealed with the following program: 95° C. for 5 min, 80-75° C. at 1° C. per 5 min, 75-30° C. at 1° C. per 15 min, and 30-25° C. at 1° C. per 10 min.

DNA DX-Tile Nanostructure Folding

Each strand of the DX-tile was mixed at an equimolar concentration (2 μM) and the same protocol of annealing was used as for origami folding. No further step of purification was needed for the DX-tile as the folding yield was close to 100%.

Purification of DNA Origami Nanostructures

The DNA origami folded with an excess of staples strands were purified using Amicon ultra 0.5 centrifugal filter with three washes of folding buffer or PBS buffer if needed for further applications. Centrifugation steps were performed at 1000 g for 30-40 minutes and the final concentration of nanostructures was determined using NanoDrop 2000.

PNA Strands Synthesis

PNA strands were synthesized manually by solid phase peptide synthesis. Lysine residues were attached at either end of the PNA sequence to improve solubility. Fmoc-PNA monomers (PNA-Bio) were coupled to a low loading Tenta-gel-S-RAM resin using 4 eq. PNA, 3.95 eq. PyBOP, and 6 eq. diisopropylethylamine (DIEA). Lysine and glycine residues were reacted in the same way. Following each coupling, the peptide was deprotected in 20% piperidine in DMF. N-maleoyl-β-alanine (Sigma) was coupled to the N-terminus under the same coupling conditions. The peptide was then cleaved from the resin in 95% trifluoroacetic acid (TFA), 2.5% $H_2O$, and 2.5% triisopropylsilane. The peptide was dissolved in an aqueous solution with 0.1% TFA, filtered, and purified by HPLC using a C-18 Gemini column (Phenomenex) with a mobile phase of acetonitrile containing 0.1% TFA. Purity of the PNA products was analyzed with MALDI-TOF mass spectrometry on a Bruker Daltonics microflex.

Antigen Modification with PNA

PNA strands were attached to eOD by reacting the maleimide onto an N-terminal cysteine of eOD. Prior to the reaction, eOD was incubated with a 10-fold molar excess of tris(2-carboxyethyl)phosphine (TCEP) for 15 minutes, and TCEP was removed using centrifugal filter. Immediately after removal of TCEP, a 2-fold molar excess of maleimide-PNA was reacted with cysteine-eOD overnight at 4 C in PBS. Unreacted PNA was then removed using an Amicon centrifugal filter (10 kDa MWCO).

Antigen Attachment to DNA Nanostructures

Purified DNA nanostructures were mixed with the PNA-antigen conjugates at a molar ratio of 5x of antigen to overhangs on DNA nanostructures. An annealing ramp is realized starting from 37 C to 4 C at 1 C for 20 min.

Structure Characterization by TEM

DNA origami nanoparticles were visualized by transmission electron microscopy (TEM), with grids prepared as described previously with minor modifications. Briefly, carbon supported grids with copper mesh (CF200H-CU; Electron Microscopy Sciences) were glow discharge and soaked in 100 μM MgCl2 and blotted prior to applying DNA origami nanoparticles. 20 ul of 10 nM nanoparticle solution was applied to a clean parafilm surface and the grid was floated for 2 minutes. While soaking, 2% uranyl formate (UF; Electron Microscopy Sciences) was neutralized with 25 mM NaOH final concentration, vortexed for 1 minute, and filtered via syringe through a 0.1 um filter (EMD Millipore) dropwise onto the clean parafilm surface. The grid was then removed and quickly dried by edge blotting with Whatman 44 ashless paper. The grid was then immediately transferred to the 2% UF solution and incubated for 30 seconds. Again, the grid was dried by blotting along the edge with Whatman paper, and left to dry in air for an additional 30 minutes prior to imaging. Imaging was done on a FEI Tecnai set to 120 kV with and Gatan camera. Images were taken at 6,500x for wide-field views and 52,000x for near-field views. Images were collected from 3-second exposures. All images were cropped in Adobe Photoshop with subsequent autocontrast applied.

Agarose Gel Electrophoresis

DNA-nanoparticles folded and conjugated with eOD-GT8-PNA were analyzed by agarose gel electrophoresis with 2% agarose gel pre-stained with SybrSafe. Samples were loaded at a concentration of 20 to 50 nM DNA-NPs, ran for 2-3 hours at 90 V at 4 C and visualized with a blue light transilluminator. For fluorescence gel analysis with the AF647 modified eOD-GT8, the image was take in a Typhoon FLA 7000 at the SybrSafe excitation wavelength (473 nm), and at the AF647 excitation wavelength (635 nm). Images were merged with the ImageJ software (3)

Fluorescent Quantification

Quantification of the eOD-GT8 conjugation to DNA-NPs was performed with a fluoromax-4 (Horiba Inc.) fluorimeter. eOD-GT8-PNA monomer was modified with AF647 dye using NHS—$NH_2$ chemistry and used for conjugation to DNA-nanoparticles. Spectra were acquired with an excitation wavelength of 630 nm (emission measured at 670 nm). A fluorescence calibration curve was realized with free eOD-GT8-PNA, conjugated with AF647 dye, at different concentrations and used to determine yield of coverage of DNA-NPs.

B Cell Calcium Flux Assay

Ramos B Cells at a concentration of 10 million cells/mL were incubated with 10 μM Fluo-4 AM (Thermo Fisher) for 30 minutes at 37 C. After washing once, flux assays were performed on a Teican plate reader at 37 C on a 96 well microplate. 160 μL of Fluo-4 labeled Ramos cells at 2 million cells/mL was added to each well. A baseline fluorescence was then recorded for 1 minute, and 40 μL of nanoparticles were added to the cells for a final concentration of 5 nM of antigen, unless otherwise stated.

Results

Figure 2A:
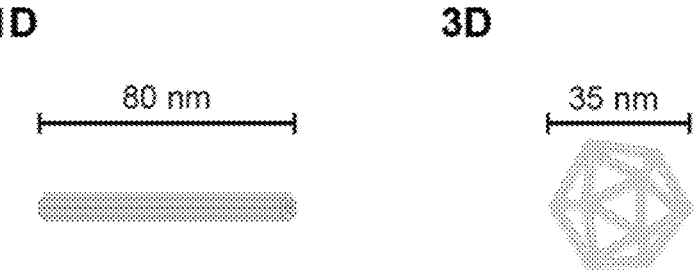
FIG. 2A is a schematic illustrating folding of the two types of DNA-NPs (6-helix bundle and DNA icosahedron) that were designed and used for 1D and 3D presentation of antigens.

The shape, monodispersity, and antigen modification of DNA-NPs were first confirmed. Negative stain transmission electron microscopy images and agarose gel electrophoresis of both 6-helix bundle structures as well as icosahedra structures (FIG. 2A) demonstrated the monodispersity of nanoparticles, their accurate folding, and their structural rigidity, consistent with previous scaffolded DNA nanostructures designed and prepared with these methods (Venziano, et al., *Science*, 352(6293):1534 (2016)). TEM images showed high folding yield and monodisperse nanoparticles.

Figure 1D:
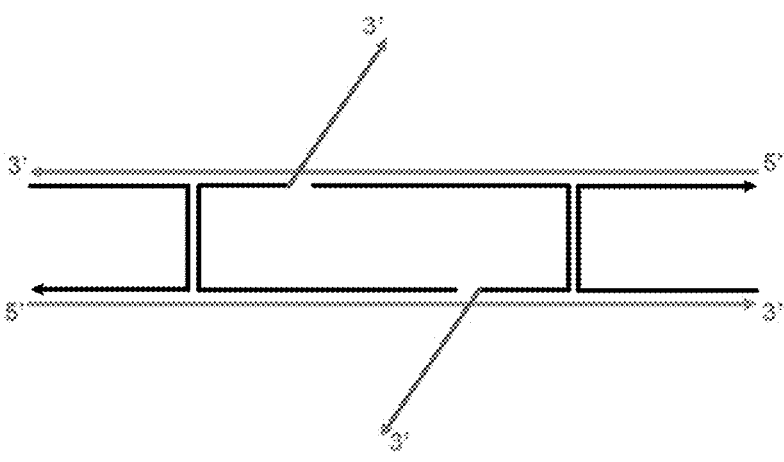
FIGS. 1D and 1E are illustrations of overhang placement on the edge of the DNA nanostructures: DNA icosahedron (FIG. 1D) DNA 6HB (FIG. 1E).
Figure 1E:
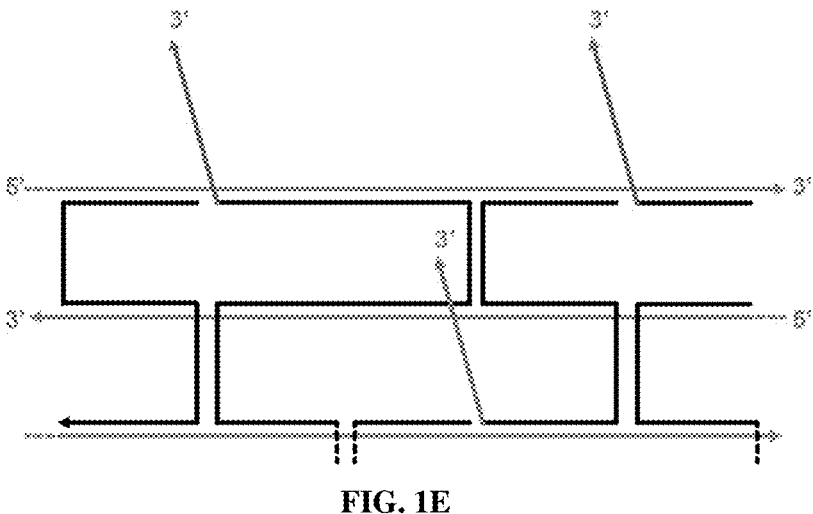
Figure 1F:
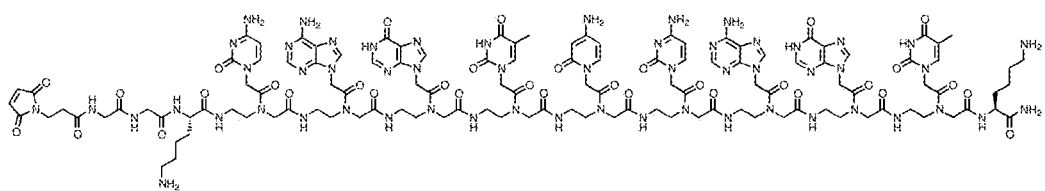
FIG. 1F is a schematic of a PNA linker designed for antigen attachment to DNA nanostructures.
Figure 2B:
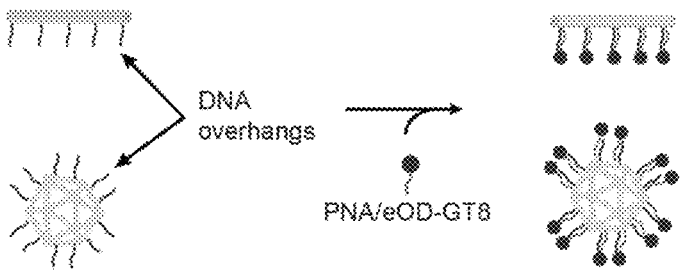
FIG. 2B is a schematic demonstrating an overview of the antigen conjugation protocol to attach eOD-GT8 antigens to the DNA nanostructures using PNA strands complementary to DNA overhangs on the DNA nanostructures.
Figure 2C:
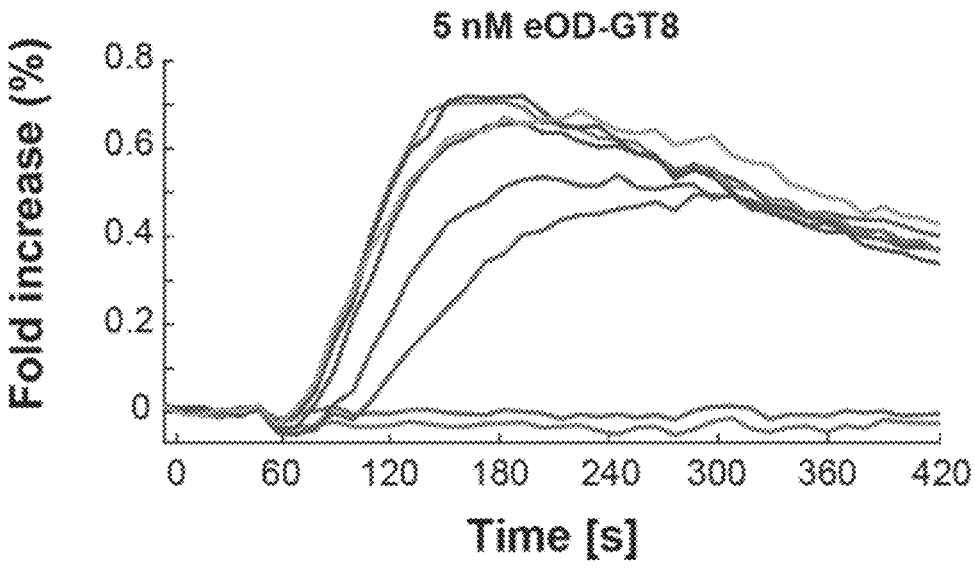
FIGS. 2C-2F are line graphs (FIGS. 2C and 2E) and bar graphs (FIGS. 2D and 2F) showing quantification of B cell (human Ramos cell) activation upon exposure to DNA NPs modified with eOD-GT8 at 5 nM (FIGS. 2C and 2D) and 0.5 nM (FIGS. 2E and 2F) eOD-GT8. Raw fluorescence of cells loaded with Fluo-4 calcium probe normalized by unstimulated levels, less buffer-only control curves (FIGS. 2C and 2E) and areas under the curves normalized to maximum in repeat (FIGS. 2D and 2F) are shown.
Figure 2D:
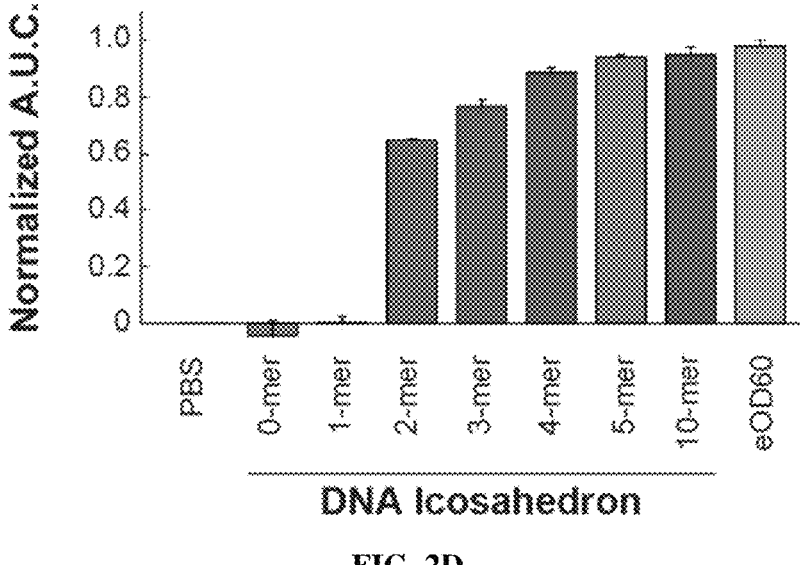
Figure 2E:
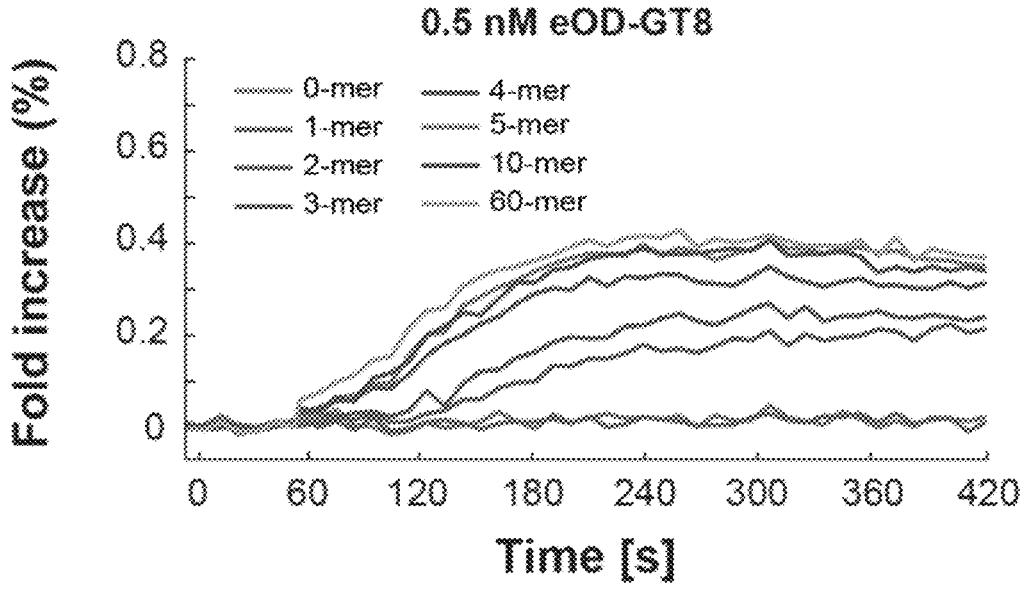
Figure 2F:
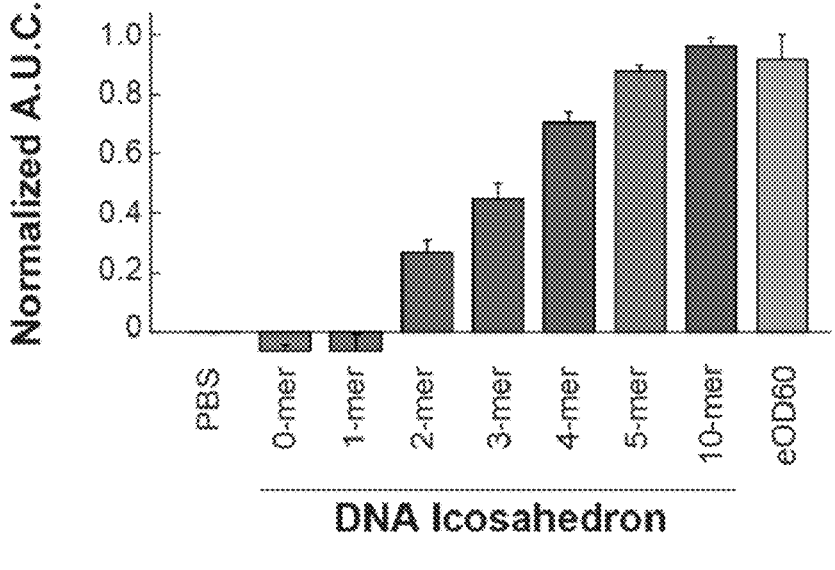

Outwardly-facing DNA overhangs were engineered at the 3' end of selected DNA nanostructure staple strands, allowing for addressable modification of DNA nanostructures through base-pairing interactions (FIGS. 1D, 1E, and 2B). A monomeric version of eOD-GT8 expressed with an N-terminal cysteine was modified with a complementary PNA strand that was functionalized with a thiol-reactive maleimide group. The purified PNA/eOD-GT8 conjugate was then added to folded and purified nanoparticles and allowed to hybridize fully before final purification and use. Gel electrophoresis assay, tryptophan fluorescence assay, and fluorimetry demonstrated the efficient complexation between the different DNA nanoparticles and PNA/eOD-GT8 (Table 2).

TABLE 2

| | | Percentage of antigen modification | | | |
|---|---|---|---|---|---|
| DNA-NPs | Fluorescence intensity | Concentration DNA | Number of antigens | Concentration antigen (nM) | Coverage (%) |
| 30 mer | 2131936.4 | 54.0 | 30 | 1455.3 | 89.8 |
| 60 mer | 3161241.1 | 46.5 | 60 | 2158.0 | 77.3 |
| 5 mer | 1883754.7 | 250.1 | 5 | 1285.9 | 102.8 |
| 1 mer | 67475.9 | 43.0 | 1 | 46.1 | 107.1 |
| 6HB 5 mer | 1045677.6 | 136.0 | 5 | 713.8 | 105.0 |
| 6HB 2 mer | 297036.7 | 107.0 | 2 | 202.8 | 94.8 |
| 6HB 1 mer | 359982.8 | 238.0 | 1 | 245.7 | 103.3 |

Figure 2G:
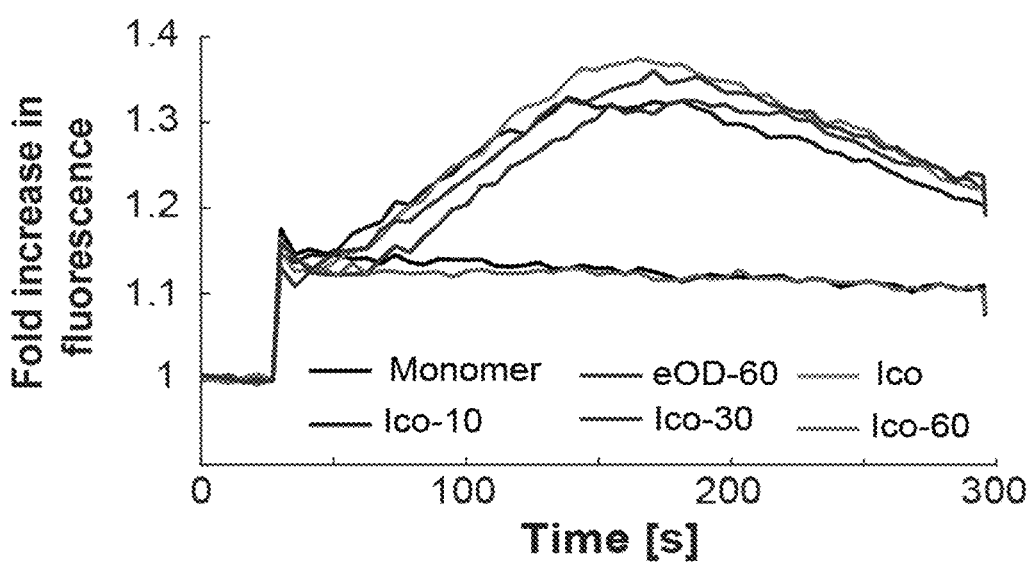
FIG. 2G is a line graph showing the effect of valency of eOD-GT8 on DNA icosahedron antigen presentation.

The effect of antigen valency was evaluated by comparing icosahedral DNA NP bearing 0, 1, 2, 3, 4, 5, or 10 eOD-GT8 ([0-10]-mer) with the 60-mer protein nanoparticle (eOD60) while keeping the total amount of eOD-GT8 constant, and observing calcium release in a human Ramos cell line stably expressing the germline VRCO1 IgM. While DNA NP modified with a single eOD-GT8, and unmodified DNA NP did not stimulate cells, increasing antigen valency yielded robust cellular responses from 2-mer DNA NP to 10-mer DNA NP (FIGS. 2C-2F). This dependence on valency was even more apparent at a lower concentration of eOD-GT8 (0.5 nM). It was observed that 5-mer and 10-mer eOD-DNA NP resulted in calcium release nearly identical to eOD60 protein nanoparticle, which has a much higher antigen valency. Moreover, using a higher valency on the DNA icosahedron (30- and 60-mer) did not lead to an increase of the cellular response (FIG. 2G). These results indicate that increasing the number of antibody binding sites per nanoparticle above 5 does not lead to stronger cellular responses, and that many antigen sites on eOD60 are dispensable for B cell activation by high affinity antigen.

Example 2: Increasing Inter-Antigen Distance on a Rigid Scaffold Initially Increases B Cell Receptor Response Methods and Materials Preparation of DNA nanostructures including folding and purification, and attachment of the DNA nanostructures to PNA-antigen conjugates was performed as described in Example 1.

Antigens and Cell Lines

Ramos B cells expressing VRC01 germline B cell receptor were provided by Daniel Lingwood (Ragon Institute).

B Cell Calcium Flux Assay

Ramos B Cells at a concentration of 10 million cells/mL were incubated with 10 μM Fluo-4 AM (Thermo Fisher) for 30 minutes at 37 C. After washing once, flux assays were performed on a Teican plate reader at 37 C on a 96 well microplate. 160 μL of Fluo-4 labeled Ramos cells at 2 million cells/mL was added to each well. A baseline fluorescence was then recorded for 1 minute, and L of nanoparticles were added to the cells for a final concentration of 5 nM of antigen, unless otherwise stated.

Results

Figure 3A:
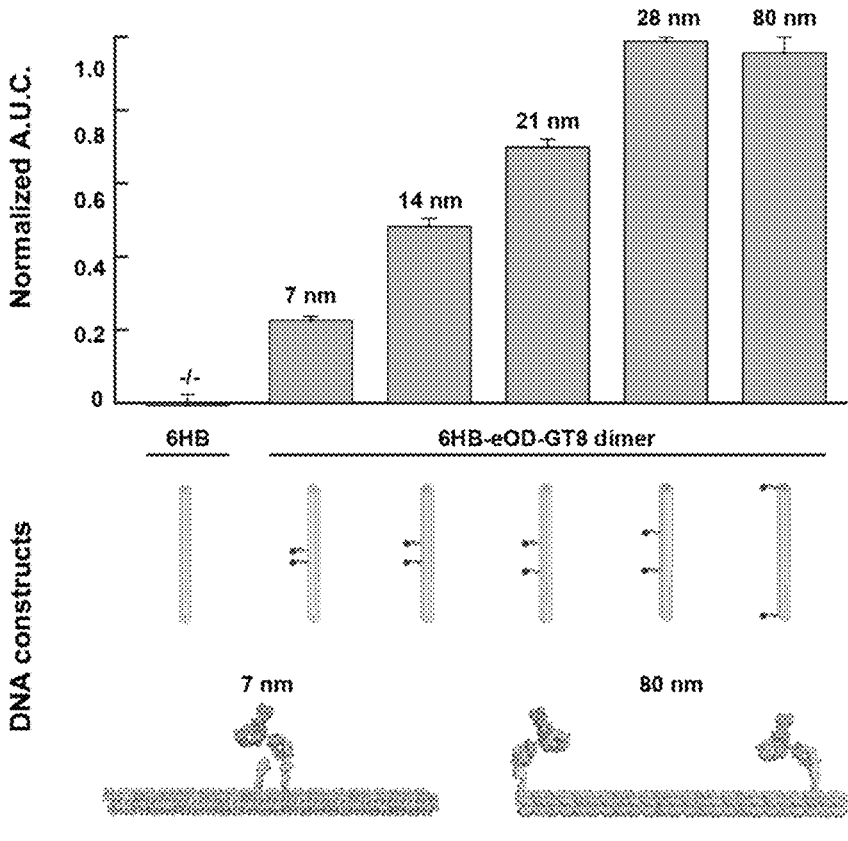
FIG. 3A is a graph showing quantification of B cell activation (assayed through Calcium release) upon exposure to DNA NP eOD-GT8 dimers having inter-antigen distances between 7 nm and 80 nm. The bottom schematic illustrates possible organizations of VRC01 antibodies on 6HB displaying eOD-GT8 dimers at 7 and 80 nm.

Previous results have indicated that inter-antigen distances impact receptor signaling for both the IgE Fc receptor (Sil, et al., *ACS Chem. Biol.*, 2(10):674-84 (2007)) and the T cell antigen receptor (Cochran, et al., *J. Biol. Chem.*, 276(30):28068-28074 (2001)), and that the B cell receptor oligomeric organization impacts receptor activation (Yang, et al., *Nature*, 467(7314):465-469 (2010)). The impact of spacing between epitopes on B cell receptor engagement was explored by systematically varying inter-antigen distance on a rigid and linear 6 helical DNA NP rods templating two eOD-GT8 per nanoparticle (FIG. 3A). For distances less than 28 nm, calcium responses were systematically lowered as inter-antigen distance decreased. A decrease in cellular response with longer inter-antigen distances up to 80 nm, the full length of the nanoparticle rod, was not observed even though this distance is well beyond the size where two separate immunoglobulin Iga/P pairs could be interacting (FIG. 3A; bottom inset).

Figure 3B:
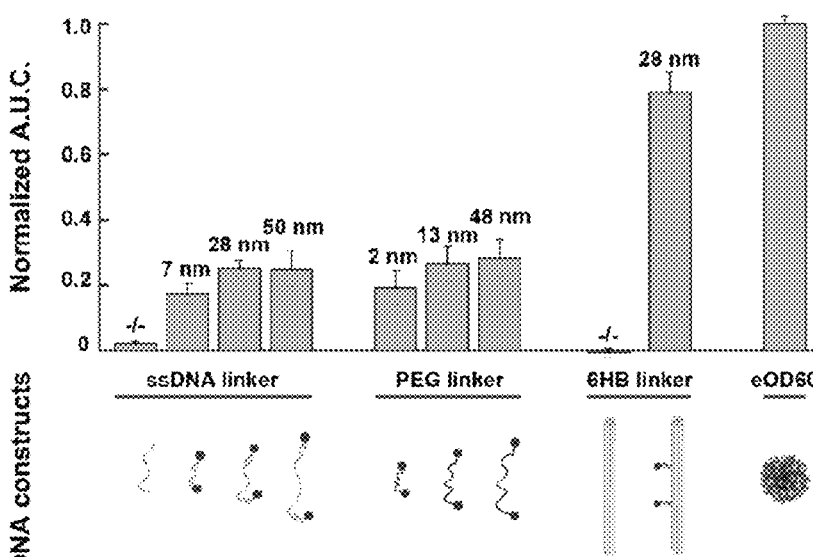
FIG. 3B is a graph showing quantification of B cell activation (assayed through Calcium release) upon exposure to eOD-GT8 dimers attached either to flexible polymeric scaffolds (ssDNA or PEG) or rigid 6HB DNA NP eOD-GT8 dimer structures. Numbers above the bars indicate the full extended length of the polymeric scaffold or the inter-antigen distance on 6HB DNA NP eOD-GT8 dimers.

To explore whether the observed B cell response was reliant on DNA NP rigidity, eOD-GT8 dimers were created on flexible polymeric ssDNA linkers and PEG linkers having comparable extended length as the DNA NP 6-helix bundle structure (FIG. 3B, Table 3).

TABLE 3

| | | Linker characteristics | | | |
|---|---|---|---|---|---|
| Linker material | Linker name | MW (Da) | Number of units (Bases or PEG units) | Linker length (nm) | Flory radius (nm) |
| ssDNA | SsDNA5 | 8930.9 | 5 | 3.2 | N/A |
| ssDNA | ssDNA12 | 11123.3 | 12 | 7.6 | N/A |
| SsDNA | SSDNA24 | 14881.8 | 24 | 15 | N/A |
| ssDNA | ssDNA35 | 18210.9 | 35 | 22 | N/A |
| SsDNA | ssDNA47 | 21916.2 | 47 | 30 | N/A |
| ssDNA | SSDNA83 | 30767.9 | 83 | 52 | N/A |
| PEG | Bis-Mal-PEG-2 | 308.3 | 2 | 0.6 | 0.5 |
| PEG | Bis-Mal-PEG-3 | 352.3 | 3 | 0.8 | 0.5 |
| PEG | Bis-Mal-PEG-4 | 2000 | 45 | 12.6 | 2.8 |
| PEG | Bis-Mal-PEG-5 | 3500 | 80 | 22.4 | 3.9 |

TABLE 3-continued

| | | | Linker characteristics | | |
|---|---|---|---|---|---|
| Linker material | Linker name | MW (Da) | Number of units (Bases or PEG units) | Linker length (nm) | Flory radius (nm) |
| PEG | Bis-Mal-PEG-6 | 5000 | 114 | 31.9 | 4.8 |
| PEG | Bis-Mal-PEG-7 | 7500 | 170 | 47.7 | 6.1 |

Flexible polymer dimers gave a drastically reduced cellular response compared to the rigid DNA NP dimers, indicating the importance of structural form and rigidity during B cell receptor responses to antigen.

Example 3: Clustering of Antigens on One Face of an Icosahedron does not Improve B Cell Receptor Responses Compared to Positioning on a Linear Rod Methods and Materials Preparation of DNA nanostructures including folding and purification, and attachment of the DNA nanostructures to PNA-antigen conjugates was performed as described in Example 1.

Antigens and Cell Lines

Ramos B cells expressing VRC01 germline B cell receptor were provided by Daniel Lingwood (Ragon Institute).

B Cell Calcium Flux Assay

Ramos B Cells at a concentration of 10 million cells/mL were incubated with 10 µM Fluo-4 AM (Thermo Fisher) for 30 minutes at 37 C. After washing once, flux assays were performed on a Teican plate reader at 37 C on a 96 well microplate. 160 µL of Fluo-4 labeled Ramos cells at 2 million cells/mL was added to each well. A baseline fluorescence was then recorded for 1 minute, and L of nanoparticles were added to the cells for a final concentration of 5 nM of antigen, unless otherwise stated.

Results

Figures 4A, 4B, 4C, 4D, 4E:
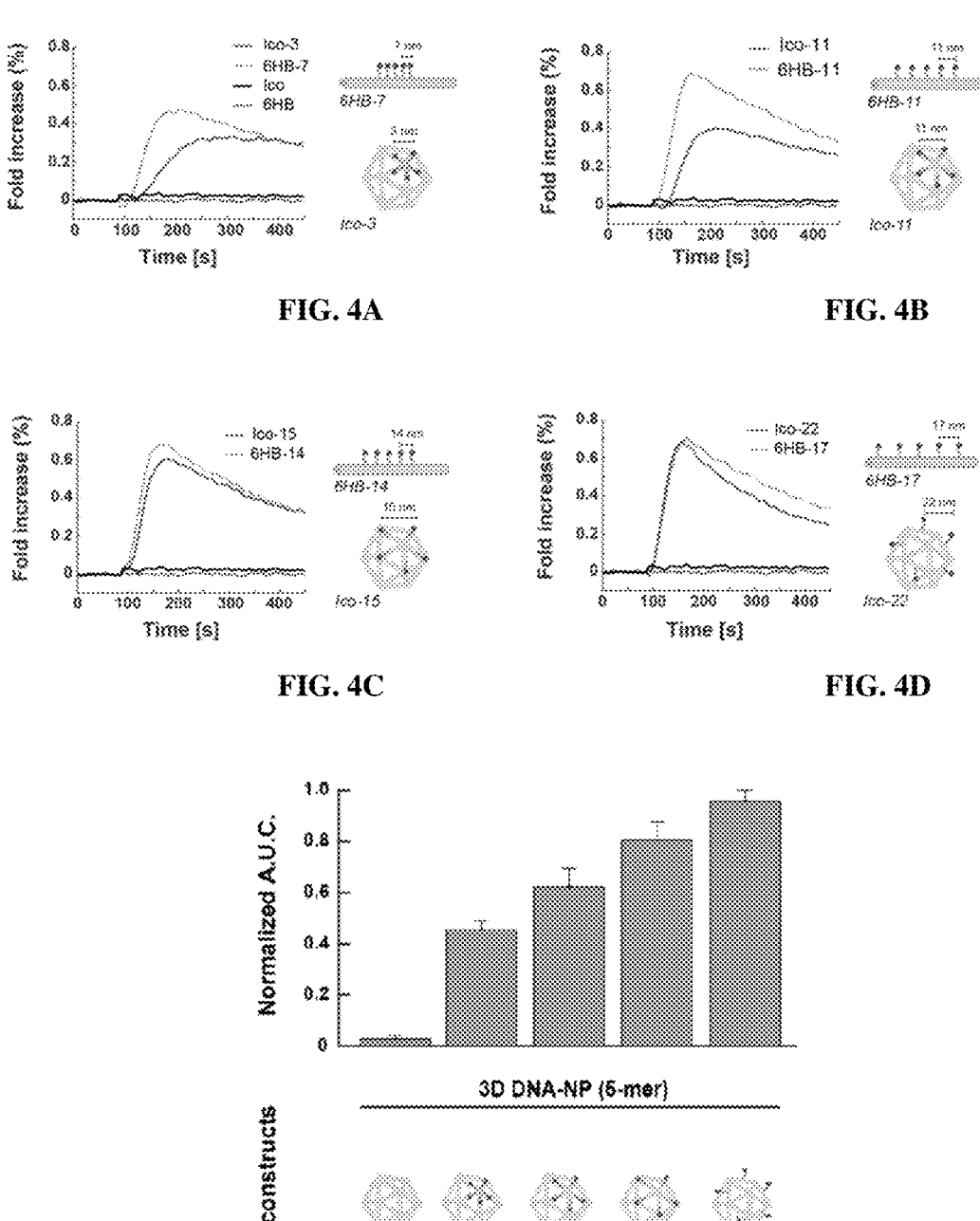
FIGS. 4A-4D are graphs showing comparisons of B cell activation (assayed through Calcium release) upon exposure to 6 helical bundle (6HB) or icosahedral (Ico) structures presenting the eOD-GT8 antigens at various inter-antigen distances including, 7 and 3 nm respectively (FIG. 4A), 11 and 11 nm respectively (FIG. 4B), 14 and 15 nm respectively (FIG. 4C), and 17 and 22 nm respectively (FIG. 4D).
FIGS. 4E-4F are graphs showing quantification of B cell activation upon exposure to 3D (FIG. 4E) and 1D (FIG. 4F) DNA NP structures presenting 5 eOD-GT8 antigens (5-mer).
Figure 4F:
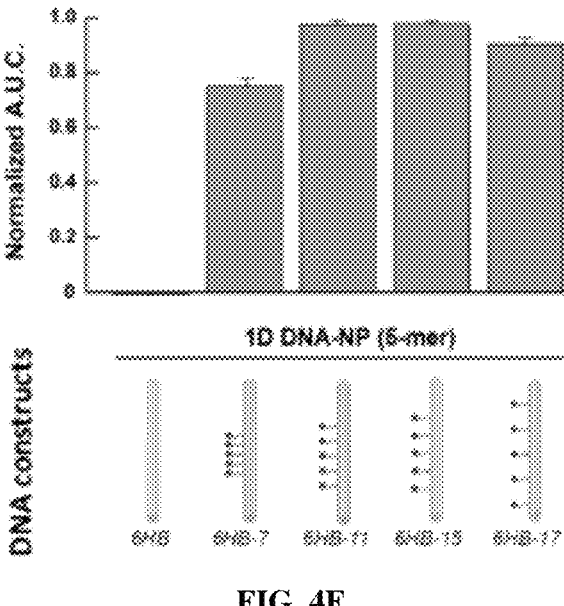

The results described in Example 2 indicate that tight clustering of antigen may limit B cell receptor responses due to close inter-antigen distances, in contrast to a model where tight clustering of antigen leads to maximal B cell receptor responses by facilitating inter-BCR cooperativity. To further test this, a linear placement of five eOD-GT8 antigens on a 6HB DNA NP was compared to a clustered placement of five eOD-GT8 antigens around one face of the icosahedron DNA NP for different inter-antigen distances between ~5 nm and 22 nm (FIGS. 4A and B). Notably, the average distance between all antigen sites on the icosahedron 5-mer is ~⅔ that of the 6HB linear rod 5-mer. It was observed that for the large inter-antigen distances, 22 nm and 15 nm, clustering on both linear and planar structures led to an equivalent cellular response (FIGS. 4C-4D). However, when inter-antigen distance is small, such as 11 nm and 3 nm, linear placement of eOD-GT8 antigens yielded a greater response than a clustered planar placement of antigens (FIGS. 4A-4B). Further, decreasing the distance between antigens in both the planar and the linear presentation yielded a decreased cellular response, consistent with previous results from dimer DNA NP structures (FIGS. 4E-4F).

Example 4: Immunogen Presenting Nanoparticles Facilitate Specific Binding and Activation of the B Cell Receptor Methods and Materials Preparation of DNA nanostructures including folding and purification, and attachment of the DNA nanostructures to PNA-antigen conjugates was performed as described in Example 1.

Antigens and Cell Lines

Ramos B cells expressing VRC01 germline B cell receptor were provided by Daniel Lingwood (Ragon Institute).

Antigen Conjugation with AF647 Dye

The eOD-PNA conjugate was modified with the fluorescent label AlexaFluor 647-NHS (AF647). The conjugate was incubated with 5 molar equivalents of AF647-NHS in 10 mM sodium bicarbonate buffer for 2 hours at room temperature. Unreacted dye was removed using centrifugal filtration (10 kDa MWCO).

B Cell Imaging: Sample Preparation for Confocal Microscopy

Ramos cells were labeled on ice at a concentration of 5 million/mL and protected from light for 30 minutes in Hank's Buffered Sterile Saline (HBSS) with 20 g/mL human anti IgM f(Ab)₁ fragment (Jackson 109-007-043) conjugated to Janelia Fluor 549. Cells were spun down and resuspended in warm HBSS at a concentration of 2 million/mL. Antigens were added to a final concentration of 5 nM by adding 50 µL antigen solution to a volume of cells between 175 µL and 400 µL, and cells were kept at 37 C by incubation in a thermal bead bath. At timepoints following the addition of antigen, 100 µL of cells were removed and placed into 200 µL of 6% warm PFA solution and allowed to fix for 10 minutes at 37 C. Following fixation, fixed cells were diluted in 4.5 mL HBSS and centrifuged at 600 g for 5 minutes. Cells were then labeled for 5 hours at 4 C in 50 µL HBSS with 5 mg/mL bovine serum albumin (BSA, Sigma) with 10 µg/mL wheat-germ agglutinin (WGA) conjugated to Alexa 488 (ThermoFisher W11261), and a 1:50 dilution of Phalloidin conjugated to Alexa 405 (material from Sudha). Cells were diluted into 4.5 mL HBSS and centrifuged at 600 g for 5 minutes, and resuspended in 4.5 mL HBSS and centrifuged again to wash before being resuspended in 100 µL HBSS. Cells were then plated onto LabTech II 8-well glass bottom chambers modified with 0.1% Poly-L-Lysine (PLL, Sigma P8920) and allowed to adhere for at least 4 hours at 4 C before performing confocal microscopy.

Confocal Microscopy Imaging

Confocal microscopy was performed on a Zeiss AxioVert 200M inverted microscope stand with Yokogawa CSU-22 spinning disk confocal scan head with Andor *Borealis* multi point confocal system. Probes were excited by 4 laser lines in the Andor/Spectral applied Research Integrated Laser Engine: 405 nm 100 mW OPSL, 488 nm 150 mW OPSL, 561 nm 100 mW OPSL, and 642 nm 110 mW OPSL. Multipass dichroic mirror 405/488/568/647 and emission filters 450/50 nm, 525/50 nm, 605/70 nm, and 700/75 nm were used for each emission channel, respectively. Sample was imaged through a 63× oil Plan Apochromat objective with an effective pixel size of 0.092 m/pixel. Images were captured through a Hamamatsu Orca-ER cooled CCD, and instrumentation was controlled through MetaMorph software. For each image, 9 z-planes having separation of 1.5 m were acquired between the top and bottom of the cell, and approximately 10 fields of view were acquired for each sample.

Image Analysis 16-bit images were read into MATLAB and converted to double precision. For each field of view, a maximum intensity projection (MIP) was calculated for the phalloidin channel. This was then binarized using adaptive thresholding, cleaned of stray pixels, and then morphological opening and closing was performed. Holes within this binarization were then filled, and discreet objects within this binarization were labeled as individual cells. For each cell in a field of view, z-planes were binarized as above using the phalloidin channel, and these z-plane binarizations were restricted to the limit of the MIP binarization for each cell. The convex hull of this z-plane binarization was used to estimate the extent of the cell, and the cell surface was estimated by selecting the perimeter of the z-plane binarization and dilating this 25 times in a 4-connected neighborhood and subsequent restriction by the undilated cell extent binarization. Total probes intensity and surface probes intensity of cells was calculated through summation through all z-stacks after logical indexing of the background-subtracted raw z-plane images, where background was estimated to be a constant through all z-planes and channels. Pixel-based correlation was performed through pairwise linear correlation of pixel values between channels following logical indexing. Average intensity values shown are an average over cells, and errorbars shown are the standard error of the mean, given by the standard deviation divided by sqrt ($N_{cells}$). Internalized fraction of probe intensity for a single cell is given by (total cell intensity−surface cell intensity)/ total cell intensity.

Results

Figure 5A:
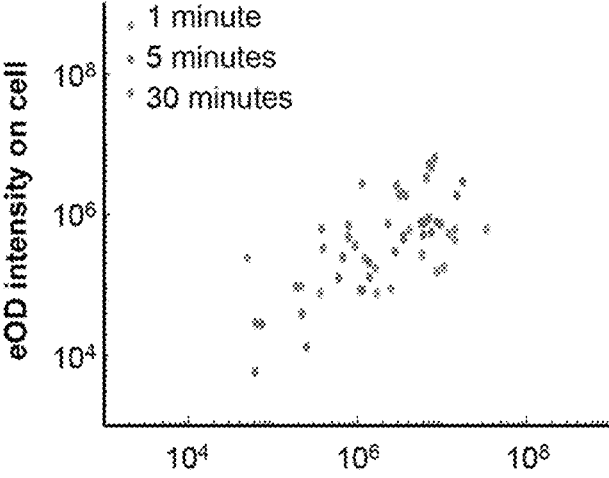
FIG. 5A is a scatter plot showing that the total intensity of eOD-GT8 is highly correlated with the intensity of the B cell receptor (BCR), confirming specific binding of nanoparticles to the B cell receptor.
Figure 5B:
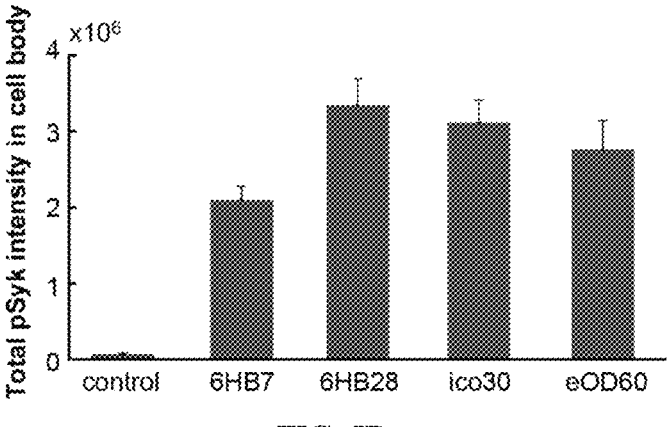
FIG. 5B is a bar graph showing quantification of total pSyk intensity per cell upon exposure to the indicated DNA NP eOD structures. Ramos cells were labeled with an anti-phospho-Syk antibody after fixation and the total pSyk intensity per cell was determined.
Figure 5C:
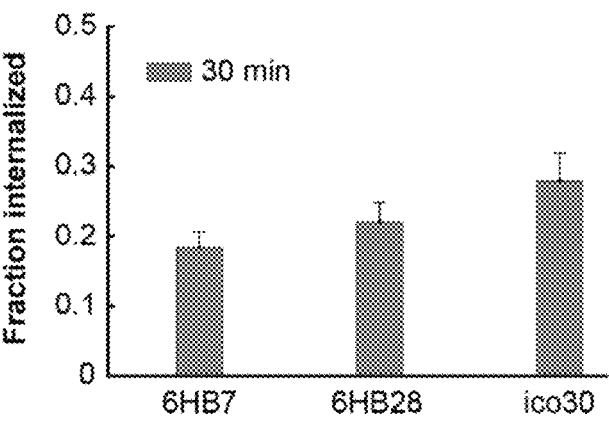
FIG. 5C is a bar graph showing quantification of the internalized fraction of eOD estimated by segmenting the cell surface using phalloidin staining. Total internal eOD fluorescence was divided by total cellular eOD fluorescence on a cell-by-cell basis. Error bars denote the standard error of the mean fluorescence between the cells.
Figure 5D:
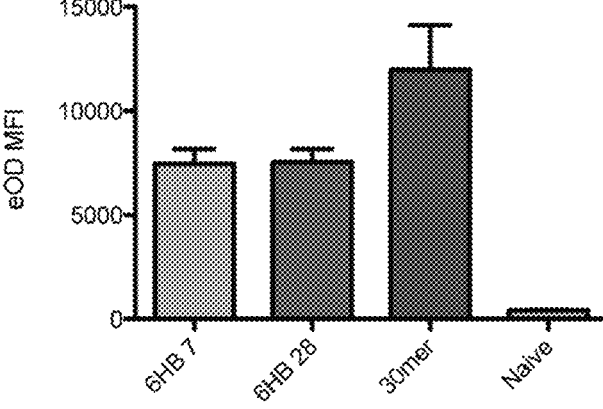
FIG. 5D is a bar graph showing quantification of flow cytometry of labeled eOD-DNA nanostructures (eOD 30mer, 6 HB 7, and 6HB 28) binding to B cells.
Figure 5E:
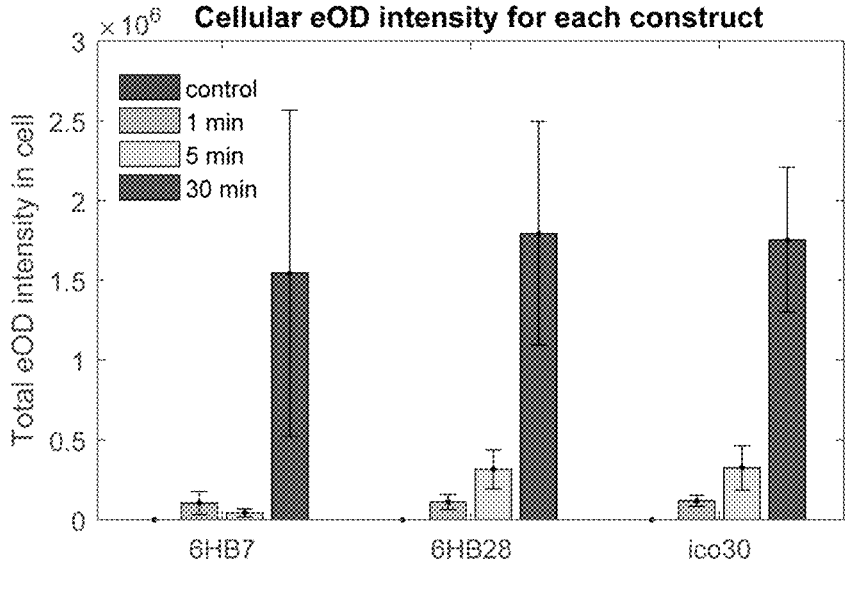
FIG. 5E is a bar graph showing cellular eOD intensity (in cell) for each construct (6HB7, 6HB28, ico30) at (from left-to-right for each construct) control, 1 minute, 5 minutes, and 30 minutes).
Figure 5F:
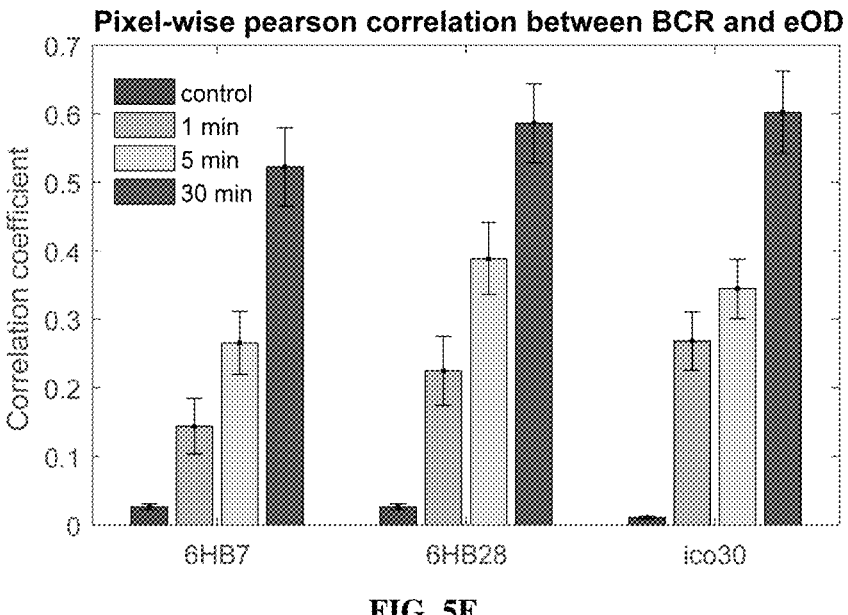
FIG. 5F is a bar graph showing pixel-wise pearson correlation between B cell receptor and eOD intensity (correlation coefficient) for each construct (6HB7, 6HB28, ico30) at (from left-to-right for each construct) control, 1 minute, 5 minutes, and 30 minutes).

Three eOD-GT8 DNA NP constructs (Icosahedron-30 mer eOD-GT8, six-helix bundle dimer with 28 nm spacing, and six-helix bundle dimer with 7 nm spacing) were chosen to examine in more detail through confocal microscopy using a fluorescent eOD that was labeled with Alexa Fluor 647. DNA NP eOD constructs bound to Ramos cells in an approximately equal fashion and were correlated in space with the B cell receptor on cell surfaces and were co-internalized at long times (FIGS. 5D-5F). eOD binding was highly correlated with VRC01 IgM expression, and cells lacking IgM expression failed to bind eOD (FIG. 5A). Antibody staining of phosphorylated Syk kinase (pSyk) revealed a sharp increase in pSyk phosphorylation after 1 minute of DNA NP or eOD60 addition for all DNA NP constructs (FIG. 5B). Dimer eOD separated by short distances (6HB7, 7 nm dimer) resulted in significantly less pSyk binding as compared to the dimer eOD separated by long distance (6HB28, 28 nm dimer) and the icosahedron bearing 30 eOD (ico30) (FIG. 5B). The internalization of eOD was also examined by use of the phalloidin stain to estimate cellular boundary. Compared to the 6HB7, it was observed that eOD internalization improved for longer inter-antigen distances and the icosahedron 30-mer (FIG. 5C).

The disclosed compositions include materials, compounds, and components that can be used for the disclosed methods. Various exemplary combinations, subsets, interactions, groups, etc. of these materials are described in more above. However, it will be appreciated that each of the other various individual and collective combinations and permutations of these compounds that are not described in detail are nonetheless specifically contemplated and disclosed herein. For example, if one or more nucleic acid nanostructures are described and discussed and a number of substitutions of one or more of the structural or sequence parameters are discussed, each and every combination and permutation of the structural or sequence parameters possible are specifically contemplated unless specifically indicated to the contrary.

These concepts apply to all aspects of this disclosure including, but not limited to, steps in *methods* of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Example 5: Immunogen Presented by Pentagonal Bipyramidal Architectures Efficiently Activated B Cell In Vitro Methods and Materials Experimental procedures are identical to those described under Example 1 with the following additions and modifications.

Chemicals and Kits

Pluronic F-127 (10% (w/v) solution) was obtained from Sigma Aldrich. Corning Spin-X UF-0.5 ml centrifugal filters (MWCO 100 kDa) were obtained from Sigma Aldrich.

ssDNA Scaffold Synthesis

Custom circular ssDNA scaffolds of lengths matching the corresponding nucleic acid nanostructure architectures were produced in a phage-based approach as previously described (see Shepherd, *Sci Rep,* 9(1):61212 (2019)). Briefly, SS320 (Lucigen) *E. coli* were fist transformed with the M13cp helper plasmid and subsequently with the ssDNA encoding phagemids phPB84 and phI52. For milligram-scale production of synthetic miniphage, a Stedium Sartorius fermenter was used for growing 5 L of culture. For 1 L cultures production was conducted in regular culture flasks and the following steps were carried out in analogy to the 5 L culture. An overnight culture of phage-producing colonies, as determined by PCR, gel visualization, and sequencing results, was grown in 2×YT supplemented with 100 µg/mL Ampicillin and 15 µg/mL of chloramphenicol and 5 µg/mL of tetracycline and diluted to O.D. 600 of 0.05 for inoculating 5 L of media. The growth media for the batch fermentation was also 2×YT supplemented with 100 µg/mL Ampicillin and g/mL of chloramphenicol and 5 µg/mL of tetracycline. Oxygen and pH were monitored throughout the growth, and the pH was maintained at 7.0 with phosphoric acid and ammonium hydroxide, with a constant agitation of 400 RPM. At 8 h, the phage-containing bacteria culture was harvested and processed. For milligram-scale purification of ssDNA, 900 mL batches of liquid culture bacteria were processed as follows. Bacteria were pelleted by centrifuging twice at 4,000×g for 20 min, followed by 0.45 m cellulose acetate filtration. Phage from clarified media were precipitated by adding 6% w/v of polyethylene glycol-8000 (PEG-8000) and 3% w/v of NaCl and stirring continuously at 4° C. for 1 h. Precipitated phage were collected by centrifuging at 12,000×g for 1 h, and the PEG-8000 supernatant was removed completely, and pellet was resuspended in 30 mL of 10 mM Tris-HCl pH 8.0, 1 mM Ethylenediaminetetraacetic acid (EDTA) buffer (TE buffer). The phage was then processed using an EndoFree Maxiprep (Qiagen, Germany) column-based purification, following the manufacturer's protocol with two adjustments. First, proteinase K (20 µg/mL final) was added to EndoFree Buffer P1 and incubated at 37° C. for 1 h before addition of EndoFree Buffer P2 and incubation at 70° C. for 10 min. The lysed phage was returned to room temperature before proceeding. Second, after removal of endotoxins, 0.2 v/v of 100% ethanol was added to the clarified sample, before applying to the EndoFree Maxiprep column to increase ssDNA binding. All other steps remained the same, and the circular ssDNA was eluted in 1 mL of endotoxin-free TE buffer. The amount of collected DNA was judged by absorbance at A280, and the purity was judged by running on a 1% agarose gel in 1×TAE stained with ethidium bromide.

DNA Origami Nanostructure Folding

In addition to the protocol described under Example 1, guard staples complementary to the overhangs sequence were added prior to thermal annealing at 5-fold excess to ensure monodispersed assembly of the DNA origami nanostructures.

Purification of Functionalized DNA Origami Nanostructures

Antigen-functionalized DNA origami nanostructures were purified using Spin-X UF-0.5 ml centrifugal filters (MWCO 100 kDa). Prior to use for purification, the filter membrane was passivated with 5% (w/v) Pluronic F-127 for 30 min at room temperature and subsequently washed three times with PBS at pH 7.4.

Characterization of Functionalized DNA Origami Nanostructures

In addition to the methods described under Example 1 to validate purity, structural integrity and immunogen copy number, functionalized DNA origami nanostructures were additionally analyzed by dynamic light scattering and atomic force microscopy.

Results

Figure 6A:
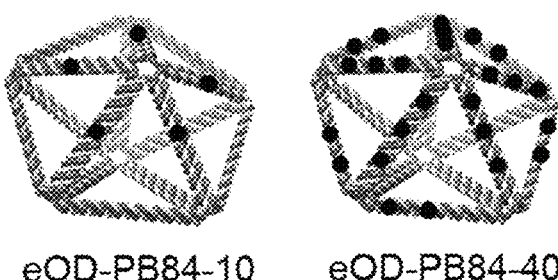
FIGS. 6A-6D are line graphs (FIGS. 6A and 6C) and bar graphs (FIGS. 6B and 6D) showing quantification of B cell (human Ramos cell) activation upon exposure to pentagonal bipyramid DNA NPs modified with eOD-GT8 at 5 nM (FIGS. 6A and 6B) and 1 nM (FIGS. 6C and 6D) eOD-GT8.
Figure 6A:
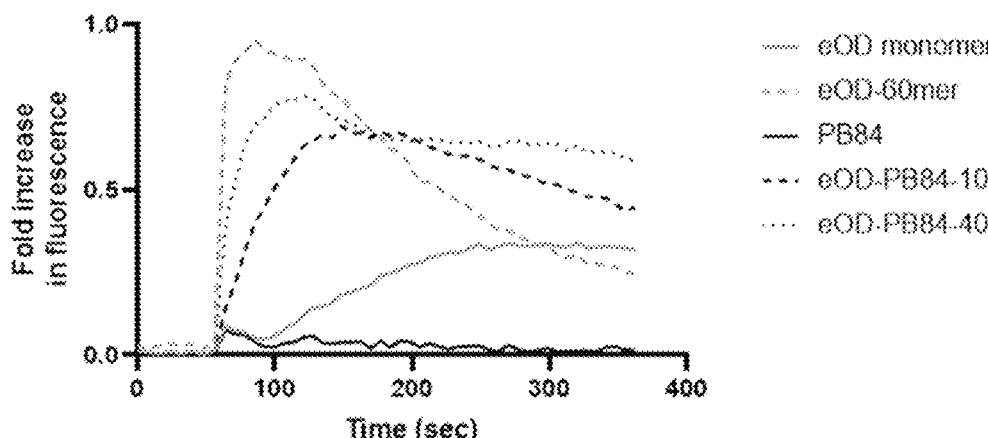
Figure 6B:
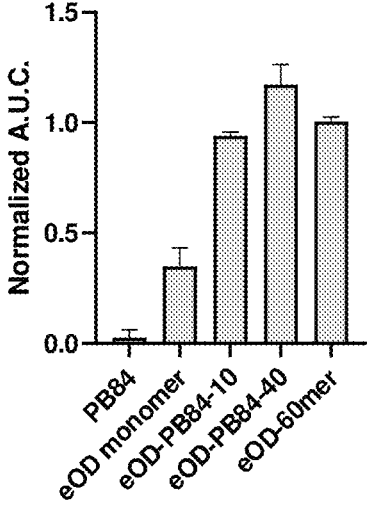
Figure 6C:
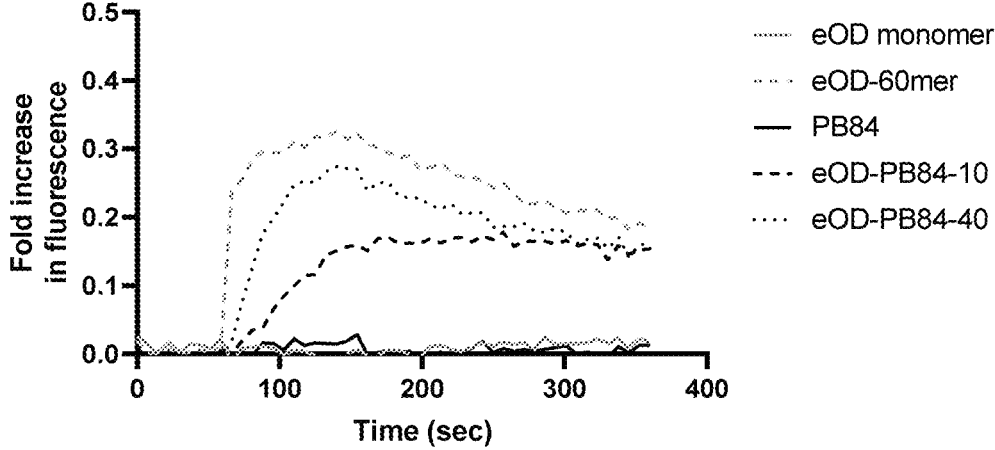
Figure 6D:
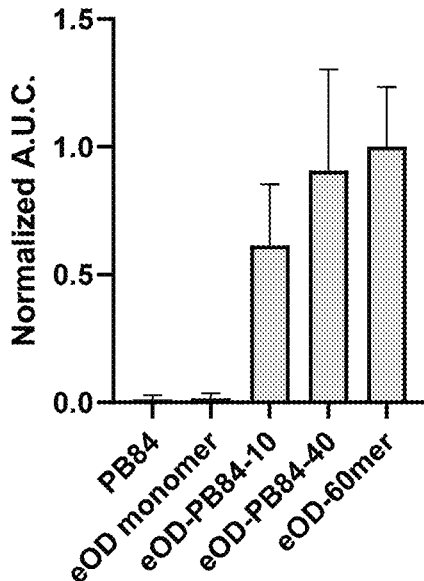

Purity, structural integrity, immunogen copy number and monodispersity were characterized for both the icosahedron and the pentagonal bipyramid as described under Example 1. Initially, the activation of human Ramos B cells by a pentagonal bipyramid with 84 bp edge length carrying 10 or 40 copies of eOD-GT8 was assayed in a calcium flux assay. Activation levels were compared to the eOD-GT8-60mer protein nanoparticle at total immunogen concentrations of 5 nM (FIGS. 6A and B) and 1 nM (FIGS. 6C and D). As observed for the icosahedral architecture, the pentagonal bipyramid efficiently activated B cell in vitro. At 5 nM immunogen concentration, activation levels saturate for both 10 and 40 copies of immunogen and are comparable to or higher than the eOD-GT8-60mer protein nanoparticle reference. At lower immunogen concentrations, the activation level for 10 copies of immunogen is decreased, while the 40 copy DNA nanostructure activates B cells comparably to the eOD-GT8-60mer protein nanoparticle.

Figure 6E:
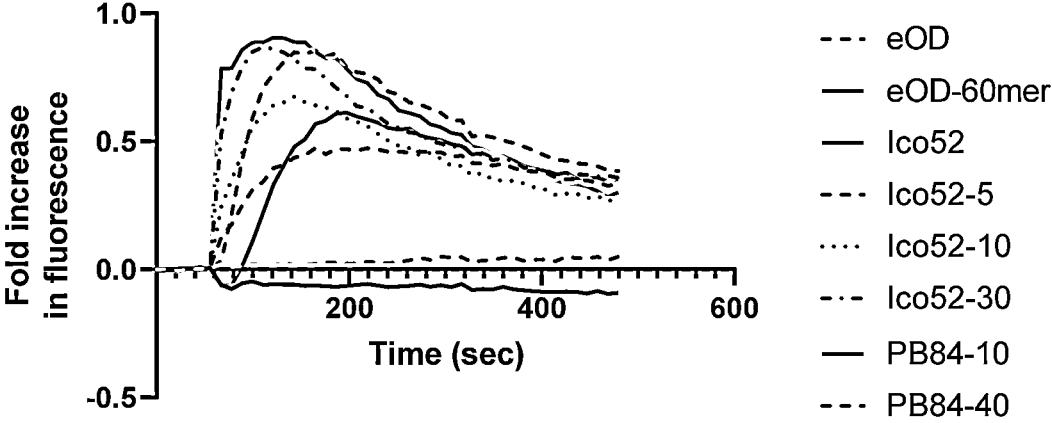
FIG. 6E is a line graph and FIG. 6F is a bar graph showing quantification of B cell (human Ramos cell) activation upon exposure to icosahedral and pentagonal bipyramid DNA NPs modified with eOD-GT8 at 2 nM eOD-GT8. Raw fluorescence of cells loaded with Fluo-4 calcium probe normalized by unstimulated levels, buffer-only control curves (FIGS. 6A, 6C and 6E) and areas under the curves normalized to the maximum in repeat (FIGS. 6B, 6D and 6F) are shown.
Figure 6F:
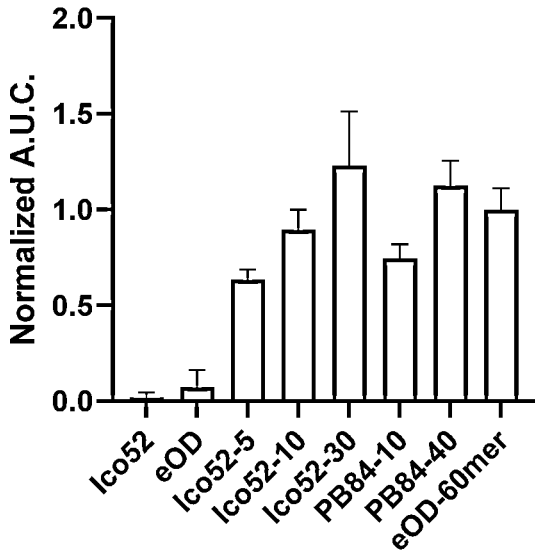

The direct comparison between the pentagonal bipyramidal architecture with the icosahedron at total immunogen concentrations of 2 nM revealed that the latter activates B cells more efficiently in vitro (FIGS. 6E and F). Activation at both low (10 copies) and high (30 and 40 copies) valency are increased for the icosahedral architecture. While results for nanostructures with different copy numbers are difficult to compare, in part due to different nanostructure concentrations in the experiment, an assessment of inter-immunogen distance histograms for 10 copy nanostructures for the icosahedron and pentagonal bipyramid is helpful to interpret these observations. The distance histograms reveal that the distribution is skewed towards larger values for both minimal and maximal distances in case of the icosahedron (FIGS. 6G and 6H). This correlates with stronger activation and is in accordance with the observations made in Examples 1 to 3.

The results indicate that icosahedral architectures are superior to pentagonal bipyramidal architectures for immunogen presentation.

Example 6: Peptide Immunogen Presentation on Nucleic Acid Nanostructures is Comparable to Liposomal Formulations Methods and Materials Experimental procedures are identical to those described under Examples 1 and 6 with the following additions and modifications.

Chemicals and Kits

Peptide-PNA-Alexa Fluor 647 conjugates were obtained from PNA Bio. Peptides for conjugation to liposomes were obtained from GenScript.

Liposome Synthesis

Lipids 1,2-dioleoyl-sn-glycero-3-phosphocholine (DOPC), 1,2-dimyristoyl-sn-glycero-3-phosphocholine (DMPC), 1,2-dioleoyl-sn-glycero-3-phospho-(1'-rac-glycerol) (DOPG), 1,2-distearoyl-sn-glycero-3-phosphoethanolamine-N-[maleimide(polyethylene glycol)-2000] (PEG-DSPE-mal), and monophosphoryl lipid A (MPLA) were obtained from Avanti Polar Lipids. Peptide-conjugated liposomes were prepared as previously described with some modifications (see Tokatlian et al., Enhancing Humoral Responses Against HIV Envelope Trimers via Nanoparticle Delivery with Stabilized Synthetic Liposomes. *Scientific Reports* 8, (2018)). Unilamellar liposomes formed of DOPC:DMPC:DOPG:PEG-DPSE-mal:MPLA lipids in a 37.8:37.8:18.9:5:0.5 molar ratio were synthesized by lipid film rehydration and membrane extrusion using a 100 nm membrane, followed by post-synthesis binding of cysteine-terminated peptides for 2 hours at room temperature in PBS. Unconjugated peptide was removed via dialysis using 10 kDa cutoff membranes in 1 L PBS baths with three bath exchanges over 36 hours. Liposome size and uniformity was assessed via dynamic light scattering, and peptide conjugation was quantified via tryptophan fluorescence.

Antigens and Cell Lines

Peptide sequences were chosen from a previously reported set of H-2K$^k$ MHC class I-derived molecules which can induce HIV antigen-specific B cell responses (see Kouskoff, et al, *Journal of Experimental Medicine*, 188(8): 1453-64 (1998)). In particular, one high-affinity peptide, p31, and one intermediate affinity peptide, p5, were chosen. Peptides were C-terminally conjugated to the PNA sequence using an amide-DEG linker. The PNA sequence itself bears a C-terminal AF647 label that enables the validation of copy number on the DNA nanostructures. Peptide-PNA-Alexa Fluor 647 conjugates were dissolved in DMF:H$_2$O such that the final DMF concentration during hybridization of the PNA to the overhang staple on the nucleic acid nanostructure was less than 5%.

Primary 3-83 splenocytes were obtained from NOD.D2 (B10)-Tg(Igh2$^k$3-83)1Nemz/Dvs mice (The Jackson Laboratory). This mouse strain produces only a single B cell receptor with known specificity for a series of previously defined peptide antigens (see Kouskoff, et al, *Journal of Experimental Medicine*, 188(8):1453-64 (1998)).

B Cell Calcium Flux Assay

Primary 3-83 splenocytes at a concentration of 10 million cells/mL were incubated with 10 μM Fluo-4 AM (Thermo Fisher) for 30 minutes at 37 C. After washing once, flux assays were performed on a Teican plate reader at 37 C on a 96 well microplate. 160 μL of Fluo-4 labeled 3-83 cells at 2 million cells/mL was added to each well. A baseline fluorescence was then recorded for 1 minute, and 40 μL of nanoparticles were added to the cells for a final concentration of 1 nM of antigen, unless otherwise stated.

Results

Purity, structural integrity, immunogen copy number and monodispersity were characterized for both the icosahedron and the pentagonal bipyramid as described under Examples 1 and 5. Both the pentagonal bipyramid functionalized with 45 copies of the high-affinity peptide p31 and the intermediate-affinity peptide p5 efficiently activated 3-83 cells in vitro compared to the liposome reference. Notably, the activation kinetics are faster for the nucleic acid nanostructures and resemble those observed for the presentation of eOD-GT8 antigens on nucleic acid and protein nanostructures, corroborating the proposed favorable effect of rigid presentation. Furthermore, the high-affinity peptide p31 displayed stronger activation compared to p5. Overall, these results demonstrate the suitability of the DNA origami platform for presentation of different classes of antigens including both proteins and peptides. See, e.g., FIGS. 7A and 7B.

Example 7: Probing and Programming Innate Immune Stimulation with 3D Wireframe DNA Origami The immunological properties of unmodified 3D wireframe origami NANPs were demonstrated by first examining the effects of NANP geometry and structuring on isolated immune pathways using reporter cell lines expressing TLR9 and cGAS-STING, and subsequently assessing cytokine induction in human PBMCs. The relative impacts of immunostimulatory motif valency and spatial distancing on immune pathway activation were assessed by presenting discrete copy numbers of CpG oligos at precise locations on DNA NANPs and evaluating the effects of these design parameters on the magnitude of TLR9 activation and interferon production.

Methods and Materials

Scaffold Synthesis.

The circular ssDNA scaffolds used to fold all variants of a pentagonal bipyramid with 84 base pairs per edge (PB84) and an icosahedron with 42 base pairs per edge (ICO42), were produced using the methods described above, using a method of bacterial production (Shepherd, et al., *Scientific Reports*, 9 (1), 6121 (2019)). *E. coli* SS320 cells (Lucigen) containing the circular phagemid comprising the target scaffold sequence and a M13cp helper plasmid, were grown overnight in 25 mL 2×YT broth supplemented with 100 ug/mL ampicillin (Sigma-Aldrich, cat. Code A5354-10ML), 15 μg/mL chloramphenicol (Sigma-Aldrich, cat. Code C0378-25G) and 5 μg/mL tetracycline (Sigma-Aldrich, cat. Code T7660) in a 200 mL flask shaken at 200 RPM at 37 C. After 16 hours, the overnight was diluted to an OD600 of 0.05 in 2×YT broth containing the same supplements and grown for 8 hours at 200 RPM at 37 C.

Scaffold Purification

Bacterial cultures were centrifuged at 4,000×g for 30 minutes at 4 C, transferred into a clean bottle, and subjected to an identical centrifugation step. The clarified supernatant was then filtered with a 0.45 μm cellulose acetate filter (Sigma-Aldrich, cat. Code CLS430516-12EA), poured into a sterile 750 mL bottle along with 6% w/v PEG-8000 (Sigma-Aldrich, cat. Code P2139-500G) and 3% w/v NaCl and stirred continuously for 16 hours at 4 C. Following PEG precipitation, phage was harvested by centrifuging the solution at 20,000×g for 30 hours at 4 C and discarding the supernatant. The phage-containing pellet was then processed using an Endofree Plasmid Giga Kit (Qiagen, cat. Code 12391), with the following adjustments: a final concentration of 20 ug/mL Proteinase K was added to Buffer P1, and the solution was incubated at 37 C for 1 hour prior to addition of Buffer P2. Following Buffer P2 addition, the solution was heated to 70 C for 10 minutes and allowed to cool back to room temperature before proceeding with the rest of the standard protocol. Finally, after addition of Buffer ER, 200 mL of 100% ethanol was added to improve ssDNA binding. All remaining steps are left unchanged. The concentration of purified ssDNA was determined by measuring absorbance at 280 nm using a Nanodrop, and the purity of the sample was evaluated by running it on a 1% agarose gel in 1×TAE stained with SybrSafe. A quantitative measure of sample endotoxin level was determined using Endosafe LAL cartridges with the Endosafe nexgen-PTS system, and Rapid single-test LAL vials (Charles River Laboratories) were used to establish qualitatively whether sample endotoxin levels were below a pre-specified threshold. Both endotoxin assays were performed according to manufacturer protocols.

Endotoxin Purification

In the cases when additional endotoxin purification was needed, chilled 10% v/v Triton X-114 was added to the sample to a final concentration of 2% v/v Triton X-114. The sample was placed on a rocker at 4 C for 30 minutes, then transferred to a rocker at 37 C for 5 minutes. Lastly, the sample was centrifuged at 30,790×g for 30 minutes at 37 C. The sample was then carefully removed from the centrifuge and the top layer of the phase-separated sample was gently pipetted into an endotoxin-free microcentrifuge tube. This process was repeated until sample endotoxin levels were below the desired threshold for subsequent assays.

Synthesis and Purification of DNA NANPs

NANPs were designed using DAEDALUS, with modifications to add ssDNA overhangs being carried out in Tiamat or UCSF Chimera. Briefly, to design inward- or outward-facing overhangs, the locations of nick positions were shifted by the required number of bases to ensure that the 3' ends of staples would be pointing perpendicularly inward or outward with respect to the center of the nanostructure. No additional nicks were created and all new nick positions were located such that at least 8 bases separated the nick position from the location of the nearest crossover. The modified NANP designs were exported into Excel, and the staples chosen to be functionalized with ssDNA overhangs were extended by concatenating the sequence of the overhang to the 3' end of the existing staple sequence (see Tables 1-11). To fold NANPs, a circular exact size bacterially produced ssDNA scaffold was mixed with a 5× excess of ssDNA staples, 1×TAE, 12 mM MgCl2, and nuclease-free water, and folded through a 13 hour thermal annealing process in which the temperature was gradually ramped down from 95 C to 25 C as described in previous literature (Veneziano, et al., *Science*, 352 (6293), 1534-1534 (2016)). To remove the excess staples and buffer exchange into sterile PBS, nanostructures were pipetted into Amicon Ultra 100 kDa MWCO centrifugal filters (Sigma-Aldrich, cat. Code UFC810024) and spun at 1,000×g for 30 minutes at room temperature for up to 5 rounds. In between each round, the flow-through was discarded and additional PBS was added. Staples were purchased through Integrated DNA Technologies (IDT) or synthesized in-house using a Dr. Oligo synthesizer following the recommended protocol and purified using a size exclusion column with a Waters HPLC. Phosphoramidites for in-house synthesis of the phosphorothioated CpG overhang containing staples (see Tables 1-11) were ordered from Glen Research.

The nucleic acid scaffold sequence used in the fabrication of DNA nanoparticles is:

(SEQ ID NO: 5)
GAGCGCAACGCAATTAATGTGCGCCCTGATGCGGCGCATTAAGCGCGGC

GGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCC

GCTTTCCCCGTCAAGCTCTAAATCGGGGGCTCCCTTTAGGGTTCCGATT

TAGTGCTTTACGGCACCTCGACCCCAAAAAACTTGATTAGGGTGATGGT

TCACGTAGTGGGCCATCGCCCTGATAGACGGTTTTTCGCCCTTTGACGT

TGGAGTCCACGTTCTTTAATAGTGGACTCTTGTTCCAAACTGGAACAAC

ACTCAACCCTATCTCGGTCTATTCTTTTGATTTATAAGGGATTTTGCCG

ATTTCGGCCTATTGGTTAAAAAATGAGCTGATTTAACAAAAATTTAACG

CGAATTACAACGGGGGTACATATGATTGGGGTCTGACGCTCAGTGGAAC

GAAAACTCACGTTAAGGGATTTTGGTCATGAGATCTAAAGTATATATGA

GTAAACTTGGTCTGACAGTTACCAATGCTTAATCAGTGAGGCACCTATC

TCAGCGATCTGTCTATTTCGTTCATCCATAGTTGCCTGACTCCCCGTCG

TGTAGATAACTACGATACGGGAGGGCTTACCATCTGGCCCCAGTGCTGC

AATGATACCGCGAGACCCACGCTCACCGGCTCCAGATTTATCAGCAATA

AACCAGCCAGCCGGAAGGGCGGAGCGCAtAAGTGGTCCTGCAACTTTAT

CCGCCTCCATCCAGTCTATTAATTGTTGCCGGGAAGCTAGAGTAAGTAG

TTCGCCAGTTAATAGTTTGCGCAACGTTGTTGCCATTGCTACAGGCATC

GTGGTGTCACGCTCGTCGTTTGGTATGGCTTCATTCAGCTCCGGTTCCC

AACGATCAAGGCCAGTTACATGATCCCCCATGTTGTGCAAAAAAGCGGT

TAGCTCCTTCGGTCCTCCGATCGTTGTCAGAAGTAAGTTGGCCGCAGTG

TTATCACTCATGGTTATGGCAGCACTGCATAATTCTCTTACTGTCATGC

CATCCGTAAGATGCTTTTCTGTGACTGGTGAGTACTCAACCAAGTCATT

CTGAGAATAGTGTATGCGGCGACCGAGTTGCTCTTGCCCGGCGTCAATA

-continued

CGGGATAATACCGCGCCACATAGCAGAACTTTAAAAGTGCTCATCATTG

GAAAACGTTCTTCGGGGCGAAAACTCTCAAGGATCTTACCGCTGTTGAG

ATCCAGTTCGATGTAACCCACTCGTGCACCCAACTGATCTTCAGCATCT

TTTACTTTCACCAGCGTTTCTGGGTGAGCAAAAACAGGAAGGCAAAATG

CCGCAAAAAAGGGAATAAGGGCGACACGGAAATGTTGAATACTCATACT

CTTCCTTTTTCAATATTATTGAAGCATTTATCAGGGTTATTGTCTCATG

AGCGGATACATATTTGAATGTATTTAGAAAAATAAACAAATAGGGGTTC

CGCGCACATTTCCCCGAAAAGTGCCACCTGACGTCTAAGAAACCATTAT

TATCATGACATTAACCTATAAAAATAGGCGTATCACGAGGCCCTTTCGT

CGAATTCGTCGTCGTCCCCTCAAACTCTTGGGTGGAGAGGCTATTCGTT

TAAGGTCACATCGCATGTAATTTACTTATTCTCTGTTGTTGAGCCACCC

GGGCGCCAGATTTTGTTTAAAGCTTTGTCTCTTAGTTTGTATAGACAGA

TTCAGAGTGCAAGGTTTCGTTCGCTCGTACCTGGTTTTCCCTGGTTCTT

CACAGATAGGATTTGACTTTCTACAACACTTATGCGGCTTCCTACCCGT

TTGAAGGCCGATACAGGTGCTGCGCAAAATGCGGGCGAACATAGAGTAT

CAAAACAACGCCTTCTAATCTAGGAATATAGGGAAGATACGTATTTGCT

ACCATGCTTTCTTGGGTCATTAACGACCAACCTCTTTTCTTTTAAAGTA

GGATTGCACAATGAATGAATACACGTGGTCCGATAACTGACCAAGTAAC

ATGGTTATCACTaGATGTCCGCCAGACGTGTGCAAACCAACCCGGGAGT

TACGTCACTAATCCTTCGCTACGTCGTGAAGATATTTACTTGTGAATAT

CGAGGGTAATAAGATAATAGACTGTGACTAGTATTGCCAGACTGTCGCT

ACCTGCAACACATAACTATCCTGAGGTTACTGCATAGTACTGATTACAC

CCGAGTCAAAATTTCTAACTTCTAACATGTACCTAGTAACCAGCTCAAT

AATTATGTCAGAATATAGCTCTGGGAACCCTCGGACAATTATGATACAC

GGTATTAATATCTTGCTTGCGTTAGCCACTTCTCATCTTTGGATACCGA

TTCTATTTTGCATAGCAGTTCCTTTTACACATATAAGAATTTCGCCATA

GGTATGCTGCAG.

TABLE 4

Staple sequences for unmodified PB84

| Name | Sequence | SEQ ID Number |
|------|----------|---------------|
| PB84_staple2 | ATAAAGTTTTGCGTTGCGCTCCTGCAGCATGGATGGAGGCCGG | SEQ ID NO: 6 |
| PB84_staple3 | TGCGCTCGCCGCTACAGGGCGCACATTAAGCAGGACCACTTA | SEQ ID NO: 7 |
| PB84_staple4 | GCTGGTTTACACCCGCCGCGCTTAATGCGGCCCTTCCGGCTG | SEQ ID NO: 8 |
| PB84_staple5 | GTCACGCTGCGTTTTTCGTAACCACCATTGCTGATAATTTTTATCT GGAGCCCACGACGGGGATTTTTGTCAGGCAAC | SEQ ID NO: 9 |
| PB84_staple6 | GTGTAGCGAGCCGGCGAACGTGGCCAGAAAGGGCGCTGGCAA | SEQ ID NO: 10 |
| PB84_staple7 | CGGGCGCTAGGAAGGGAAGAAAGCAGCTATAT | SEQ ID NO: 11 |
| PB84_staple8 | TCTGACATGTCCGAGGGTTCCCAGGAAAGGAG | SEQ ID NO: 12 |
| PB84_staple9 | CATTGGTAACTTTTTTGTCAGACCAAGATTTAGAGCTTTTTTTGACGGGGAA | SEQ ID NO: 13 |
| PB84_staple10 | TACTTTAGGGAACCCTAAAGGGAGCCCCCGTTTACTCATATA | SEQ ID NO: 14 |

TABLE 4-continued

Staple sequences for unmodified PB84

| Name | Sequence | SEQ ID Number |
|------|----------|---------------|
| PB84_staple11 | TTCATTTTGGTGCCGTAAAGCACTAAATCATTGATTTAAAAC | SEQ ID NO: 15 |
| PB84_staple12 | TCTAGGTGAATCAAGTTTTTTGGGGTCGATAATTTAAAAGGA | SEQ ID NO: 16 |
| PB84_staple13 | GTTGAGTGTTGTTTTTTTCCAGTTTGCACTACGTGAATTTTTCCATCACCCT | SEQ ID NO: 17 |
| PB84_staple14 | CGATGGCCGAACAAGAGTCCACTATTAAACCGTCTATCAGGG | SEQ ID NO: 18 |
| PB84_staple15 | GCGAAAAAGAACGTGGACTCCAACAATCAGTA | SEQ ID NO: 19 |
| PB84_staple16 | CTATGCAGATTTTGACTCGGGTGTGTCAAAGG | SEQ ID NO: 20 |
| PB84_staple17 | GAGATAGGATCAGCTCATTTTTTAACCAAAAAAGAATAGACC | SEQ ID NO: 21 |
| PB84_staple18 | TATAAATCTAGGCCGAAATCGGCATGTTGTAG | SEQ ID NO: 22 |
| PBS4_staple19 | AAAGTCAATAGGAAGCCGCATAAGAAATCCCT | SEQ ID NO: 23 |
| PB84_staple20 | AAGATCCTTTTTTTTTTGATAATCTCTTCGCGTTAAATTTTTTTTTGTTAA | SEQ ID NO: 24 |
| PB84_staple21 | GGTTGTAAATGACCAAAATCCCTTAACGTTCATATGTACCCC | SEQ ID NO: 25 |
| PB84_staple22 | GACCCCAAGAGTTTTCGTTCCACTCCCGTATT | SEQ ID NO: 26 |
| PB84_staple23 | GACGCCGGTGTGGCGCGGTATTATGAGCCGTCA | SEQ ID NO: 27 |
| PBS4_staple24 | ACTGATTAAGTATGGATGAA | SEQ ID NO: 28 |
| PB84_staple25 | GGTGCCTCCGAAATAGACAGATCGAAAAGCAT | SEQ ID NO: 29 |
| PB84_slaple26 | CTTACGGATACTCACCAGTCACAGCTGAGATA | SEQ ID NO: 30 |
| PB84_staple27 | GTTATCTAGGTGAGCGTGGGTCTCGCGGTCTCCCGTATCGTA | SEQ ID NO: 31 |
| PB84_staple28 | GGTAAGCCATCATTGCAGCACTGGAACCGGAG | SEQ ID NO: 32 |
| PB84_staple29 | CTGAATGACSCCTTGATCGTTGGGGGCCAGAT | SEQ ID NO: 33 |
| PB84_staple30 | TCCCGGCAACATTTTTATTAATAGACTACCTATGGCGTTTTTAAATTCTTAT | SEQ ID NO: 34 |
| PB84_staple31 | AATGTGCGGGCGAACTACTTACTCTAGCTCACTTTTCGGGGA | SEQ ID NO: 35 |
| PB84_staple32 | TGTTTATTACGTTGCGCAAACTATTAACTCGGAACCCCTATT | SEQ ID NO: 36 |
| PB84_staple33 | TCAAATATATGCCTGTAGCAATGGCAACATTTCTAAATACAT | SEQ ID NO: 37 |
| PB84_staple34 | AACGACGAGCGTTTTTTGACACCACGGTATCCGCTCATTTTTTGAGACAATA | SEQ ID NO: 38 |
| PB84_staple35 | AGCCATACCATCATGTAACT | SEQ ID NO: 39 |
| PB84_staple36 | CATTTCCGTGTTTTTTCGCCCTTATTTTTTTTGCACATTTTTACATGGGGGA | SEQ ID NO: 40 |
| PB84_staple37 | CATTTTGCAGGACCGAAGGAGCTAACCGCCCCTTTTTTGCGG | SEQ ID NO: 41 |
| PB84_staple38 | CTCACCCACTTACTTCTGACAACCATCGGCTTCCTGTTTTTTG | SEQ ID NO: 42 |
| PB84_staple39 | AAGTAAAAGAGTGATAACACTGCGGCCAAGAAACCCTGGTGA | SEQ ID NO: 43 |
| PB84_staple40 | CTCGGTCGCCGTTTTTCATACACTATATGCAGTGCTGTTTTTCCATAACCAT | SEQ ID NO: 44 |
| PB84_staple41 | AGAGAATTTCTCAGAATGACTTGGTTGAGTGGCATGACAGTA | SEQ ID NO: 45 |
| PB84_staple42 | GCAAGAGCAAAGTTCTGCTA | SEQ ID NO: 46 |
| PB84_staple43 | GATGCTGAAGATTTTTTCAGTTGGGTTCCAATGATGATTTTTGCACTTTTAA | SEQ ID NO: 47 |
| PB84_staple44 | GAACGTTTGCACGAGTGGGTTACATCGAATTTTCGCCCCGAA | SEQ ID NO: 48 |
| PB84_staple45 | CTTGAGAGCTGGATCTCAACAGCCTGAATCTG | SEQ ID NO: 49 |
| PB84_staple46 | TCTATACAACGAAACCTTGCACTCGTAAGATC | SEQ ID NO: 50 |
| PB84_staple47 | GAGTATTCAAACCCTGATAA | SEQ ID NO: 51 |
| PB84_staple48 | AAGAGTATATGCTTCAATAATATTACATGCGA | SEQ ID NO: 52 |

TABLE 4-continued

Staple sequences for unmodified PB84

| Name | Sequence | SEQ ID Number |
|---|---|---|
| PB84_staple49 | TGTGACCTAGAGAATAAGTAAATTGAAAAAGG | SEQ ID NO: 53 |
| PB84_staple50 | TTATCGGACCATTTTTCGTGTATTCAGGTTTCTTAGATTTTTCGTCAGGTGG | SEQ ID NO: 54 |
| PB84_staple51 | CCTACTTTGGTTAATGTCATGATAATAATTTCATTGTGCAAT | SEQ ID NO: 55 |
| PB84_staple52 | TTGGTCGTCGTGATACGCCTATTTTTATAAAAAGAAAAGAGG | SEQ ID NO: 56 |
| PB84_staple53 | AAGCATGGACGAATTCGACGAAAGGGCCTTAATGACCCAAGA | SEQ ID NO: 57 |
| PB84_staple54 | CAAAGCTTTAATTTTTACAAAATCTGCAAGAGTTTGATTTTTGGGGACGAC GTAGCAAATACGTTTTTTATCTTTCCCT | SEQ ID NO: 58 |
| PB84_staple55 | TCTTCCACCGCGCCCGGGTGGCTCAACAACTAAACGAATAGCC | SEQ ID NO: 59 |
| PB84_staple56 | AACTAAGAGAGTACGAGCGA | SEQ ID NO: 60 |
| PB84_staple57 | TGCGCAGCACCTTTTTTGTATCGGCCTGAAGAACCAGTTTTTGGAAAACCAG | SEQ ID NO: 61 |
| PB84_staple58 | ATCCTATCTGTTCAAACGGG | SEQ ID NO: 62 |
| PBS4_staple59 | GCCCGCATTTATATTCCTAG | SEQ ID NO: 63 |
| PB84_staple60 | CTATGTTCATTAGAAGGCGTTGTTATTACCCT | SEQ ID NO: 64 |
| PB84_staple61 | CGATATTCCACAGTCTATTATCTTTTGATACT | SEQ ID NO: 65 |
| PB84_staple62 | ACTGCTATATAACCATGTTACTTGGTCAGATGTGTAAAAGGA | SEQ ID NO: 66 |
| PB84_staple63 | GGTATCCAACGTCTGGCGGACATCTAGTGGCAAAATAGAATC | SEQ ID NO: 67 |
| PB84_staple64 | GCTAACGCAACTCCCGGGTTGGTTTGCACAAGATGAGAAGTG | SEQ ID NO: 68 |
| PB84_staple65 | GTAGCGAAGGATTTTTTTAGTGACGTAAGCAAGATATTTTTTTAATACCGTG | SEQ ID NO: 69 |
| PB84_staple66 | TTCACGACCGACAGTCTGGCAATACTAGTACAAGTAAATATC | SEQ ID NO: 70 |
| PB84_staple67 | CTGGTTACTAGTTTTTGTACATGTTAATAGTTATGTGTTTTTTTGCAGGTAG | SEQ ID NO: 71 |
| PB84_staple68 | TAACCTCAGGGAAGTTAGAA | SEQ ID NO: 72 |
| PB84_staple69 | AATTATTGAGTATCATAATT | SEQ ID NO: 73 |

TABLE 5

STaple sequences for PB84 including CpG motifs

| Name | Sequence | SEQ ID NO: |
|---|---|---|
| PB84_CpG_motiftest_staple2v1 | ATAAAGTTTTGCGTTGCGCTCCTGCAGCATGGATGGAGGCGGTGGCATTGT ACCATTCTAAGGCTA | 74 |
| PB84_CpG_motifiest_staple7v1 | CGGGCGCTAGGAAGGGAAGAAAGCAGCTATATTGGCATTGTACCATTCTAA GGCTA | 75 |
| PB84_CpG_motiftest_stale12v1 | TCTAGGTGAATCAAGTTTTTTGGGGTCGATAATTTAAAAGGATGGCATTGTA CCATTCTAAGGCTA | 76 |
| PB84_CpG_motiftest_staple17v1 | GAGATAGGATCAGCTCATTTTTTAACCAAAAAAGAATAGACCTGGCATTGTA CCATTCTAAGGCTA | 77 |
| PB84_CpG_motiftest_staple28v1 | GGTAAGCCATCATTGCAGCACTGGAACCGGAGTGGCATTGTACCATTCTAA GGCTA | 78 |
| PB84_CpG_motiftest_staple41v1 | AGAGAATTTCTCAGAATGACTTGGTTGAGTGGCATGACAGTATGGCATTGT ACCATTCTAAGGCTA | 79 |
| PB84_CpG_motiftest_staple44v1 | GAACGTTTGCACGAGTGGGTTACATCGAATTTTCGCCCCGAATGGCATTGT ACCATTCTAAGGCTA | 80 |
| PB84_CpG_mofifiest_staple49v1 | TGTGACCTAGAGAATAAGTAAATTGAAAAAGGTGGCATTGTACCATTCTAAG GCTA | 81 |

TABLE 5-continued

| Name | Sequence | SEQ ID NO: |
|---|---|---|
| PB84_CpG_motiftest_staple51v1 | CCTACTTTGGTTAATGTCATGATAATAATTTCATTGTGCAATTGGCATTGTAC CATTCTAAGGCTA | 82 |
| PB84_CpG_motiftest_staple66v1 | TTCACGACCGACAGTCTGGCAATACTAGTACAAGTAAATATCTGGCATTGTA CCATTCTAAGGCTA | 83 |
| PB84_CpG motifiest_staple2v2 | ATAAAGTTTTGCGTTGCGCTCCTGCAGCATGGATGGAGGCGCGTGGCATTGT ACCATTCTTTGTCGTT | 84 |
| PB84_CpG_motiftest_staple7v2 | CGGGCGCTAGGAAGGGAAGAAAGCAGCTATATTGGCATTGTACCATTCTTT GTCGTT | 85 |
| PB84_CpG_motiftest_staple12v2 | TCTAGGTGAATCAAGTTTTTTGGGGTCGATAATTTAAAAGGATGGCATTGTA CCATTTCTTTGTCGTT | 86 |
| PB84_CpG motifiest_staple17v2 | GAGATAGGATCAGCTCATTTTTTAACCAAAAAAAGAATAGACCTGGCATTGTA CCATTCTTTGTCGTT | 87 |
| PB84_CpG_motiftest_staple28v2 | GGTAAGCCATCATTGCAGCACTGGAACCGGAGTGGCATTGTACCATTCTTT GTCGTT | 88 |
| PB84_CpG_motifiest_staple41v2 | AGAGAATTTCTCAGAATGACTTGGTTGAGTGGCATGACAGTATGGCATTGT ACCATTCTTTGTCGTT | 89 |
| PB84_CpG_motiftest_staple44v2 | GAACGTTTGCACGAGTGGGTTACATCGAATTTTCGCCCCGAATGGCATTGT ACCATTCTTTGTCGTT | 90 |
| PB84_CpG_motiftest_staple49v2 | TGTGACCTAGAGAATAAGTAAATTGAAAAGGTGGCATTGTACCATTCTTTG TCGTT | 91 |
| PB84_CpG_motiftest staple51v2 | CCTACTTTGGTTAATGTCATGATAATAATTTCATTGTGCAATTGGCATTGTAC CATTCTTTGTCOGTT | 92 |
| PB84_CpG_motiftest_staple66v2 | TTCACGACCGACAGTCTGGCAATACTAGTACAAGTAAATATCTGGCATTGTA CCATTCTTTTGTCGTT | 93 |
| PB84_CpG_motfest_staple2v3 | ATAAAGTTTTGCGTTGCGCTCCTGCAGCATGGATGGAGGCGGTGGCATTGT TGTGGTTTTAGGCTA | 94 |
| PB84_CpG_motiftest_staple7v3 | CGGGCGCTAGGAAGGGAAGAAAGCAGCTATATTGGCATTGTTTGTCGTTTTA GGCTA | 95 |
| PB84_CpG_motiftest_staple12v3 | TCTAGGTGAATCAAGTTTTTTGGGGTCGATAATTTAAAAGGATGGCATTTGTT GTCGTTTTAGGCTA | 96 |
| PB84_CpG_motiftest_staple17v3 | GAGATAGGATCAGCTCATTTTTTAACCAAAAAAGAATAGACCTGGCATTGTT GTCGTTTTAGGCTA | 97 |
| PB84_CpG_motifiest_staple28v3 | GGTAAGCCATCATTGCAGCACTGGAACCGGAGTGGCATTGTTGTCGTTTTA GGCTA | 98 |
| PB84_CpG_motiftest_staple41v3 | AGAGAATTTCTCAGAATGACTTGGTTGAGTGGCATGACAGTATGGCATTGT TGTCGTTTTAGGCTA | 99 |
| PB84_CpG_motiftest_stapled44v3 | GAACGTTTGCACGAGTGGGTTACATCGAATTTTCGCCCCGAATGGCATTGT TGTCGTTTTAGGCTA | 100 |
| PB84_CpG_motifiest_staple49v3 | TGTGACCTAGAGAATAAGTAAATTGAAAAGGTGGCATTGTTGTCGTTTTAG GCTA | 101 |
| PB8B4_CpG _motiftest_staple51v3 | CCTACTTTGGTTAATGTCATGATAATAATTTCATTGTGCAATTGGCATTGTTG TCGTTTTAGGCTA | 102 |
| PB84_CpG_motiftest_staple66v3 | TTCACGACCGACAGTCTGGCAATACTAGTACAAGTAAATATCTGGCATTGTT GTCGTTTTAGGCTA | 103 |
| PB84_CpG_motiftest_staple2v4 | ATAAAGTTTTGCGTTGCGCTCCTGCAGCATGGATGGAGGCGGTCGTCGTTT TCCATTCTAAGGCTA | 104 |
| PB84_CpG_motiftest_staple7v4 | CGGGCGCTAGGAAGGGAAGAAAGCAGCTATATTCGTCGTTTTCCATTCTAA GGCTA | 105 |
| PB84_CpG_motiftest_staple12v4 | TCTAGGTGAATCAAGTTTTTTGGGGTCGATAATTTAAAAGGATCGTCGTTTT CCATTCTAAGGCTA | 106 |

TABLE 5-continued

| | STaple sequences for PB84 including CpG motifs | |
|---|---|---|
| Name | Sequence | SEQ ID NO: |
| PB84_CpG_moliftest_staple17v4 | GAGATAGGATCAGCTCATTTTTTAACCAAAAAAGAATAGACCTCGTCGTTTT CCATTCTAAGGCTA | 107 |
| PBB84_CpG_motifiest_staple28v4 | GGTAAGCCATCATTGCAGCACTGGAACCGGAGTCGTCGTTTTCCATTCTAA GGCTA | 108 |
| PB84_CpG_motifest_stapled41v4 | AGAGAATTTCTCAGAATGACTTGGTTGAGTGGCATGACAGTATCGTCGTTTT CCATTCTAAGGCTA | 109 |
| PB84_CpG_motiftest_staple44v4 | GAACGTTTGCACGAGTGGGTTACATCGAATTTTCGCCCCGAATCGTCGTTT TCCATTCTAAGGCTA | 110 |
| PB84_CpG_motiftest_staple49v4 | TGTGACCTAGAGAATAAGTAAATTGAAAAAGGTCGTCGTTTTCCATTCTAAG GCTA | 111 |
| PB84_CpG_motiftest_staple51v4 | CCTACTTTGGTTAATGTCATGATAATAATTTCATTGTGCAATTCGTCGTTTTC CATTTCTAAGGCTA | 112 |
| PB84_CpG_motiftest_staple66v4 | TTCACGACCGACAGTCTGGCAATACTAGTACAAGTAAATATCTCGTCGTTTT CCATTCTAAGGCTA | 113 |
| PB84_CpG_motiftest_staple2v5 | ATAAAGTTTTGCGTTGCGCTCCTGCAGCATGGATGGAGGCGGTGGCATTGT TGTCGTTTTGTCGTT | 114 |
| PB84_CpG_motiftest_staple7v5 | CGGGCGCTAGGAAGGGAAGAAAGCAGCTATATTGGCATTGTTGTCGTTTTC TCGTT | 115 |
| PB84_CpG_motiftest_staple12v5 | TCTAGGTGAATCAAGTTTTTTGGGGTCGATAATTTAAAAGGATGGCATTGTT GTCGTTTTGTCGTT | 116 |
| PB84_CpG_motiftest_staple17v5 | GAGATAGGATCAGCTCATTTTTTAACCAAAAAAGAATAGACCTGGCATTGTT GTCGTTTTGTCGTT | 117 |
| PB84_CpG_motiftest_staple28v5 | GGTAAGCCATCATTGCAGCACTGGAACCGGAGTGGCATTGTTGTCGTTTTG TCGTT | 118 |
| PB84_CpG_motiftest_staple41v5 | AGAGAATTTCTCAGAATGACTTGGTTGAGTGGCATGACAGTATGGCATTGT TGTCGTTTTGTCGTT | 119 |
| PB84_CpG_motiftest_staple44v5 | GAACGTTTGCACGAGTGGGTTACATCGAATTTTCGCCCCGAATGGCATTGT TGTCGTTTTTGTCGTT | 120 |
| PB84_CpG_motiftest_staple49v5 | TGTGACCTAGAGAATAAGTAAATTGAAAAAGGTGGCATTGTTGTCGTTTTGT CGTT | 121 |
| PB84_CpG_motiftest_staple51v5 | CCTACTTTGGTTAATGTCATGATAATAATTTCATTGTGCAATTGGCAT-TTGTTG TCGTTTTGTCGTT | 122 |
| PB84_CpG_motiftest_staple66v5 | TTCACGACCGACAGTCTGGCAATACTAGTACAAGTAAATATCTGGCATTGTT GTCGTTTGTCGTT | 123 |
| PB84_CpG_motiftest_staple2v6 | ATAAAGTTTTGCGTTGCGCTCCTGCAGCATGGATGGAGGCGGTCGTCGTTT TGTCGTTTTAGGCTA | 124 |
| PB84_CpG_motiftest_staple7v6 | CGGGCGCTAGGAAGGGAAGAAAGCAGCTATATTCGTCGTTTTGTCGTTTTA GGCTA | 125 |
| PB84_CpG_motiftest_staple12v6 | TCTAGGTGAATCAAGTTTTTTGGGGTCGATAATTTAAAAGGATCGTCGTTTT GTCGTTTTAGGCTA | 126 |
| PB84_CpG_motiftest_staple17v6 | GAGATAGGATCAGCTCATTTTTTAACCAAAAAAGAATAGACCTCGTCGTTTT GTCGTTTTAGGCTA | 127 |
| PB84_CpG_motiftest_staple28v6 | GGTAAGCCATCATTGCAGCACTGGAACCGGAGTCGTCGTTTTGTCGTTTTA GGCTA | 128 |
| PB84_CpG_molifiest_staple41v6 | AGAGAATTTCTCAGAATGACTTGGTTGAGTGGCATGACAGTATCGTCGTTTT GTCGTTTTAGGCTA | 129 |
| PB84_CpG_motiftest_staed44v6 | GAACGTTTGCACGAGTGGGTTACATCGAATTTTCGCCCCGAATCGTCGTTT TGTCGTTTTAGGCTA | 130 |
| PB84_CpG_motiftest_stapled49v6 | TGTGACCTAGAGAATAAGTAAATTGAAAAAGGTCGTCGTTTTGTCGTTTTAG GCTA | 131 |

TABLE 5-continued

STaple sequences for PB84 including CpG motifs

| Name | Sequence | SEQ ID NO: |
|------|----------|------------|
| PB84_CpG_motiftest_staple51v6 | CCTACTTTGGTTAATGTCATGATAATAATTTCATTGTGCAATTCGTCGTTTTG TCGTTTTAGGCTA | 132 |
| PB84_CpG_motiftest_staple66v6 | TTCACGACCGACAGTCTGGCAATACTAGTACAAGTAAATATCTCGTCGTTTT GTCGTTTTAGGCTA | 133 |
| PB8B4_CpG_motiftest_staple2v7 | ATAAAGTTTTGCGTTGCGCTCCTGCAGCATGGATGGAGGCGGTCGTCGTTT TCCATTCTTGTCGTT | 134 |
| PB84_CpG_motiftest_staple7v7 | CGGGCGCTAGGAAGGGAAGAAAGCAGCTATATTCGTCGTTTTCCATTCTTG TCGTT | 135 |
| PB84_CpG_motiftest_staple12v7 | TCTAGGTGAATCAAGTTTTTTGGGGTCGATAATTTAAAAGGATCGTCGTTTT CCATTCTTGTCGTT | 136 |
| PB84_CpG_motiftest_staple17v7 | GAGATAGGATCAGCTCATTTTTTAACCAAAAAAGAATAGACCTCGTCGTTTT CCATTCTTGTCGTT | 137 |
| PB84_CpG_motiftest_staple28v7 | GGTAAGCCATCATTGCAGCACTGGAACCGGAGTCGTCGTTTTTCCATTCTTG TCGTT | 138 |
| PBS4_CpG_motiftest_staple41v7 | AGAGAATTTCTCAGAATGACTTGGTTGAGTGGCATGACAGTATCGTCGTTTT CCATTCTTGTCGTT | 139 |
| PB84_CpG_motiftest_staple44v7 | GAACGTTTGCACGAGTGGGTTACATCGAATTTTCGCCCCGAATCGTCGTTT TCCATTCTTGTCGTT | 140 |
| PB84_CpG_motiftest_stapled49v7 | TGTGACCTAGAGAATAAGTAAATTGAAAAAGGTCGTCGTTTTCCATTCTTGT CGTT | 141 |
| PB84_CpG_motiftest_staple51v7 | CCTACTTTGGTTAATGTCATGATAATAATTTCATTGTGCAATTCGTCGTTTTC CATTCTTGTCGTT | 142 |
| PB84_CpG_motiftest_staple66v7 | TTCACGACCGACAGTCTGGCAATACTAGTACAAGTAAATATCTCGTCGTTTT CCATTCTTGTCGTT | 143 |
| PB84_CpG_motiftest_staple2v8 | ATAAAGTTTTGCGTTGCGCTCCTGCAGCATGGATGGAGGCGGTCGTCGTTT TGTCGTTTTGTCGTT | 144 |
| PB84_CpG_motiftest_staple7v8 | CGGGCGCTAGGAAGGGAAGAAAGCAGCTATATTCGTCGTTTTGTCGTTTTG TCGTT | 145 |
| PB84_CpG_moliftest_staple12v8 | TCTAGGTGAATCAAGTTTTTTGGGGTCGATAATTTAAAAGGATCGTCGTTTT GTCGTTTGTCGTT | 146 |
| PB84_CpG_motiftest_staple17v8 | GAGATAGGATCAGCTCATTTTTTAACCAAAAAAGAATAGACCTCGTCGTTTT GTCGTTTTGTCGTT | 147 |
| PB84_CpG_motiftest_staple28v8 | GGTAAGCCATCATTGCAGCACTGGAACCGGAGTCGTCGTTTTGTCGTTTTG TCGTT | 148 |
| PB84_CpG_motiftest_staple41v8 | AGAGAATTTCTCAGAATGACTTGGTTGAGTGGCATGACAGTATCGTCGTTTT GTCGTTTGTCGTT | 149 |
| PB84_CpG_motiftest_staple44v8 | GAACGTTTGCACGAGTGGGTTACATCGAATTTTCGCCCCGAATCGTCGTTT TGTCGTTTTGTCGTT | 150 |
| PB84_CpG_motiftest_staple49vB | TGTGACCTAGAGAATAAGTAAATTGAAAAAGGTCGTCGTTTTGTCGTTTTGT CGTT | 151 |
| PB84_CpG_motiftest_staple51v8 | CCTACTTTGGTTAATGTCATGATAATAATTTCATTGTGCAATTCGTCGTTTTG TCGTTTTGTCGTT | 152 |
| PB84_CpG_motiftest_staple66v8 | TTCACGACCGACAGTCTGGCAATACTAGTACAAGTAAATATCTCGTCGTTTT GTCGTTTTGTCGTT | 153 |

TABLE 6

Staple sequences for PB84 including outward facing CpG motifs
PB84, CpG containing, Outward facing.

| Name | Sequence | |
|---|---|---|
| PB84_CpG_out_staple2 | ATAAAGTTTTGCGTTGCGCTCCTGCAGCATGGATGGAGGCGGTCGTCGTTTTGT CGTTTTGTCGTT | SEQ ID NO: 154 |
| PB84_CpG_out_staple3 | TGCGCTCGCCGCTACAGGGCGCACATTAAGCAGGACCACTTATCGTCGTTTG" CGTTTTGTCGTT | SEQ ID NO: 155 |
| PB84_CpG_out_staple4 | GCTGGTTTACACCCGCCGCGCTTAATGCGGCCCTTCCGGCTGTCGTCGTTTTGT CGTTTTGTCGTT | SEQ ID NO: 156 |
| PB84_CpG_out_staple6 | GTGTAGCGAGCCGGCGAACGTGGCGAGAAAGGGCGCTGGCAATCGTCGTTTTG TCGTTTTGTCGTT | SEQ ID NO: 157 |
| PB84_CpG_out_staple7 | CGGGCGCTAGGAAGGGAAGAAAGCAGCTATATTCGTCGTTTTTGTCGTTTGTCC TT | SEQ ID NO: 158 |
| PB84_CpG_out_staple8 | TCTGACATGTCCGAGGGTTCCCAGGAAAGGAGTCGTCGTTTTGTCGTTTTTGTCG TT | SEQ ID NO: 159 |
| PB84_CpG_out_staple10 | TACTTTAGGGAACCCTAAAGGGAGCCCCCGTTTACTCATATATCGTCGTTTTGTC GTTTTGTCGTT | SEQ ID NO: 160 |
| PB84_CpG_out_staple11 | TTCATTTTGGTGCCGTAAAGCACTAAATCATTGATTTAAAACTCGTCGTTTTGTCG TTTTGTCGTT | SEQ ID NO: 161 |
| PB84_CpG_out_staple12 | TCTAGGTGAATCAAGTTTTTTGGGGTCGATAATTTAAAAGGATCGTCGTTTTGTC GTTTTCGTT | SEQ ID NO: 162 |
| PB84_CpG_out_staple14 | CGATGGCCGAACAAGAGTCCACTATTAAACCGTCTATCAGGGTCGTCGTTTTGT CGTTTTGTCGTT | SEQ ID NO: 163 |
| PB84_CpG_out_staple15 | GCGAAAAAGAACGTGGACTCCAACAATCAGTATCGTCGTTTTGTCGTTTTGTTCG" T | SEQ ID NO: 164 |
| PB84_CpG_out_staple17 | GAGATAGGATCAGCTCATTTTTTAACCAAAAAAGAATAGACCTCGTCGTTTTGTC GTTTTGTCGTT | SEQ ID NO: 165 |
| PB84_CpG_out_staple18 | TATAAATCTAGGCCGAAATCGGCATGTTGTAGTCGTCGTTTTGTCGTTTGTCGT T | SEQ ID NO: 166 |
| PB84_CpG_out_staple19 | AAAGTCAATAGGAAGCCGCATAAGAAATCCCTTCGTCGTTTTGTCGTTTTGTCGT T | SEQ ID NO: 167 |
| PB84_CpG_out_staple21 | GGTTGTAAATGACCAAAATCCCTTAACGTTCATATGTACCCCTCGTCGTTTGTC GTTTTGTCGTT | SEQ ID NO: 168 |
| PB84_CpG_out_staple22 | GACCCCAAGAGTTTTCGTTCCACTCCCGTATTCGTCGTTTTCGTCGTTTGTCGT T | SEQ ID NO: 169 |
| PB84_CpG_out_staple25 | GGTGCCTCCGAAATAGACAGATCGAAAAGCATTCGTCGTTTTGTTCGTTTTGTCGT T | SEQ ID NO: 170 |
| PB84_CpG_out_staple26 | CTTACGGATACTCACCAGTCACAGCTGAGATATCGTCGTTTTGTCGTTTTGTCGT T | SEQ ID NO: 171 |
| PB84_CpG_out_staple27 | GTTATCTAGGTGAGCGTGGGTCTCGCGGTCTCCCGTATCGTATCGTCGTTTGT CGTTTTGTCGTT | SEQ ID NO: 172 |
| PB84_CpG_out_staple28 | GGTAAGCCATCATTGCAGCACTGGAACCGGAGTCGTCGTTTTGTCGTTTTGTCG TT | SEQ ID NO: 173 |
| PB84_CpG_out_staple29 | CTGAATGACGCCTTGATCGTTGGGGGCCAGATTCGTCGTTTTGTCGTTGTCG TT | SEQ ID NO: 174 |
| PB84_CpG_out_staple31 | AATGTGCGGGCGAACTACTTACTCTAGCTCACTTTTCGGGGATCGTCGTTTTTGT CGTTTTGTCGTT | SEQ ID NO: 175 |
| PB84_CpG_out_staple33 | TCAAATATATGCCTGTAGCAATGGCAACATTTCTAAATACATTCGTCGTTTTGTCG TTTTGTCGTT | SEQ ID NO: 176 |
| PB84_CpG_out_staple37 | CATTTTGCAGGACCGAAGGAGCTAACCGCCCCTTTTTGCGGTCGTCGTTTTGT CGTTTTGTCGTT | SEQ ID NO: 177 |
| PB84_CpG_out_staple39 | AAGTAAAAGAGTGATAACACTGCGGCCAAGAAACGCTGGTGATCGTCGTTTTGT CGTTTTGTCGTT | SEQ ID NO: 178 |

TABLE 6-continued

Staple sequences for PB84 including outward facing CpG motifs
PB84, CpG containing, Outward facing.

| Name | Sequence | |
|------|----------|---|
| PB84_CpG_out_staple41 | AGAGAATTTCTCAGAATGACTTGGTTGAGTGGCATGACAGTATCGTCGTTTTGTC<br>GTTTTTGTCGTT | SEQ ID NO: 179 |
| PB84_CpG_out_staple44 | GAACGTTTGCACGAGTGGGTTACATCGAATTTTCGCCCCGAATCGTCGTTTTGT<br>CGTTTTGTCGTT | SEQ ID NO: 180 |
| PB84_CpG_out_staple45 | CTTGAGAGCTGGATCTCAACAGCGTGAATCTGTCGTCGTTTGTCGTTTTTGTCGT<br>T | SEQ ID NO: 181 |
| PB84_CpG_out_staple46 | TCTATACAACGAAACCTTGCACTCGTAAGATCTCGTCGTTTTGTCGTTTGTCGT<br>T | SEQ ID NO: 182 |
| PB84_CpG_out_staple48 | AAGAGTATATGCTTCAATAATATTACATGCGATCGTCGTTTTTGTCGTTTTGTCGTT | SEQ ID NO: 183 |
| PB84_CpG_out_staple49 | TGTGACCTAGAGAATAAGTAAATTGAAAAAGGTCGTCGTTTGTCGTTTTGTCGT<br>T | SEQ ID NO: 184 |
| PB84_CpG_out_staple51 | CCTACTTTGGTTAATGTCATGATAATAATTTCATTGTGCAATTTCGTCGTTTTGTCG<br>TTTTGTCGTT | SEQ ID NO: 185 |
| PB84_CpG_out_staple52 | TTGGTCGTCGTGATACGCCTATTTTTATAAAAAGAAAAAAGAGGTCGTCGTTTTGTC<br>GTTTTGTCGTT | SEQ ID NO: 186 |
| PB84_CpG_out_staple53 | AAGCATGGACGAATTCGACGAAAGGGCCTTAATGACCCAAGATCGTCGTTTGT<br>CGTTTTGTCGTT | SEQ ID NO: 187 |
| PB84_CpG_out_staple55 | TCTCCACCGCGCCCGGGTGGCTCAACAACTAAACGAATAGCCTCGTCGTTTTG"<br>CGTTTTGTCGTT | SEQ ID NO: 188 |
| PB84_CpG_out_staple60 | CTATGTTCATTAGAAGGCGTTGTTATTACCCTTCGTCGTTTTGTCGTTTGTCGTT | SEQ ID NO: 189 |
| PB84_CpG_out_staple61 | CGATATTCCACAGTCTATTATCTTTTGATACTTCGTCEGTTTTGTCGTTTTGTCGTT | SEQ ID NO: 190 |
| PB84_CpG_out_staple62 | ACTGCTATATAACCATGTTACTTGGTCAGATGTGTAAAAGGATCGTCGTTTGTC<br>GTTTTGTCGTT | SEQ ID NO: 191 |
| PB84_CpG_out_staple64 | GCTACGCAACTCCCGGCTTGGTTTGCACAAGATGAGACTCTCCTCGTTTTGT<br>CGTTTTGTCGTT | SEQ ID NO: 192 |
| PB84_CpG_out_staple66 | TTCACGACCGACAGTCTGGCAATACTAGTACAAGTAAATATCTCGTCGTTTTGTC<br>GTTTTGTCGTT | SEQ ID NO: 193 |

TABLE 7

Staple sequences for PB84 including CpG free outward facing motifs

| Name | Sequence | |
|------|----------|---|
| PB84_CpGfree_out_staple2 | ATAAAGTTTTGCGTTGCGCTCCTGCAGCATGGATGGAGGCGGCCCGATACTCG<br>CCATAGACGGCAA | SEQ ID NO: 194 |
| PB84_CpGfree_out_staple3 | TGCGCTCGCCGCTACAGGGCGCACATTAAGCAGGACCACTTACCCGATACTG<br>CCATAGACGGCAA | SEQ ID NO: 195 |
| PB84_CpGfree_out_staple4 | GCTGGTTTACACCCGCCGCGCTTAATGCGGCCCTTCCGGCTGCCCGATACTG<br>CCATAGACGGCAA | SEQ ID NO: 196 |
| PB84_CpGfree_out_staple6 | GTGTAGCGAGCCGGCGAACGTGGCGAGAAAGGGCGCTGGCAACCCGATAC"<br>GCCATAGACGGCAA | SEQ ID NO: 197 |
| PB84_CpGfree_out_staple7 | CGGGCGCTAGGAAGGGAAGAAAGCAGCTATATCCCGATACTGCCATAGACG<br>GCAA | SEQ ID NO: 198 |
| PB84_CpGfree_out_staple8 | TCTTGACATGTCCGAGGGTTCCCAGGAAAGGAGCCCGATACTGCCATAGACGG<br>CAA | SEQ ID NO: 199 |
| PB84_CpGfree_out_staple10 | TACTTTAGGGAACCCTAAAGGGAGCCCCCGTTTACTCATATACCCGATACTGC<br>CATAGACGGCAA | SEQ ID NO: 200 |
| PB84_CpGfree_out_staple11 | TTCATTTTGGTGCCGTAAAGCACTAAATCATTGATTTAAAACCCCGATACTGCC<br>ATAGACGGCAA | SEQ ID NO: 201 |

TABLE 7-continued

| Staple sequences for PB84 including CpG free outward facing motifs | | |
|---|---|---|
| Name | Sequence | |
| PB84_CpGfree_out_staple12 | TCTAGGTGAATCAAGTTTTTTGGGGTCGATAATTTAAAAGGACCCGATACTGC CATAGACGGCAA | SEQ ID NO: 202 |
| PB84_CpGfree_out_staple14 | CGATGGCCGAACAAGAGTCCACTATTAAACCGTCTATCAGGGCCCGATACTG CCATAGACGGCAA | SEQ ID NO: 203 |
| PB84_CpGfree_out_staple15 | GCGAAAAGAACGTGGACTCCAACAATCAGTACCCGATACTGCCATAGACGC CAA | SEQ ID NO: 204 |
| PB84_CpGfree_out_staple17 | GAGATAGGATCAGCTCATTTTTTAACCAAAAAGAATAGACCCCGATACTGC CATAGACGGCAA | SEQ ID NO: 205 |
| PB84_CpGfree_out_staple18 | TATAAATCTAGGCCGAAATCGGCATGTTGTAGCCCGATACTGCCATAGACGG CAA | SEQ ID NO: 206 |
| PB84_CpGfree_out_staple19 | AAAGTCAATAGGAAGCCGCATAAGAAATCCCTCCCGATACTGCCATAGACGG CA | SEQ ID NO: 207 |
| PB84_CpGfree_out_staple21 | GGTTGTAAATGACCAAAATCCCTTAACGTTCATATGTACCCCCCCGATACTGC CATAGACGGCAA | SEQ ID NO: 208 |
| PB84_CpGfree_out_staple22 | GACCCCAAGAGTTTTCGTTCCACTCCCGTATTCCCGATACTGCCATAGACGG CAA | SEQ ID NO: 209 |
| PB84_CpGfree_out_staple25 | GGTGCCTCCGAAATAGACAGATCGAAAAGCATCCCGATACTGCCATAGACGC CA | SEQ ID NO: 210 |
| PB84_CpGfree_out_staple26 | CTTACGGATACTCACCAGTCACAGCTGAGATACCCGATACTGCCATAGACGG CAA | SEQ ID NO: 211 |
| PB84_CpGfree_out_staple27 | GTTATCTAGGTGAGCGTGGGTCTCGCGGTCTCCCGTATCGTACCCGATACTG CCATAGACGGCAA | SEQ ID NO: 212 |
| PB84_CpGfree_out_staple28 | GGTAAGCCATCATTGCAGCACTGGAACCGGAGCCCGATACTGCCATAGACGG CAA | SEQ ID NO: 213 |
| PB84_CpGfree_out_staple29 | CTGAATGACGCCTTGATCGTTGGGGGCCAGATCCCGATACTGCCATAGACGG CAA | SEQ ID NO: 214 |
| PB84_CpGfree_out_staple31 | AATGTGCGGGCGAACTACTTACTCTAGCTCACTTTTTCGGGGACCCGATACTG CCATAGACGGCAA | SEQ ID NO: 215 |
| PB84_CpGfree_out_staple33 | TCAAATATATGCCTGTAGCAATGGCAACATTTCTAAATACATCCCGATACTGCC ATAGACGGCAA | SEQ ID NO: 216 |
| PB84_CpGfree_out_staple37 | CATTTTGCAGGACCGAAGGAGCTAACCGCCCCTTTTTTGCGGCCCGATACTG CCATAGACGGCAA | SEQ ID NO: 217 |
| PB84_CpGfree_out_staple39 | AAGTAAAAGAGTGATAACACTGCGGCCAAGAAACGCTGGTGACCCGATACTG CCATAGACGGCAA | SEQ ID NO: 218 |
| PB84_CpGfree_out_staple41 | AGAGAATTTCTCAGAATGACTTGGTTGAGTGGCATGACAGTACCCGATACTGC CATAGACGGCAA | SEQ ID NO: 219 |
| PB84_CpGfree_out_staple44 | GAACGTTTGCACGAGTGGGTTACATCGAATTTTCGCCCCGAACCCGATACTG CCATAGACGGCAA | SEQ ID NO: 220 |
| PB84_CpGfree_out_staple45 | CTTGAGAGCTGGATCTCAACAGCGTGAATCTGCCCGATACTGCCATAGACGCG CA | SEQ ID NO: 221 |
| PB84_CpGfree_out_staple46 | TCTATACAACGAAACCTTGCACTCGTAAGATCCCCGATACTGCCATAGACGGC AA | SEQ ID NO: 222 |
| PB84_CpGfree_out_staple48 | AAGAGTATATGCTTCAATAATATTACATGCGACCCGATACTGCCATAGACGGC AA | SEQ ID NO: 223 |
| PB84_CpGfree_out_staple49 | TGTGACCTAGAGAATAAGTAAATTGAAAAAGGCCCGATACTGCCATAGACGG CA | SEQ ID NO: 224 |
| PB84_CpGfree_out_staple51 | CCTACTTTGGTTAATGTCATGATAATAATTTCATTGTGCAATCCCGATACTGCC ATAGACGGCAA | SEQ ID NO: 225 |
| PB84_CpGfree_out_staple52 | TTGGTCGTTCGTGATACGCCTATTTTTATAAAAAGAAAAAGACGGCCCGATACTGC CATAGACGGCAA | SEQ ID NO: 226 |

TABLE 7-continued

Staple sequences for PB84 including CpG free outward facing motifs

| Name | Sequence | |
|------|----------|---|
| PB84_CpGfree_out_staple53 | AAGCATGGACGAATTCGACGAAAGCGCCTTAATGACCCAAGACCCGATACTG CCATAGACGGCA | SEQ ID NO: 227 |
| PB84_CpGfree_out_staple55 | TCTCGACCGCGCCCGGGTGGCTCAACAACTAAACGAATAGCCCCCGATACTG CCATAGACGGCAA | SEQ ID NO: 228 |
| PB84_CpGfree_out_staple60 | CTATGTTCATTAGAAGGCGTTGTTATTACCCTCCCGATACTGCCATAGACGGC AA | SEQ ID NO: 229 |
| PB84_CpGfree_out_staple61 | CGATATTCCACAGTCTATTATCTTTTGATACTCCCGATACTGCCATAGACGGC AA | SEQ ID NO: 230 |
| PB84_CpGfree_out_staple62 | ACTGCTATATAACCATGTTACTTGGTCAGATGTGTAAAAGGACCCGATACTGC CATAGACGGCAA | SEQ ID NO: 231 |
| PB84_CpGfree_out_staple64 | GCTAACGCAACTCCCGGGTTGGTTTGCACAAGATGAGAAGTGCCCGATACTG CCATAGACGGCA | SEQ ID NO: 232 |
| PB84_CpGfree_out_staple66 | TTGCACGACCGACAGTCTGGCAATACTAGTACAAGTAAATATCCCCGATACTGC CATAGACGGCAA | SEQ ID NO: 233 |

TABLE 8

Staple sequences for PB84 including CpG-containing, inward facing
motifs

| Name | Sequences | SEQ ID NO: |
|------|-----------|-----------|
| PB84_CpG_in_staple2 | GGCGGATAAAGTTTTGCGTTGCGCTCCTGCAGCATGGATGGATCGTCGT TTGTCGTTTTGTCGTT | 234 |
| PB84_CpG_in_staple3 | ACTTATGCGCTCGCCGCTACAGGGCGCACATTAAGCAGGACCTCGTCGT TTTGTTCGTTTTGTCGTT | 235 |
| PB84_CpG_in_staple4 | GGCTGGCTGGTTTACACCCGCCGCGCTTAATGCGGCCCTTCCTCGTCG TTTTGTCGTTTTGTCGTT | 236 |
| PB84_CpG_in_staple6 | GGCAAGTGTAGCGAGCCGGCGAACGTGGCGAGAAAGGGCGCTTCGTC GTTTTGTCGTTTTGTCGTT | 237 |
| PB84_CpG_in_staple7 | GTTCCCAGGAAAGGAGCGGGCGCTAGGAAGGGTCGTCGTTTTGTCGTT TTGTCGTT | 238 |
| PB84_CpG_in_staple8 | AAGAAAGCAGCTATATTCTGACATGTCCGAGGTCGTCGTTTTGTCGTTTT GTCGTT | 239 |
| PB84_CpG_in_staple10 | ATATATACTTTAGGGAACCCTAAAGGGAGCCCCCGTTTACTCTCGTCGTT TTGTCGTTTTGTCGTT | 240 |
| PB84_CpG_in_staple11 | AAAACTTCATTTTGGTGCCGTAAAGCACTAAATCATTGATTTTCGTCGTTT TGTCGTTTTGTCGTT | 241 |
| PB84_CpG_in_staple12 | AAGGATCTAGGTGAATCAAGTTTTTTGGGGTCGATAATTTAATCGTCGTT TTGTCGTTTTGTCGTT | 242 |
| PB84_CpG_in_staple14 | CAGGGCGATGGCCGAACAAGAGTCCACTATTAAACCGTCTATTCGTCGT TTTGTCGTTTTGTCGTT | 243 |
| PB84_CpG_in_staple16 | ACTCCAACAATCAGTACTATGCAGATTTTGACTCGTCGTTTTGTCGTTTT GTCGTT | 244 |
| PB84_CpG_in_staple17 | AGACCGAGATAGGATCAGCTCATTTTTTAACCAAAAAAGAATTCGTCGTT TTGTCGTTTTGTCGTT | 245 |
| PB84_CpG_in_staple18 | CSCATAAGAAATCCCTTATAAATCTAGGCCGATCGTCGTTTTGTCGTTTT GTCGTT | 246 |
| PB84_CpG_in_staple19 | AATCGGCATGTTGTAGAAAGTCAATAGGAAGCTCGTCGTTTTGTCGTTTT GTCGTT | 247 |
| PB84_CpG_in_staple21 | ACCCCGGTTGTAAATGACCAAAATCCCTTAACGTTCATATGTTCGTCGTT TTGTTCGTTTTGTTCGTT | 248 |

TABLE 8-continued

Staple sequences for PB84 including CpG-containing, inward facing
motifs

| Name | Sequences | SEQ ID NO: |
|---|---|---|
| PB84_CpG_in_staple23 | GTTCCACTCCCGTATTGACGCCGGTGTGGCGCTCGTCGTTTTGTCGTTT TGTCGTT | 249 |
| PB84_CpG_in_staple25 | AGTCACAGCTGAGATAGGTGCCTCCGAAATAGTCGTCGTTTTGTCGTTTT GTCGTT | 250 |
| PB84_CpG_in_staple26 | ACAGATCGAAAAGCATCTTACGGATACTCACCTCGTCGTTTTGTCGTTTT GTCGTT | 251 |
| PB84_CpG_in_staple27 | TCGTAGTTATCTAGGTGAGCGTGGGTCTCGCGGTCTCCCGTATCGTCGT TTTGTCGTTTTTGTCGTT | 252 |
| PB84_CpG_in_staple28 | TCGTTGGGGGCCAGATGGTAAGCCATCATTGCTCGTCGTTTTTGTCGTTT TGTCGTT | 253 |
| PB84_CpG_in_staple29 | AGCACTGGAACCGGAGCTGAATGACGCCTTGATCGTCGTTTTGTCGTTT TGTCGTT | 254 |
| PB84_CpG_in_staple31 | GGGGAAATGTGCGGGCGAACTACTTACTCTAGCTCACTTTTCTCGTCGT TTTGTCGTTTTGTCGTT | 255 |
| PB84_CpG_in_staple33 | TACATTCAAATATATGCCTGTAGCAATGGCAACATTTCTAAATCGTCGTTT TGTCGTTTTGTCGTT | 256 |
| PB84_CpG_in_staple37 | TGCGGCATTTTGCAGGACCGAAGGAGCTAACCGCCCCTTTTTTCGTCGT TTTGTCGTTTTGTCGTT | 257 |
| PB84_CpG_in_staple39 | GGTGAAAGTAAAAGAGTGATAACACTGCGGCCAAGAAACGCTTCGTCGT TTTGTCGTTTTGTCGTT | 258 |
| PB84_CpG_in_staple41 | CAGTAAGAGAATTTCTCAGAATGACTTGGTTGAGTGGCATGATCGTCGTT TGTTCGTTTTGTCGTT | 259 |
| PB84_CpG_in_staple44 | CCGAAGAACGTTTGCACGAGTGGGTTACATCGAATTTTCGCCTCGTCGT TTTGTCGGTTTTGTTCGTT | 260 |
| PB84_CpG_in_staple45 | TTGCACTCGTAAGATCCTTGAGAGCTGGATCTTCGTCGTTTTGTCGTT GTCGTT | 261 |
| PB84_CpG_in_staple46 | CAACAGCGTGAATCTGTCTATACAACGAAACCTCGTCGTTTTGTCGTTTT GTCGTT | 262 |
| PB84_CpG_in_staple48 | AGTAAATTGAAAAAGGAAGAGTATATGCTTCATCGTCGTTTTGTCGTTTT GTCGTT | 263 |
| PB84_CpG_in_staple49 | ATAATATTACATGCGATGTGACCTAGAGAATATCGTCGTTTTGTCGTTTT GTCGTT | 264 |
| PB84_CpG_in_staple51 | GCAATCCTACTTTGGTTAATGTCATGATAATAATTTCATTGTTCGTCGTTT TGTCGTTTTGTCGTT | 265 |
| PB84_CpG_in_staple52 | AGAGGTTGGTCGTCGTGATACGCCTATTTTTATAAAAAGAAATCGTCGTT TTGTCGTTTTGTCGTT | 266 |
| PB84_CpG_in_staple53 | CAAGAAAGCATGGACGAATTCGACGAAAGGGCCTTAATGACCTCGTCGT TTTGTCGTTTTGTCGTT | 267 |
| PB84_CpG_in_staple55 | TAGCCTCTCCACCGCGCCCGGGTGGCTCAACAACTAAACGAATCGTCGT TTTGTCGTTTTGTCGTT | 268 |
| PB84_CpG_in_staple60 | ATTATCTTTTGATACTCTATGTTCATTAGAAGTCGTCGTTTTTGTCGTT TTGTCGTT | 269 |
| PB84_CpG_in_staple61 | GCGTTGTTATTACCCTCGATATTTCCACAGTCTTCGTCGTTTTGTCGTTTT GTCGTT | 270 |
| PB84_CpG_in_staple62 | AAGGAACTGCTATATAACCATGTTACTTGGTCAGATGTGTAATCGTCGTT TTGTCGTTTTGTCGTT | 271 |
| PB84_CpG_in_staple64 | AAGTGGCTAACGCAACTCCCGGGTTGGTTTGCACAAGATGAGTCGTCGT TTTGTCGTTTTGTCGTT | 272 |
| PB84_CpG_in_staple64 | ATATCTTCACGACCGACAGTCTGGCAATACTAGTACAAGTAATCGTCGTT TTGTCGTTTTGTCGTT | 273 |

TABLE 9

| Staple sequences for CpG free, inward facing motifs | | |
|---|---|---|
| Name | Sequence | SEQ ID NO: |
| PB84_CpGfree_in_staple2 | GGCGGATAAAGTTTTTGCGTTGCGCTCCTGCAGCATGGATGGACCCGATACT GCCATAGACGGCAA | 274 |
| PB84_CpGfree_in_staple3 | ACTTATGCGCTCGCCGCTACAGGGCGCACATTAAGCAGGACCCCCGATACTG CCATAGACGGCAA | 275 |
| PB84_CpGfree_in_staple4 | GGCTGGCTGGTTTACACCCGCCGCGCTTAATGCGGCCCTTCCCCCGATACTG CCATAGACGGCAA | 276 |
| PB84_CpGfree_in_staple6 | GGCAAGTGTAGCGAGCCGGCGAACGTGGCGAGAAAGGGCGCTCCCGATACT GCCATAGACGGCAA | 277 |
| PB84_CpGfree_in_staple7 | GTTCCCAGGAAAGGAGCGGGCGCTAGGAAGGGCCCGATACTGCCATAGACG GCAA | 278 |
| PB84_CpGfree_in_staple8 | AAGAAAGCAGCTATATTCTGACATGTCCGAGGCCCGATACTGCCATAGACGG CAA | 279 |
| PB84_CpGfree_in_staple10 | ATATATACTTTAGGGAACCCTAAAGGGAGCCCCCGTTTACTCCCCGATACTG CCATAGACGGCAA | 280 |
| PB84_CpGfree_in_staple11 | AAAACTTCATTTTGGTGCCGTAAAGCACTAAATCATTGATTTCCCGATACTG CCATAGACGGCAA | 281 |
| PB84_CpGfree_in_staple12 | AAGGATCTAGGTGAATCAAGTTTTTTGGGGTCGATAATTTAACCCGATACTGC CATAGACGGCAA | 282 |
| PB84_CpGfree_in_staple14 | CAGGGCGATGGCCGAACAAGAGTCCACTATTAAACCGTCTATCCCGATACTG CCATAGACGGCAA | 283 |
| PB84_CpGfree_in_staple16 | ACTCCAACAATCAGTACTATGCAGATTTTGACCCCGATACTGCCATAGACGGC AA | 284 |
| PB84_CpGfree_in_staple17 | AGACCGAGATAGGATCAGCTCATTTTTTAACCAAAAAAGAATCCCGATACTGC CATAGACGGCAA | 285 |
| PB84_CpGfree_in_staple18 | CGCATAAGAAATCCCTTATAAATCTAGGCCGACCCGATACTGCCATAGACGGC AA | 286 |
| PB84_CpGfree_in_staple19 | AATCGGCATGTTGTAGAAAGTCAATAGGAAGCCCCGATACTGCCATAGACGG CAA | 287 |
| PB84_CpGfree_in_staple21 | ACCCCGGTTGTAAATGACCAAAATCCCTTAACGTTCATATGTCCCGATACTGC CATAGACGGCAA | 288 |
| PB84_CpGfree_in_staple23 | GTTCCACTCCCGTATTGACGCCGGTGTGGCGCCCCGATACTGCCATAGACGG CAA | 289 |
| PB84_CpGfree_in_staple25 | AGTCACAGCTGAGATAGGTGCCTCCGAAATAGCCCGATACTGCCATAGACGG CAA | 290 |
| PB84_CpGfree_in_staple26 | ACAGATCGAAAAGCATCTTACGGATACTCACCCCCGATACTGCCATAGACGG CAA | 291 |
| PB84_CpGfree_in_staple27 | TCGTAGTTATCTAGGTGAGCGTGGGTCTCGCGGTCTCCCGTACCCGATACTG CCATAGACGGCAA | 292 |
| PB84_CpGfree_in_staple28 | TCGTTGGGGGCCAGATGGTAAGCCATCATTGCCCCGATACTGCCATAGACGG CAA | 293 |
| PB84_CpGfree_in_staple29 | AGCACTGGAACCGGAGCTGAATGACGCCTTGACCCGATACTGCCATAGACGG CAA | 294 |
| PB84_CpGfree_in_staple31 | GGGGAAATGTGCGGGCGAACTACTTACTCTAGCTCACTTTTCCCCGATACTGC CATAGACGGCAA | 295 |
| PB84_CpGfree_in_staple33 | TACATTCAAATATATGCCTGTAGCAATGGCAACATTTCTAAACCCGATACTG CCATAGACGGCAA | 296 |
| PB84_CpGfree_in_staple37 | TGCGGCATTTTGCAGGACCGAAGGAGCTAACCGCCCCTTTTTCCCGATACTG CCATAGACGGCAA | 297 |
| PB84_CpGfree_in_staple39 | GGTGAAAGTAAAAGAGTGATAACACTGCGGCCAAGAAACGCTCCCGATACTG CCATAGACGGCAA | 298 |

TABLE 9-continued

Staple sequences for CpG free, inward facing motifs

| Name | Sequence | SEQ ID NO: |
|---|---|---|
| PB84_CpGfree_in_staple41 | CAGTAAGAGAATTTCTCAGAATGACTTGGTTGAGTGGCATGACCCGATACTGC CATAGACGGCAA | 299 |
| PB84_CpGfree_in_staple44 | CCGAAGAACGTTTGCACGAGTGGGTTACATCGAATTTTCGCCCCCGATACTG CCATAGACGGCAA | 300 |
| PB84_CpGfree_in_staple45 | TTGCACTCGTAAGATCCTTGAGAGCTGGATCTCCCGATACTGCCATAGACGG CAA | 301 |
| PB84_CpGfree_in_staple46 | CAACAGCGTGAATCTGTCTATACAACGAAACCCCCGATACTGCCATAGACGG CAA | 302 |
| PB84_CpGfree_in_staple48 | AGTAAATTGAAAAAGGAAGAGTATATGCTTCACCCGATACTGCCATAGACGGC AA | 303 |
| PB84_CpGfree_in_staple49 | ATAATATTACATGCGATGTGACCTAGAGAATACCCGATACTGCCATAGACGGC AA | 304 |
| PB84_CpGfree_in_staple51 | GCAATCCTACTTTGGTTAATGTCATGATAATAATTTCATTGTCCCGATACTG CCATAGACGGCAA | 305 |
| PB84_CpGfree_in_staple52 | AGAGGTTGGTCGTCGTGATACGCCTATTTTTATAAAAAGAAACCCGATACTGC CATAGACGGCAA | 306 |
| PB84_CpGfree_in_staple53 | CAAGAAAGCATGGACGAATTCGACGAAAGGGCCTTAATGACCCCCGATACTG CCATAGACGGCAA | 307 |
| PB84_CpGfree_in_staple55 | TAGCCTCTCCACCGCGCCCGGGTGGCTCAACAACTAAACGAACCCGATACTG CCATAGACGGCAA | 308 |
| PB84_CpGfree_in_staple60 | ATTATCTTTTGATACTCTATGTTCATTAGAAGCCCGATACTGCCATAGACGG CAA | 309 |
| PB84_CpGfree_in_staple61 | GCGTTGTTATTACCCTCGATATTCCACAGTCTCCCGATACTGCCATAGACGGC AA | 310 |
| PB84_CpGfree_in_staple62 | AAGGAACTGCTATATAACCATGTTACTTGGTCAGATGTGTAACCCGATACTGC CATAGACGGCAA | 311 |
| PB84_CpGfree_in_staple64 | AAGTGGCTAACGCAACTCCCGGGTTGGTTTGCACAAGATGAGCCCGATACTG CCATAGACGGCAA | 312 |
| PB84_CpGfree_in_staple66 | ATATCTTCACGACCGACAGTCTGGCAATACTAGTACAAGTAACCCGATACTGC CATAGACGGCAA | 313 |

TABLE 10

Staple sequences for unmodified ICO42 variants.

| Name | Sequence | SEQ ID NO: |
|---|---|---|
| ICO42_staple2 | CCCTAAAGTTGCGTTGCGCTCCTGCAGCACACTAAATCGGAA | 314 |
| ICO42_staple3 | CCGCTACAGGGTTTTTCGCACATTAAGGAGCCCCCGATTTTTTTTAGAGCTT | 315 |
| ICO42_staple4 | CAAGATATAAGATGAGAAGTGGCTATGCSGCTTAAACGCAAG | 317 |
| ICO42_staple5 | GAAGGGAAGAATTTTTAGCGAAAGGAGGGCGCTGGCATTTTTAGTGTAGCGGCG TAACCACCATTTTTCACCCGCCGC | 318 |
| ICO42_staple6 | TTAGAAATTGGTTACTAGGTACATCTGCGTCACGGTTAGAAG | 319 |
| ICO42_staple7 | TCTATTATACAGTCTGGCAATACTCGCTAGCGGGAGTCACAG | 320 |
| ICO42_staple8 | CGAGAAAGGACGGGGAAAGCCGGCTCAGGGTCTAGAACCGTGG | 321 |
| ICO42_staple9 | TGGGGTCGAGGTTTTTTGCCGTAAAGTACCTATGGCGTTTTTAAATTCTTATGCTT TAAACAATTTTTAATCTGGCGC | 322 |
| ICO42_staple10 | TCATTTTTCATCACCCTAATCAAGTTTTTTTGTTAAATCAGC | 323 |
| ICO42_staple11 | GCGATGGCCCATTTTTCTACGTGAACTAACCAATAGGTTTTTCCGAAATCGG | 324 |

TABLE 10-continued

Staple sequences for unmodified ICO42 variants.

| Name | Sequence | SEQ ID NO: |
|---|---|---|
| ICO42_staple12 | AGATAGGGTTGTTTTTAGTGTTGTTTCCAAGAGTCCACTTTTTTATTAAAGAAAACCT CAAAGGTTTTTGCGAAAAACC | 325 |
| ICO42_staple13 | GAAGGATTAAGTAAATATCTTCACACTCCCGTGGGACCTAGC | 326 |
| ICO42_staple14 | TCAACAGCGAGTGGGTTACATCGATGGAACAGTTACTGGATC | 327 |
| ICO42_staple15 | ATAGACCGCAAAATCCCTTATAAATGAGTTAACGTCAAAAGA | 328 |
| ICO42_staple16 | GGCAACTATGGTTTTTATGAACGAAAGTTGTAATTCGTTTTTCGTTAAATTT | 329 |
| ICO42_staple17 | GAGATAGGACCCCAATCATATGTACCCCGTAGACAGATCGCT | 330 |
| ICO42_staple18 | TTTCGTTCCACTTTTTTGAGCGTCAGTGCCTCACTGATTTTTTTAAGCATTG | 331 |
| ICO42_staple19 | TTTAGATTGATTTTTTTTAAAACTTCTAAAAGGATCTTTTTTAGGTGAAGATAATCTC ATGACTTTTTCAAAATCCCT | 332 |
| ICO42_staple20 | ATGAGCACCGCCCCGAAGAACGTTTTGATCCTTTTTCCAATG | 333 |
| ICO42_staple21 | GGCTGGCTACCACTTATGCGCTCGTAATTATTTTGCCCTTCC | 334 |
| ICO42_staple22 | ATATATACGTAACTGTCAGACCAAGATGGGGCCAGTTTACTC | 335 |
| ICO42_staple23 | CAACAGAGTATCTACACGACGGGGAGTCACCGGGTGGCTCAA | 336 |
| ICO42_staple24 | TAAGCCCTCCCTTTTTGTATCGTAGTAATAAGTAAATTTTTTTACATGCGAT | 337 |
| ICO42_staple25 | ACGAATAGCCTTTTTTCTCCACCCAAACCGGAGCTGATTTTTATGAAGCCATGCGG TATCATTTTTTTTGCAGCACTGG | 338 |
| ICO42_staple26 | CGTGACACGAGCCGGTGAGCGTGGGTCTCACCAAACCGACGAG | 339 |
| ICO42_staple27 | GGAGGCGGATATTTTTAAGTTGCAGGGGTTTATTGCTTTTTTGATAAATCTGCACG ATGCCTGTTTTTTAGCAATGGC | 340 |
| ICO42_staple28 | CGGGCAAGCGCGGTATTATCCCGTTGGATTAGACATTGACGC | 341 |
| ICO42_staple29 | CGCAAACTATTTTTTTAACTGGCGAATAGCTTCCCGGTTTTTCAACAATTAA | 342 |
| ICO42_staple30 | CAGTAAGAAAAAGCATCTTACGGATACTCCTACTTGGCATGA | 343 |
| ICO42_staple31 | GCTTTTTTATCGGAGGACCGAAGGCGTTGAACAAAGCTAACC | 344 |
| ICO42_staple32 | CGACGACGAACTCGCCTTGATCGTTGGGAGAGTTTGAGGGGA | 345 |
| ICO42_staple33 | GCACAACATGGTTTTTGSGATCATGTAATTCGACGAATTTTTAGGGCCTCGTTAAT AATGGTTTTTTTTCTTTAGACGT | 346 |
| ICO42_staple34 | TTTTCGGGGAATTTTTATGTGCGCGGGCCAACTTACTTTTTTTCTGACAACG | 347 |
| ICO42_staple35 | TTATTTTTACCATGAGTGATAACACTGCGAACCCCTATTTGT | 348 |
| ICO42_staple36 | GAATTATGCAGTTTTTGCTGCCATACTAAATACATTTTTTTCAAATATGTA | 349 |
| ICO42_staple37 | TTCAATAATATTTTTTTGAAAAAGGACTTATTCCCTTTTTTTTTTTGCGGCATTGAGT ACTCATTTTTCCAGTCACAG | 350 |
| ICO42_staple38 | TGACTTGGTTTTGCCTTCCTGTTTTTGCTACTATTCTCAGAA | 351 |
| ICO42_staple39 | TTTTAAAGTTCTTTTTTGCTATGTGGAGCAACTCGGTTTTTTCGCCGCATACCACC CAGAAACTTTTTGCTGGTGAA | 352 |
| ICO42_staple40 | CTGAAGATCAGTTTTTTTGGGTGCACGGTAAGATCCTTTTTTTTGAGAGTTTT | 353 |
| ICO42_staple41 | TAGTGATAGTTTGCACACGTCTGGAGATGGTAAACGGACATC | 354 |
| ICO42_staple42 | GTGTCGCCAGAGTATGAGTATTCACCACGTCGGAACATTTCC | 355 |
| ICO42_staple43 | ATAAATGCTCCGCTCATGAGACAATGGTAAAGCATAACCCTG | 356 |
| ICO42_staple44 | TTGATACTATTCCTAGATTAGAAGGGCACCAGGTGCGTTGTT | 357 |
| ICO42_staple45 | TGTCATGAGATACGCCTATTTTTATGTAGAGTGTTAGGTTAA | 358 |
| ICO42_staple46 | GCGAACGAAGAACCAGGGAAAACCCTTAAGTGACAGGTACGA | 359 |

TABLE 10-continued

Staple sequences for unmodified ICO42 variants.

| Name | Sequence | SEQ ID NO: |
|------|----------|------------|
| ICO42_staple47 | ACTGCTATCTATACAAACTAAGAGACAAAATGTGTAAAAGGA | 360 |
| ICO42_staple48 | AAAGTCAAATCTTTTTCTATCTGTGAAACCTTGCACTTTTTTCTGAATCTGT | 361 |
| ICO42_staple49 | GCAAAATAGAATTTTTTCGGTATCCATAATACCGTGTTTTTTATCATAATTGAAACG GGTAGGTTTTTAAGCCGCATA | 362 |
| ICO42_staple50 | AGAGCTATGCAGCACCTGTATCGGCCTTCTCCGAGGGTTCCC | 363 |
| ICO42_staple51 | GCAAATACGTATTTTTTCTTCCCTATCTATGTTCGCCTTTTCGCATTTTTGC | 364 |
| ICO42_staple52 | ATTCTGACATATTTTTATTATTGAGCTTTGACTCGGGTTTTTTGTAATCAGTTTGGT CGTTAATTTTTTGACCCAAGA | 365 |
| ICO42_staple53 | AAAAGAGGACTATGCAGTAACCTCAGGATCCTACTTTAAAAG | 366 |
| ICO42_staple54 | AGTGACGTAACTTTTTTCCCGGGTTGACCATGTTACTTTTTTTTGGTCAGTTATGTAT TCATTCTTTTTATTTGTGCAAT | 367 |
| ICO42_staple55 | AGTTATGTGTTTTTTTGCAGGTAGCGCTTATTACCCTTTTTTCGATATTCAC | 368 |

TABLE 11

CpG containing, Outward facing Staple sequences for ICO42 variants.

| Name | Sequence | SEQ ID NO: |
|------|----------|------------|
| ICO42_CpG_out_staple2 | CCCTAAAGTTGCGTTGCGCTCCTGCAGCACACTAAATCGGAATCGTCGTTTTGT CGTTTTGTTCGTTT | 369 |
| ICO42_CpG_out_staple4 | CAAGATATAAGATGAGAAGTGGCTATGCGGCTTAAACGCAAGTCGTCGTTTTGT CGTTTTGTTCGTT | 370 |
| ICO42_CpG_out_staple6 | TTAGAAATTGGTTACTAGGTACATCTGCGTCACGGTTAGAAGTCGTCGTTTTGT CGTTTTGTTCGTT | 371 |
| ICO42_CpG_out_staple7 | TCTATTATACAGTCTGGCAATACTCGCTAGCGGGAGTCACAGTCGTCGTTTTGT CGTTTTGTTCGTT | 372 |
| ICO42_CpG_out_staple8 | CGAGAAAAGGACGGGGAAAGCCGGCTCAGGCGTCTAGAACGTGGTCGTCGTTTT GTCGTTTTGTCGTT | 393 |
| ICO42_CpG_out_staple10 | TCATTTTTTCATCACCCTAATCAAGTTTTTTTGTTAAATCAGCTCGTCGTTTTGTCG TTTTGTTCGTT | 374 |
| ICO42_CpG_out_staple13 | GAAGGATTAAGTAAATATCTTCACACTCCCGTGGGACGTAGCTCGTCGTTTTGT CGTTTTGTTCGTT | 375 |
| ICO42_CpG_out_staple14 | TCAACAGCGAGTGGGTTACATCGATGGAACAGTTACTGGATCTCGTCGTTTTTGT CGTTTGTTCGTT | 376 |
| ICO42_CpG_out_staple15 | ATAGACCGCAAAATCCCTTATAAATGAGTTAACGTCAAAAGATCGTCGTTTTGTC GTTTTGTCGTT | 377 |
| ICO42_CpG_out_staple17 | GAGATAGGACCCCAATCATATGTACCCCGTAGACAGATCGCTTCGTCGTTTTGT CGTTTTGTCGTTT | 378 |
| ICO42_CpG_out_staple20 | ATGAGCACCGCCCCGAAGAACGTTTTGATCCTTTTTCCAATGTCGTCGTTTTGT CGTTTTGTCGTT | 379 |
| ICO42_CpG_out_staple21 | GGCTGGCTACCACTTATGCGCTCGTAATTATTTTTGCCCTTCCTCGTCGTTTTTGT CGTTTTGTCGTT | 380 |
| ICO42_CpG_out_staple22 | ATATATACGTAACTGTCAGACCAAGATGGGGCCAGTTTACTCTCGTCGTTTTGT CGTTTTGTEGTT | 381 |
| ICO42_CpG_out_staple23 | CAACAGAGTATCTACACGACGGGGAGTCACCGGGTGGCTCAATCGTCGTTTTG TCGTTTTGTCGTT | 382 |
| ICO42_CpG_out_staple26 | CGTGACACGAGCCGGTGAGCGTGGGTCTCACCAAACGACGAGTCGTCGTTTTCE TCGTTTTGTCGTT | 383 |

TABLE 11-continued

| Name | Sequence | SEQ ID NO: |
|------|----------|-----------|
| CpG containing, Outward facing Staple sequences for ICO42 variants. | | |
| ICO42_CpG_out_staple28 | CGGGCAAGCGCGGTATTATCCCGTTGGATTAGACATTTGACGCTCGTCGTTTTGT CcGTTTTGTCGTT | 384 |
| ICO42_CpG_out_staple30 | CAGTAAGAAAAAGCATCTTACGGATACTCCTACTTGGCATGATCGTCGTTTTGT CGTTTTGTCGTT | 385 |
| ICO42_CpG_out_staple31 | GCTTTTTTATCGGAGGACCGAAGGCGTTGAACAAAGCTAACCTCGTCGTTTTGT CGTTTTGTCGTT | 386 |
| ICO42_CpG_out_staple32 | CGACGACGAACTCGCCTTGATCGTTGGGAGAGTTTGAGGGGATCGTCGTTTTG TCGTTTTGTCGTT | 387 |
| ICO42_CpG_out_staple35 | TTATTTTTACCATGAGTGATAACACTGCGAACCCCTATTTGTTCGTCGTTTTGTC GTTTGTCGTT | 388 |
| ICO42_CpG_out_staple38 | TGACTTGGTTTTGCCTTCCTGTTTTTGCTACTATTTCTCAGAATCGTCGTTTTGTC GTTTTGTTCGTT | 389 |
| ICO42_CpG_out_staple41 | TAGTGATAGTTTGCACACGTCTGGAGATGGTAAACGGACATCTCGTCGTTTTGT CGTTTTGTCGTT | 390 |
| ICO42_CpG_out_staple42 | GTGTCGCCAGAGTATGAGTATTCACCACGTCGGAACATTTCCTCGTCGTTTTGT CGTTTTGTCGTT | 391 |
| ICO42_CpG_out_staple43 | ATAAATGCTCCGCTCATGAGACAATGGTAAAGCATAACCCTGTCGTCGTTTTGT CGTTTTGTCGTT | 392 |
| ICO42_CpG_out_staple44 | TTGATACTATTCCTAGATTAGAAGGGCACCAGGTGCGTTGTTTCGTCGTTTTGT CGTTTTGTCGTT | 393 |
| ICO42_CpG_out_staple45 | TGTCATGAGATACGCCTATTTTTATGTAGAGTGTTAGGTTTAATCGTCGTTTTGTC GTTTTGTTCGTT | 394 |
| ICO42_CpG_out_staple46 | GCGAACGAAGAACCAGGGAAAACCCTTAAGTGACAGGTACGATCGTCGTTTTG TCGTTTTGTCGTT | 395 |
| ICO42_CpG_out_staple47 | ACTGCTATCTATACAAACTAAGAGACAAAATGTGTAAAAGGATCGTCGTTTTGTC GTTTTGTCGTT | 396 |
| ICO42_CpG_out_staple50 | AGAGCTATGCAGCACCTGTATCGGCCTTCTCCGAGGGTTCCCTCGTCGTTTTGT CGTTTTGTCGTT | 397 |
| ICO42_CpG_out_staple53 | AAAAGAGGACTATGCAGTAACCTCAGGATCCTACTTTAAAAGTCGTCGTTTTGT CGTTTTGTCGTT | 398 |

TABLE 12

| Name | Sequence | SEQ ID NO: |
|------|----------|-----------|
| CpG free, Outward facing Staple sequences for ICO42 variants. | | |
| ICO42_CpGfree_out_staple2 | CCCTAAAGTTGCGTTGCGCTCCTGCAGCACACTAAATCGGAACCCGATACT GCCATAGACGGCAA | 399 |
| ICO42_CpGfree_out_staple4 | CAAGATATAAGATGAGAAGTGGCTATGCGGCTTAAACGCAAGCCCGATACT GCCATAGACGGCAA | 400 |
| ICO42_CpGfree_out_staple6 | TTAGAAATTGGTTACTAGGTACATCTGCGTCACGGTTAGAAGCCCGATACTG CCATAGACGGCAA | 401 |
| ICO42_CpGfree_out_staple7 | TCTATTATACAGTCTGGCAATACTCGCTAGCGGGAGTCACAGCCCGATACTC:CCATAGACGGCAA | 402 |
| ICO42_CpGfree_out_staple8 | CGAGAAAGGACGGGGAAAGCCGGCTCAGGGTCTAGAACGTGGCCCGATAC TGCCATAGACGGCAA | 403 |
| ICO42_CpGfree_out_staple10 | TCATTTTTCATCACCCTAATCAAGTTTTTTTGTTAAATCAGCCCCGATACTGC CATAGACGGCAA | 404 |
| ICO42_CpGfree_out_staple13 | GAAGGATTAAGTAAATATCTTCACACTCCCGTGGGACGTAGCCCCGATACTC CCATAGACGGCAA | 405 |

TABLE 12-continued

CpG free, Outward facing Staple sequences for ICO42 variants.

| Name | Sequence | SEQ ID NO: |
| --- | --- | --- |
| ICO42_CpGfree_out_staple14 | TCAACAGCGAGTGGGTTACATCGATGGAACAGTTACTGGATCCCCGATACT GCCATAGACGGCAA | 406 |
| ICO42_CpGfree_out_staple15 | ATAGACCGCAAAATCCCTTATAAATGAGTTAACGTCAAAAGACCCGATACTG CCATAGACGGCAA | 407 |
| ICO42_CpGfree_out_staple17 | GAGATAGGACCCCAATCATATGTACCCCGTAGACAGATCGCTCCCGATACT GCCATAGACGGCAA | 408 |
| ICO42_CpGfree_out_staple20 | ATGAGCACCGCCCCGAAGAACGTTTTGATCCTTTTTCCAATGCCCGATACTG GCATAGACGGCAA | 409 |
| ICO42_CpGfree_out_staple21 | GGCTGGCTACCACTTATGCGCTCGTAATTATTTTGCCCTTCCCCCGATACTG CCATAGACGGCAA | 410 |
| ICO42_CpGfree_out_staple22 | ATATATACGTAACTGTCAGACCAAGATGGGGCCAGTTTACTCCCCGATACTG CCATAGACGGCAA | 411 |
| ICO42_CpGfree_out_staple23 | CAACAGAGTATCTACACGACGGGGAGTCACCGGGTGGCTCAACCCGATACT GCCATAGACGGCAA | 412 |
| ICO42_CpGfree_out_staple26 | CGTGACACGAGCCGGTGAGCGTGGGTCTCACCAAACGACGAGCCCGATAC TGCCATAGACGGCAA | 413 |
| ICO42_CpGfree_out_staple28 | CGGGCAAGCGCGGTATTATCCCGTTGGATTAGACATTGACGCCCCGATACT GCCATAGACGGCAA | 414 |
| ICO42_CpGfree_out_staple30 | CAGTAAGAAAAAGCATCTTACGGATACTCCTACTTGGCATGACCCGATACTG CCATAGACGGCAA | 415 |
| ICO42_CpGfree_out_staple31 | GCTTTTTTATCGGAGGACCGAAGGCGTTGAACAAAGCTAACCCCCGATACT GCCATAGACGGCAA | 416 |
| ICO42_CpGfree_out_staple32 | CGACGACGAACTCGCCTTGATCGTTGGGAGAGTTTGAGGGGACCCGATACT GCCATAGACGGCAA | 417 |
| ICO42_CpGfree_out_staple35 | TTATTTTTACCATGAGTGATAACACTGCGAACCCCTATTTGTCCCGATACTGC CATAGACGGCAA | 418 |
| ICO42_CpGfree_out_staple38 | TGACTTTGGTTTTGCCTTCCTGTTTTTGCTACTATTCTCAGAACCCGA-TACTGC CATAGACGGCAA | 419 |
| ICO42_CpGfree_out_staple41 | TAGTGATAGTTTGCACACGTCTGGAGATGGTAAACGGACATCCCCGATACT GCCATAGACGGCAA | 420 |
| ICO42_CpGfree_out_staple42 | GTGTCGCCAGAGTATGAGTATTCACCACGTCGGAACATTTCCCCCGATACT GCCATAGACGGCAA | 421 |
| ICO42_CpGfree_out_staple43 | ATAAATGCTCCGCTCATGAGACAATGGTAAAGCATAACCCTGCCCGATACTG CCATAGACGGCAA | 422 |
| ICO42_CpGfree_out_staple44 | TTGATACTATTCCTAGATTAGAAGGGCACCAGGTGCGTTGTTCCCGATACTG CCATAGACGGCAA | 423 |
| ICO42_CpGfree_out_staple45 | TGTCATGAGATACGCCTATTTTTATGTAGAGTGTTAGGTTAACCCGATACTG CCATAGACGGCAA | 424 |
| ICO42_CpGfree_out_staple46 | GCGAACGAAGAACCAGGGAAAACCCTTAAGTGACAGGTACGACCCGATACT GCCATAGACGGCAA | 425 |
| ICO42_CpGfree_out_staple47 | ACTGCTATCTATACAAACTAAGAGACAAAATGTGTAAAAGGACCCGATACTG CCATAGACGGCAA | 426 |
| ICO42_CpGfree_out_staple50 | AGAGCTATGCAGCACCTGTATCGGCCTTCTCCGAGGGTTCCCCCCGATACT GCCATAGACGGCAA | 427 |
| ICO42_CpGfree_out_staple53 | AAAAGAGGACTATGCAGTAACCTCAGGATCCTACTTTAAAAGCCCGATACTG CCATAGACGGCAA | 428 |

TABLE 13

| CpG containing, inward facing Staple sequences for ICO42 variants. | | |
| --- | --- | --- |
| Name | Sequence | SEQ ID NO: |
| ICO42_CpG_in_staple2 | CGGAACCCTAAAGTTGCGTTGCGCTCCTGCAGCACACTAAATTCGTCGT TTTGTCGTTTTTGTCG | 429 |
| ICO42_CpG_in_staple4 | AAGTGGCTATGCGGCTTAAACGCAAGCAAGATATAAGATGAGTCGTCGT TTTGTCGTTTTGTTCGTT | 430 |
| ICO42_CpG_in_staple6 | AGGTACATCTGCGTCACGGTTAGAAGTTAGAAATTGGTTACTTCGTCGTT TTGTCGTTTGTCGTT | 431 |
| ICO42_CpG_in_staple7 | GCAATACTCGCTAGCGGGAGTCACAGTCTATTATACAGTCTGTCGTCGT TTTGTCGTTTTGTCGTT | 432 |
| ICO42_CpG_in_staple8 | AAGCCGGCTCAGGGTCTAGAACGTGGCGAGAAAGGACGGGCGATCGTC GTTTTTGTCGTTTTGTCGTT | 433 |
| ICO42_CpG_in_staple10 | TCAGCTCATTTTTCATCACCCTAATCAAGTTTTTTTGTTAAATCGTCGT TTTGTCGTTTTGTCGTT | 434 |
| ICO42_CpG_in_staple13 | GTAGCGAAGGATTAAGTAAATATCTTCACACTCCCGTGGGACTCGTCGT TTTGTCGTTTTGTCGTT | 435 |
| ICO42_CpG_in_staple14 | TACATCGATGGAACAGTTACTGGATCTCAACAGCGAGTGGGTTCGTCGT TTTGTCGTTTTGTCGTT | 436 |
| ICO42_CpG_in_staple15 | CTTATAAATGAGTTAACGTCAAAAGAATAGACCGCAAAATCCTCGTCGTT TTGTCGTTTTTGTCGTT | 437 |
| ICO42_CpG_in_staple17 | TCGCTGAGATAGGACCCCAATCATATGTACCCCGTAGACAGATCGTCGT TTTGTCGTTTTGTCGTT | 438 |
| ICO42_CpG_in_staple20 | AGAACGTTTTGATCCTTTTTCCAATGATGAGCACCGCCCCGATCGTCGTT TTGTCGTTTTGTCGTT | 439 |
| ICO42_CpG_in_staple21 | CTTCCGGCTGGCTACCACTTATGCGCTCGTAATTATTTTGCCTCGTCGTT TTGTCGTTTTGTCGTT | 440 |
| ICO42_CpG_in_staple22 | CAGACCAAGATGGGGCCAGTTTACTCATATATACGTAACTGTTCGTCGTT TTGTCGTTTTGTCGTT | 441 |
| ICO42_CpG_in_staple23 | CTCAACAACAGAGTATCTACACGACGGGGAGTCACCGGGTGGTCGTCG TTTTGTCGTTTTGTCGTT | 442 |
| ICO42_CpG_in_staple26 | ACGAGCGTGACACGAGCCGGTGAGCGTGGGTCTCACCAAACGTCGTCG TTTTGTCGTTTTGTCGTT | 443 |
| ICO42_CpG_in_staple28 | TATCCCGTTGGATTAGACATTGACGCCGGGCAAGCGCGGTATTCGTCGT TTTGTCGTTTTGTCGTT | 444 |
| ICO42_CpG_in_staple30 | CTTACGGATACTCCTACTTGGCATGACAGTAAGAAAAAGCATTCGTCGTT TTGTCGTTTGTCGTT | 445 |
| ICO42_CpG_in_staple31 | ACCGAAGGCGTTGAACAAAGCTAACCGCTTTTTTATCGGAGGTCGTCGT TTTGTCGTTTTGTCGTT | 446 |
| ICO42_CpG_in_staple32 | GGGGACGACGACGAACTCGCCTTGATCGTTGGGAGAGTTTGATCGTCG TTTTGTTCGTTTTGTCGTT | 447 |
| ICO42_CpG_in_staple35 | TTTGTTTATTTTTACCATGAGTGATAACACTGCGAACCCCTATCGTCGTTT TGTCGTTTTGTCGTT | 448 |
| ICO42_CpG_in_staple38 | CAGAATGACTTGGTTTTTGCCTTCCTGTTTTTGCTACTATTCTTCGTCGT TTTGTTCGTTTTGTTCGTT | 449 |
| ICO42_CpG_in_staple41 | ACGTCTGGAGATGGTAAACGGACATCTAGTGATAGTTTGCACTCGTCGT TTGTCGTTTTGTCGTT | 450 |
| ICO42_CpG_in_staple42 | AGTATTCACCACGTCGGAACATTTCCGTGTCGCCAGAGTATGTCGTCGT TTTGTCGTTTTGTCGTT | 451 |
| ICO42_CpG_in_staple43 | TGAGACAATGGTAAAGCATAACCCTGATAAATGCTCCGCTCATCGTCGTT TTGTCGTTTTGTCGT | 452 |
| ICO42_CpG_in_staple44 | ATTAGAAGGGCACCAGGTGCGTTGTTTTGATACTATTCCTAGTCGTCGTT TTGTCGTTTTGTCGTT | 453 |

TABLE 13-continued

CpG containing, inward facing Staple sequences for ICO42 variants.

| Name | Sequence | SEQ ID NO: |
|------|----------|-----------|
| ICO42_CpG_in_staple45 | TATTTTTATGTAGAGTGTTAGGTTAATGTCATGAGATACGCCTCGTCGTTT<br>TGTCGTTTGTTCGTT | 454 |
| ICO42_CpG_in_staple46 | GGAAAACCCTTAAGTGACAGGTACGAGCGAACGAAGAACCAGTCGTCG<br>TTTTGTCGTTTTGTCGTT | 455 |
| ICO42_CpG_in_staple47 | AAGGAACTGCTATCTATACAAACTAAGAGACAAAATGTGTAATCGTCGTT<br>TTGTTCGTTTTTGTTCGTT | 456 |
| ICO42_CpG_in_staple50 | TTCCCAGAGCTATGCAGCACCTGTATCGGCCTTCTCCGAGGGTCGTCGT<br>TTTGTTCGTTTTGTTCGTT | 457 |
| ICO42_CpG_in_staple53 | GTAACCTCAGGATCCTACTTTAAAAGAAAAGAGGACTATGCATCGTCGTT<br>TTGTCGTTTTGTTCGTT | 458 |

TABLE 14

CpG free, inward facing Staple sequences for ICO42 variants.

| Name | Sequence | SEQ ID NO: |
|------|----------|-----------|
| ICO42_CpG_in_staple2 | CGGAACCCTAAAGTTGCGTTGCGCTCCTGCAGCACACTAAATCCCGATACTG<br>CCATAGACGGCAA | 459 |
| ICO42_CpG_in_staple4 | AAGTGGCTATGCGGCTTAAACGCAAGCAAGATATAAGATGAGCCCGATACTG<br>CCATAGACGGCAA | 460 |
| ICO42_CpG_in_staple6 | AGGTACATCTGCGTCACGGTTAGAAGTTAGAAATTGGTTACTCCCGATACTGC<br>CATAGACGGCAA | 461 |
| ICO42_CpG_in_staple7 | GCAATACTCGCTAGCGGGAGTCACAGTCTATTATACAGTCTGCCCGATACTGC:<br>CATAGACGGCAA | 462 |
| ICO42_CpG_in_staple8 | AAGCCGGCTCAGGGTCTAGAACGTGGCGAGAAAGGACGGGGACCCGATACT<br>GCCATAGACGGCAA | 463 |
| ICO42_CpG_in_staple10 | TCAGCTCATTTTTCATCACCCTAATCAAGTTTTTTTGTTTAAACCCGATACTGCC<br>ATAGACGGGCAA | 464 |
| ICO42_CpG_in_staple13 | GTAGCGAAGGATTAAGTAAATATCTTCACACTCCCGTGGGACCCGATACTGC.<br>CATAGACGGCAA | 465 |
| ICO42_CpG_in_staple14 | TACATCGATGGAACAGTTACTGGATCTCAACAGCGAGTGGGTCCCGATACTG<br>CCATAGACGGCAA | 466 |
| ICO42_CpG_in_staple15 | CTTATAAATGAGTTAACGTCAAAAGAATAGACCGCAAAATCCCCGATACTGC<br>CATAGACGGCAA | 467 |
| ICO42_CpG_in_staple17 | TCGCTGAGATAGGACCCCAATCATATGTACCCCGTAGACAGACCCGATACTG<br>CCATAGACGGCAA | 468 |
| ICO42_CpG_in_staple20 | AGAACGTTTTGATCCTTTTTCCAATGATGAGCACCGCCCCGACCCGATACTGC<br>CATAGACGGCAA | 469 |
| ICO42_CpG_in_staple21 | CTTCCGGCTGGCTACCACTTATGCGCTCGTAATTATTTTGCCCCCGATACTGC<br>CATAGACGGCAA | 470 |
| ICO42_CpG_in_staple22 | CAGACCAAGATGGGGCCAGTTTACTCATATATACGTAACTGTCCCGATACTGC<br>CATAGACGGCAA | 471 |
| ICO42_CpG_in_staple23 | CTCAACAACAGAGTATCTACACGACGGGGAGTCACCGGGTGGCCCGATACTC<br>CCATAGACGGCAA | 472 |
| ICO42_CpG_in_staple26 | ACGAGCGTGACACGAGCCGGTGAGCGTGGGTCTCACCAAACGCCCGATACT<br>GCCATAGACGGCAA | 473 |
| ICO42_CpG_in_staple28 | TATCCCGTTGGATTAGACATTGACGCCGGGCAAGCGCGGTATCCCGATACTG<br>CCATAGACGGCAA | 474 |
| ICO42_CpG_in_staple30 | CTTACGGATACTCCTACTTGGCATGACAGTAAGAAAAAGCATCCCGATACTGC<br>CATAGACGGCAA | 475 |
| ICO42_CpG_in_staple31 | ACCGAAGGCGTTGAACAAAGCTAACCGCTTTTTTATCGGAGGCCCGATACTG<br>CCATAGACGGCAA | 476 |

TABLE 14-continued

CpG free, inward facing Staple sequences for ICO42 variants.

| Name | Sequence | SEQ ID NO: |
|------|----------|------------|
| ICO42_CpG_in_staple32 | GGGGACGACGACGAACTCGCCTTGATCGTTGGGAGAGTTTGACCCGATACTG CCATAGACGGCAA | 477 |
| ICO42_CpG_in_staple35 | TTTGTTTATTTTTACCATGAGTGATAACACTGCGAACCCCTACCCGATACTGCC ATAGACGGCAA | 478 |
| ICO42_CpG_in_staple38 | CAGAATGACTTGGTTTTGCCTTCCTGTTTTTGCTACTATTTCTCCCGATACTGCC479 ATAGACGGCAA | 479 |
| ICO42_CpG_in_staple41 | ACGTCTGGAGATGGTAAACGGACATCTAGTGATAGTTTGCACCCCGATACTGC CATAGACGGCAA | 480 |
| ICO42_CpG_in_staple42 | AGTATTCACCACGTCGGAACATTTCCGTGTCGCCAGAGTATGCCCGATACTGC CATAGACGGCAA | 481 |
| ICO42_CpG_in_staple43 | TGAGACAATGGTAAAGCATAACCCTGATAAATGCTCCGCTCACCCGATACTGC CATAGACGGCAA | 482 |
| ICO42_CpG_in_staple44 | ATTAGAAGGGCACCAGGTGCGTTGTTTTGATACTATTTCCTAGCCCGATACTGC CATAGACGGCAA | 483 |
| ICO42_CpG_in_staple45 | TATTTTTATGTAGAGTGTTAGGTTAATGTCATGAGATACGCCCCCGATACTGCC ATAGACGGCAA | 484 |
| ICO42_CpG_in_staple46 | GGAAAACCCTTAAGTGACAGGTACGAGCGAACGAAGAACCAGCCCGATACTG CCATAGACGGCAA | 485 |
| ICO42_CpG_in_staple47 | AAGGAACTGCTATCTATACAAACTAAGAGACAAAATGTGTAACCCGATACTGC CATAGACGGCAA | 486 |
| ICO42_CpG_in_staple50 | TTCCCAGAGCTATGCAGCACCTGTATCGGCCTTCTCCGAGGGCCCGATACTG CCATAGACGGCAA | 487 |
| ICO42_CpG_in_staple53 | GTAACCTCAGGATCCTACTTTAAAAGAAAAGAGGACTATGCACCCGATACTGC CATAGACGGCAA | 488 |

Gel Shift Assay, Dynamic Light Scattering, Fluorimetry

Agarose gel electrophoresis was used to analyze degree of NANP folding. 1.5% low melt agarose was dissolved in buffer containing 1×TAE and 12 mM $MgCl_2$ and slowly heated to boiling, then cooled back to room temperature. SybrSafe was mixed into the gel according to manufacturer protocols and the gel was allowed to set for at least 45 minutes at room temperature or 4 C prior to gel electrophoresis. 100 ng of DNA NANP sample was mixed with gel loading buffer (final concentration 1×) with water to make up the necessary volume. The gel was placed in a chamber containing pre-chilled gel running buffer consisting of 1×TAE and 12 mM $MgCl_2$, and once the samples were loaded, the gel was run at 85 V for 120 minutes at 4 C. Images were captured using a Typhoon. DLS was used for validation of NANP monodispersity: samples were diluted to 50 nM in PBS, and 50 uL of each sample was loaded into a plastic cuvette to be evaluated on a ZetaSizer. Samples were analyzed in triplicate using single angle scattering. Quantification of CpG copy number on NANPs was measured using a Tecan Spark. A Cy5-conjugated ssDNA oligo purchased from IDT was hybridized to folded NANPs via a 4 hour thermal annealing ramp during which the sample temperature was decreased incrementally from 37 C to 25 C. Fluorescently labeled NANPs were purified using the spin purification method described above and concentration was determined using UV-Vis measurements taken on a Nanodrop with absorbances set to 260 nm and 647 nm. A fluorescent calibration curve was produced using serial dilutions of the free CpG overhang hybridized to the Cy5-conjugated ssDNA oligo and measured with the Tecan Spark to produce a regression line with which the coverage of CpGs on each NANP variant was determined.

Reporter Cell Assays

HEK-Blue TLR9 reporter cells and THP1-Dual reporter cells were purchased from Invivogen and cultured according to manufacturer protocols. One day prior to cell assays, TLR9 cells were detached from the flask, centrifuged at 250×g for 5 minutes at room temperature and resuspended in fresh growth medium, consisting of Dulbecco's Modified Eagle Medium with 4.5 g/L glucose (Sigma-Aldrich, cat. Code D6546-6×500ML), 10% heat-inactivated FBS (Fisher Scientific, cat. Code SH3007002HI), 100 U/mL penicillin, 100 ug/mL streptomycin (Life Technologies, cat. Code 15140148), 100 ug/mL Normocin (manufacturer, cat. Code) and 2 mM L-glutamine (Fisher Scientific, cat. Code SH3003401). Cells were counted using a Nexcelom Cellometer Auto 2000 and 80,000 cells in 160 uL media were seeded into a flat-bottom 96-well plate. Cells were allowed to adhere for 24 hours prior to removal of growth medium from each well and subsequent addition of 160 uL of prewarmed HEK Blue Detection Medium. 40 μL of NANP sample was added to each well, with each sample being tested in triplicate, and cells were incubated at 37 C and 5% $CO_2$ for 20-24 hours. TLR9 activation levels were quantified by reading the absorbance of the 96-well plate at 620-655 nm using a spectrophotometer and normalized to a PBS negative control. For cGAS-STING assays, THP1-Dual reporter cells were centrifuged at 250×g for 5 minutes at room temperature and resuspended in fresh test medium, consisting of RPMI 1640 (Life Technologies, cat. Code 11875093), 2 mM L-glutamine, 25 mM HEPES, 10% heat-inactivated FBS, 100 U/mL penicillin, and 100 ug/mL streptomycin. 100,000 cells in 160 uL media were seeded into a flat-bottom 96-well plate and 40 μL of NANP sample was added to each well, with each sample being tested in triplicate. Cells were incubated at 37 C and 5% CO2 for 20-24 hours, after which 20 uL of cell supernatant was carefully transferred into an opaque white 96-well plate. 50 uL of QUANTI-Luc assay solution (Invivogen, cat. Code repqlc1) was added to each row of the 96-well plate, the plate was gently tapped several times on each side to mix, and luminescence readings were quantified using a luminometer set to a 0.1 second reading time. Positive controls for TLR9 and cGAS-STING assays were not complexed with lipofectamine prior to incubation with PBMCs.

PBMC Isolation, Stimulation, and Multiplex ELISA

Research donor blood was obtained from anonymous healthy donor volunteers under the IRB approved NCIat-Frederick Protocol OH9-C-N046 and the IRB approved exemption E-3359. PBMCs were isolated from three separate human donor buffy coats following the NCL protocol ITA-10 and tested following protocol ITA-2753. Briefly, blood was mixed at a 1:1 ratio with fresh PBS and gently layered onto Ficoll-Paque (Fisher Scientific, cat. Code 45001751) at a ratio of 3 mL Ficoll-Paque to 4 mL diluted blood in a 50 mL Falcon tube. Tubes were centrifuged at 900×g for 30 minutes with minimum acceleration and with the brakes off, after which the PBMC layer was gently pipetted into a new 50 mL tube. PBMCs were washed three times with HBSS (Life Technologies, cat. Code 24020117) and resuspended in complete RPMI. Cells were counted using a Nexcelom Cellometer Auto 2000 and $1.25 \times 10^6$ cells in 160 uL media were seeded into a flat-bottom 96-well plate. NANP samples were complexed with Lipofectamine 2000 (Life Technologies, cat. Code 11668027) at a ratio of 4:1 and incubated at room temperature for 30 minutes, after which OptiMEM (Life Technologies, cat. Code 31985062) was added to dilute the NANPs to the correct working concentration. 40 uL of the lipofectamine-complexed NANP sample was added to each well, with each sample being tested in triplicate, and cells were incubated at 37 C and 5% CO2 for 20-24 hours. 150 uL of cell supernatant was carefully transferred into a new 96-well plate, and the plate was flash frozen and stored at −80 C. Supernatant was then shipped on dry ice to Quansys Biosciences, which analyzed production of IFNα, IFNλ, IFNβ, and IFNω using multiplex ELISA.

Results

Design and Characterization of Wireframe DNA NANPs

Figure 8A:
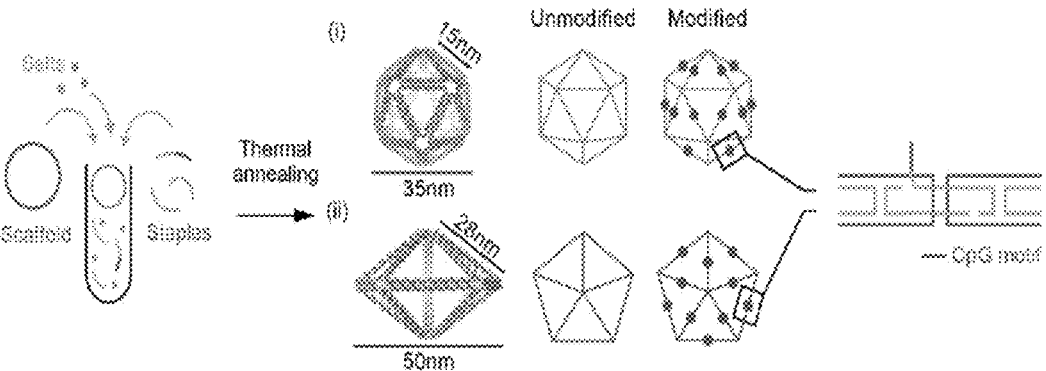
FIGS. 8A-8B are schematics illustrating design, production, and antigen presentation by nucleic acid nanostructures.
Figure 8B:
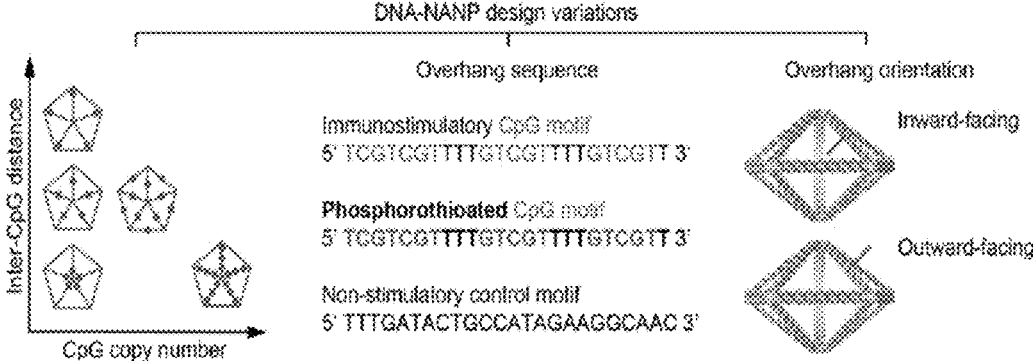

Wireframe DNA origami NANPs were designed using DAEDALUS and folded from a bacterially produced synthetic circular scaffold and an excess of short single-stranded staples via thermal annealing (Shepherd, et al., *Scientific Reports,* 9 (1), 6121 (2019)). In order to systematically evaluate the immunostimulatory properties of these NANPs, which are composed of dual-duplex DNA edges and additionally contain 262 CpG dinucleotides scattered throughout the scaffold and staples (Tables 4-14), multiple variations of one primary NANP, a pentagonal bipyramid with 84 base pairs per edge (PB84), were analyzed. As a comparative construct to investigate the effects of geometry on TLR9 and cGAS-STING activation, an icosahedron with 42 base pairs per edge (ICO42) was also fabricated, which was designed using the same scaffold as PB84 to eliminate potential effects of sequence variation on innate immune signaling (FIG. 8A). In addition to the unmodified NANPs that was used to probe the intrinsic immunogenicity of these wireframe structures, PB84 and ICO42 constructs in which select staples were extended on the 3' end to expose a 20-nt single-stranded overhang comprising the CpG sequence ODN 2006/7909 was also fabricated, a class B CpG ODN containing three repeats of an optimized hexamer known to strongly activate human TLR9. This approach was used to display CpG motifs at defined spatial locations on the NANP constructs in order to interrogate the effects of CpG copy number, spacing, and organization on TLR9 activation (FIG. 8B).

DNA NANPs of varying sizes and geometries were fabricated with staples containing ssDNA CpG motif overhangs to control the copy number of CpGs displayed from NANP edges in the form of (i) an Icosahedron displaying up to 30 CpG overhangs; and (ii) pentagonal bipyramid displaying up to 40 CpG overhangs. Design variations were used to explore the effects of CpG overhang copy number, inter-CpG distance, orientation, and sequence.

Validation of proper NANP self-assembly was first performed using agarose gel electrophoresis, in which successful folding was indicated by an upward shift of the folded NANP band relative to the scaffold band, with this shift enhanced by the addition of ssDNA overhangs. A fluorescent agarose gel shift assay was used to analyze the quality of NANP folding after spin column purification. Pentagonal bipyramids displaying 0, 10, 20, or 40 ssDNA overhangs hybridized to complementary Cy5-modified oligos show gel shifts corresponding to their increasing molecular weight on the SybrSafe channel, while the gel image taken in the Cy5 channel exhibits an increase in band intensity due to the successive increase in Cy5-CpG copy number on each NANP.

Figure 8C:
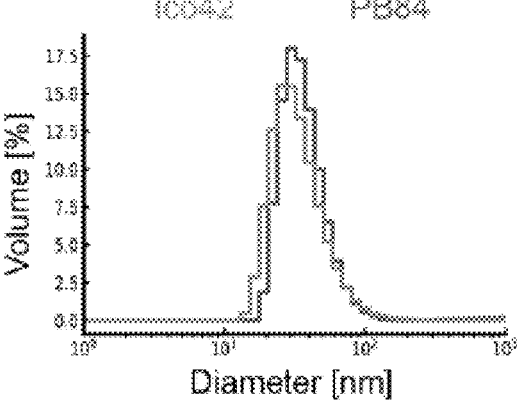
FIG. 8C is a graph of dynamic light scattering (DLS) to evaluate NANP hydrodynamic diameter and Polydispersity, with representative DLS measurements of an unmodified pentagonal bipyramid and an icosahedron, showing volume (%) over Diameter (nm) for each of the ICO42 and PB84 NANP, respectively.
Figure 13A:
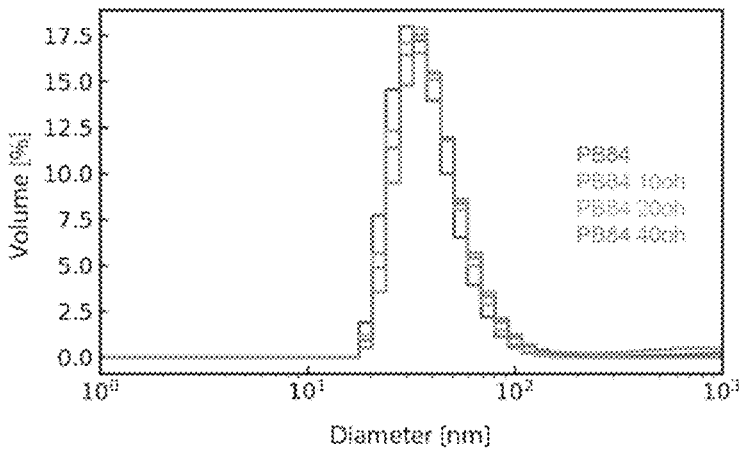
FIGS. 13A-13B are graphs of dynamic light scattering (DLS) measurements to evaluate NANP hydrodynamic diameter and polydispersity of variants of PB84 (FIG. 13A), and ICO42 (FIG. 13B), showing volume (%) over Diameter (nm) for each of the ICO42 and PB84 NANP un-modified, as well as modified with 10 (10 oh), 20 (20 oh) or 30 (30 oh)
Figure 13B:
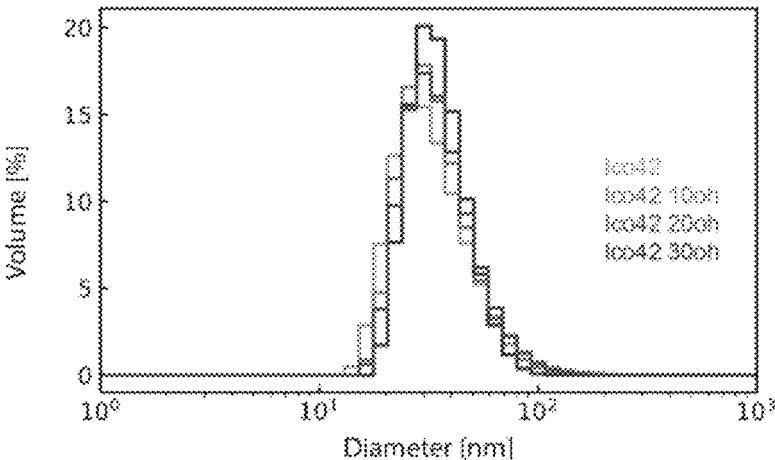

NANP monodispersity was evaluated using dynamic light scattering (DLS), and the hydrodynamic diameter of each sample was measured to validate batch to batch consistency in NANP folding (FIG. 8C, FIGS. 13A-13B). Dynamic light scattering (DLS) was used to evaluate NANP hydrodynamic diameter and polydispersity.

Fluorimetry using Cy5-labeled oligos hybridized to CpG overhangs confirmed the capability of this approach to present the expected copy numbers of CpGs on each NANP variant. A gel clot endotoxin test was used to verify that the endotoxin level of each sample was below a threshold of 1.5 EU/mL prior to its application in cell assays.

Innate Immune Stimulation by Unmodified DNA NANPs In Vitro

To characterize the baseline immunostimulatory properties of NANPs the effect of unmodified PB84 and ICO42 on TLR9 and cGAS-STING pathway activation was investigated in vitro. HEK-Blue reporter cells expressing stably transfected human TLR9 were incubated with 10 nM PB84 and ICO42, and to assess the impact of NANP structuring, equivalent concentrations of the scaffold (phPB84) as well as the PB84 and ICO42 staple sets were also tested as non-structured controls. Consistent with results from previous literature (Hong, et al., *Nano Letters,* 18 (7), 4309-4321 (2018)), NANPs that were not complexed with lipofectamine prior to incubation with reporter cells failed to elicit an innate immune response. Thus, for all experiments described herein, all constructs were co-complexed with lipofectamine to enable transfection, and a lipofectamine-only control was also included in each assay (pathway activation is not observed in response to transfection of PB84, ICO42 or the unfolded control into HEK293T cells without transfected TLR9, or cGAS-knockout THP1-Dual cells).

Figure 9A:
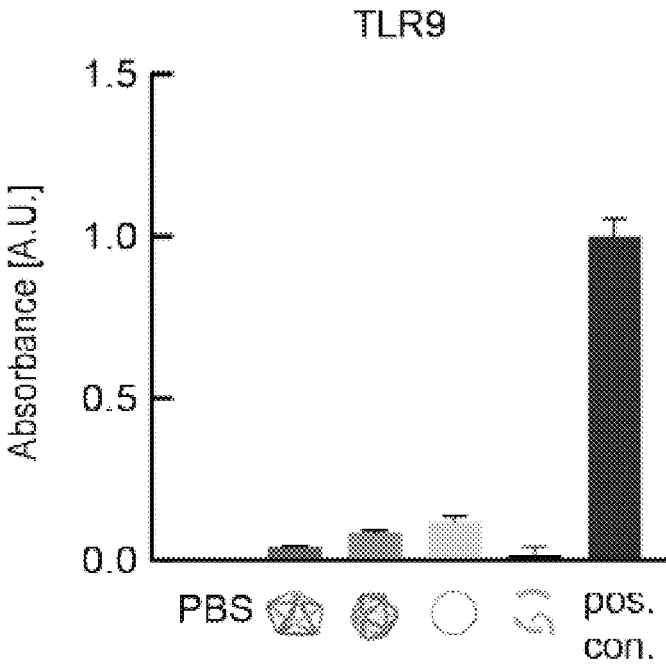
FIGS. 9A-9B are bar graphs of cellular immunostimulation by unfunctionalized NANPs in vitro, showing Absorbance [0-1.5 A.U.] following TLR activation (FIG. 9A) and luminescence [0-2.0 R.L.U.] following cGAS-STING pathway activation (FIG. 9B) for each of PBS (control), PB84, ICO42, scaffold DNA, staple strands, and a positive control, respectively.

After incubation of TLR9 cells with all NANP samples for 24 hours, TLR9 activation was evaluated and it was found that structured constructs resulted in minimal activation of the TLR9 pathway, whereas the unstructured scaffold induced slightly stronger TLR9 activation (FIG. 9A). Importantly, the phPB84 scaffold and the PB84/ICO42 staple sets from which the NANPs were folded contained several hundred CpG dinucleotides, although only three sets of these CpG dinucleotides could be considered strongly stimulatory CpG motifs according to previously identified sequence requirements (Pohar, et al., *The Journal of Immunology*, 194 (8), 3901-3908 (2015), Vollmer, et al., *Journal of Immunology*, 34 (1), 251-262 (2004)). Notwithstanding, this result still suggests that such CpGs, which are typically inaccessible in fully folded NANPs and might not be sufficiently exposed to induce TLR9 engagement and downstream pathway activation even after NANP degradation by Dnases, may induce low levels of TLR9 activation when presented in unstructured formulations.

Figure 9B:
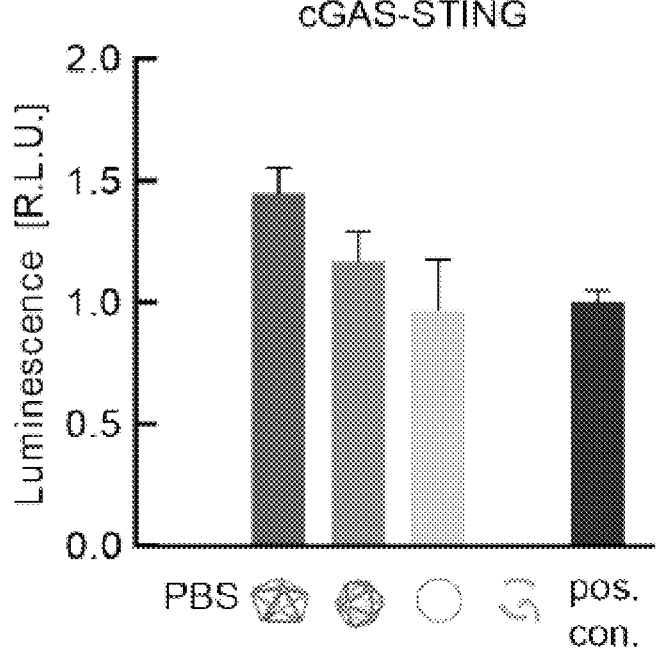

Unlike TLR9, which requires specific sequence contexts for binding and activation, cGAS responds to cytosolic dsDNA in a primarily sequence-independent manner. As a result, while neither of the unmodified PB84 nor ICO42 constructs induced strong TLR9 signaling, they might instead elicit a substantial cGAS-STING response. To test this, PB84, ICO42, and their respective unstructured controls were transfected into THP1-Dual reporter cells. After a 24-hour incubation, cells treated with structured NANPs were observed to be strongly activated the cGAS-STING pathway, while staples alone did not induce cGAS activation (FIG. 9B). Surprisingly, moderate levels of immune activation were observed in response to transfected phPB84 scaffold. As some sections of the scaffold have potential for self-dimerization, this might have occurred during incubation, resulting in stretches of dsDNA becoming available for cGAS binding.

To verify that the observed responses to these NANPs were indeed mediated by the TLR9 and cGAS-STING pathways, the same set of experiments were performed in the Null 1 and THP1-KO-cGAS cell lines, which do not express TLR9 and have a stable cGAS knockout, respectively (FIGS. 14A-14B). All formulations failed to elicit a response, confirming the role of these innate immune pathways in the NANP-induced responses.

Interferon Response Towards Unmodified DNA NANPs in Primary Cells

Having evaluated the responses of isolated innate immune pathways to DNA-based NANPs, the effects of these nanostructures on PBMCs was Investigated. PBMCs contain many critical immune cell subtypes such as lymphocytes, monocytes, and dendritic cells and therefore represent a more complete model system of the innate immune response. PB84, ICO42, scaffold, and staples were transfected into PBMCs and recovered cell supernatant after a 20-hour incubation (Dobrovolskaia & Afonin, *Nature Protocols*, 15 (11), 3678-3698 (2020)). The immunostimulatory activity of each construct was quantified using a multiplex enzyme-linked immunosorbent assay (ELISA) to measure secretion of IFNα, IFNλ, IFNβ, and IFNω, interferons which are known to be expressed in response to intracellular nucleic acids (Schlee & Hartmann, *Nature Reviews Immunology*, 16 (9), 566-580 (2016), Paludan, *Microbiology and Molecular Biology Reviews*, 79 (2), 225-241 (2015)). Increases in production of all interferons were observed in response to both PB84 and ICO42, as well as weaker but consistently elevated levels of IFN expression in response to the pHPB84 scaffold (FIGS. 11A-11M). The staples alone induced much higher levels of IFN production compared to the other NANP formulations, even though all of the constructs have the same sequence composition. This may be due to the fact that the staples are much smaller than the folded constructs and the scaffold, potentially allowing for higher transfection efficiency and therefore higher concentrations of CpG-containing oligos available for TLR9 binding. This result highlights the ability of nanostructuring to modulate the properties of the individual components: once these highly immunostimulatory staples are folded into a wireframe NANP, whether because of a decrease in transfection efficiency or reduced accessibility of CpG dinucleotides within the scaffold and staples to TLR9, the folded NANP is much less immunostimulatory than the sum of its parts.

Taken together with the results from the reporter cell lines, these data suggest that while the immune response towards the unstructured scaffold and staples can be attributed towards both TLR9 and cGAS-STING, the immune response towards the structured NANPs is largely independent of the TLR9 pathway and may primarily be mediated by cGAS-STING. This suggests that the immunostimulatory profile of the individual NANP components is affected by sequence composition and self-dimerization potential, whereas properties which affect cGAS activation such as NANP duplex edge length might have the greatest influence on the immune response towards intact, unmodified DNA NANPs.

Designing DNA NANPs for Controllable Immunostimulation

The ability of 3D wireframe DNA NANPs to trigger programmable activation of the innate immune response through rationally designed display of immunostimulatory motifs was investigated. Since significant stimulation of the TLR9 pathway by unmodified structured PB84 was not observed in previous reporter assays, this structure was immunologically inert in the context of TLR9 reporter cells. This NANP could then be controllably functionalized with immunostimulatory motifs to systematically investigate the relative impacts of various parameters of nanoscale display without any confounding levels of baseline TLR9 activation. To this end, PB84 variants displaying 0, 10, 20, or 40 copies of CpG-OH distributed evenly across the exterior of the NANP (FIG. 8B) were fabricated. Nanostructures displaying corresponding copy numbers of CpG-free overhangs (CpG-f-OH) of identical length and GC content served as comparative controls.

Figure 10A:
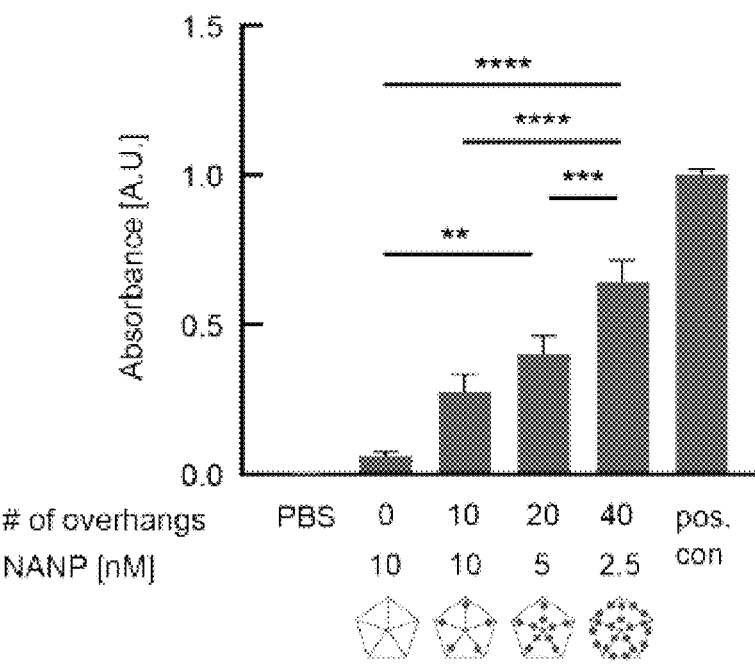
FIGS. 10A-10B are bar graphs of cellular immunostimulation by unfunctionalized and CpG-functionalized NANPs in vitro, showing absorbance [0-1.5 A.U.] following TLR activation for each of ICO42 and PB84, respectively, with different numbers (0, 10, 20, or 40 total) and concentrations (10, 10, 5, or 2.5 nM) of CpG motifs, respectively.

Each of the test formulations were transfected into HEK-Blue TLR9 cells, and following a 24-hour incubation period, PB84 was verified as displaying 0 copies of CpG-OH and did not activate TLR9. In contrast, each of the constructs displaying 10, 20, or 40 copies of CpG-OH induced TLR9 activation, and furthermore, the strength of TLR9 activation was directly correlated with the CpG-OH copy number on the nanostructure (FIG. 10A). Importantly, the total concentration of CpG motifs was held constant across these samples, indicating that the magnitude of TLR9 activation is dependent not only on the CpG concentration, but also on the valency of CpG motifs per NANP. Neither PB84 nor ICO42 induce expression of Type I or Type III IFNs if they are not complexed with lipofectamine prior to incubation with PBMCs. (FIG. 15) All constructs displaying CpG-f-OH, regardless of copy number per NANP, did not induce significantly higher levels of TLR9 activation compared with the unmodified nanostructure, which shows that changes in non-CpG-containing total DNA content have no effect on TLR9 signaling (10 nM equivalent of PB84 scaffold, staples, and folded PB84 were not complexed with lipofectamine prior to incubation with HEK-Blue TLR9 cells for 24 hours. No activation of TLR9 was observed for the staple and PB84 samples, and very minimal TLR9 activation was induced in response to the scaffold sample.).

Figure 10B:
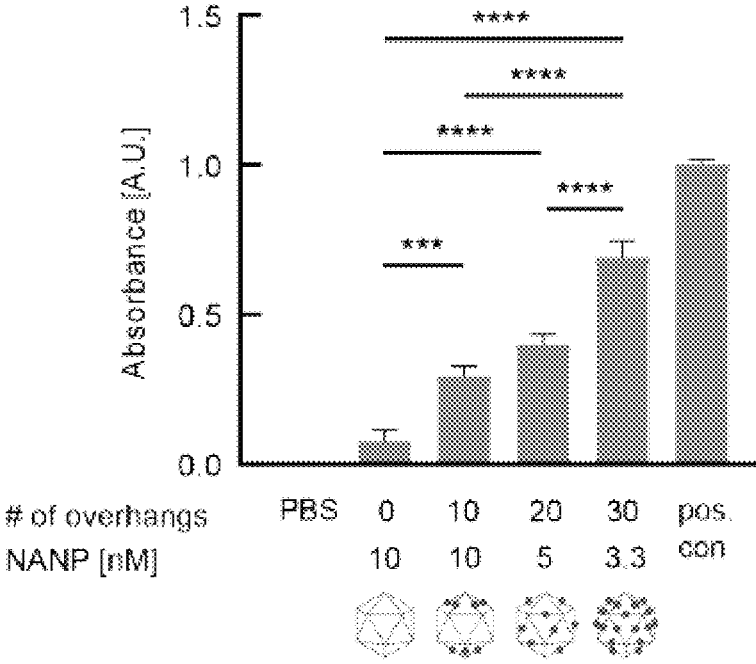
Figures 11A, 11B, 11C, 11D, 11E, 11F, 11G, 11H, 11I:
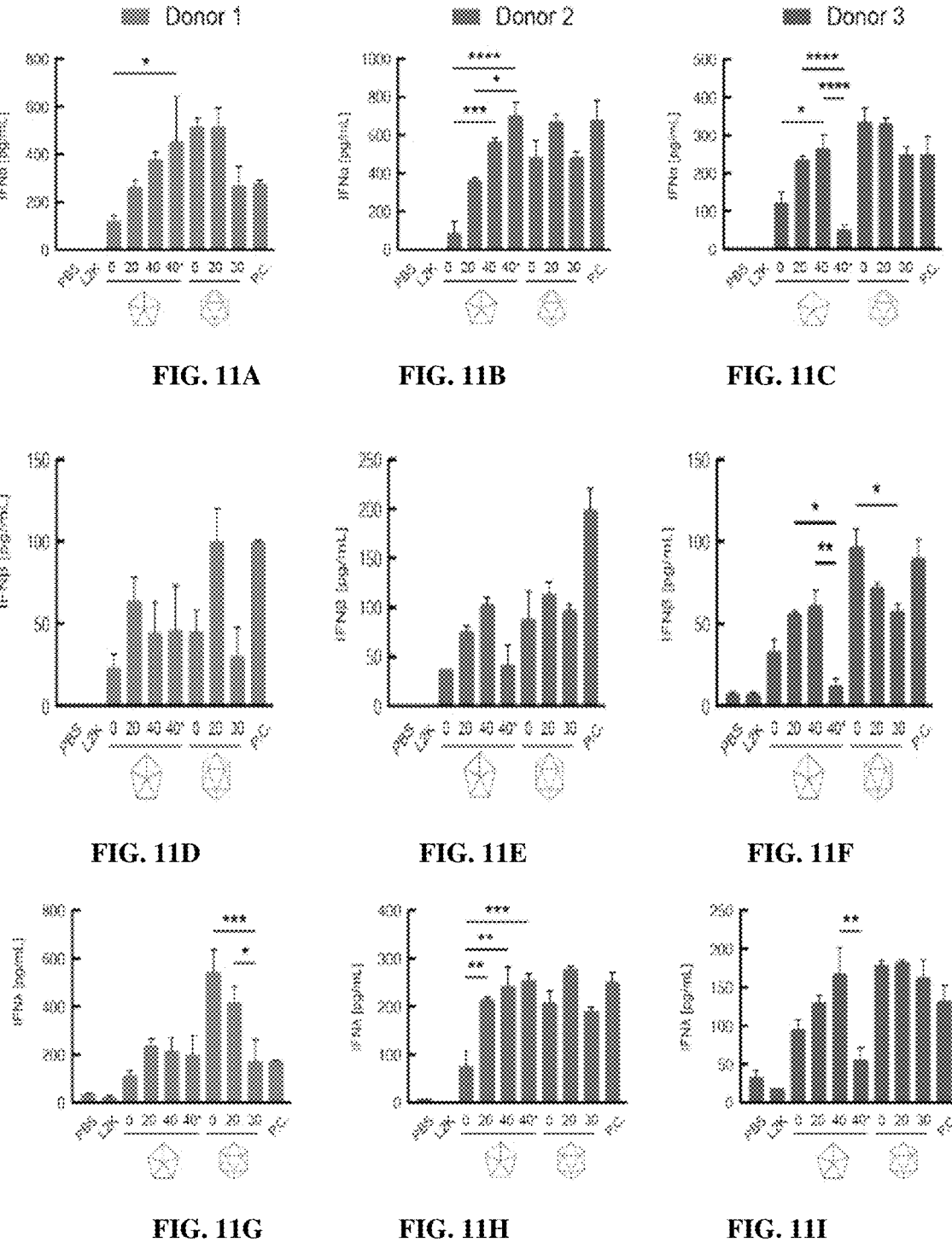
FIGS. 11A-11I are bar graphs of innate immune response of PBMCs in response to engineered immunostimulatory NANPs, showing expression (pg/ml) of IFNα (FIGS. 11A-11C), IFNλ (FIGS. 11D-11F), IFNβ (FIGS. 11G-11I) and IFNω (FIGS. 11J-11L), following TLR activation for each of PB84 displaying 0, 20, or 40 copies of CpG, respectively, and ICO42 displaying 0, 20, or 30 copies of CpG, respectively, as well as negative (PBS) and positive (P.C.) controls for each of samples obtained from three different donors, respectively. Each bar represents averaged triplicate data from a single donor, where n=3 donors.
Figures 11J, 11K, 11L:
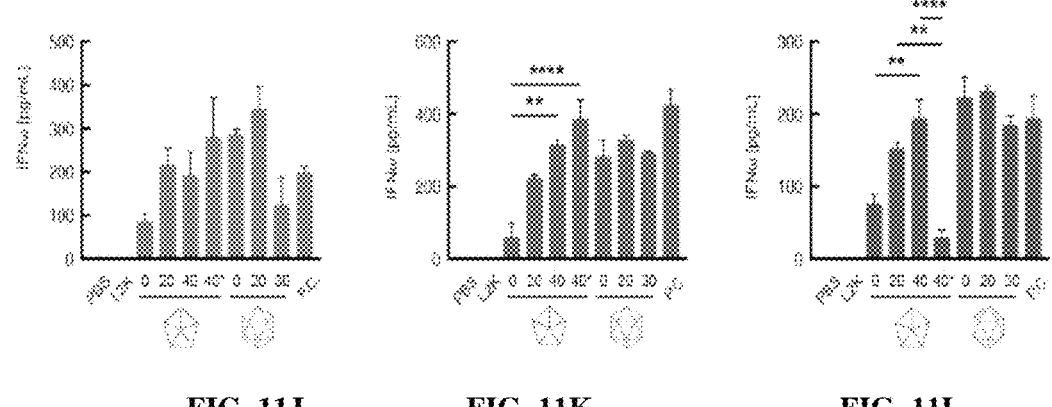
FIG. 11M is a shaded heat map depicting interferon expression in response to unmodified DNA NANPs in PBMCs, showing NANP-induced expression levels of IFNα, IFNλ, IFNβ, and IFNω in PBMCs analyzed separately for each donor and all IFN expression levels were normalized to the corresponding positive control, ODN2216. Data in all assays were calculated from samples in triplicate, where n=3 biologically independent assays.
Figure 11M:
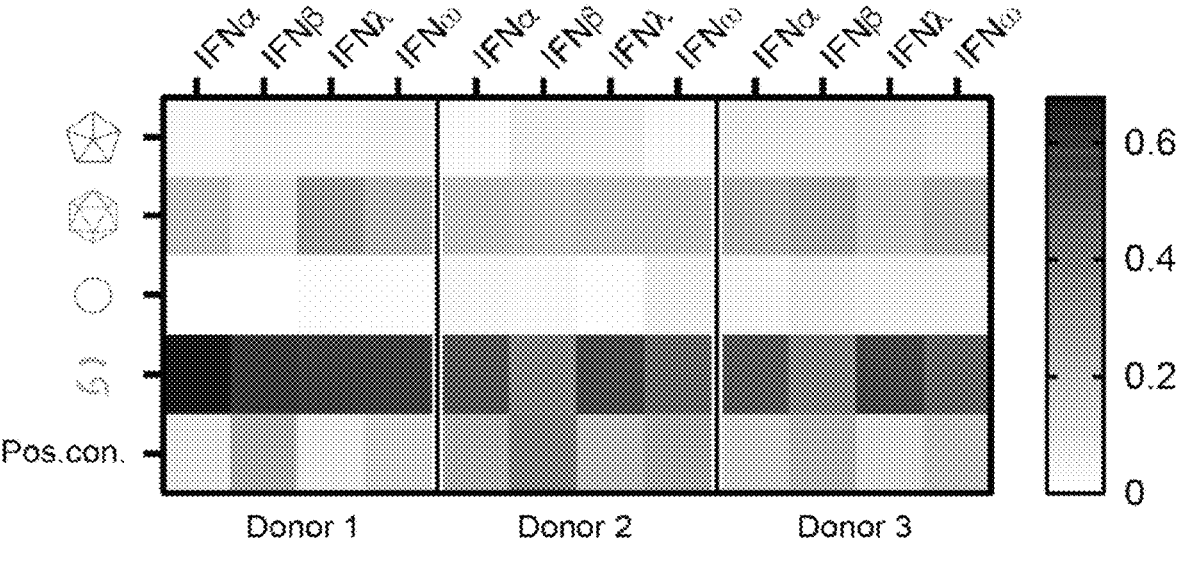

To test whether this method of controllable immunostimulation was applicable to more than a single type of NANP, ICO42 displaying 0, 10, 20, or 30 copies of CpG-OH was also fabricated. As with PB84, the magnitude of TLR9 activation was dependent on the copy number of CpG-OH presented by the NANP (FIG. 10B). However, the magnitude at which the TLR9 pathway was activated by ICO42 and PB84 constructs displaying identical copy numbers of CpG-OH was not the same, suggesting that the spatial organization of CpG overhangs on the nanostructures may influence TLR9 activation levels as well.

To investigate whether the ability of these NANPs to controllably modulate immune pathway activation was reproducible outside of reporter cell lines, the capability of these NANPs to induce interferon production in primary immune cells was evaluated. PB84 with 0, 20, and 40 copies of CpG-OH and ICO42 with 0, 20, and 30 copies of CpG-OH were transfected into PBMCs, where the total concentration of CpG-Ohs in each sample was held constant at 10 nM. After incubation for 20 hours, subsequent multiplex ELISA analysis of cell supernatant showed that for all analytes tested, CpG-OH-displaying PB84 constructs induced significantly higher interferon expression compared to their unmodified counterparts (FIGS. 11A-11M). Additionally, interferon production was generally higher in response to PB84 displaying 40 copies of CpG-OH compared to PB84 with 20 copies of CpGOH.

Interestingly, unlike what was seen in the reporter cell assays, the increase in IFN response towards ICO42 displaying CpG-Ohs appeared to saturate at 20 CpG-Ohs. In most cases, ICO42 displaying 30 copies of CpGOH induced similar levels of IFNs to the unmodified ICO42, and in a few cases, IFN expression in response to ICO42 with 30 CpG-Ohs was actually lower than the unmodified NANP. Because the baseline immunostimulation induced by ICO42, likely mediated by cGAS-STING, was already quite high, it's possible that the addition of 20 CpG overhangs elicited an increase in TLR9 activation while minimally affecting cGAS binding, whereas the addition of 30 CpG overhangs significantly hindered the ability of cGAS to bind to ICO42, so much so that the increase in TLR9 activation was not sufficient to compensate for the loss of cGAS-STING activation. These results imply that CpG valency and spatial organization can indeed be tuned to controllably modulate the strength of the NANP-mediated activation of TLR9, but the specific levels of each parameter may need to be optimized for different NANP geometries. However, as with the reporter cell assays, NANPs that were not complexed with lipofectamine did not elicit cytokine production, suggesting that these nanostructures may not be natively taken up by any immune cell populations within PBMCs at sufficient levels to activate immune signaling, and therefore may be largely immunologically inert in the absence of functionalizations enabling cellular uptake and internalization, minimizing the potential for off-target immunostimulation.

Investigating the Parameters Controlling DNA NANP-Mediated Immune Activation

It has been demonstrated that these NANPs can be modified with CpGs to tune TLR9 activation and modulate the resulting innate immune response. To elucidate the roles of the NANP design parameters contributing to this controllable immunostimulation. Because NANP structuring significantly affected the intensity of TLR9 signaling, further investigation of the role of NANPs in TLR9 activation was done. As precise control over directionality and spatial positioning is one unique advantage of wireframe DNA origami, whether the orientation of CpG-OH presentation on NANPs affected TLR9 activation was assessed.

Interestingly, it was found that there were no significant differences in TLR9 signaling between PB84 constructs displaying CpG-Ohs on the exterior versus interior of the NANP (FIG. 17). This may be the result of the flexibility of the 20-nt ssDNA overhang and the wireframe structure of NANPs; because only the duplex edges are solid, the 3' terminus of the inward-facing overhangs may in fact end up on the exterior of the NANP, and vice versa. Regardless of the copy number of CpG-free overhangs displayed on PB84, there is no significant difference between the level of TLR9 activation induced by those constructs compared to non-modified PB84 (FIG. 18). To further understand the contribution of the NANP itself to TLR9 activation, HEK-Blue TLR9 cells were treated with free CpG-OH and found that there was no TLR9 signaling in response to free CpG-OH at any of the tested concentrations, even though the same concentrations of CpG-OH displayed on NANPs induced strong TLR9 activation (FIG. 19). To test whether this lack of activation may be due to degradation of free CpG-Ohs by intracellular Dnases, HEK-Blue TLR9 cells were incubated with phosphorothioate-stabilized free CpG-Ohs (pCpG-Ohs). Unlike the non-stabilized CpG-Ohs, the magnitude of TLR9 activation was correlated with the concentration of pCpG-Ohs delivered (FIGS. 14A-19). As phosphorothioate stabilization of CpG-Ohs was able to rescue their ability to activate TLR9, this suggests that CpG oligo degradation significantly impacts TLR9 activation, corroborating an earlier hypothesis. When CpG-Ohs were displayed on NANPs, they were able to induce similar levels of TLR9 activation as their free pCpG-OH counterparts. These results demonstrate that in terms of the ability to activate the TLR9 pathway, attachment of CpG-Ohs to DNA NANPs produces a similar effect to phosphorothioate stabilization, suggesting either that NANP-bound CpGOHs may be less susceptible to Dnase degradation, or alternatively that the effects of NANP-mediated CpG-OH clustering may be able to compensate for the limited stability of phosphodiester CpG overhangs. Finally, the effect of the proximity between the CpG motif and the NANP was tested by varying the location of the CpG along the ssDNA overhang. NANPs where the CpG motif was furthest away from the NANP induced significantly higher levels of TLR9 activation compared to NANPs where the CpG motif was spatially closer along the ssDNA overhang (FIGS. 16A-16B). This suggests that the NANP may provide a steric hindrance towards CpGTLR9 binding when there is not sufficient distance between the dual-duplex edge of the NANP and the CpG motif, which highlights spatial distancing as another parameter that can be tuned to influence the magnitude of TLR9 activation.

Figure 12A:
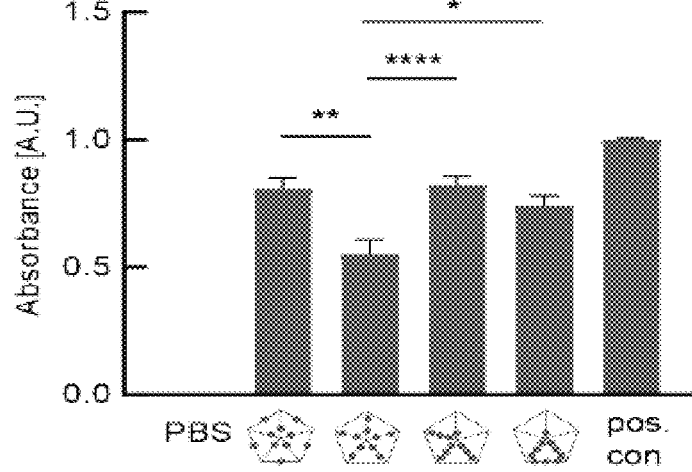
FIGS. 12A-12B are bar graphs of TLR9 activation is dependent on CpG-OH valency, inter-CpG distance, and nanoscale organization of CpG-OHs, showing Absorbance [0-1.5 A.U.] measured in response to TLR9 stimulation with PB84 displaying 10 CpG-OHs (•) at varying densities (FIG. 12A), and Absorbance [0-1.5 A.U.] measured in response to TLR9 stimulation by PB84 constructs in which either one or both sides of the NANP displays 5 CpG-OHs (•) (FIG. 12B), respectively. PBS is a negative control; ODN2006 is a positive control (pos. con.). Data show the average absorbance of samples in triplicate with standard error, where n=3 biologically independent assays. P values are from a one-sided analysis of variance (ANOVA) with correction for multiple comparisons (*: P≤0.05; : P≤0.01, *: P≤0.001, ****: P≤0.0001). All unlabeled pair-wise comparisons are not significant.
Figure 12B:
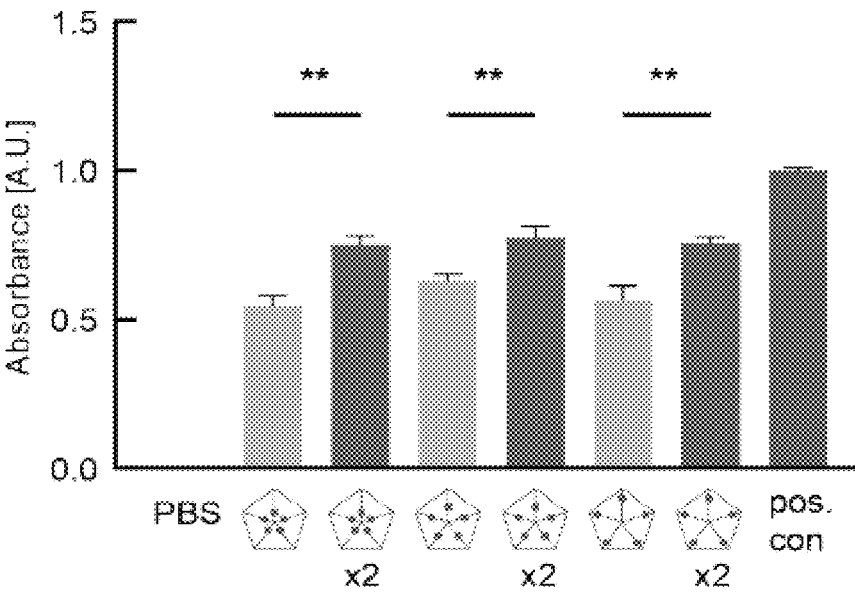

In the previous assays, the CpG-OH valency, inter-CpG distance, and pattern of presentation were all unique for each of the NANPs tested (FIG. 15). As such, any or all of these properties could theoretically be a potential determinant of the strength of TLR9 activation. However, as these variables are interdependent, it is difficult to evaluate any of these properties in isolation using the current system. To partially circumvent this technical limitation, the complexity of the system was reduced by holding a single variable constant and analyzing the effects of the remaining parameters on the TLR9 pathway, starting with the CpG-OH copy number. Three PB84 constructs were fabricated, each displaying 10 copies of CpG-OH, in which the distances between adjacent CpG overhangs progressively decreased between constructs (FIG. 12A). Upon transfecting these samples into HEKBlue TLR9 cells, the NANP in which the distance between adjacent CpG-Ohs was the smallest induced a significantly higher level of TLR9 activation compared to the constructs in which the CpG-Ohs were clustered less tightly together. Additionally, PB84 constructs with five CpG-Ohs displayed at low, medium, and high clustering densities on either one or both sides of the NANP were synthesized. Interestingly, in contrast to the previous result, no significant difference between the magnitude of TLR9 activation induced by any of the five CpG-OH constructs was observed (FIG. 12B). This may suggest that at this low valency of CpG-Ohs, the clustering density has very low impact on the level of TLR9 activation, whereas at higher copy numbers such as 10+CpGOHs, the impact of clustering becomes much stronger. However, there was a significant difference in TLR9 signaling between each of the five CpG-OH constructs and their corresponding 10 CpG-OH counterparts, even though the total CpG concentration and the density of CpG-OH motifs was held constant for each pair of NANPs. As clustering of multiple activated TLR dimers in close proximity has been shown in previous studies to mediate enhanced downstream signaling, the ability of the 10 CpG-OH construct to coordinate binding of more dimers than its five CpG-OH counterpart may explain the observed increase in TLR9 activation levels.

The magnitude of TLR9 signaling decreases as the CpG motif is shifted closer to the nanoparticle (FIGS. 20A-20B).

Increasing the number of CpG motifs on each overhang results in a corresponding increase in TLR9 activation.

SUMMARY

Baseline immunostimulatory effects of wireframe DNA NANPs in reporter cell lines were characterized and the immune response towards these nanostructures was primarily driven by the cGAS-STING pathway, while intact nanostructures do not induce a TLR9 response. Nanostructures functionalized with immunostimulatory CpG overhangs demonstrated that both TLR9 activation levels and the downstream production of Type I and III IFNs can be controllably modulated by adjusting critical design parameters. These parameters included CpG valency, clustering density, and pattern of presentation, as well as NANP geometry and CpG motif stabilization. Lastly, several physical parameters regulating intra-versus inter-TLR9 dimer binding were demonstrated (FIGS. 14A-20B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A nucleic acid nanostructure comprising
(i) nucleic acid(s) folded into a defined three-dimensional geometric shape, and
(ii) two or more copies of an immunostimulatory agent,
wherein the two or more copies of the immunostimulatory agent are conjugated to, bound to, or otherwise associated with the nucleic acid(s),
wherein the distance between adjacent copies of the immunostimulatory agent is from 1 nm to 500 nm, inclusive, and
wherein the number of copies of the immunostimulatory agent, the distance between adjacent copies of the immunostimulatory agent, the location of the immunostimulatory agent on the nanostructure, the rigidity/flexibility of the immunostimulatory agent, the dimensionality of the immunostimulatory agent, the topology of the nanostructure, the ultra-structural organization of the nanostructure, the geometric shape of the nanostructure, or a combination thereof improves an immune response induced by the immunostimulatory agent relative to a control having an equal amount of the same immunostimulatory agent,
wherein the control comprises the same nucleic acid nanostructure comprising a single copy of the same immunostimulatory agent.

2. The nanostructure of claim 1, wherein the nanostructure comprises a single stranded nucleic acid scaffold sequence and one or more single stranded nucleic acid staple strands that hybridize to the scaffold sequence to form the three-dimensional nanostructure having a defined geometric shape.

3. The nanostructure of claim 1, wherein the number of copies of the immunostimulatory agent is 2 to 1,000, or 2 to 100, or 3 to 75, or 4 to 60, or 5 to 50, or 10 to 50, or 5 to 25, or 5 to 10, inclusive.

4. The nanostructure of claim 1, wherein the distance between adjacent copies of the immunostimulatory agent is from 1 to 100 Angstroms, or 1 to 40 Angstroms, or from 1 nm to 150 nm, or 10 nm to 80 nm, or 15 nm to 50 nm, or 25 nm to 30 nm, inclusive.

5. The nanostructure of claim 1, wherein the geometric shape is selected from the group consisting of a helix bundle, cuboidal structure, icosahedral structure, tetrahedral structure, cuboctahedral structure, octahedral structure, and hexahedral structure.

6. The nanostructure of claim 1, wherein the copies of the immunostimulatory agent are covalently or non-covalently bound to the nanostructure.

7. The nanostructure of claim 6, wherein the copies of the immunostimulatory agent are indirectly or directly associated with the nanostructure via nucleic acid overhangs extending from the 3' or 5' ends of one or more selected staple strands of the nanostructure,
optionally wherein the nucleic acid overhangs hybridize to complementary target RNA, DNA or PNA covalently linked to, or incorporating the immunostimulatory agent.

8. The nanostructure of claim 6, wherein the covalent linkage is formed by maleimide-thiol coupling.

9. The nanostructure of claim 1, comprising two or more structurally different immunostimulatory agents.

10. The nanostructure of claim 1, wherein one or more of the immunostimulatory agent(s) is selected from an antigen, an adjuvant, a TLR agonist and a cGAS ligand,
optionally wherein the TLR agonist is selected from the group consisting of BCG; Poly I: C, Poly ICLC; MPL; LPS; Imiquimod; 852A; Resiquimod; VTX-2337 and an immunostimulatory CpG motif.

11. The nanostructure of claim 10, wherein the immunostimulatory agent(s) is a TLR9 agonist.

12. The nanostructure of claim 10, wherein the immunostimulatory agent comprises an immunostimulatory CpG motif that is capable of binding to a TLR,
optionally wherein the immunostimulatory CpG motif is located within a single stranded nucleic acid overhang associated with a staple strand within the nanostructure, optionally wherein the nanostructure comprises a total of from 1 to 1,000 CpG motifs, inclusive.

13. The nanostructure of claim 12, comprising
(i) from 2 to 100, from 2 to 50, from 2 to 30, from 2 to 20, or from 2 to 10 immunostimulatory CpG motifs, inclusive, or
(ii) from 2 to less than 10 immunostimulatory CpG motifs, or
(iii) comprising 10 or more immunostimulatory CpG motifs, or
(iv) comprising between 1 and 10 immunostimulatory CpG motifs within at least one staple strand, or
(v) comprising 1, 2 or 3 immunostimulatory CpG motifs within at least one staple strand.

14. The nanostructure of claim 13, wherein the two or more copies of immunostimulatory CpG motifs are separated by a distance of at least 40 angstroms.

15. The nanostructure of claim 1, further comprising a targeting molecule,
optionally, wherein the targeting molecule directs the nanostructure to the cell cytosol.

16. The nanostructure of claim 1, further comprising a therapeutic agent.

17. The nanostructure of claim 1, wherein the nanostructure is coated with a coating agent,
optionally, wherein the coating agent is a naturally occurring or synthetic cationic oligomer or polymer or co-oligomer, optionally comprising or consisting of PEG moieties,
further optionally, wherein the coating agent comprises or consists of
(a) 10 lysine units optionally conjugated terminally to a linear PEG moiety,
optionally wherein the PEG has a molecular weight of approximately 5000 Da;
(b) poly (2-dimethylaminoethyl methacrylate (PD-MAEMA), or a PEG copolymer thereof,
optionally having a molecular weight range between 5000 Da to 20000 Da;
(c) linear polyethyleneimine (PEI), optionally, in a molecular weight range between 5000 Da and 10000 Da; or
(d) chitosan, optionally having a molecular weight range between 4000 Da and 6000 Da, optionally with deacetylation of more than 90%.

18. The nanostructure of claim 17, wherein the coating agent comprises or consists of a minor groove binder,
optionally wherein the minor groove binder increases stabilization,
optionally wherein the stabilization comprises protecting the protection for endonuclease.

19. The nanostructure of claim 2, wherein
(i) one or more of the single stranded nucleic acid overhang extending from the 3' or 5' end of one or more selected staple strands of the nanostructure face inwards towards the center of the nanostructure; or
(ii) one or more of the single stranded nucleic acid overhang extending from the 3' or 5' end of one or more selected staple strands of the nanostructure face outwards away from the nanostructure.

20. The nanostructure of claim 2, comprising a nucleic acid scaffold sequence of SEQ ID NO:5.

21. The nanostructure of claim 7, comprising a nucleic staple sequence from any one of SEQ ID NOs: 6-488.

22. The nanostructure of claim 20, wherein the nanostructure comprises a pentagonal bipyramid with 84 base pairs per edge, comprising one or more staple sequence from any one or more of SEQ ID NOs: 74-193, and 234-273,
optionally comprising 20, 30, or 40 immunostimulatory CpG motifs.

23. The nanostructure of claim 20, wherein the nanostructure comprises an icosahedron with 42 base pairs per edge,
comprising one or more staple sequence from any one or more of SEQ ID NOs: 314-398, and 429-458, optionally comprising 10, 20, or 30 immunostimulatory CpG motifs.

24. A nucleic acid nanostructure comprising a defined geometric shape and two or more copies of an adjuvant bound to the surface of the nanostructure,
wherein the distance between adjacent copies of the adjuvant is from 1 nm to 500 nm, inclusive, and
wherein the number of copies of the adjuvant, the distance between adjacent copies of the adjuvant, the location of the adjuvant on the nanostructure, the rigidity/flexibility of the adjuvant, the dimensionality of the adjuvant, the topology of the nanostructure, the ultra-structural organization of the nanostructure, the geometric shape of the nanostructure, or a combination thereof improves an immune response induced by the adjuvant relative to a control nucleic acid nanostructure comprising one copy of the same adjuvant.

25. A nucleic acid nanostructure comprising
(i) a pentagonal bipyramid with 84 base pairs per edge, or an icosahedron with 42 base pairs per edge; and
(ii) two or more, up to 40 copies of single stranded DNA including an immunostimulatory CpG motif bound to, or otherwise associated with the-nanostructure,
wherein the distance between adjacent copies of the immunostimulatory CpG motif is from 1 to 100 Angstroms, inclusive, and
wherein the number of copies of the immunostimulatory CpG motif, the distance between adjacent copies of the immunostimulatory CpG motifs, the location of the immunostimulatory CpG motifs on the nanostructure, the rigidity/flexibility of the single stranded DNA including a immunostimulatory CpG motif, the dimensionality of the immunostimulatory CpG motifs, the topology of the nanostructure, the ultra-structural organization of the nanostructure, the geometric shape of the nanostructure, or a combination thereof improves an immune response induced by the immunostimulatory CpG motifs relative to a control,
wherein the control comprises the same nucleic acid nanostructure comprising a single copy of the immunostimulatory CpG,
wherein the nanostructure comprises a single stranded nucleic acid scaffold sequence and one or more single stranded nucleic acid staple strands that hybridize to the scaffold sequence to form the three-dimensional nanostructure having a defined geometric shape, and
wherein the two or more copies of single stranded DNA including an immunostimulatory CpG motif are located within one or more single stranded nucleic acid overhang extending from the 3' or 5' end of one or more selected staple strand of the nanostructure.

26. A liposomal composition, comprising the nanostructure of claim 1, wherein the nanostructure is encapsulated within the liposome.

27. A pharmaceutical composition comprising the nucleic acid nanostructure of claim 1 in an effective amount to induce an immune response in a subject in need thereof, with or without the aid of an adjuvant and/or antigen, and a pharmaceutically acceptable carrier, diluent, preservative, excipient, or combination thereof, optionally further comprising an adjuvant and/or antigen.

28. A method of inducing or enhancing an immune response in a subject comprising administering to the subject an effective amount of the pharmaceutical composition of claim 27, optionally further comprising administering to the subject an antigen.

29. A method of inducing a TLR9 response in a subject, comprising administering to the subject an effective amount of the pharmaceutical composition of claim 27, optionally wherein the method does not include administering an antigen to the subject.

30. A method of inducing an innate immune response in a subject, comprising administering to the subject an effective amount of a nucleic acid nanostructure comprising (i) nucleic acids folded into a defined three-dimensional geometric shape, and (ii) two or more immunostimulatory agents, wherein the immunostimulatory agents comprise two or more CpG motifs, and/or a double stranded nucleic acid structure suitable for stimulating an innate immune response.

31. The method of claim 30, wherein the nanostructure comprises a single stranded nucleic acid scaffold sequence and one or more single stranded nucleic acid staple strands that hybridize to the scaffold sequence to form the defined three-dimensional geometric shape, wherein the two or more immunostimulatory agent form part of the scaffold and/or staple sequence, optionally wherein the nanostructure is free from immunostimulatory agents extending from the scaffold sequence by hybridization to staple strand overhangs.

32. The method of claim 30, wherein the nanostructure comprises a single-stranded nucleic acid scaffold sequence and one or more single stranded nucleic acid staple strands that hybridize to the scaffold sequence to form the defined three-dimensional geometric shape, wherein the immunostimulatory agent(s) extend from the scaffold sequence by hybridization to staple strand overhangs, optionally wherein the immunostimulatory agents comprise single or double stranded oligonucleotide(s).

33. The method of claim 30, wherein the innate immune response comprises TLR9 activation, a cGAS-STING-dependent immune response, or a combination thereof.

34. The method of claim 33, comprising (i) TLR9 activation, wherein the nanostructure comprises immunostimulatory agent(s) extending from the scaffold sequence by hybridization to staple strand overhangs, optionally wherein the immunostimulatory agent is single or double stranded oligonucleotide(s); or (ii) a cGAS-STING-dependent immune response, wherein the nanostructure is free (ii) from immunostimulatory agent(s) extending from the scaffold sequence by hybridization to staple strand overhangs, optionally wherein the immunostimulatory agent forms part of the scaffold sequence and/or staple strand(s), optionally wherein the immunostimulatory agent is single or double stranded oligonucleotide(s).

35. The method of claim 30, wherein the method is free from administration of antigen to the subject.

36. The nanostructure of claim 1, wherein the number of copies of the immunostimulatory agent is 2, 3, 4, 5, 6, 7, 8, 9, or 10.

37. The method of claim 32, wherein the immunostimulatory agent comprises one or more CpG motifs.

38. The method of claim 34, wherein the immunostimulatory agent comprises one or more CpG motifs.

* * * * *

SEQUENCE LISTING

```
Sequence total quantity: 491
SEQ ID NO: 1              moltype = DNA   length = 20
FEATURE                   Location/Qualifiers
source                    1..20
                          mol_type = other DNA
                          organism = synthetic construct
SEQUENCE: 1
ccctttaggg ttccgattta                                          20

SEQ ID NO: 2              moltype = DNA   length = 20
FEATURE                   Location/Qualifiers
source                    1..20
                          mol_type = other DNA
                          organism = unidentified
SEQUENCE: 2
tctttgcctt gcctgtatga                                          20

SEQ ID NO: 3              moltype = DNA   length = 20
FEATURE                   Location/Qualifiers
source                    1..20
                          mol_type = other DNA
                          organism = synthetic construct
SEQUENCE: 3
gctgaaaagg tggcatcaat                                          20

SEQ ID NO: 4              moltype = DNA   length = 19
FEATURE                   Location/Qualifiers
source                    1..19
                          mol_type = other DNA
                          organism = synthetic construct
SEQUENCE: 4
gctaacgagc gtctttcca                                           19

SEQ ID NO: 5              moltype = DNA   length = 2520
FEATURE                   Location/Qualifiers
source                    1..2520
                          mol_type = other DNA
                          organism = synthetic construct
SEQUENCE: 5
gagcgcaacg caattaatgt gcgccctgta gcggcgcatt aagcgcggcg ggtgtggtgg  60
```

```
ttacgcgcag cgtgaccgct acacttgcca gcgccctagc gcccgctcct ttcgctttct   120
tcccttcctt tctcgccacg ttcgccggct ttccccgtca agctctaaat cgggggctcc   180
ctttagggtt ccgatttagt gctttacggc acctcgaccc caaaaaactt gattagggtg   240
atggttcacg tagtgggcca tcgccctgat agacggtttt tcgccctttg acgttggagt   300
ccacgttctt taatagtgga ctcttgttcc aaactggaac aacactcaac cctatctcgg   360
tctattcttt tgatttataa gggattttgc cgatttcggc ctattggtta aaaaatgagc   420
tgatttaaca aaaatttaac gcgaattaca accggggtac atatgattgg ggtctgacgc   480
tcagtggaac gaaaactcac gttaagggat tttggtcatg agattatcaa aaaggatctt   540
cacctagatc cttttaaatt aaaaatgaag ttttaaatca atctaaagta tatatgagta   600
aacttggtct gacagttacc aatgcttaat cagtgaggca cctatctcag cgatctgtct   660
atttcgttca tccatagttg cctgactccc cgtcgtgtag ataactacga tacgggaggg   720
cttaccatct ggccccagtg ctgcaatgat accgcgagac ccacgctcac cggctccaga   780
tttatcagca ataaaccagc cagccggaag ggccgagcgc ataagtggtc ctgcaactt    840
atccgcctcc atccagtcta ttaattgttg ccgggaagct agagtaagta gttcgccagt   900
taatagtttg cgcaacgttg ttgccattgc tacaggcatc gtggtgtcac gctcgtcgtt   960
tggtatggct tcattcagct ccggttccca acgatcaagg cgagttacat gatcccccat  1020
gttgtgcaaa aaagcggtta gctccttcgg tcctccgatc gttgtcagaa gtaagttggc  1080
cgcagtgtta tcactcatgg ttatggcagc actgcataat tctcttactg tcatgccatc  1140
cgtaagatgc ttttctgtga ctggtgagta ctcaaccaag tcattctgag aatagtgtat  1200
gcggcgaccg agttgctctt gcccggcgtc aatacgggat aataccgcgc cacatagcag  1260
aactttaaaa gtgctcatca ttggaaaacg ttcttcgggg cgaaaactct caaggatctt  1320
accgctgttg agatccagtt cgatgtaacc cactcgtgca cccaactgat cttcagcatc  1380
ttttactttc accagcgttt ctgggtgagc aaaaacagga aggcaaaatg ccgcaaaaaa  1440
gggaataagg cgacacggaa aatgttgaat actcatactc ttcctttttc aatattattg  1500
aagcatttat cagggttatt gtctcatgag cggatacata tttgaatgta tttagaaaaa  1560
taaacaaata ggggttccgc gcacatttcc ccgaaaagtg ccacctgacg tctaagaaac  1620
cattattatc atgacattaa cctataaaaa taggcgtatc acgaggccct ttcgtcgaat  1680
tcgtcgtcgt cccctcaaac tcttgggtgg agaggctatt cgtttaaggt cacatcgcat  1740
gtaatttact tattctctgt tgttgagcca cccgggcgcc agattttgtt taaagctttg  1800
tctcttagtt tgtatagaca gattcagagt gcaaggtttc gttcgctcgt acctggtttt  1860
ccctggttct tcacagatag gatttgactt tctacaacac ttatgcggct tcctacccgt  1920
ttgaaggccg atacaggtgc tgcgcaaaat gcgggcgaac atagagtatc aaaacaacgc  1980
cttctaatct aggaatatag ggaagatacg tatttgctac catgctttct tgggtcatta  2040
acgaccaacc tctttttctt taaagtagga ttgcacaatg aatgaataca cgtggtccga  2100
taactgacca agtaacatgg ttatcactag atgtccgcca gacgtgtgca aaccaacccg  2160
ggagttacgt cactaatcct tcgctacgtc gtgaagatat ttacttgtga atatcgaggg  2220
taataagata atagactgtg actagtattg ccagactgtc gctacctgca acacataact  2280
atcctgaggt tactgcatag tactgattac acccgagtca aaatttctaa cttctaacat  2340
gtacctagta accagctcaa taattatgtc agaatatagc tctgggaacc ctcggacaat  2400
tatgatacac ggtattaata tcttgcttgc gttagccact tctcatcttt ggataccgat  2460
tctattttgc atagcagttc cttttacaca tataagaatt cgccataggg tatgctgcag  2520
```

```
SEQ ID NO: 6              moltype = DNA  length = 42
FEATURE                   Location/Qualifiers
source                    1..42
                          mol_type = other DNA
                          organism = synthetic construct
SEQUENCE: 6
ataaagtttt gcgttgcgct cctgcagcat ggatggaggc gg                        42

SEQ ID NO: 7              moltype = DNA  length = 42
FEATURE                   Location/Qualifiers
source                    1..42
                          mol_type = other DNA
                          organism = synthetic construct
SEQUENCE: 7
tgcgctcgcc gctacagggc gcacattaag caggaccact ta                        42

SEQ ID NO: 8              moltype = DNA  length = 42
FEATURE                   Location/Qualifiers
source                    1..42
                          mol_type = other DNA
                          organism = synthetic construct
SEQUENCE: 8
gctggtttac acccgccgcg cttaatgcgg cccttccggc tg                        42

SEQ ID NO: 9              moltype = DNA  length = 78
FEATURE                   Location/Qualifiers
source                    1..78
                          mol_type = other DNA
                          organism = synthetic construct
SEQUENCE: 9
gtcacgctgc gtttttcgta accaccattg ctgataattt ttatctggag cccacgacgg    60
ggattttttgt caggcaac                                                  78

SEQ ID NO: 10             moltype = DNA  length = 42
FEATURE                   Location/Qualifiers
source                    1..42
                          mol_type = other DNA
```

-continued

```
                        organism = synthetic construct
SEQUENCE: 10
gtgtagcgag ccggcgaacg tggcgagaaa gggcgctggc aa                    42

SEQ ID NO: 11          moltype = DNA   length = 32
FEATURE                Location/Qualifiers
source                 1..32
                       mol_type = other DNA
                       organism = synthetic construct
SEQUENCE: 11
cgggcgctag gaagggaaga aagcagctat at                               32

SEQ ID NO: 12          moltype = DNA   length = 32
FEATURE                Location/Qualifiers
source                 1..32
                       mol_type = other DNA
                       organism = synthetic construct
SEQUENCE: 12
tctgacatgt ccgagggttc ccaggaaagg ag                               32

SEQ ID NO: 13          moltype = DNA   length = 52
FEATURE                Location/Qualifiers
source                 1..52
                       mol_type = other DNA
                       organism = synthetic construct
SEQUENCE: 13
cattggtaac ttttttgtca gaccaagatt tagagctttt tttgacgggg aa         52

SEQ ID NO: 14          moltype = DNA   length = 42
FEATURE                Location/Qualifiers
source                 1..42
                       mol_type = other DNA
                       organism = synthetic construct
SEQUENCE: 14
tactttaggg aaccctaaag ggagcccccg tttactcata ta                   42

SEQ ID NO: 15          moltype = DNA   length = 42
FEATURE                Location/Qualifiers
source                 1..42
                       mol_type = other DNA
                       organism = synthetic construct
SEQUENCE: 15
ttcattttgg tgccgtaaag cactaaatca ttgatttaaa ac                   42

SEQ ID NO: 16          moltype = DNA   length = 42
FEATURE                Location/Qualifiers
source                 1..42
                       mol_type = other DNA
                       organism = synthetic construct
SEQUENCE: 16
tctaggtgaa tcaagttttt tggggtcgat aatttaaaag ga                   42

SEQ ID NO: 17          moltype = DNA   length = 52
FEATURE                Location/Qualifiers
source                 1..52
                       mol_type = other DNA
                       organism = synthetic construct
SEQUENCE: 17
gttgagtgtt gttttttttcc agtttgcact acgtgaattt ttccatcacc ct        52

SEQ ID NO: 18          moltype = DNA   length = 42
FEATURE                Location/Qualifiers
source                 1..42
                       mol_type = other DNA
                       organism = synthetic construct
SEQUENCE: 18
cgatggccga acaagagtcc actattaaac cgtctatcag gg                   42

SEQ ID NO: 19          moltype = DNA   length = 32
FEATURE                Location/Qualifiers
source                 1..32
                       mol_type = other DNA
                       organism = synthetic construct
SEQUENCE: 19
gcgaaaaaga acgtggactc caacaatcag ta                              32

SEQ ID NO: 20          moltype = DNA   length = 32
FEATURE                Location/Qualifiers
source                 1..32
```

-continued

```
                        mol_type = other DNA
                        organism = synthetic construct
SEQUENCE: 20
ctatgcagat tttgactcgg gtgtgtcaaa gg                                     32

SEQ ID NO: 21          moltype = DNA   length = 42
FEATURE                Location/Qualifiers
source                 1..42
                        mol_type = other DNA
                        organism = synthetic construct
SEQUENCE: 21
gagataggat cagctcattt tttaaccaaa aaagaataga cc                          42

SEQ ID NO: 22          moltype = DNA   length = 32
FEATURE                Location/Qualifiers
source                 1..32
                        mol_type = other DNA
                        organism = synthetic construct
SEQUENCE: 22
tataaatcta ggccgaaatc ggcatgttgt ag                                     32

SEQ ID NO: 23          moltype = DNA   length = 32
FEATURE                Location/Qualifiers
source                 1..32
                        mol_type = other DNA
                        organism = synthetic construct
SEQUENCE: 23
aaagtcaata ggaagccgca taagaaatcc ct                                     32

SEQ ID NO: 24          moltype = DNA   length = 52
FEATURE                Location/Qualifiers
source                 1..52
                        mol_type = other DNA
                        organism = synthetic construct
SEQUENCE: 24
aagatccttt ttttttgat aatctcttcg cgttaaattt ttttttgtt aa                 52

SEQ ID NO: 25          moltype = DNA   length = 42
FEATURE                Location/Qualifiers
source                 1..42
                        mol_type = other DNA
                        organism = synthetic construct
SEQUENCE: 25
ggttgtaaat gaccaaaatc ccttaacgtt catatgtacc cc                          42

SEQ ID NO: 26          moltype = DNA   length = 32
FEATURE                Location/Qualifiers
source                 1..32
                        mol_type = other DNA
                        organism = synthetic construct
SEQUENCE: 26
gaccccaaga gttttcgttc cactcccgta tt                                     32

SEQ ID NO: 27          moltype = DNA   length = 32
FEATURE                Location/Qualifiers
source                 1..32
                        mol_type = other DNA
                        organism = synthetic construct
SEQUENCE: 27
gacgccggtg tggcgcggta ttatgagcgt ca                                     32

SEQ ID NO: 28          moltype = DNA   length = 20
FEATURE                Location/Qualifiers
source                 1..20
                        mol_type = other DNA
                        organism = synthetic construct
SEQUENCE: 28
actgattaag tatggatgaa                                                   20

SEQ ID NO: 29          moltype = DNA   length = 32
FEATURE                Location/Qualifiers
source                 1..32
                        mol_type = other DNA
                        organism = synthetic construct
SEQUENCE: 29
ggtgcctccg aaatagacag atcgaaaagc at                                     32

SEQ ID NO: 30          moltype = DNA   length = 32
FEATURE                Location/Qualifiers
```

-continued

```
source                  1..32
                        mol_type = other DNA
                        organism = synthetic construct
SEQUENCE: 30
cttacggata ctcaccagtc acagctgaga ta                              32

SEQ ID NO: 31           moltype = DNA   length = 42
FEATURE                 Location/Qualifiers
source                  1..42
                        mol_type = other DNA
                        organism = synthetic construct
SEQUENCE: 31
gttatctagg tgagcgtggg tctcgcggtc tcccgtatcg ta                   42

SEQ ID NO: 32           moltype = DNA   length = 32
FEATURE                 Location/Qualifiers
source                  1..32
                        mol_type = other DNA
                        organism = synthetic construct
SEQUENCE: 32
ggtaagccat cattgcagca ctggaaccgg ag                              32

SEQ ID NO: 33           moltype = DNA   length = 32
FEATURE                 Location/Qualifiers
source                  1..32
                        mol_type = other DNA
                        organism = synthetic construct
SEQUENCE: 33
ctgaatgacg ccttgatcgt tgggggccag at                              32

SEQ ID NO: 34           moltype = DNA   length = 52
FEATURE                 Location/Qualifiers
source                  1..52
                        mol_type = other DNA
                        organism = synthetic construct
SEQUENCE: 34
tcccggcaac atttttatta atagactacc tatggcgttt ttaaattctt at        52

SEQ ID NO: 35           moltype = DNA   length = 42
FEATURE                 Location/Qualifiers
source                  1..42
                        mol_type = other DNA
                        organism = synthetic construct
SEQUENCE: 35
aatgtgcggg cgaactactt actctagctc acttttcggg ga                   42

SEQ ID NO: 36           moltype = DNA   length = 42
FEATURE                 Location/Qualifiers
source                  1..42
                        mol_type = other DNA
                        organism = synthetic construct
SEQUENCE: 36
tgtttattac gttgcgcaaa ctattaactc ggaacccta tt                    42

SEQ ID NO: 37           moltype = DNA   length = 42
FEATURE                 Location/Qualifiers
source                  1..42
                        mol_type = other DNA
                        organism = synthetic construct
SEQUENCE: 37
tcaaatatat gcctgtagca atggcaacat ttctaaatac at                   42

SEQ ID NO: 38           moltype = DNA   length = 52
FEATURE                 Location/Qualifiers
source                  1..52
                        mol_type = other DNA
                        organism = synthetic construct
SEQUENCE: 38
aacgacgagc gttttttgac accacggtat ccgctcattt tttgagacaa ta        52

SEQ ID NO: 39           moltype = DNA   length = 20
FEATURE                 Location/Qualifiers
source                  1..20
                        mol_type = other DNA
                        organism = synthetic construct
SEQUENCE: 39
agccatacca tcatgtaact                                            20

SEQ ID NO: 40           moltype = DNA   length = 52
```

-continued

```
FEATURE              Location/Qualifiers
source               1..52
                     mol_type = other DNA
                     organism = synthetic construct
SEQUENCE: 40
catttccgtg tttttcgcc cttatttttt ttgcacattt ttacatgggg ga          52

SEQ ID NO: 41        moltype = DNA   length = 42
FEATURE              Location/Qualifiers
source               1..42
                     mol_type = other DNA
                     organism = synthetic construct
SEQUENCE: 41
cattttgcag gaccgaagga gctaaccgcc ccttttttgc gg                     42

SEQ ID NO: 42        moltype = DNA   length = 42
FEATURE              Location/Qualifiers
source               1..42
                     mol_type = other DNA
                     organism = synthetic construct
SEQUENCE: 42
ctcacccact tacttctgac aacgatcggc ttcctgtttt tg                     42

SEQ ID NO: 43        moltype = DNA   length = 42
FEATURE              Location/Qualifiers
source               1..42
                     mol_type = other DNA
                     organism = synthetic construct
SEQUENCE: 43
aagtaaaaga gtgataacac tgcggccaag aaacgctggt ga                     42

SEQ ID NO: 44        moltype = DNA   length = 52
FEATURE              Location/Qualifiers
source               1..52
                     mol_type = other DNA
                     organism = synthetic construct
SEQUENCE: 44
ctcggtcgcc gttttttcata cactatatgc agtgctgttt ttccataacc at         52

SEQ ID NO: 45        moltype = DNA   length = 42
FEATURE              Location/Qualifiers
source               1..42
                     mol_type = other DNA
                     organism = synthetic construct
SEQUENCE: 45
agagaatttc tcagaatgac ttggttgagt ggcatgacag ta                     42

SEQ ID NO: 46        moltype = DNA   length = 20
FEATURE              Location/Qualifiers
source               1..20
                     mol_type = other DNA
                     organism = synthetic construct
SEQUENCE: 46
gcaagagcaa agttctgcta                                              20

SEQ ID NO: 47        moltype = DNA   length = 52
FEATURE              Location/Qualifiers
source               1..52
                     mol_type = other DNA
                     organism = synthetic construct
SEQUENCE: 47
gatgctgaag attttttcag ttgggttcca atgatgattt ttgcactttt aa         52

SEQ ID NO: 48        moltype = DNA   length = 42
FEATURE              Location/Qualifiers
source               1..42
                     mol_type = other DNA
                     organism = synthetic construct
SEQUENCE: 48
gaacgtttgc acgagtgggt tacatcgaat tttcgccccg aa                     42

SEQ ID NO: 49        moltype = DNA   length = 32
FEATURE              Location/Qualifiers
source               1..32
                     mol_type = other DNA
                     organism = synthetic construct
SEQUENCE: 49
cttgagagct ggatctcaac agcgtgaatc tg                                32
```

```
SEQ ID NO: 50          moltype = DNA   length = 32
FEATURE                Location/Qualifiers
source                 1..32
                       mol_type = other DNA
                       organism = synthetic construct
SEQUENCE: 50
tctatacaac gaaaccttgc actcgtaaga tc                                    32

SEQ ID NO: 51          moltype = DNA   length = 20
FEATURE                Location/Qualifiers
source                 1..20
                       mol_type = other DNA
                       organism = synthetic construct
SEQUENCE: 51
gagtattcaa accctgataa                                                  20

SEQ ID NO: 52          moltype = DNA   length = 32
FEATURE                Location/Qualifiers
source                 1..32
                       mol_type = other DNA
                       organism = synthetic construct
SEQUENCE: 52
aagagtatat gcttcaataa tattacatgc ga                                    32

SEQ ID NO: 53          moltype = DNA   length = 32
FEATURE                Location/Qualifiers
source                 1..32
                       mol_type = other DNA
                       organism = synthetic construct
SEQUENCE: 53
tgtgacctag agaataagta aattgaaaaa gg                                    32

SEQ ID NO: 54          moltype = DNA   length = 52
FEATURE                Location/Qualifiers
source                 1..52
                       mol_type = other DNA
                       organism = synthetic construct
SEQUENCE: 54
ttatcggacc atttttcgtg tattcaggtt tcttagattt ttcgtcaggt gg              52

SEQ ID NO: 55          moltype = DNA   length = 42
FEATURE                Location/Qualifiers
source                 1..42
                       mol_type = other DNA
                       organism = synthetic construct
SEQUENCE: 55
cctactttgg ttaatgtcat gataataatt tcattgtgca at                        42

SEQ ID NO: 56          moltype = DNA   length = 42
FEATURE                Location/Qualifiers
source                 1..42
                       mol_type = other DNA
                       organism = synthetic construct
SEQUENCE: 56
ttggtcgtcg tgatacgcct attttttataa aaagaaaaga gg                       42

SEQ ID NO: 57          moltype = DNA   length = 42
FEATURE                Location/Qualifiers
source                 1..42
                       mol_type = other DNA
                       organism = synthetic construct
SEQUENCE: 57
aagcatggac gaattcgacg aaagggcctt aatgacccaa ga                        42

SEQ ID NO: 58          moltype = DNA   length = 78
FEATURE                Location/Qualifiers
source                 1..78
                       mol_type = other DNA
                       organism = synthetic construct
SEQUENCE: 58
caaagcttta atttttacaa aatctgcaag agtttgattt ttggggacga cgtagcaaat 60
acgttttta tcttccct                                                    78

SEQ ID NO: 59          moltype = DNA   length = 42
FEATURE                Location/Qualifiers
source                 1..42
                       mol_type = other DNA
                       organism = synthetic construct
SEQUENCE: 59
```

-continued

```
tctccaccgc gcccgggtgg ctcaacaact aaacgaatag cc                          42

SEQ ID NO: 60          moltype = DNA   length = 20
FEATURE                Location/Qualifiers
source                 1..20
                       mol_type = other DNA
                       organism = synthetic construct
SEQUENCE: 60
aactaagaga gtacgagcga                                                   20

SEQ ID NO: 61          moltype = DNA   length = 52
FEATURE                Location/Qualifiers
source                 1..52
                       mol_type = other DNA
                       organism = synthetic construct
SEQUENCE: 61
tgcgcagcac ctttttgta tcggcctgaa gaaccagttt ttggaaaacc ag               52

SEQ ID NO: 62          moltype = DNA   length = 20
FEATURE                Location/Qualifiers
source                 1..20
                       mol_type = other DNA
                       organism = synthetic construct
SEQUENCE: 62
atcctatctg ttcaaacggg                                                   20

SEQ ID NO: 63          moltype = DNA   length = 20
FEATURE                Location/Qualifiers
source                 1..20
                       mol_type = other DNA
                       organism = synthetic construct
SEQUENCE: 63
gcccgcattt atattcctag                                                   20

SEQ ID NO: 64          moltype = DNA   length = 32
FEATURE                Location/Qualifiers
source                 1..32
                       mol_type = other DNA
                       organism = synthetic construct
SEQUENCE: 64
ctatgttcat tagaaggcgt tgttattacc ct                                     32

SEQ ID NO: 65          moltype = DNA   length = 32
FEATURE                Location/Qualifiers
source                 1..32
                       mol_type = other DNA
                       organism = synthetic construct
SEQUENCE: 65
cgatattcca cagtctatta tcttttgata ct                                     32

SEQ ID NO: 66          moltype = DNA   length = 42
FEATURE                Location/Qualifiers
source                 1..42
                       mol_type = other DNA
                       organism = synthetic construct
SEQUENCE: 66
actgctatat aaccatgtta cttggtcaga tgtgtaaaag ga                          42

SEQ ID NO: 67          moltype = DNA   length = 42
FEATURE                Location/Qualifiers
source                 1..42
                       mol_type = other DNA
                       organism = synthetic construct
SEQUENCE: 67
ggtatccaac gtctggcgga catctagtgg caaaatagaa tc                          42

SEQ ID NO: 68          moltype = DNA   length = 42
FEATURE                Location/Qualifiers
source                 1..42
                       mol_type = other DNA
                       organism = synthetic construct
SEQUENCE: 68
gctaacgcaa ctcccgggtt ggtttgcaca agatgagaag tg                          42

SEQ ID NO: 69          moltype = DNA   length = 52
FEATURE                Location/Qualifiers
source                 1..52
                       mol_type = other DNA
                       organism = synthetic construct
```

```
SEQUENCE: 69
gtagcgaagg atttttttag tgacgtaagc aagatatttt tttaataccg tg              52

SEQ ID NO: 70           moltype = DNA   length = 42
FEATURE                 Location/Qualifiers
source                  1..42
                        mol_type = other DNA
                        organism = synthetic construct
SEQUENCE: 70
ttcacgaccg acagtctggc aatactagta caagtaaata tc                        42

SEQ ID NO: 71           moltype = DNA   length = 52
FEATURE                 Location/Qualifiers
source                  1..52
                        mol_type = other DNA
                        organism = synthetic construct
SEQUENCE: 71
ctggttacta gttttgtac atgttaatag ttatgtgttt ttttgcaggt ag              52

SEQ ID NO: 72           moltype = DNA   length = 20
FEATURE                 Location/Qualifiers
source                  1..20
                        mol_type = other DNA
                        organism = synthetic construct
SEQUENCE: 72
taacctcagg gaagttagaa                                                 20

SEQ ID NO: 73           moltype = DNA   length = 20
FEATURE                 Location/Qualifiers
source                  1..20
                        mol_type = other DNA
                        organism = synthetic construct
SEQUENCE: 73
aattattgag tatcataatt                                                 20

SEQ ID NO: 74           moltype = DNA   length = 66
FEATURE                 Location/Qualifiers
source                  1..66
                        mol_type = other DNA
                        organism = synthetic construct
SEQUENCE: 74
ataaagtttt gcgttgcgct cctgcagcat ggatggaggc ggtggcattg taccattcta     60
aggcta                                                                66

SEQ ID NO: 75           moltype = DNA   length = 56
FEATURE                 Location/Qualifiers
source                  1..56
                        mol_type = other DNA
                        organism = synthetic construct
SEQUENCE: 75
cgggcgctag gaagggaaga aagcagctat attggcattg taccattcta aggcta         56

SEQ ID NO: 76           moltype = DNA   length = 66
FEATURE                 Location/Qualifiers
source                  1..66
                        mol_type = other DNA
                        organism = synthetic construct
SEQUENCE: 76
tctaggtgaa tcaagttttt tggggtcgat aatttaaaag gatggcattg taccattcta     60
aggcta                                                                66

SEQ ID NO: 77           moltype = DNA   length = 66
FEATURE                 Location/Qualifiers
source                  1..66
                        mol_type = other DNA
                        organism = synthetic construct
SEQUENCE: 77
gagataggat cagctcattt tttaaccaaa aaagaataga cctggcattg taccattcta     60
aggcta                                                                66

SEQ ID NO: 78           moltype = DNA   length = 56
FEATURE                 Location/Qualifiers
source                  1..56
                        mol_type = other DNA
                        organism = synthetic construct
SEQUENCE: 78
ggtaagccat cattgcagca ctggaaccgg agtggcattg taccattcta aggcta         56

SEQ ID NO: 79           moltype = DNA   length = 66
```

-continued

```
FEATURE                  Location/Qualifiers
source                   1..66
                         mol_type = other DNA
                         organism = synthetic construct
SEQUENCE: 79
agagaatttc tcagaatgac ttggttgagt ggcatgacag tatggcattg taccattcta   60
aggcta                                                                66

SEQ ID NO: 80            moltype = DNA   length = 66
FEATURE                  Location/Qualifiers
source                   1..66
                         mol_type = other DNA
                         organism = synthetic construct
SEQUENCE: 80
gaacgtttgc acgagtgggt tacatcgaat tttcgccccg aatggcattg taccattcta   60
aggcta                                                                66

SEQ ID NO: 81            moltype = DNA   length = 56
FEATURE                  Location/Qualifiers
source                   1..56
                         mol_type = other DNA
                         organism = synthetic construct
SEQUENCE: 81
tgtgacctag agaataagta aattgaaaaa ggtggcattg taccattcta aggcta         56

SEQ ID NO: 82            moltype = DNA   length = 66
FEATURE                  Location/Qualifiers
source                   1..66
                         mol_type = other DNA
                         organism = synthetic construct
SEQUENCE: 82
cctactttgg ttaatgtcat gataataatt tcattgtgca attggcattg taccattcta   60
aggcta                                                                66

SEQ ID NO: 83            moltype = DNA   length = 66
FEATURE                  Location/Qualifiers
source                   1..66
                         mol_type = other DNA
                         organism = synthetic construct
SEQUENCE: 83
ttcacgaccg acagtctggc aatactagta caagtaaata tctggcattg taccattcta   60
aggcta                                                                66

SEQ ID NO: 84            moltype = DNA   length = 67
FEATURE                  Location/Qualifiers
source                   1..67
                         mol_type = other DNA
                         organism = synthetic construct
SEQUENCE: 84
ataaagtttt gcgttgcgct cctgcagcat ggatggaggc ggtggcattg taccattctt   60
tgtcgtt                                                               67

SEQ ID NO: 85            moltype = DNA   length = 57
FEATURE                  Location/Qualifiers
source                   1..57
                         mol_type = other DNA
                         organism = synthetic construct
SEQUENCE: 85
cgggcgctag gaagggaaga aagcagctat attggcattg taccattctt tgtcgtt       57

SEQ ID NO: 86            moltype = DNA   length = 67
FEATURE                  Location/Qualifiers
source                   1..67
                         mol_type = other DNA
                         organism = synthetic construct
SEQUENCE: 86
tctaggtgaa tcaagttttt tggggtcgat aatttaaaag gatggcattg taccattctt   60
tgtcgtt                                                               67

SEQ ID NO: 87            moltype = DNA   length = 67
FEATURE                  Location/Qualifiers
source                   1..67
                         mol_type = other DNA
                         organism = synthetic construct
SEQUENCE: 87
gagataggat cagctcattt tttaaccaaa aaagaataga cctggcattg taccattctt   60
tgtcgtt                                                               67

SEQ ID NO: 88            moltype = DNA   length = 57
```

-continued

```
FEATURE             Location/Qualifiers
source              1..57
                    mol_type = other DNA
                    organism = synthetic construct
SEQUENCE: 88
ggtaagccat cattgcagca ctggaaccgg agtggcattg taccattctt tgtcgtt        57

SEQ ID NO: 89       moltype = DNA   length = 67
FEATURE             Location/Qualifiers
source              1..67
                    mol_type = other DNA
                    organism = synthetic construct
SEQUENCE: 89
agagaatttc tcagaatgac ttggttgagt ggcatgacag tatggcattg taccattctt    60
tgtcgtt                                                                67

SEQ ID NO: 90       moltype = DNA   length = 67
FEATURE             Location/Qualifiers
source              1..67
                    mol_type = other DNA
                    organism = synthetic construct
SEQUENCE: 90
gaacgtttgc acgagtgggt tacatcgaat tttcgccccg aatggcattg taccattctt    60
tgtcgtt                                                                67

SEQ ID NO: 91       moltype = DNA   length = 57
FEATURE             Location/Qualifiers
source              1..57
                    mol_type = other DNA
                    organism = synthetic construct
SEQUENCE: 91
tgtgacctag agaataagta aattgaaaaa ggtggcattg taccattctt tgtcgtt        57

SEQ ID NO: 92       moltype = DNA   length = 67
FEATURE             Location/Qualifiers
source              1..67
                    mol_type = other DNA
                    organism = synthetic construct
SEQUENCE: 92
cctactttgg ttaatgtcat gataataatt tcattgtgca attggcattg taccattctt    60
tgtcgtt                                                                67

SEQ ID NO: 93       moltype = DNA   length = 67
FEATURE             Location/Qualifiers
source              1..67
                    mol_type = other DNA
                    organism = synthetic construct
SEQUENCE: 93
ttcacgaccg acagtctggc aatactagta caagtaaata tctggcattg taccattctt    60
tgtcgtt                                                                67

SEQ ID NO: 94       moltype = DNA   length = 66
FEATURE             Location/Qualifiers
source              1..66
                    mol_type = other DNA
                    organism = synthetic construct
SEQUENCE: 94
ataaagtttt gcgttgcgct cctgcagcat ggatggaggc ggtggcattg ttgtcgtttt    60
aggcta                                                                66

SEQ ID NO: 95       moltype = DNA   length = 56
FEATURE             Location/Qualifiers
source              1..56
                    mol_type = other DNA
                    organism = synthetic construct
SEQUENCE: 95
cgggcgctag gaagggaaga aagcagctat attggcattg ttgtcgtttt aggcta         56

SEQ ID NO: 96       moltype = DNA   length = 66
FEATURE             Location/Qualifiers
source              1..66
                    mol_type = other DNA
                    organism = synthetic construct
SEQUENCE: 96
tctaggtgaa tcaagttttt tggggtcgat aatttaaaag gatggcattg ttgtcgtttt    60
aggcta                                                                66

SEQ ID NO: 97       moltype = DNA   length = 66
FEATURE             Location/Qualifiers
```

```
source                     1..66
                           mol_type = other DNA
                           organism = synthetic construct
SEQUENCE: 97
gagataggat cagctcattt tttaaccaaa aaagaataga cctggcattg ttgtcgtttt    60
aggcta                                                               66

SEQ ID NO: 98              moltype = DNA   length = 56
FEATURE                    Location/Qualifiers
source                     1..56
                           mol_type = other DNA
                           organism = synthetic construct
SEQUENCE: 98
ggtaagccat cattgcagca ctggaaccgg agtggcattg ttgtcgtttt aggcta        56

SEQ ID NO: 99              moltype = DNA   length = 66
FEATURE                    Location/Qualifiers
source                     1..66
                           mol_type = other DNA
                           organism = synthetic construct
SEQUENCE: 99
agagaatttc tcagaatgac ttggttgagt ggcatgacag tatggcattg ttgtcgtttt    60
aggcta                                                               66

SEQ ID NO: 100             moltype = DNA   length = 66
FEATURE                    Location/Qualifiers
source                     1..66
                           mol_type = other DNA
                           organism = synthetic construct
SEQUENCE: 100
gaacgtttgc acgagtgggt tacatcgaat tttcgccccg aatggcattg ttgtcgtttt    60
aggcta                                                               66

SEQ ID NO: 101             moltype = DNA   length = 56
FEATURE                    Location/Qualifiers
source                     1..56
                           mol_type = other DNA
                           organism = synthetic construct
SEQUENCE: 101
tgtgacctag agaataagta aattgaaaaa ggtggcattg ttgtcgtttt aggcta        56

SEQ ID NO: 102             moltype = DNA   length = 66
FEATURE                    Location/Qualifiers
source                     1..66
                           mol_type = other DNA
                           organism = synthetic construct
SEQUENCE: 102
cctactttgg ttaatgtcat gataataatt tcattgtgca attggcattg ttgtcgtttt    60
aggcta                                                               66

SEQ ID NO: 103             moltype = DNA   length = 66
FEATURE                    Location/Qualifiers
source                     1..66
                           mol_type = other DNA
                           organism = synthetic construct
SEQUENCE: 103
ttcacgaccg acagtctggc aatactagta caagtaaata tctggcattg ttgtcgtttt    60
aggcta                                                               66

SEQ ID NO: 104             moltype = DNA   length = 66
FEATURE                    Location/Qualifiers
source                     1..66
                           mol_type = other DNA
                           organism = synthetic construct
SEQUENCE: 104
ataaagtttt gcgttgcgct cctgcagcat ggatggaggc ggtcgtcgtt ttccattcta    60
aggcta                                                               66

SEQ ID NO: 105             moltype = DNA   length = 56
FEATURE                    Location/Qualifiers
source                     1..56
                           mol_type = other DNA
                           organism = synthetic construct
SEQUENCE: 105
cgggcgctag gaagggaaga aagcagctat attcgtcgtt ttccattcta aggcta        56

SEQ ID NO: 106             moltype = DNA   length = 66
FEATURE                    Location/Qualifiers
source                     1..66
```

```
                              mol_type = other DNA
                              organism = synthetic construct
SEQUENCE: 106
tctaggtgaa tcaagttttt tggggtcgat aatttaaaag gatcgtcgtt ttccattcta   60
aggcta                                                              66

SEQ ID NO: 107              moltype = DNA   length = 66
FEATURE                     Location/Qualifiers
source                      1..66
                            mol_type = other DNA
                            organism = synthetic construct
SEQUENCE: 107
gagataggat cagctcattt tttaaccaaa aaagaataga cctcgtcgtt ttccattcta   60
aggcta                                                              66

SEQ ID NO: 108              moltype = DNA   length = 56
FEATURE                     Location/Qualifiers
source                      1..56
                            mol_type = other DNA
                            organism = synthetic construct
SEQUENCE: 108
ggtaagccat cattgcagca ctggaaccgg agtcgtcgtt ttccattcta aggcta       56

SEQ ID NO: 109              moltype = DNA   length = 66
FEATURE                     Location/Qualifiers
source                      1..66
                            mol_type = other DNA
                            organism = synthetic construct
SEQUENCE: 109
agagaatttc tcagaatgac ttggttgagt ggcatgacag tatcgtcgtt ttccattcta   60
aggcta                                                              66

SEQ ID NO: 110              moltype = DNA   length = 66
FEATURE                     Location/Qualifiers
source                      1..66
                            mol_type = other DNA
                            organism = synthetic construct
SEQUENCE: 110
gaacgtttgc acgagtgggt tacatcgaat tttcgccccg aatcgtcgtt ttccattcta   60
aggcta                                                              66

SEQ ID NO: 111              moltype = DNA   length = 56
FEATURE                     Location/Qualifiers
source                      1..56
                            mol_type = other DNA
                            organism = synthetic construct
SEQUENCE: 111
tgtgacctag agaataagta aattgaaaaa ggtcgtcgtt ttccattcta aggcta       56

SEQ ID NO: 112              moltype = DNA   length = 66
FEATURE                     Location/Qualifiers
source                      1..66
                            mol_type = other DNA
                            organism = synthetic construct
SEQUENCE: 112
cctactttgg ttaatgtcat gataataatt tcattgtgca attcgtcgtt ttccattcta   60
aggcta                                                              66

SEQ ID NO: 113              moltype = DNA   length = 66
FEATURE                     Location/Qualifiers
source                      1..66
                            mol_type = other DNA
                            organism = synthetic construct
SEQUENCE: 113
ttcacgaccg acagtctggc aatactagta caagtaaata tctcgtcgtt ttccattcta   60
aggcta                                                              66

SEQ ID NO: 114              moltype = DNA   length = 66
FEATURE                     Location/Qualifiers
source                      1..66
                            mol_type = other DNA
                            organism = synthetic construct
SEQUENCE: 114
ataaagtttt gcgttgcgct cctgcagcat ggatggaggc ggtggcattg ttgtcgtttt   60
gtcgtt                                                              66

SEQ ID NO: 115              moltype = DNA   length = 56
FEATURE                     Location/Qualifiers
source                      1..56
```

-continued

```
                          mol_type = other DNA
                          organism = synthetic construct
SEQUENCE: 115
cgggcgctag gaagggaaga aagcagctat attggcattg ttgtcgtttt gtcgtt       56

SEQ ID NO: 116          moltype = DNA   length = 66
FEATURE                 Location/Qualifiers
source                  1..66
                        mol_type = other DNA
                        organism = synthetic construct
SEQUENCE: 116
tctaggtgaa tcaagttttt tggggtcgat aatttaaaag gatggcattg ttgtcgtttt   60
gtcgtt                                                               66

SEQ ID NO: 117          moltype = DNA   length = 66
FEATURE                 Location/Qualifiers
source                  1..66
                        mol_type = other DNA
                        organism = synthetic construct
SEQUENCE: 117
gagataggat cagctcattt tttaaccaaa aaagaataga cctggcattg ttgtcgtttt   60
gtcgtt                                                               66

SEQ ID NO: 118          moltype = DNA   length = 56
FEATURE                 Location/Qualifiers
source                  1..56
                        mol_type = other DNA
                        organism = synthetic construct
SEQUENCE: 118
ggtaagccat cattgcagca ctggaaccgg agtggcattg ttgtcgtttt gtcgtt       56

SEQ ID NO: 119          moltype = DNA   length = 66
FEATURE                 Location/Qualifiers
source                  1..66
                        mol_type = other DNA
                        organism = synthetic construct
SEQUENCE: 119
agagaatttc tcagaatgac ttggttgagt ggcatgacag tatggcattg ttgtcgtttt   60
gtcgtt                                                               66

SEQ ID NO: 120          moltype = DNA   length = 66
FEATURE                 Location/Qualifiers
source                  1..66
                        mol_type = other DNA
                        organism = synthetic construct
SEQUENCE: 120
gaacgtttgc acgagtgggt tacatcgaat tttcgccccg aatggcattg ttgtcgtttt   60
gtcgtt                                                               66

SEQ ID NO: 121          moltype = DNA   length = 56
FEATURE                 Location/Qualifiers
source                  1..56
                        mol_type = other DNA
                        organism = synthetic construct
SEQUENCE: 121
tgtgacctag agaataagta aattgaaaaa ggtggcattg ttgtcgtttt gtcgtt       56

SEQ ID NO: 122          moltype = DNA   length = 66
FEATURE                 Location/Qualifiers
source                  1..66
                        mol_type = other DNA
                        organism = synthetic construct
SEQUENCE: 122
cctactttgg ttaatgtcat gataataatt tcattgtgca attggcattg ttgtcgtttt   60
gtcgtt                                                               66

SEQ ID NO: 123          moltype = DNA   length = 66
FEATURE                 Location/Qualifiers
source                  1..66
                        mol_type = other DNA
                        organism = synthetic construct
SEQUENCE: 123
ttcacgaccg acagtctggc aatactagta caagtaaata tctggcattg ttgtcgtttt   60
gtcgtt                                                               66

SEQ ID NO: 124          moltype = DNA   length = 66
FEATURE                 Location/Qualifiers
source                  1..66
                        mol_type = other DNA
```

```
                         organism = synthetic construct
SEQUENCE: 124
ataaagtttt gcgttgcgct cctgcagcat ggatggaggc ggtcgtcgtt ttgtcgtttt    60
aggcta                                                                66

SEQ ID NO: 125           moltype = DNA   length = 56
FEATURE                  Location/Qualifiers
source                   1..56
                         mol_type = other DNA
                         organism = synthetic construct
SEQUENCE: 125
cgggcgctag gaagggaaga aagcagctat attcgtcgtt ttgtcgtttt aggcta           56

SEQ ID NO: 126           moltype = DNA   length = 66
FEATURE                  Location/Qualifiers
source                   1..66
                         mol_type = other DNA
                         organism = synthetic construct
SEQUENCE: 126
tctaggtgaa tcaagttttt tggggtcgat aatttaaaag gatcgtcgtt ttgtcgtttt    60
aggcta                                                                66

SEQ ID NO: 127           moltype = DNA   length = 66
FEATURE                  Location/Qualifiers
source                   1..66
                         mol_type = other DNA
                         organism = synthetic construct
SEQUENCE: 127
gagataggat cagctcattt tttaaccaaa aaagaataga cctcgtcgtt ttgtcgtttt    60
aggcta                                                                66

SEQ ID NO: 128           moltype = DNA   length = 56
FEATURE                  Location/Qualifiers
source                   1..56
                         mol_type = other DNA
                         organism = synthetic construct
SEQUENCE: 128
ggtaagccat cattgcagca ctggaaccgg agtcgtcgtt ttgtcgtttt aggcta           56

SEQ ID NO: 129           moltype = DNA   length = 66
FEATURE                  Location/Qualifiers
source                   1..66
                         mol_type = other DNA
                         organism = synthetic construct
SEQUENCE: 129
agagaatttc tcagaatgac ttggttgagt ggcatgacag tatcgtcgtt ttgtcgtttt    60
aggcta                                                                66

SEQ ID NO: 130           moltype = DNA   length = 66
FEATURE                  Location/Qualifiers
source                   1..66
                         mol_type = other DNA
                         organism = synthetic construct
SEQUENCE: 130
gaacgtttgc acgagtgggt tacatcgaat tttcgccccg aatcgtcgtt ttgtcgtttt    60
aggcta                                                                66

SEQ ID NO: 131           moltype = DNA   length = 56
FEATURE                  Location/Qualifiers
source                   1..56
                         mol_type = other DNA
                         organism = synthetic construct
SEQUENCE: 131
tgtgacctag agaataagta aattgaaaaa ggtcgtcgtt ttgtcgtttt aggcta           56

SEQ ID NO: 132           moltype = DNA   length = 66
FEATURE                  Location/Qualifiers
source                   1..66
                         mol_type = other DNA
                         organism = synthetic construct
SEQUENCE: 132
cctactttgg ttaatgtcat gataataatt tcattgtgca attcgtcgtt ttgtcgtttt    60
aggcta                                                                66

SEQ ID NO: 133           moltype = DNA   length = 66
FEATURE                  Location/Qualifiers
source                   1..66
                         mol_type = other DNA
                         organism = synthetic construct
```

```
SEQUENCE: 133
ttcacgaccg acagtctggc aatactagta caagtaaata tctcgtcgtt ttgtcgtttt    60
aggcta                                                               66

SEQ ID NO: 134        moltype = DNA   length = 66
FEATURE               Location/Qualifiers
source                1..66
                      mol_type = other DNA
                      organism = synthetic construct
SEQUENCE: 134
ataaagtttt gcgttgcgct cctgcagcat ggatggaggc ggtcgtcgtt ttccattctt    60
gtcgtt                                                               66

SEQ ID NO: 135        moltype = DNA   length = 56
FEATURE               Location/Qualifiers
source                1..56
                      mol_type = other DNA
                      organism = synthetic construct
SEQUENCE: 135
cgggcgctag gaagggaaga aagcagctat attcgtcgtt ttccattctt gtcgtt         56

SEQ ID NO: 136        moltype = DNA   length = 66
FEATURE               Location/Qualifiers
source                1..66
                      mol_type = other DNA
                      organism = synthetic construct
SEQUENCE: 136
tctaggtgaa tcaagttttt tggggtcgat aatttaaaag gatcgtcgtt ttccattctt    60
gtcgtt                                                               66

SEQ ID NO: 137        moltype = DNA   length = 66
FEATURE               Location/Qualifiers
source                1..66
                      mol_type = other DNA
                      organism = synthetic construct
SEQUENCE: 137
gagataggat cagctcattt tttaaccaaa aaagaataga cctcgtcgtt ttccattctt    60
gtcgtt                                                               66

SEQ ID NO: 138        moltype = DNA   length = 56
FEATURE               Location/Qualifiers
source                1..56
                      mol_type = other DNA
                      organism = synthetic construct
SEQUENCE: 138
ggtaagccat cattgcagca ctggaaccgg agtcgtcgtt ttccattctt gtcgtt         56

SEQ ID NO: 139        moltype = DNA   length = 66
FEATURE               Location/Qualifiers
source                1..66
                      mol_type = other DNA
                      organism = synthetic construct
SEQUENCE: 139
agagaatttc tcagaatgac ttggttgagt ggcatgacag tatcgtcgtt ttccattctt    60
gtcgtt                                                               66

SEQ ID NO: 140        moltype = DNA   length = 66
FEATURE               Location/Qualifiers
source                1..66
                      mol_type = other DNA
                      organism = synthetic construct
SEQUENCE: 140
gaacgtttgc acgagtgggt tacatcgaat tttcgccccg aatcgtcgtt ttccattctt    60
gtcgtt                                                               66

SEQ ID NO: 141        moltype = DNA   length = 56
FEATURE               Location/Qualifiers
source                1..56
                      mol_type = other DNA
                      organism = synthetic construct
SEQUENCE: 141
tgtgacctag agaataagta aattgaaaaa ggtcgtcgtt ttccattctt gtcgtt         56

SEQ ID NO: 142        moltype = DNA   length = 66
FEATURE               Location/Qualifiers
source                1..66
                      mol_type = other DNA
                      organism = synthetic construct
SEQUENCE: 142
```

-continued

```
cctactttgg ttaatgtcat gataataatt tcattgtgca attcgtcgtt ttccattctt   60
gtcgtt                                                               66

SEQ ID NO: 143          moltype = DNA   length = 66
FEATURE                 Location/Qualifiers
source                  1..66
                        mol_type = other DNA
                        organism = synthetic construct
SEQUENCE: 143
ttcacgaccg acagtctggc aatactagta caagtaaata tctcgtcgtt ttccattctt   60
gtcgtt                                                               66

SEQ ID NO: 144          moltype = DNA   length = 66
FEATURE                 Location/Qualifiers
source                  1..66
                        mol_type = other DNA
                        organism = synthetic construct
SEQUENCE: 144
ataaagtttt gcgttgcgct cctgcagcat ggatggaggc ggtcgtcgtt ttgtcgtttt   60
gtcgtt                                                               66

SEQ ID NO: 145          moltype = DNA   length = 56
FEATURE                 Location/Qualifiers
source                  1..56
                        mol_type = other DNA
                        organism = synthetic construct
SEQUENCE: 145
cgggcgctag gaagggaaga aagcagctat attcgtcgtt ttgtcgtttt gtcgtt        56

SEQ ID NO: 146          moltype = DNA   length = 66
FEATURE                 Location/Qualifiers
source                  1..66
                        mol_type = other DNA
                        organism = synthetic construct
SEQUENCE: 146
tctaggtgaa tcaagttttt tggggtcgat aatttaaaag gatcgtcgtt ttgtcgtttt   60
gtcgtt                                                               66

SEQ ID NO: 147          moltype = DNA   length = 66
FEATURE                 Location/Qualifiers
source                  1..66
                        mol_type = other DNA
                        organism = synthetic construct
SEQUENCE: 147
gagataggat cagctcattt tttaaccaaa aaagaataga cctcgtcgtt ttgtcgtttt   60
gtcgtt                                                               66

SEQ ID NO: 148          moltype = DNA   length = 56
FEATURE                 Location/Qualifiers
source                  1..56
                        mol_type = other DNA
                        organism = synthetic construct
SEQUENCE: 148
ggtaagccat cattgcagca ctggaaccgg agtcgtcgtt ttgtcgtttt gtcgtt        56

SEQ ID NO: 149          moltype = DNA   length = 66
FEATURE                 Location/Qualifiers
source                  1..66
                        mol_type = other DNA
                        organism = synthetic construct
SEQUENCE: 149
agagaatttc tcagaatgac ttggttgagt ggcatgacag tatcgtcgtt ttgtcgtttt   60
gtcgtt                                                               66

SEQ ID NO: 150          moltype = DNA   length = 66
FEATURE                 Location/Qualifiers
source                  1..66
                        mol_type = other DNA
                        organism = synthetic construct
SEQUENCE: 150
gaacgtttgc acgagtgggt tacatcgaat tttcgccccg aatcgtcgtt ttgtcgtttt   60
gtcgtt                                                               66

SEQ ID NO: 151          moltype = DNA   length = 56
FEATURE                 Location/Qualifiers
source                  1..56
                        mol_type = other DNA
                        organism = synthetic construct
SEQUENCE: 151
```

```
tgtgacctag agaataagta aattgaaaaa ggtcgtcgtt ttgtcgtttt gtcgtt         56

SEQ ID NO: 152           moltype = DNA   length = 66
FEATURE                  Location/Qualifiers
source                   1..66
                         mol_type = other DNA
                         organism = synthetic construct
SEQUENCE: 152
cctactttgg ttaatgtcat gataataatt tcattgtgca attcgtcgtt ttgtcgtttt    60
gtcgtt                                                               66

SEQ ID NO: 153           moltype = DNA   length = 66
FEATURE                  Location/Qualifiers
source                   1..66
                         mol_type = other DNA
                         organism = synthetic construct
SEQUENCE: 153
ttcacgaccg acagtctggc aatactagta caagtaaata tctcgtcgtt ttgtcgtttt    60
gtcgtt                                                               66

SEQ ID NO: 154           moltype = DNA   length = 66
FEATURE                  Location/Qualifiers
source                   1..66
                         mol_type = other DNA
                         organism = synthetic construct
SEQUENCE: 154
ataaagtttt gcgttgcgct cctgcagcat ggatggaggc ggtcgtcgtt ttgtcgtttt    60
gtcgtt                                                               66

SEQ ID NO: 155           moltype = DNA   length = 66
FEATURE                  Location/Qualifiers
source                   1..66
                         mol_type = other DNA
                         organism = synthetic construct
SEQUENCE: 155
tgcgctcgcc gctacagggc gcacattaag caggaccact tatcgtcgtt ttgtcgtttt    60
gtcgtt                                                               66

SEQ ID NO: 156           moltype = DNA   length = 66
FEATURE                  Location/Qualifiers
source                   1..66
                         mol_type = other DNA
                         organism = synthetic construct
SEQUENCE: 156
gctggtttac acccgccgcg cttaatgcgg cccttccggc tgtcgtcgtt ttgtcgtttt    60
gtcgtt                                                               66

SEQ ID NO: 157           moltype = DNA   length = 66
FEATURE                  Location/Qualifiers
source                   1..66
                         mol_type = other DNA
                         organism = synthetic construct
SEQUENCE: 157
gtgtagcgag ccggcgaacg tggcgagaaa gggcgctggc aatcgtcgtt ttgtcgtttt    60
gtcgtt                                                               66

SEQ ID NO: 158           moltype = DNA   length = 56
FEATURE                  Location/Qualifiers
source                   1..56
                         mol_type = other DNA
                         organism = synthetic construct
SEQUENCE: 158
cgggcgctag gaagggaaga aagcagctat attcgtcgtt ttgtcgtttt gtcgtt         56

SEQ ID NO: 159           moltype = DNA   length = 56
FEATURE                  Location/Qualifiers
source                   1..56
                         mol_type = other DNA
                         organism = synthetic construct
SEQUENCE: 159
tctgacatgt ccgagggttc ccaggaaagg agtcgtcgtt ttgtcgtttt gtcgtt         56

SEQ ID NO: 160           moltype = DNA   length = 66
FEATURE                  Location/Qualifiers
source                   1..66
                         mol_type = other DNA
                         organism = synthetic construct
SEQUENCE: 160
tactttaggg aaccctaaag ggagcccccg tttactcata tatcgtcgtt ttgtcgtttt    60
```

```
gtcgtt                                                              66

SEQ ID NO: 161          moltype = DNA   length = 66
FEATURE                 Location/Qualifiers
source                  1..66
                        mol_type = other DNA
                        organism = synthetic construct
SEQUENCE: 161
ttcattttgg tgccgtaaag cactaaatca ttgatttaaa actcgtcgtt ttgtcgtttt   60
gtcgtt                                                              66

SEQ ID NO: 162          moltype = DNA   length = 66
FEATURE                 Location/Qualifiers
source                  1..66
                        mol_type = other DNA
                        organism = synthetic construct
SEQUENCE: 162
tctaggtgaa tcaagttttt tggggtcgat aatttaaaag gatcgtcgtt ttgtcgtttt   60
gtcgtt                                                              66

SEQ ID NO: 163          moltype = DNA   length = 66
FEATURE                 Location/Qualifiers
source                  1..66
                        mol_type = other DNA
                        organism = synthetic construct
SEQUENCE: 163
cgatggccga acaagagtcc actattaaac cgtctatcag ggtcgtcgtt ttgtcgtttt   60
gtcgtt                                                              66

SEQ ID NO: 164          moltype = DNA   length = 56
FEATURE                 Location/Qualifiers
source                  1..56
                        mol_type = other DNA
                        organism = synthetic construct
SEQUENCE: 164
gcgaaaaaga acgtggactc caacaatcag tatcgtcgtt ttgtcgtttt gtcgtt        56

SEQ ID NO: 165          moltype = DNA   length = 66
FEATURE                 Location/Qualifiers
source                  1..66
                        mol_type = other DNA
                        organism = synthetic construct
SEQUENCE: 165
gagataggat cagctcattt tttaaccaaa aaagaataga cctcgtcgtt ttgtcgtttt   60
gtcgtt                                                              66

SEQ ID NO: 166          moltype = DNA   length = 56
FEATURE                 Location/Qualifiers
source                  1..56
                        mol_type = other DNA
                        organism = synthetic construct
SEQUENCE: 166
tataaatcta ggccgaaatc ggcatgttgt agtcgtcgtt ttgtcgtttt gtcgtt        56

SEQ ID NO: 167          moltype = DNA   length = 56
FEATURE                 Location/Qualifiers
source                  1..56
                        mol_type = other DNA
                        organism = synthetic construct
SEQUENCE: 167
aaagtcaata ggaagccgca taagaaatcc cttcgtcgtt ttgtcgtttt gtcgtt        56

SEQ ID NO: 168          moltype = DNA   length = 66
FEATURE                 Location/Qualifiers
source                  1..66
                        mol_type = other DNA
                        organism = synthetic construct
SEQUENCE: 168
ggttgtaaat gaccaaaatc ccttaacgtt catatgtacc cctcgtcgtt ttgtcgtttt   60
gtcgtt                                                              66

SEQ ID NO: 169          moltype = DNA   length = 56
FEATURE                 Location/Qualifiers
source                  1..56
                        mol_type = other DNA
                        organism = synthetic construct
SEQUENCE: 169
gaccccaaga gttttcgttc cactcccgta tttcgtcgtt ttgtcgtttt gtcgtt        56
```

-continued

```
SEQ ID NO: 170          moltype = DNA   length = 56
FEATURE                 Location/Qualifiers
source                  1..56
                        mol_type = other DNA
                        organism = synthetic construct
SEQUENCE: 170
ggtgcctccg aaatagacag atcgaaaagc attcgtcgtt ttgtcgtttt gtcgtt          56

SEQ ID NO: 171          moltype = DNA   length = 56
FEATURE                 Location/Qualifiers
source                  1..56
                        mol_type = other DNA
                        organism = synthetic construct
SEQUENCE: 171
cttacggata ctcaccagtc acagctgaga tatcgtcgtt ttgtcgtttt gtcgtt          56

SEQ ID NO: 172          moltype = DNA   length = 66
FEATURE                 Location/Qualifiers
source                  1..66
                        mol_type = other DNA
                        organism = synthetic construct
SEQUENCE: 172
gttatctagg tgagcgtggg tctcgcggtc tcccgtatcg tatcgtcgtt ttgtcgtttt     60
gtcgtt                                                                 66

SEQ ID NO: 173          moltype = DNA   length = 56
FEATURE                 Location/Qualifiers
source                  1..56
                        mol_type = other DNA
                        organism = synthetic construct
SEQUENCE: 173
ggtaagccat cattgcagca ctggaaccgg agtcgtcgtt ttgtcgtttt gtcgtt          56

SEQ ID NO: 174          moltype = DNA   length = 56
FEATURE                 Location/Qualifiers
source                  1..56
                        mol_type = other DNA
                        organism = synthetic construct
SEQUENCE: 174
ctgaatgacg ccttgatcgt tgggggccag attcgtcgtt ttgtcgtttt gtcgtt          56

SEQ ID NO: 175          moltype = DNA   length = 66
FEATURE                 Location/Qualifiers
source                  1..66
                        mol_type = other DNA
                        organism = synthetic construct
SEQUENCE: 175
aatgtgcggg cgaactactt actctagctc acttttcggg gatcgtcgtt ttgtcgtttt     60
gtcgtt                                                                 66

SEQ ID NO: 176          moltype = DNA   length = 66
FEATURE                 Location/Qualifiers
source                  1..66
                        mol_type = other DNA
                        organism = synthetic construct
SEQUENCE: 176
tcaaatatat gcctgtagca atggcaacat ttctaaatac attcgtcgtt ttgtcgtttt     60
gtcgtt                                                                 66

SEQ ID NO: 177          moltype = DNA   length = 66
FEATURE                 Location/Qualifiers
source                  1..66
                        mol_type = other DNA
                        organism = synthetic construct
SEQUENCE: 177
cattttgcag gaccgaagga gctaaccgcc cctttttgc ggtcgtcgtt ttgtcgtttt      60
gtcgtt                                                                 66

SEQ ID NO: 178          moltype = DNA   length = 66
FEATURE                 Location/Qualifiers
source                  1..66
                        mol_type = other DNA
                        organism = synthetic construct
SEQUENCE: 178
aagtaaaaga gtgataacac tgcggccaag aaacgctggt gatcgtcgtt ttgtcgtttt     60
gtcgtt                                                                 66

SEQ ID NO: 179          moltype = DNA   length = 66
FEATURE                 Location/Qualifiers
```

-continued

```
source                1..66
                      mol_type = other DNA
                      organism = synthetic construct
SEQUENCE: 179
agagaatttc tcagaatgac ttggttgagt ggcatgacag tatcgtcgtt ttgtcgtttt   60
gtcgtt                                                               66

SEQ ID NO: 180        moltype = DNA   length = 66
FEATURE               Location/Qualifiers
source                1..66
                      mol_type = other DNA
                      organism = synthetic construct
SEQUENCE: 180
gaacgtttgc acgagtgggt tacatcgaat tttcgccccg aatcgtcgtt ttgtcgtttt   60
gtcgtt                                                               66

SEQ ID NO: 181        moltype = DNA   length = 56
FEATURE               Location/Qualifiers
source                1..56
                      mol_type = other DNA
                      organism = synthetic construct
SEQUENCE: 181
cttgagagct ggatctcaac agcgtgaatc tgtcgtcgtt ttgtcgtttt gtcgtt        56

SEQ ID NO: 182        moltype = DNA   length = 56
FEATURE               Location/Qualifiers
source                1..56
                      mol_type = other DNA
                      organism = synthetic construct
SEQUENCE: 182
tctatacaac gaaaccttgc actcgtaaga tctcgtcgtt ttgtcgtttt gtcgtt        56

SEQ ID NO: 183        moltype = DNA   length = 56
FEATURE               Location/Qualifiers
source                1..56
                      mol_type = other DNA
                      organism = synthetic construct
SEQUENCE: 183
aagagtatat gcttcaataa tattacatgc gatcgtcgtt ttgtcgtttt gtcgtt        56

SEQ ID NO: 184        moltype = DNA   length = 56
FEATURE               Location/Qualifiers
source                1..56
                      mol_type = other DNA
                      organism = synthetic construct
SEQUENCE: 184
tgtgacctag agaataagta aattgaaaaa ggtcgtcgtt ttgtcgtttt gtcgtt        56

SEQ ID NO: 185        moltype = DNA   length = 66
FEATURE               Location/Qualifiers
source                1..66
                      mol_type = other DNA
                      organism = synthetic construct
SEQUENCE: 185
cctactttgg ttaatgtcat gataataatt tcattgtgca attcgtcgtt ttgtcgtttt   60
gtcgtt                                                               66

SEQ ID NO: 186        moltype = DNA   length = 66
FEATURE               Location/Qualifiers
source                1..66
                      mol_type = other DNA
                      organism = synthetic construct
SEQUENCE: 186
ttggtcgtcg tgatacgcct atttttataa aaagaaaaga ggtcgtcgtt ttgtcgtttt   60
gtcgtt                                                               66

SEQ ID NO: 187        moltype = DNA   length = 66
FEATURE               Location/Qualifiers
source                1..66
                      mol_type = other DNA
                      organism = synthetic construct
SEQUENCE: 187
aagcatggac gaattcgacg aaagggcctt aatgacccaa gatcgtcgtt ttgtcgtttt   60
gtcgtt                                                               66

SEQ ID NO: 188        moltype = DNA   length = 66
FEATURE               Location/Qualifiers
source                1..66
                      mol_type = other DNA
```

```
                             organism = synthetic construct
SEQUENCE: 188
tctccaccgc gcccgggtgg ctcaacaact aaacgaatag cctcgtcgtt ttgtcgtttt    60
gtcgtt                                                               66

SEQ ID NO: 189           moltype = DNA  length = 56
FEATURE                  Location/Qualifiers
source                   1..56
                         mol_type = other DNA
                         organism = synthetic construct
SEQUENCE: 189
ctatgttcat tagaaggcgt tgttattacc cttcgtcgtt ttgtcgtttt gtcgtt         56

SEQ ID NO: 190           moltype = DNA  length = 56
FEATURE                  Location/Qualifiers
source                   1..56
                         mol_type = other DNA
                         organism = synthetic construct
SEQUENCE: 190
cgatattcca cagtctatta tcttttgata cttcgtcgtt ttgtcgtttt gtcgtt         56

SEQ ID NO: 191           moltype = DNA  length = 66
FEATURE                  Location/Qualifiers
source                   1..66
                         mol_type = other DNA
                         organism = synthetic construct
SEQUENCE: 191
actgctatat aaccatgtta cttggtcaga tgtgtaaaag gatcgtcgtt ttgtcgtttt    60
gtcgtt                                                               66

SEQ ID NO: 192           moltype = DNA  length = 66
FEATURE                  Location/Qualifiers
source                   1..66
                         mol_type = other DNA
                         organism = synthetic construct
SEQUENCE: 192
gctaacgcaa ctcccgggtt ggtttgcaca agatgagaag tgtcgtcgtt ttgtcgtttt    60
gtcgtt                                                               66

SEQ ID NO: 193           moltype = DNA  length = 66
FEATURE                  Location/Qualifiers
source                   1..66
                         mol_type = other DNA
                         organism = synthetic construct
SEQUENCE: 193
ttcacgaccg acagtctggc aatactagta caagtaaata tctcgtcgtt ttgtcgtttt    60
gtcgtt                                                               66

SEQ ID NO: 194           moltype = DNA  length = 65
FEATURE                  Location/Qualifiers
source                   1..65
                         mol_type = other DNA
                         organism = synthetic construct
SEQUENCE: 194
ataaagtttt gcgttgcgct cctgcagcat ggatggaggc ggcccgatac tgccatagac    60
ggcaa                                                                65

SEQ ID NO: 195           moltype = DNA  length = 65
FEATURE                  Location/Qualifiers
source                   1..65
                         mol_type = other DNA
                         organism = synthetic construct
SEQUENCE: 195
tgcgctcgcc gctacagggc gcacattaag caggaccact tacccgatac tgccatagac    60
ggcaa                                                                65

SEQ ID NO: 196           moltype = DNA  length = 65
FEATURE                  Location/Qualifiers
source                   1..65
                         mol_type = other DNA
                         organism = synthetic construct
SEQUENCE: 196
gctggtttac acccgccgcg cttaatgcgg cccttccggc tgcccgatac tgccatagac    60
ggcaa                                                                65

SEQ ID NO: 197           moltype = DNA  length = 65
FEATURE                  Location/Qualifiers
source                   1..65
                         mol_type = other DNA
```

```
                              organism = synthetic construct
SEQUENCE: 197
gtgtagcgag ccggcgaacg tggcgagaaa gggcgctggc aacccgatac tgccatagac    60
ggcaa                                                                65

SEQ ID NO: 198         moltype = DNA   length = 55
FEATURE                Location/Qualifiers
source                 1..55
                       mol_type = other DNA
                       organism = synthetic construct
SEQUENCE: 198
cgggcgctag gaagggaaga aagcagctat atcccgatac tgccatagac ggcaa          55

SEQ ID NO: 199         moltype = DNA   length = 55
FEATURE                Location/Qualifiers
source                 1..55
                       mol_type = other DNA
                       organism = synthetic construct
SEQUENCE: 199
tctgacatgt ccgagggttc ccaggaaagg agcccgatac tgccatagac ggcaa          55

SEQ ID NO: 200         moltype = DNA   length = 65
FEATURE                Location/Qualifiers
source                 1..65
                       mol_type = other DNA
                       organism = synthetic construct
SEQUENCE: 200
tactttaggg aaccctaaag ggagcccccg tttactcata tacccgatac tgccatagac    60
ggcaa                                                                65

SEQ ID NO: 201         moltype = DNA   length = 65
FEATURE                Location/Qualifiers
source                 1..65
                       mol_type = other DNA
                       organism = synthetic construct
SEQUENCE: 201
ttcattttgg tgccgtaaag cactaaatca ttgatttaaa accccgatac tgccatagac    60
ggcaa                                                                65

SEQ ID NO: 202         moltype = DNA   length = 65
FEATURE                Location/Qualifiers
source                 1..65
                       mol_type = other DNA
                       organism = synthetic construct
SEQUENCE: 202
tctaggtgaa tcaagttttt tggggtcgat aatttaaaag gacccgatac tgccatagac    60
ggcaa                                                                65

SEQ ID NO: 203         moltype = DNA   length = 65
FEATURE                Location/Qualifiers
source                 1..65
                       mol_type = other DNA
                       organism = synthetic construct
SEQUENCE: 203
cgatggccga acaagagtcc actattaaac cgtctatcag ggcccgatac tgccatagac    60
ggcaa                                                                65

SEQ ID NO: 204         moltype = DNA   length = 55
FEATURE                Location/Qualifiers
source                 1..55
                       mol_type = other DNA
                       organism = synthetic construct
SEQUENCE: 204
gcgaaaaaga acgtggactc caacaatcag tacccgatac tgccatagac ggcaa          55

SEQ ID NO: 205         moltype = DNA   length = 65
FEATURE                Location/Qualifiers
source                 1..65
                       mol_type = other DNA
                       organism = synthetic construct
SEQUENCE: 205
gagataggat cagctcattt tttaaccaaa aaagaataga cccccgatac tgccatagac    60
ggcaa                                                                65

SEQ ID NO: 206         moltype = DNA   length = 55
FEATURE                Location/Qualifiers
source                 1..55
                       mol_type = other DNA
                       organism = synthetic construct
```

-continued

```
SEQUENCE: 206
tataaatcta ggccgaaatc ggcatgttgt agcccgatac tgccatagac ggcaa          55

SEQ ID NO: 207          moltype = DNA   length = 55
FEATURE                 Location/Qualifiers
source                  1..55
                        mol_type = other DNA
                        organism = synthetic construct
SEQUENCE: 207
aaagtcaata ggaagccgca taagaaatcc ctcccgatac tgccatagac ggcaa          55

SEQ ID NO: 208          moltype = DNA   length = 65
FEATURE                 Location/Qualifiers
source                  1..65
                        mol_type = other DNA
                        organism = synthetic construct
SEQUENCE: 208
ggttgtaaat gaccaaaatc ccttaacgtt catatgtacc ccccgatac tgccatagac     60
ggcaa                                                                 65

SEQ ID NO: 209          moltype = DNA   length = 55
FEATURE                 Location/Qualifiers
source                  1..55
                        mol_type = other DNA
                        organism = synthetic construct
SEQUENCE: 209
gaccccaaga gttttcgttc cactcccgta ttcccgatac tgccatagac ggcaa          55

SEQ ID NO: 210          moltype = DNA   length = 55
FEATURE                 Location/Qualifiers
source                  1..55
                        mol_type = other DNA
                        organism = synthetic construct
SEQUENCE: 210
ggtgcctccg aaatagacag atcgaaaagc atcccgatac tgccatagac ggcaa          55

SEQ ID NO: 211          moltype = DNA   length = 55
FEATURE                 Location/Qualifiers
source                  1..55
                        mol_type = other DNA
                        organism = synthetic construct
SEQUENCE: 211
cttacggata ctcaccagtc acagctgaga tacccgatac tgccatagac ggcaa          55

SEQ ID NO: 212          moltype = DNA   length = 65
FEATURE                 Location/Qualifiers
source                  1..65
                        mol_type = other DNA
                        organism = synthetic construct
SEQUENCE: 212
gttatctagg tgagcgtggg tctcgcggtc tcccgtatcg tacccgatac tgccatagac     60
ggcaa                                                                 65

SEQ ID NO: 213          moltype = DNA   length = 55
FEATURE                 Location/Qualifiers
source                  1..55
                        mol_type = other DNA
                        organism = synthetic construct
SEQUENCE: 213
ggtaagccat cattgcagca ctggaaccgg agcccgatac tgccatagac ggcaa          55

SEQ ID NO: 214          moltype = DNA   length = 55
FEATURE                 Location/Qualifiers
source                  1..55
                        mol_type = other DNA
                        organism = synthetic construct
SEQUENCE: 214
ctgaatgacg ccttgatcgt tgggggccag atcccgatac tgccatagac ggcaa          55

SEQ ID NO: 215          moltype = DNA   length = 65
FEATURE                 Location/Qualifiers
source                  1..65
                        mol_type = other DNA
                        organism = synthetic construct
SEQUENCE: 215
aatgtgcggg cgaactactt actctagctc acttttcggg gacccgatac tgccatagac     60
ggcaa                                                                 65

SEQ ID NO: 216          moltype = DNA   length = 65
```

```
FEATURE                 Location/Qualifiers
source                  1..65
                        mol_type = other DNA
                        organism = synthetic construct
SEQUENCE: 216
tcaaatatat gcctgtagca atggcaacat ttctaaatac atcccgatac tgccatagac   60
ggcaa                                                                65

SEQ ID NO: 217          moltype = DNA   length = 65
FEATURE                 Location/Qualifiers
source                  1..65
                        mol_type = other DNA
                        organism = synthetic construct
SEQUENCE: 217
cattttgcag gaccgaagga gctaaccgcc ccttttttgc ggcccgatac tgccatagac   60
ggcaa                                                                65

SEQ ID NO: 218          moltype = DNA   length = 65
FEATURE                 Location/Qualifiers
source                  1..65
                        mol_type = other DNA
                        organism = synthetic construct
SEQUENCE: 218
aagtaaaaga gtgataacac tgcggccaag aaacgctggt gacccgatac tgccatagac   60
ggcaa                                                                65

SEQ ID NO: 219          moltype = DNA   length = 65
FEATURE                 Location/Qualifiers
source                  1..65
                        mol_type = other DNA
                        organism = synthetic construct
SEQUENCE: 219
agagaatttc tcagaatgac ttggttgagt ggcatgacag tacccgatac tgccatagac   60
ggcaa                                                                65

SEQ ID NO: 220          moltype = DNA   length = 65
FEATURE                 Location/Qualifiers
source                  1..65
                        mol_type = other DNA
                        organism = synthetic construct
SEQUENCE: 220
gaacgtttgc acgagtgggt tacatcgaat tttcgccccg aacccgatac tgccatagac   60
ggcaa                                                                65

SEQ ID NO: 221          moltype = DNA   length = 55
FEATURE                 Location/Qualifiers
source                  1..55
                        mol_type = other DNA
                        organism = synthetic construct
SEQUENCE: 221
cttgagagct ggatctcaac agcgtgaatc tgcccgatac tgccatagac ggcaa          55

SEQ ID NO: 222          moltype = DNA   length = 55
FEATURE                 Location/Qualifiers
source                  1..55
                        mol_type = other DNA
                        organism = synthetic construct
SEQUENCE: 222
tctatacaac gaaaccttgc actcgtaaga tccccgatac tgccatagac ggcaa          55

SEQ ID NO: 223          moltype = DNA   length = 55
FEATURE                 Location/Qualifiers
source                  1..55
                        mol_type = other DNA
                        organism = synthetic construct
SEQUENCE: 223
aagagtatat gcttcaataa tattacatgc gacccgatac tgccatagac ggcaa          55

SEQ ID NO: 224          moltype = DNA   length = 55
FEATURE                 Location/Qualifiers
source                  1..55
                        mol_type = other DNA
                        organism = synthetic construct
SEQUENCE: 224
tgtgacctag agaataagta aattgaaaaa ggcccgatac tgccatagac ggcaa          55

SEQ ID NO: 225          moltype = DNA   length = 65
FEATURE                 Location/Qualifiers
source                  1..65
```

-continued

```
                         mol_type = other DNA
                         organism = synthetic construct
SEQUENCE: 225
cctactttgg ttaatgtcat gataataatt tcattgtgca atcccgatac tgccatagac    60
ggcaa                                                                 65

SEQ ID NO: 226          moltype = DNA   length = 65
FEATURE                 Location/Qualifiers
source                  1..65
                        mol_type = other DNA
                        organism = synthetic construct
SEQUENCE: 226
ttggtcgtcg tgatacgcct atttttataa aaagaaaaga ggcccgatac tgccatagac    60
ggcaa                                                                 65

SEQ ID NO: 227          moltype = DNA   length = 65
FEATURE                 Location/Qualifiers
source                  1..65
                        mol_type = other DNA
                        organism = synthetic construct
SEQUENCE: 227
aagcatggac gaattcgacg aaagggcctt aatgacccaa gacccgatac tgccatagac    60
ggcaa                                                                 65

SEQ ID NO: 228          moltype = DNA   length = 65
FEATURE                 Location/Qualifiers
source                  1..65
                        mol_type = other DNA
                        organism = synthetic construct
SEQUENCE: 228
tctccaccgc gcccgggtgg ctcaacaact aaacgaatag cccccgatac tgccatagac    60
ggcaa                                                                 65

SEQ ID NO: 229          moltype = DNA   length = 55
FEATURE                 Location/Qualifiers
source                  1..55
                        mol_type = other DNA
                        organism = synthetic construct
SEQUENCE: 229
ctatgttcat tagaaggcgt tgttattacc ctcccgatac tgccatagac ggcaa         55

SEQ ID NO: 230          moltype = DNA   length = 55
FEATURE                 Location/Qualifiers
source                  1..55
                        mol_type = other DNA
                        organism = synthetic construct
SEQUENCE: 230
cgatattcca cagtctatta tcttttgata ctcccgatac tgccatagac ggcaa         55

SEQ ID NO: 231          moltype = DNA   length = 65
FEATURE                 Location/Qualifiers
source                  1..65
                        mol_type = other DNA
                        organism = synthetic construct
SEQUENCE: 231
actgctatat aaccatgtta cttggtcaga tgtgtaaaag gacccgatac tgccatagac    60
ggcaa                                                                 65

SEQ ID NO: 232          moltype = DNA   length = 65
FEATURE                 Location/Qualifiers
source                  1..65
                        mol_type = other DNA
                        organism = synthetic construct
SEQUENCE: 232
gctaacgcaa ctcccgggtt ggtttgcaca agatgagaag tgcccgatac tgccatagac    60
ggcaa                                                                 65

SEQ ID NO: 233          moltype = DNA   length = 65
FEATURE                 Location/Qualifiers
source                  1..65
                        mol_type = other DNA
                        organism = synthetic construct
SEQUENCE: 233
ttcacgaccg acagtctggc aatactagta caagtaaata tccccgatac tgccatagac    60
ggcaa                                                                 65

SEQ ID NO: 234          moltype = DNA   length = 66
FEATURE                 Location/Qualifiers
source                  1..66
```

-continued

```
                       mol_type = other DNA
                       organism = synthetic construct
SEQUENCE: 234
ggcggataaa gttttgcgtt gcgctcctgc agcatggatg gatcgtcgtt ttgtcgtttt   60
gtcgtt                                                               66

SEQ ID NO: 235         moltype = DNA   length = 66
FEATURE                Location/Qualifiers
source                 1..66
                       mol_type = other DNA
                       organism = synthetic construct
SEQUENCE: 235
acttatgcgc tcgccgctac agggcgcaca ttaagcagga cctcgtcgtt ttgtcgtttt   60
gtcgtt                                                               66

SEQ ID NO: 236         moltype = DNA   length = 66
FEATURE                Location/Qualifiers
source                 1..66
                       mol_type = other DNA
                       organism = synthetic construct
SEQUENCE: 236
ggctggctgg tttcacuccg ccgcgcttaa tgcggccctt cctcgtcgtt ttgtcgtttt   60
gtcgtt                                                               66

SEQ ID NO: 237         moltype = DNA   length = 66
FEATURE                Location/Qualifiers
source                 1..66
                       mol_type = other DNA
                       organism = synthetic construct
SEQUENCE: 237
ggcaagtgta gcgagccggc gaacgtggcg agaaagggcg cttcgtcgtt ttgtcgtttt   60
gtcgtt                                                               66

SEQ ID NO: 238         moltype = DNA   length = 56
FEATURE                Location/Qualifiers
source                 1..56
                       mol_type = other DNA
                       organism = synthetic construct
SEQUENCE: 238
gttcccagga aaggagcggg cgctaggaag ggtcgtcgtt ttgtcgtttt gtcgtt       56

SEQ ID NO: 239         moltype = DNA   length = 56
FEATURE                Location/Qualifiers
source                 1..56
                       mol_type = other DNA
                       organism = synthetic construct
SEQUENCE: 239
aagaaagcag ctatattctg acatgtccga ggtcgtcgtt ttgtcgtttt gtcgtt       56

SEQ ID NO: 240         moltype = DNA   length = 66
FEATURE                Location/Qualifiers
source                 1..66
                       mol_type = other DNA
                       organism = synthetic construct
SEQUENCE: 240
atatatactt tagggaaccc taaagggagc ccccgtttac tctcgtcgtt ttgtcgtttt   60
gtcgtt                                                               66

SEQ ID NO: 241         moltype = DNA   length = 66
FEATURE                Location/Qualifiers
source                 1..66
                       mol_type = other DNA
                       organism = synthetic construct
SEQUENCE: 241
aaaacttcat tttggtgccg taaagcacta aatcattgat tttcgtcgtt ttgtcgtttt   60
gtcgtt                                                               66

SEQ ID NO: 242         moltype = DNA   length = 66
FEATURE                Location/Qualifiers
source                 1..66
                       mol_type = other DNA
                       organism = synthetic construct
SEQUENCE: 242
aaggatctag gtgaatcaag ttttttgggg tcgataattt aatcgtcgtt ttgtcgtttt   60
gtcgtt                                                               66

SEQ ID NO: 243         moltype = DNA   length = 66
FEATURE                Location/Qualifiers
source                 1..66
```

```
                              mol_type = other DNA
                              organism = synthetic construct
SEQUENCE: 243
cagggcgatg gccgaacaag agtccactat taaaccgtct attcgtcgtt ttgtcgtttt    60
gtcgtt                                                                66

SEQ ID NO: 244           moltype = DNA   length = 56
FEATURE                  Location/Qualifiers
source                   1..56
                         mol_type = other DNA
                         organism = synthetic construct
SEQUENCE: 244
actccaacaa tcagtactat gcagattttg actcgtcgtt ttgtcgtttt gtcgtt         56

SEQ ID NO: 245           moltype = DNA   length = 66
FEATURE                  Location/Qualifiers
source                   1..66
                         mol_type = other DNA
                         organism = synthetic construct
SEQUENCE: 245
agaccgagat aggatcagct cattttttaa ccaaaaaaga attcgtcgtt ttgtcgtttt    60
gtcgtt                                                                66

SEQ ID NO: 246           moltype = DNA   length = 56
FEATURE                  Location/Qualifiers
source                   1..56
                         mol_type = other DNA
                         organism = synthetic construct
SEQUENCE: 246
cgcataagaa atcccttata aatctaggcc gatcgtcgtt ttgtcgtttt gtcgtt         56

SEQ ID NO: 247           moltype = DNA   length = 56
FEATURE                  Location/Qualifiers
source                   1..56
                         mol_type = other DNA
                         organism = synthetic construct
SEQUENCE: 247
aatcggcatg ttgtagaaag tcaataggaa gctcgtcgtt ttgtcgtttt gtcgtt         56

SEQ ID NO: 248           moltype = DNA   length = 66
FEATURE                  Location/Qualifiers
source                   1..66
                         mol_type = other DNA
                         organism = synthetic construct
SEQUENCE: 248
accccggttg taaatgacca aaatccctta acgttcatat gttcgtcgtt ttgtcgtttt    60
gtcgtt                                                                66

SEQ ID NO: 249           moltype = DNA   length = 56
FEATURE                  Location/Qualifiers
source                   1..56
                         mol_type = other DNA
                         organism = synthetic construct
SEQUENCE: 249
gttccactcc cgtattgacg ccggtgtggc gctcgtcgtt ttgtcgtttt gtcgtt         56

SEQ ID NO: 250           moltype = DNA   length = 56
FEATURE                  Location/Qualifiers
source                   1..56
                         mol_type = other DNA
                         organism = synthetic construct
SEQUENCE: 250
agtcacagct gagataggtg cctccgaaat agtcgtcgtt ttgtcgtttt gtcgtt         56

SEQ ID NO: 251           moltype = DNA   length = 56
FEATURE                  Location/Qualifiers
source                   1..56
                         mol_type = other DNA
                         organism = synthetic construct
SEQUENCE: 251
acagatcgaa aagcatctta cggatactca cctcgtcgtt ttgtcgtttt gtcgtt         56

SEQ ID NO: 252           moltype = DNA   length = 66
FEATURE                  Location/Qualifiers
source                   1..66
                         mol_type = other DNA
                         organism = synthetic construct
SEQUENCE: 252
tcgtagttat ctaggtgagc gtgggtctcg cggtctcccg tatcgtcgtt ttgtcgtttt    60
```

-continued

```
gtcgtt                                                          66

SEQ ID NO: 253        moltype = DNA   length = 56
FEATURE               Location/Qualifiers
source                1..56
                      mol_type = other DNA
                      organism = synthetic construct
SEQUENCE: 253
tcgttggggg ccagatggta agccatcatt gctcgtcgtt ttgtcgtttt gtcgtt     56

SEQ ID NO: 254        moltype = DNA   length = 56
FEATURE               Location/Qualifiers
source                1..56
                      mol_type = other DNA
                      organism = synthetic construct
SEQUENCE: 254
agcactggaa ccggagctga atgacgcctt gatcgtcgtt ttgtcgtttt gtcgtt     56

SEQ ID NO: 255        moltype = DNA   length = 66
FEATURE               Location/Qualifiers
source                1..66
                      mol_type = other DNA
                      organism = synthetic construct
SEQUENCE: 255
ggggaaatgt gcgggcgaac tacttactct agctcacttt tctcgtcgtt ttgtcgtttt  60
gtcgtt                                                          66

SEQ ID NO: 256        moltype = DNA   length = 66
FEATURE               Location/Qualifiers
source                1..66
                      mol_type = other DNA
                      organism = synthetic construct
SEQUENCE: 256
tacattcaaa tatatgcctg tagcaatggc aacatttcta aatcgtcgtt ttgtcgtttt  60
gtcgtt                                                          66

SEQ ID NO: 257        moltype = DNA   length = 66
FEATURE               Location/Qualifiers
source                1..66
                      mol_type = other DNA
                      organism = synthetic construct
SEQUENCE: 257
tgcggcattt tgcaggaccg aaggagctaa ccgccccttt tttcgtcgtt ttgtcgtttt  60
gtcgtt                                                          66

SEQ ID NO: 258        moltype = DNA   length = 66
FEATURE               Location/Qualifiers
source                1..66
                      mol_type = other DNA
                      organism = synthetic construct
SEQUENCE: 258
ggtgaaagta aaagagtgat aacactgcgg ccaagaaacg cttcgtcgtt ttgtcgtttt  60
gtcgtt                                                          66

SEQ ID NO: 259        moltype = DNA   length = 66
FEATURE               Location/Qualifiers
source                1..66
                      mol_type = other DNA
                      organism = synthetic construct
SEQUENCE: 259
cagtaagaga atttctcaga atgacttggt tgagtggcat gatcgtcgtt ttgtcgtttt  60
gtcgtt                                                          66

SEQ ID NO: 260        moltype = DNA   length = 66
FEATURE               Location/Qualifiers
source                1..66
                      mol_type = other DNA
                      organism = synthetic construct
SEQUENCE: 260
ccgaagaacg tttgcacgag tgggttacat cgaattttcg cctcgtcgtt ttgtcgtttt  60
gtcgtt                                                          66

SEQ ID NO: 261        moltype = DNA   length = 56
FEATURE               Location/Qualifiers
source                1..56
                      mol_type = other DNA
                      organism = synthetic construct
SEQUENCE: 261
ttgcactcgt aagatccttg agagctggat cttcgtcgtt ttgtcgtttt gtcgtt     56
```

-continued

```
SEQ ID NO: 262           moltype = DNA   length = 56
FEATURE                  Location/Qualifiers
source                   1..56
                         mol_type = other DNA
                         organism = synthetic construct
SEQUENCE: 262
caacagcgtg aatctgtcta tacaacgaaa cctcgtcgtt ttgtcgtttt gtcgtt        56

SEQ ID NO: 263           moltype = DNA   length = 56
FEATURE                  Location/Qualifiers
source                   1..56
                         mol_type = other DNA
                         organism = synthetic construct
SEQUENCE: 263
agtaaattga aaaggaaga gtatatgctt catcgtcgtt ttgtcgtttt gtcgtt          56

SEQ ID NO: 264           moltype = DNA   length = 56
FEATURE                  Location/Qualifiers
source                   1..56
                         mol_type = other DNA
                         organism = synthetic construct
SEQUENCE: 264
ataatattac atgcgatgtg acctagagaa tatcgtcgtt ttgtcgtttt gtcgtt        56

SEQ ID NO: 265           moltype = DNA   length = 66
FEATURE                  Location/Qualifiers
source                   1..66
                         mol_type = other DNA
                         organism = synthetic construct
SEQUENCE: 265
gcaatcctac tttggttaat gtcatgataa taatttcatt gttcgtcgtt ttgtcgtttt   60
gtcgtt                                                               66

SEQ ID NO: 266           moltype = DNA   length = 66
FEATURE                  Location/Qualifiers
source                   1..66
                         mol_type = other DNA
                         organism = synthetic construct
SEQUENCE: 266
agaggtggt cgtcgtgata cgcctatttt tataaaaga aatcgtcgtt ttgtcgtttt     60
gtcgtt                                                               66

SEQ ID NO: 267           moltype = DNA   length = 66
FEATURE                  Location/Qualifiers
source                   1..66
                         mol_type = other DNA
                         organism = synthetic construct
SEQUENCE: 267
caagaaagca tggacgaatt cgacgaaagg gccttaatga cctcgtcgtt ttgtcgtttt   60
gtcgtt                                                               66

SEQ ID NO: 268           moltype = DNA   length = 66
FEATURE                  Location/Qualifiers
source                   1..66
                         mol_type = other DNA
                         organism = synthetic construct
SEQUENCE: 268
tagcctctcc accgcgcccg ggtggctcaa caactaaacg aatcgtcgtt ttgtcgtttt   60
gtcgtt                                                               66

SEQ ID NO: 269           moltype = DNA   length = 56
FEATURE                  Location/Qualifiers
source                   1..56
                         mol_type = other DNA
                         organism = synthetic construct
SEQUENCE: 269
attatctttt gatactctat gttcattaga agtcgtcgtt ttgtcgtttt gtcgtt       56

SEQ ID NO: 270           moltype = DNA   length = 56
FEATURE                  Location/Qualifiers
source                   1..56
                         mol_type = other DNA
                         organism = synthetic construct
SEQUENCE: 270
gcgttgttat taccctcgat attccacagt cttcgtcgtt ttgtcgtttt gtcgtt       56

SEQ ID NO: 271           moltype = DNA   length = 66
FEATURE                  Location/Qualifiers
```

-continued

```
source                  1..66
                        mol_type = other DNA
                        organism = synthetic construct
SEQUENCE: 271
aaggaactgc tatataacca tgttacttgg tcagatgtgt aatcgtcgtt ttgtcgtttt   60
gtcgtt                                                             66

SEQ ID NO: 272          moltype = DNA   length = 66
FEATURE                 Location/Qualifiers
source                  1..66
                        mol_type = other DNA
                        organism = synthetic construct
SEQUENCE: 272
aagtggctaa cgcaactccc gggttggttt gcacaagatg agtcgtcgtt ttgtcgtttt   60
gtcgtt                                                             66

SEQ ID NO: 273          moltype = DNA   length = 66
FEATURE                 Location/Qualifiers
source                  1..66
                        mol_type = other DNA
                        organism = synthetic construct
SEQUENCE: 273
atatcttcac gaccgacagt ctggcaatac tagtacaagt aatcgtcgtt ttgtcgtttt   60
gtcgtt                                                             66

SEQ ID NO: 274          moltype = DNA   length = 65
FEATURE                 Location/Qualifiers
source                  1..65
                        mol_type = other DNA
                        organism = synthetic construct
SEQUENCE: 274
ggcggataaa gttttgcgtt gcgctcctgc agcatggatg gacccgatac tgccatagac   60
ggcaa                                                              65

SEQ ID NO: 275          moltype = DNA   length = 65
FEATURE                 Location/Qualifiers
source                  1..65
                        mol_type = other DNA
                        organism = synthetic construct
SEQUENCE: 275
acttatgcgc tcgccgctac agggcgcaca ttaagcagga cccccgatac tgccatagac   60
ggcaa                                                              65

SEQ ID NO: 276          moltype = DNA   length = 65
FEATURE                 Location/Qualifiers
source                  1..65
                        mol_type = other DNA
                        organism = synthetic construct
SEQUENCE: 276
ggctggctgg tttacacccg ccgcgcttaa tgcggccctt cccccgatac tgccatagac   60
ggcaa                                                              65

SEQ ID NO: 277          moltype = DNA   length = 65
FEATURE                 Location/Qualifiers
source                  1..65
                        mol_type = other DNA
                        organism = synthetic construct
SEQUENCE: 277
ggcaagtgta gcgagccggc gaacgtggcg agaaagggcg ctcccgatac tgccatagac   60
ggcaa                                                              65

SEQ ID NO: 278          moltype = DNA   length = 55
FEATURE                 Location/Qualifiers
source                  1..55
                        mol_type = other DNA
                        organism = synthetic construct
SEQUENCE: 278
gttcccagga aaggagcggg cgctaggaag ggcccgatac tgccatagac ggcaa         55

SEQ ID NO: 279          moltype = DNA   length = 55
FEATURE                 Location/Qualifiers
source                  1..55
                        mol_type = other DNA
                        organism = synthetic construct
SEQUENCE: 279
aagaaagcag ctatattctg acatgtccga ggcccgatac tgccatagac ggcaa         55

SEQ ID NO: 280          moltype = DNA   length = 65
FEATURE                 Location/Qualifiers
```

-continued

```
source                1..65
                      mol_type = other DNA
                      organism = synthetic construct
SEQUENCE: 280
atatatactt tagggaaccc taaagggagc ccccgtttac tccccgatac tgccatagac   60
ggcaa                                                               65

SEQ ID NO: 281        moltype = DNA   length = 65
FEATURE               Location/Qualifiers
source                1..65
                      mol_type = other DNA
                      organism = synthetic construct
SEQUENCE: 281
aaaacttcat tttggtgccg taaagcacta aatcattgat ttcccgatac tgccatagac   60
ggcaa                                                               65

SEQ ID NO: 282        moltype = DNA   length = 65
FEATURE               Location/Qualifiers
source                1..65
                      mol_type = other DNA
                      organism = synthetic construct
SEQUENCE: 282
aaggatctag gtgaatcaag ttttttgggg tcgataattt aacccgatac tgccatagac   60
ggcaa                                                               65

SEQ ID NO: 283        moltype = DNA   length = 65
FEATURE               Location/Qualifiers
source                1..65
                      mol_type = other DNA
                      organism = synthetic construct
SEQUENCE: 283
cagggcgatg gccgaacaag agtccactat taaaccgtct atcccgatac tgccatagac   60
ggcaa                                                               65

SEQ ID NO: 284        moltype = DNA   length = 55
FEATURE               Location/Qualifiers
source                1..55
                      mol_type = other DNA
                      organism = synthetic construct
SEQUENCE: 284
actccaacaa tcagtactat gcagattttg accccgatac tgccatagac ggcaa         55

SEQ ID NO: 285        moltype = DNA   length = 65
FEATURE               Location/Qualifiers
source                1..65
                      mol_type = other DNA
                      organism = synthetic construct
SEQUENCE: 285
agaccgagat aggatcagct cattttttaa ccaaaaaaga atcccgatac tgccatagac   60
ggcaa                                                               65

SEQ ID NO: 286        moltype = DNA   length = 55
FEATURE               Location/Qualifiers
source                1..55
                      mol_type = other DNA
                      organism = synthetic construct
SEQUENCE: 286
cgcataagaa atcccttata aatctaggcc gacccgatac tgccatagac ggcaa         55

SEQ ID NO: 287        moltype = DNA   length = 55
FEATURE               Location/Qualifiers
source                1..55
                      mol_type = other DNA
                      organism = synthetic construct
SEQUENCE: 287
aatcggcatg ttgtagaaag tcaataggaa gccccgatac tgccatagac ggcaa         55

SEQ ID NO: 288        moltype = DNA   length = 65
FEATURE               Location/Qualifiers
source                1..65
                      mol_type = other DNA
                      organism = synthetic construct
SEQUENCE: 288
accccggttg taaatgacca aaatccctta acgttcatat gtcccgatac tgccatagac   60
ggcaa                                                               65

SEQ ID NO: 289        moltype = DNA   length = 55
FEATURE               Location/Qualifiers
source                1..55
```

-continued

```
                              mol_type = other DNA
                              organism = synthetic construct
SEQUENCE: 289
gttccactcc cgtattgacg ccggtgtggc gccccgatac tgccatagac ggcaa          55

SEQ ID NO: 290          moltype = DNA   length = 55
FEATURE                 Location/Qualifiers
source                  1..55
                        mol_type = other DNA
                        organism = synthetic construct
SEQUENCE: 290
agtcacagct gagataggtg cctccgaaat agcccgatac tgccatagac ggcaa          55

SEQ ID NO: 291          moltype = DNA   length = 55
FEATURE                 Location/Qualifiers
source                  1..55
                        mol_type = other DNA
                        organism = synthetic construct
SEQUENCE: 291
acagatcgaa aagcatctta cggatactca cccccgatac tgccatagac ggcaa          55

SEQ ID NO: 292          moltype = DNA   length = 65
FEATURE                 Location/Qualifiers
source                  1..65
                        mol_type = other DNA
                        organism = synthetic construct
SEQUENCE: 292
tcgtagttat ctaggtgagc gtgggtctcg cggtctcccg tacccgatac tgccatagac     60
ggcaa                                                                  65

SEQ ID NO: 293          moltype = DNA   length = 55
FEATURE                 Location/Qualifiers
source                  1..55
                        mol_type = other DNA
                        organism = synthetic construct
SEQUENCE: 293
tcgttggggg ccagatggta agccatcatt gccccgatac tgccatagac ggcaa          55

SEQ ID NO: 294          moltype = DNA   length = 55
FEATURE                 Location/Qualifiers
source                  1..55
                        mol_type = other DNA
                        organism = synthetic construct
SEQUENCE: 294
agcactggaa ccggagctga atgacgcctt gacccgatac tgccatagac ggcaa          55

SEQ ID NO: 295          moltype = DNA   length = 65
FEATURE                 Location/Qualifiers
source                  1..65
                        mol_type = other DNA
                        organism = synthetic construct
SEQUENCE: 295
ggggaaatgt gcgggcgaac tacttactct agctcacttt tccccgatac tgccatagac     60
ggcaa                                                                  65

SEQ ID NO: 296          moltype = DNA   length = 65
FEATURE                 Location/Qualifiers
source                  1..65
                        mol_type = other DNA
                        organism = synthetic construct
SEQUENCE: 296
tacattcaaa tatatgcctg tagcaatggc aacatttcta aacccgatac tgccatagac     60
ggcaa                                                                  65

SEQ ID NO: 297          moltype = DNA   length = 65
FEATURE                 Location/Qualifiers
source                  1..65
                        mol_type = other DNA
                        organism = synthetic construct
SEQUENCE: 297
tgcggcattt tgcaggaccg aaggagctaa ccgccccttt ttcccgatac tgccatagac     60
ggcaa                                                                  65

SEQ ID NO: 298          moltype = DNA   length = 65
FEATURE                 Location/Qualifiers
source                  1..65
                        mol_type = other DNA
                        organism = synthetic construct
SEQUENCE: 298
```

-continued

```
ggtgaaagta aaagagtgat aacactgcgg ccaagaaacg ctcccgatac tgccatagac   60
ggcaa                                                               65

SEQ ID NO: 299          moltype = DNA  length = 65
FEATURE                 Location/Qualifiers
source                  1..65
                        mol_type = other DNA
                        organism = synthetic construct
SEQUENCE: 299
cagtaagaga atttctcaga atgacttggt tgagtggcat gacccgatac tgccatagac   60
ggcaa                                                               65

SEQ ID NO: 300          moltype = DNA  length = 65
FEATURE                 Location/Qualifiers
source                  1..65
                        mol_type = other DNA
                        organism = synthetic construct
SEQUENCE: 300
ccgaagaacg tttgcacgag tgggttacat cgaattttcg cccccgatac tgccatagac   60
ggcaa                                                               65

SEQ ID NO: 301          moltype = DNA  length = 55
FEATURE                 Location/Qualifiers
source                  1..55
                        mol_type = other DNA
                        organism = synthetic construct
SEQUENCE: 301
ttgcactcgt aagatccttg agagctggat ctcccgatac tgccatagac ggcaa        55

SEQ ID NO: 302          moltype = DNA  length = 55
FEATURE                 Location/Qualifiers
source                  1..55
                        mol_type = other DNA
                        organism = synthetic construct
SEQUENCE: 302
caacagcgtg aatctgtcta tacaacgaaa cccccgatac tgccatagac ggcaa        55

SEQ ID NO: 303          moltype = DNA  length = 55
FEATURE                 Location/Qualifiers
source                  1..55
                        mol_type = other DNA
                        organism = synthetic construct
SEQUENCE: 303
agtaaattga aaaaggaaga gtatatgctt cacccgatac tgccatagac ggcaa        55

SEQ ID NO: 304          moltype = DNA  length = 55
FEATURE                 Location/Qualifiers
source                  1..55
                        mol_type = other DNA
                        organism = synthetic construct
SEQUENCE: 304
ataatattac atgcgatgtg acctagagaa tacccgatac tgccatagac ggcaa        55

SEQ ID NO: 305          moltype = DNA  length = 65
FEATURE                 Location/Qualifiers
source                  1..65
                        mol_type = other DNA
                        organism = synthetic construct
SEQUENCE: 305
gcaatcctac tttggttaat gtcatgataa taatttcatt gtcccgatac tgccatagac   60
ggcaa                                                               65

SEQ ID NO: 306          moltype = DNA  length = 65
FEATURE                 Location/Qualifiers
source                  1..65
                        mol_type = other DNA
                        organism = synthetic construct
SEQUENCE: 306
agaggttggt cgtcgtgata cgcctatttt tataaaaga aacccgatac tgccatagac    60
ggcaa                                                               65

SEQ ID NO: 307          moltype = DNA  length = 65
FEATURE                 Location/Qualifiers
source                  1..65
                        mol_type = other DNA
                        organism = synthetic construct
SEQUENCE: 307
caagaaagca tggacgaatt cgacgaaagg gccttaatga cccccgatac tgccatagac   60
ggcaa                                                               65
```

```
SEQ ID NO: 308          moltype = DNA   length = 65
FEATURE                 Location/Qualifiers
source                  1..65
                        mol_type = other DNA
                        organism = synthetic construct
SEQUENCE: 308
tagcctctcc accgcgcccg ggtggctcaa caactaaacg aacccgatac tgccatagac   60
ggcaa                                                               65

SEQ ID NO: 309          moltype = DNA   length = 55
FEATURE                 Location/Qualifiers
source                  1..55
                        mol_type = other DNA
                        organism = synthetic construct
SEQUENCE: 309
attatctttt gatactctat gttcattaga agcccgatac tgccatagac ggcaa         55

SEQ ID NO: 310          moltype = DNA   length = 55
FEATURE                 Location/Qualifiers
source                  1..55
                        mol_type = other DNA
                        organism = synthetic construct
SEQUENCE: 310
gcgttgttat taccctcgat attccacagt ctcccgatac tgccatagac ggcaa         55

SEQ ID NO: 311          moltype = DNA   length = 65
FEATURE                 Location/Qualifiers
source                  1..65
                        mol_type = other DNA
                        organism = synthetic construct
SEQUENCE: 311
aaggaactgc tatataacca tgttacttgg tcagatgtgt aacccgatac tgccatagac   60
ggcaa                                                               65

SEQ ID NO: 312          moltype = DNA   length = 65
FEATURE                 Location/Qualifiers
source                  1..65
                        mol_type = other DNA
                        organism = synthetic construct
SEQUENCE: 312
aagtggctaa cgcaactccc gggttggttt gcacaagatg agcccgatac tgccatagac   60
ggcaa                                                               65

SEQ ID NO: 313          moltype = DNA   length = 65
FEATURE                 Location/Qualifiers
source                  1..65
                        mol_type = other DNA
                        organism = synthetic construct
SEQUENCE: 313
atatcttcac gaccgacagt ctggcaatac tagtacaagt aacccgatac tgccatagac   60
ggcaa                                                               65

SEQ ID NO: 314          moltype = DNA   length = 42
FEATURE                 Location/Qualifiers
source                  1..42
                        mol_type = other DNA
                        organism = synthetic construct
SEQUENCE: 314
ccctaaagtt gcgttgcgct cctgcagcac actaaatcgg aa                       42

SEQ ID NO: 315          moltype = DNA   length = 52
FEATURE                 Location/Qualifiers
source                  1..52
                        mol_type = other DNA
                        organism = synthetic construct
SEQUENCE: 315
ccgctacagg gtttttcgca cattaaggag cccccgattt tttttagagc tt            52

SEQ ID NO: 316          moltype = DNA   length = 42
FEATURE                 Location/Qualifiers
source                  1..42
                        mol_type = other DNA
                        organism = synthetic construct
SEQUENCE: 316
caagatataa gatgagaagt ggctatgcgg cttaaacgca ag                       42

SEQ ID NO: 317          moltype = DNA   length = 78
FEATURE                 Location/Qualifiers
```

```
source                      1..78
                            mol_type = other DNA
                            organism = synthetic construct
SEQUENCE: 317
gaagggaaga attttttagcg aaaggagggc gctggcattt ttagtgtagc ggcgtaacca  60
ccatttttca cccgccgc                                                  78

SEQ ID NO: 318              moltype = DNA  length = 78
FEATURE                     Location/Qualifiers
source                      1..78
                            mol_type = other DNA
                            organism = synthetic construct
SEQUENCE: 318
gaagggaaga attttttagcg aaaggagggc gctggcattt ttagtgtagc ggcgtaacca  60
ccatttttca cccgccgc                                                  78

SEQ ID NO: 319              moltype = DNA  length = 42
FEATURE                     Location/Qualifiers
source                      1..42
                            mol_type = other DNA
                            organism = synthetic construct
SEQUENCE: 319
tctattatac agtctggcaa tactcgctag cgggagtcac ag                       42

SEQ ID NO: 320              moltype = DNA  length = 42
FEATURE                     Location/Qualifiers
source                      1..42
                            mol_type = other DNA
                            organism = synthetic construct
SEQUENCE: 320
cgagaaagga cggggaaagc cggctcaggg tctagaacgt gg                       42

SEQ ID NO: 321              moltype = DNA  length = 42
FEATURE                     Location/Qualifiers
source                      1..42
                            mol_type = other DNA
                            organism = synthetic construct
SEQUENCE: 321
cgagaaagga cggggaaagc cggctcaggg tctagaacgt gg                       42

SEQ ID NO: 322              moltype = DNA  length = 78
FEATURE                     Location/Qualifiers
source                      1..78
                            mol_type = other DNA
                            organism = synthetic construct
SEQUENCE: 322
tggggtcgag gttttttgcc gtaaagtacc tatggcgttt ttaaattctt atgctttaaa  60
caatttttaa tctggcgc                                                  78

SEQ ID NO: 323              moltype = DNA  length = 42
FEATURE                     Location/Qualifiers
source                      1..42
                            mol_type = other DNA
                            organism = synthetic construct
SEQUENCE: 323
tcatttttca tcaccctaat caagtttttt tgttaaatca gc                       42

SEQ ID NO: 324              moltype = DNA  length = 42
FEATURE                     Location/Qualifiers
source                      1..42
                            mol_type = other DNA
                            organism = synthetic construct
SEQUENCE: 324
tcatttttca tcaccctaat caagtttttt tgttaaatca gc                       42

SEQ ID NO: 325              moltype = DNA  length = 78
FEATURE                     Location/Qualifiers
source                      1..78
                            mol_type = other DNA
                            organism = synthetic construct
SEQUENCE: 325
agatagggtt gttttttagtg ttgttccaag agtccacttt tttattaaag aaaacgtcaa  60
aggttttttgc gaaaaacc                                                 78

SEQ ID NO: 326              moltype = DNA  length = 42
FEATURE                     Location/Qualifiers
source                      1..42
                            mol_type = other DNA
                            organism = synthetic construct
```

-continued

```
SEQUENCE: 326
gaaggattaa gtaaatatct tcacactccc gtgggacgta gc                        42

SEQ ID NO: 327            moltype = DNA   length = 42
FEATURE                  Location/Qualifiers
source                   1..42
                         mol_type = other DNA
                         organism = synthetic construct
SEQUENCE: 327
tcaacagcga gtgggttaca tcgatggaac agttactgga tc                        42

SEQ ID NO: 328            moltype = DNA   length = 42
FEATURE                  Location/Qualifiers
source                   1..42
                         mol_type = other DNA
                         organism = synthetic construct
SEQUENCE: 328
atagaccgca aaatccctta taaatgagtt aacgtcaaaa ga                        42

SEQ ID NO: 329            moltype = DNA   length = 52
FEATURE                  Location/Qualifiers
source                   1..52
                         mol_type = other DNA
                         organism = synthetic construct
SEQUENCE: 329
ggcaactatg gtttttatga acgaaagttg taattcgttt ttcgttaaat tt            52

SEQ ID NO: 330            moltype = DNA   length = 42
FEATURE                  Location/Qualifiers
source                   1..42
                         mol_type = other DNA
                         organism = synthetic construct
SEQUENCE: 330
gagataggac cccaatcata tgtaccccgt agacagatcg ct                        42

SEQ ID NO: 331            moltype = DNA   length = 52
FEATURE                  Location/Qualifiers
source                   1..52
                         mol_type = other DNA
                         organism = synthetic construct
SEQUENCE: 331
tttcgttcca cttttttgag cgtcagtgcc tcactgattt ttttaagcat tg            52

SEQ ID NO: 332            moltype = DNA   length = 78
FEATURE                  Location/Qualifiers
source                   1..78
                         mol_type = other DNA
                         organism = synthetic construct
SEQUENCE: 332
tttagattga tttttttttaa aacttctaaa aggatctttt ttaggtgaag ataatctcat   60
gactttttca aaatccct                                                   78

SEQ ID NO: 333            moltype = DNA   length = 42
FEATURE                  Location/Qualifiers
source                   1..42
                         mol_type = other DNA
                         organism = synthetic construct
SEQUENCE: 333
atgagcaccg ccccgaagaa cgttttgatc ctttttccaa tg                        42

SEQ ID NO: 334            moltype = DNA   length = 42
FEATURE                  Location/Qualifiers
source                   1..42
                         mol_type = other DNA
                         organism = synthetic construct
SEQUENCE: 334
ggctggctac cacttatgcg ctcgtaatta ttttgccctt cc                        42

SEQ ID NO: 335            moltype = DNA   length = 42
FEATURE                  Location/Qualifiers
source                   1..42
                         mol_type = other DNA
                         organism = synthetic construct
SEQUENCE: 335
atatatacgt aactgtcaga ccaagatggg gccagtttac tc                        42

SEQ ID NO: 336            moltype = DNA   length = 42
FEATURE                  Location/Qualifiers
source                   1..42
```

-continued

```
                          mol_type = other DNA
                          organism = synthetic construct
SEQUENCE: 336
caacagagta tctacacgac ggggagtcac cgggtggctc aa                       42

SEQ ID NO: 337           moltype = DNA   length = 52
FEATURE                  Location/Qualifiers
source                   1..52
                          mol_type = other DNA
                          organism = synthetic construct
SEQUENCE: 337
taagccctcc ctttttgtat cgtagtaata agtaaatttt tttacatgcg at           52

SEQ ID NO: 338           moltype = DNA   length = 78
FEATURE                  Location/Qualifiers
source                   1..78
                          mol_type = other DNA
                          organism = synthetic construct
SEQUENCE: 338
acgaatagcc ttttttctcc acccaaaccg gagctgattt ttatgaagcc atgcggtatc   60
attttttttgc agcactgg                                                 78

SEQ ID NO: 339           moltype = DNA   length = 42
FEATURE                  Location/Qualifiers
source                   1..42
                          mol_type = other DNA
                          organism = synthetic construct
SEQUENCE: 339
cgtgacacga gccggtgagc gtgggtctca ccaaacgacg ag                       42

SEQ ID NO: 340           moltype = DNA   length = 78
FEATURE                  Location/Qualifiers
source                   1..78
                          mol_type = other DNA
                          organism = synthetic construct
SEQUENCE: 340
ggaggcggat atttttaagt tgcaggggtt tattgctttt ttgataaatc tgcacgatgc   60
ctgtttttta gcaatggc                                                  78

SEQ ID NO: 341           moltype = DNA   length = 42
FEATURE                  Location/Qualifiers
source                   1..42
                          mol_type = other DNA
                          organism = synthetic construct
SEQUENCE: 341
cgggcaagcg cggtattatc ccgttggatt agacattgac gc                       42

SEQ ID NO: 342           moltype = DNA   length = 52
FEATURE                  Location/Qualifiers
source                   1..52
                          mol_type = other DNA
                          organism = synthetic construct
SEQUENCE: 342
cgcaaactat ttttttaact ggcgaatagc ttcccggttt ttcaacaatt aa           52

SEQ ID NO: 343           moltype = DNA   length = 42
FEATURE                  Location/Qualifiers
source                   1..42
                          mol_type = other DNA
                          organism = synthetic construct
SEQUENCE: 343
cagtaagaaa aagcatctta cggatactcc tacttggcat ga                       42

SEQ ID NO: 344           moltype = DNA   length = 42
FEATURE                  Location/Qualifiers
source                   1..42
                          mol_type = other DNA
                          organism = synthetic construct
SEQUENCE: 344
gctttttttat cggaggaccg aaggcgttga acaaagctaa cc                      42

SEQ ID NO: 345           moltype = DNA   length = 42
FEATURE                  Location/Qualifiers
source                   1..42
                          mol_type = other DNA
                          organism = synthetic construct
SEQUENCE: 345
cgacgacgaa ctcgccttga tcgttgggag agtttgaggg ga                       42
```

-continued

```
SEQ ID NO: 346          moltype = DNA   length = 78
FEATURE                 Location/Qualifiers
source                  1..78
                        mol_type = other DNA
                        organism = synthetic construct
SEQUENCE: 346
gcacaacatg gtttttggga tcatgtaatt cgacgaattt ttagggcctc gttaataatg    60
gtttttttc ttagacgt                                                   78

SEQ ID NO: 347          moltype = DNA   length = 52
FEATURE                 Location/Qualifiers
source                  1..52
                        mol_type = other DNA
                        organism = synthetic construct
SEQUENCE: 347
ttttcgggga atttttatgt gcgcgggcca acttactttt tttctgacaa cg            52

SEQ ID NO: 348          moltype = DNA   length = 42
FEATURE                 Location/Qualifiers
source                  1..42
                        mol_type = other DNA
                        organism = synthetic construct
SEQUENCE: 348
ttatttttac catgagtgat aacactgcga acccctattt gt                       42

SEQ ID NO: 349          moltype = DNA   length = 52
FEATURE                 Location/Qualifiers
source                  1..52
                        mol_type = other DNA
                        organism = synthetic construct
SEQUENCE: 349
gaattatgca gttttttgct gccatactaa atacattttt ttcaaatatg ta            52

SEQ ID NO: 350          moltype = DNA   length = 78
FEATURE                 Location/Qualifiers
source                  1..78
                        mol_type = other DNA
                        organism = synthetic construct
SEQUENCE: 350
ttcaataata ttttttgaa aaaggactta ttcccttttt tttttgcgg cattgagtac      60
tcatttttcc agtcacag                                                  78

SEQ ID NO: 351          moltype = DNA   length = 42
FEATURE                 Location/Qualifiers
source                  1..42
                        mol_type = other DNA
                        organism = synthetic construct
SEQUENCE: 351
tgacttggtt ttgccttcct gttttgcta ctattctcag aa                        42

SEQ ID NO: 352          moltype = DNA   length = 78
FEATURE                 Location/Qualifiers
source                  1..78
                        mol_type = other DNA
                        organism = synthetic construct
SEQUENCE: 352
ttttaaagtt cttttttgct atgtggagca actcggtttt ttcgccgcat accacccaga    60
aactttttgc tggtgaaa                                                  78

SEQ ID NO: 353          moltype = DNA   length = 52
FEATURE                 Location/Qualifiers
source                  1..52
                        mol_type = other DNA
                        organism = synthetic construct
SEQUENCE: 353
ctgaagatca gtttttttgg gtgcacggta agatcctttt tttgagagtt tt            52

SEQ ID NO: 354          moltype = DNA   length = 42
FEATURE                 Location/Qualifiers
source                  1..42
                        mol_type = other DNA
                        organism = synthetic construct
SEQUENCE: 354
tagtgatagt ttgcacacgt ctggagatgg taaacggaca tc                       42

SEQ ID NO: 355          moltype = DNA   length = 42
FEATURE                 Location/Qualifiers
source                  1..42
                        mol_type = other DNA
```

-continued

```
                        organism = synthetic construct
SEQUENCE: 355
gtgtcgccag agtatgagta ttcaccacgt cggaacattt cc                         42

SEQ ID NO: 356          moltype = DNA   length = 42
FEATURE                 Location/Qualifiers
source                  1..42
                        mol_type = other DNA
                        organism = synthetic construct
SEQUENCE: 356
ataaatgctc cgctcatgag acaatggtaa agcataaccc tg                         42

SEQ ID NO: 357          moltype = DNA   length = 42
FEATURE                 Location/Qualifiers
source                  1..42
                        mol_type = other DNA
                        organism = synthetic construct
SEQUENCE: 357
ttgatactat tcctagatta gaagggcacc aggtgcgttg tt                         42

SEQ ID NO: 358          moltype = DNA   length = 42
FEATURE                 Location/Qualifiers
source                  1..42
                        mol_type = other DNA
                        organism = synthetic construct
SEQUENCE: 358
tgtcatgaga tacgcctatt tttatgtaga gtgttaggtt aa                         42

SEQ ID NO: 359          moltype = DNA   length = 42
FEATURE                 Location/Qualifiers
source                  1..42
                        mol_type = other DNA
                        organism = synthetic construct
SEQUENCE: 359
gcgaacgaag aaccagggaa aacccttaag tgacaggtac ga                         42

SEQ ID NO: 360          moltype = DNA   length = 42
FEATURE                 Location/Qualifiers
source                  1..42
                        mol_type = other DNA
                        organism = synthetic construct
SEQUENCE: 360
actgctatct atacaaacta agagacaaaa tgtgtaaaag ga                         42

SEQ ID NO: 361          moltype = DNA   length = 52
FEATURE                 Location/Qualifiers
source                  1..52
                        mol_type = other DNA
                        organism = synthetic construct
SEQUENCE: 361
aaagtcaaat ctttttctat ctgtgaaacc ttgcactttt ttctgaatct gt             52

SEQ ID NO: 362          moltype = DNA   length = 52
FEATURE                 Location/Qualifiers
source                  1..52
                        mol_type = other DNA
                        organism = synthetic construct
SEQUENCE: 362
aaagtcaaat ctttttctat ctgtgaaacc ttgcactttt ttctgaatct gt             52

SEQ ID NO: 363          moltype = DNA   length = 78
FEATURE                 Location/Qualifiers
source                  1..78
                        mol_type = other DNA
                        organism = synthetic construct
SEQUENCE: 363
gcaaaataga attttttcgg tatccataat accgtgtttt ttatcataat tgaaacgggt     60
aggttttttaa gccgcata                                                   78

SEQ ID NO: 364          moltype = DNA   length = 42
FEATURE                 Location/Qualifiers
source                  1..42
                        mol_type = other DNA
                        organism = synthetic construct
SEQUENCE: 364
agagctatgc agcacctgta tcggccttct ccgagggttc cc                        42

SEQ ID NO: 365          moltype = DNA   length = 52
FEATURE                 Location/Qualifiers
```

-continued

```
source                    1..52
                          mol_type = other DNA
                          organism = synthetic construct
SEQUENCE: 365
gcaaatacgt atttttctt ccctatctat gttcgccttt ttcgcatttt gc          52

SEQ ID NO: 366           moltype = DNA   length = 78
FEATURE                  Location/Qualifiers
source                    1..78
                          mol_type = other DNA
                          organism = synthetic construct
SEQUENCE: 366
attctgacat attttattta ttgagctttg actcgggttt tttgtaatca gtttggtcgt  60
taatttttg acccaaga                                                 78

SEQ ID NO: 367           moltype = DNA   length = 42
FEATURE                  Location/Qualifiers
source                    1..42
                          mol_type = other DNA
                          organism = synthetic construct
SEQUENCE: 367
aaaagaggac tatgcagtaa cctcaggatc ctactttaaa ag                     42

SEQ ID NO: 368           moltype = DNA   length = 52
FEATURE                  Location/Qualifiers
source                    1..52
                          mol_type = other DNA
                          organism = synthetic construct
SEQUENCE: 368
agttatgtgt ttttttgcag gtagcgctta ttaccctttt ttcgatattc ac          52

SEQ ID NO: 369           moltype = DNA   length = 66
FEATURE                  Location/Qualifiers
source                    1..66
                          mol_type = other DNA
                          organism = synthetic construct
SEQUENCE: 369
ccctaaagtt gcgttgcgct cctgcagcac actaaatcgg aatcgtcgtt ttgtcgtttt  60
gtcgtt                                                             66

SEQ ID NO: 370           moltype = DNA   length = 66
FEATURE                  Location/Qualifiers
source                    1..66
                          mol_type = other DNA
                          organism = synthetic construct
SEQUENCE: 370
caagatataa gatgagaagt ggctatgcgg cttaaacgca agtcgtcgtt ttgtcgtttt  60
gtcgtt                                                             66

SEQ ID NO: 371           moltype = DNA   length = 66
FEATURE                  Location/Qualifiers
source                    1..66
                          mol_type = other DNA
                          organism = synthetic construct
SEQUENCE: 371
ttagaaattg gttactaggt acatctgcgt cacggttaga agtcgtcgtt ttgtcgtttt  60
gtcgtt                                                             66

SEQ ID NO: 372           moltype = DNA   length = 66
FEATURE                  Location/Qualifiers
source                    1..66
                          mol_type = other DNA
                          organism = synthetic construct
SEQUENCE: 372
tctattatac agtctggcaa tactcgctag cgggagtcac agtcgtcgtt ttgtcgtttt  60
gtcgtt                                                             66

SEQ ID NO: 373           moltype = DNA   length = 66
FEATURE                  Location/Qualifiers
source                    1..66
                          mol_type = other DNA
                          organism = synthetic construct
SEQUENCE: 373
cgagaaagga cggggaaagc cggctcaggg tctagaacgt ggtcgtcgtt ttgtcgtttt  60
gtcgtt                                                             66

SEQ ID NO: 374           moltype = DNA   length = 66
FEATURE                  Location/Qualifiers
source                    1..66
```

-continued

```
                             mol_type = other DNA
                             organism = synthetic construct
SEQUENCE: 374
tcatttttca tcaccctaat caagtttttt tgttaaatca gctcgtcgtt ttgtcgtttt    60
gtcgtt                                                               66

SEQ ID NO: 375          moltype = DNA   length = 66
FEATURE                 Location/Qualifiers
source                  1..66
                        mol_type = other DNA
                        organism = synthetic construct
SEQUENCE: 375
gaaggattaa gtaaatatct tcacactccc gtgggacgta gctcgtcgtt ttgtcgtttt    60
gtcgtt                                                               66

SEQ ID NO: 376          moltype = DNA   length = 66
FEATURE                 Location/Qualifiers
source                  1..66
                        mol_type = other DNA
                        organism = synthetic construct
SEQUENCE: 376
tcaacagcga gtgggttaca tcgatggaac agttactgga tctcgtcgtt ttgtcgtttt    60
gtcgtt                                                               66

SEQ ID NO: 377          moltype = DNA   length = 66
FEATURE                 Location/Qualifiers
source                  1..66
                        mol_type = other DNA
                        organism = synthetic construct
SEQUENCE: 377
atagaccgca aaatccctta taaatgagtt aacgtcaaaa gatcgtcgtt ttgtcgtttt    60
gtcgtt                                                               66

SEQ ID NO: 378          moltype = DNA   length = 66
FEATURE                 Location/Qualifiers
source                  1..66
                        mol_type = other DNA
                        organism = synthetic construct
SEQUENCE: 378
gagataggac cccaatcata tgtaccccgt agacagatcg cttcgtcgtt ttgtcgtttt    60
gtcgtt                                                               66

SEQ ID NO: 379          moltype = DNA   length = 66
FEATURE                 Location/Qualifiers
source                  1..66
                        mol_type = other DNA
                        organism = synthetic construct
SEQUENCE: 379
atgagcaccg ccccgaagaa cgttttgatc ctttttccaa tgtcgtcgtt ttgtcgtttt    60
gtcgtt                                                               66

SEQ ID NO: 380          moltype = DNA   length = 66
FEATURE                 Location/Qualifiers
source                  1..66
                        mol_type = other DNA
                        organism = synthetic construct
SEQUENCE: 380
ggctggctac cacttatgcg ctcgtaatta ttttgccctt cctcgtcgtt ttgtcgtttt    60
gtcgtt                                                               66

SEQ ID NO: 381          moltype = DNA   length = 66
FEATURE                 Location/Qualifiers
source                  1..66
                        mol_type = other DNA
                        organism = synthetic construct
SEQUENCE: 381
atatatacgt aactgtcaga ccaagatggg gccagtttac tctcgtcgtt ttgtcgtttt    60
gtcgtt                                                               66

SEQ ID NO: 382          moltype = DNA   length = 66
FEATURE                 Location/Qualifiers
source                  1..66
                        mol_type = other DNA
                        organism = synthetic construct
SEQUENCE: 382
caacagagta tctacacgac ggggagtcac cgggtggctc aatcgtcgtt ttgtcgtttt    60
gtcgtt                                                               66

SEQ ID NO: 383          moltype = DNA   length = 66
```

-continued

```
FEATURE               Location/Qualifiers
source                1..66
                      mol_type = other DNA
                      organism = synthetic construct
SEQUENCE: 383
cgtgacacga gccggtgagc gtgggtctca ccaaacgacg agtcgtcgtt ttgtcgtttt   60
gtcgtt                                                               66

SEQ ID NO: 384        moltype = DNA   length = 66
FEATURE               Location/Qualifiers
source                1..66
                      mol_type = other DNA
                      organism = synthetic construct
SEQUENCE: 384
cgggcaagcg cggtattatc ccgttggatt agacattgac gctcgtcgtt ttgtcgtttt   60
gtcgtt                                                               66

SEQ ID NO: 385        moltype = DNA   length = 66
FEATURE               Location/Qualifiers
source                1..66
                      mol_type = other DNA
                      organism = synthetic construct
SEQUENCE: 385
cagtaagaaa aagcatctta cggatactcc tacttggcat gatcgtcgtt ttgtcgtttt   60
gtcgtt                                                               66

SEQ ID NO: 386        moltype = DNA   length = 66
FEATURE               Location/Qualifiers
source                1..66
                      mol_type = other DNA
                      organism = synthetic construct
SEQUENCE: 386
gctttttat cggaggaccg aaggcgttga acaaagctaa cctcgtcgtt ttgtcgtttt    60
gtcgtt                                                               66

SEQ ID NO: 387        moltype = DNA   length = 66
FEATURE               Location/Qualifiers
source                1..66
                      mol_type = other DNA
                      organism = synthetic construct
SEQUENCE: 387
cgacgacgaa ctcgccttga tcgttgggag agtttgaggg gatcgtcgtt ttgtcgtttt   60
gtcgtt                                                               66

SEQ ID NO: 388        moltype = DNA   length = 66
FEATURE               Location/Qualifiers
source                1..66
                      mol_type = other DNA
                      organism = synthetic construct
SEQUENCE: 388
ttatttttac catgagtgat aacactgcga acccctattt gttcgtcgtt ttgtcgtttt   60
gtcgtt                                                               66

SEQ ID NO: 389        moltype = DNA   length = 66
FEATURE               Location/Qualifiers
source                1..66
                      mol_type = other DNA
                      organism = synthetic construct
SEQUENCE: 389
tgacttggtt ttgccttcct gttttttgcta ctattctcag aatcgtcgtt ttgtcgtttt  60
gtcgtt                                                               66

SEQ ID NO: 390        moltype = DNA   length = 66
FEATURE               Location/Qualifiers
source                1..66
                      mol_type = other DNA
                      organism = synthetic construct
SEQUENCE: 390
tagtgatagt ttgcacacgt ctggagatgg taaacggaca tctcgtcgtt ttgtcgtttt   60
gtcgtt                                                               66

SEQ ID NO: 391        moltype = DNA   length = 66
FEATURE               Location/Qualifiers
source                1..66
                      mol_type = other DNA
                      organism = synthetic construct
SEQUENCE: 391
gtgtcgccag agtatgagta ttcaccacgt cggaacattt cctcgtcgtt ttgtcgtttt   60
gtcgtt                                                               66
```

-continued

```
SEQ ID NO: 392            moltype = DNA   length = 66
FEATURE                   Location/Qualifiers
source                    1..66
                          mol_type = other DNA
                          organism = synthetic construct
SEQUENCE: 392
ataaatgctc cgctcatgag acaatggtaa agcataaccc tgtcgtcgtt ttgtcgtttt    60
gtcgtt                                                                66

SEQ ID NO: 393            moltype = DNA   length = 66
FEATURE                   Location/Qualifiers
source                    1..66
                          mol_type = other DNA
                          organism = synthetic construct
SEQUENCE: 393
ttgatactat tcctagatta gaagggcacc aggtgcgttg tttcgtcgtt ttgtcgtttt    60
gtcgtt                                                                66

SEQ ID NO: 394            moltype = DNA   length = 66
FEATURE                   Location/Qualifiers
source                    1..66
                          mol_type = other DNA
                          organism = synthetic construct
SEQUENCE: 394
tgtcatgaga tacgcctatt tttatgtaga gtgttaggtt aatcgtcgtt ttgtcgtttt    60
gtcgtt                                                                66

SEQ ID NO: 395            moltype = DNA   length = 66
FEATURE                   Location/Qualifiers
source                    1..66
                          mol_type = other DNA
                          organism = synthetic construct
SEQUENCE: 395
gcgaacgaag aaccagggaa aacccttaag tgacaggtac gatcgtcgtt ttgtcgtttt    60
gtcgtt                                                                66

SEQ ID NO: 396            moltype = DNA   length = 66
FEATURE                   Location/Qualifiers
source                    1..66
                          mol_type = other DNA
                          organism = synthetic construct
SEQUENCE: 396
actgctatct atacaaacta agagacaaaa tgtgtaaaag gatcgtcgtt ttgtcgtttt    60
gtcgtt                                                                66

SEQ ID NO: 397            moltype = DNA   length = 66
FEATURE                   Location/Qualifiers
source                    1..66
                          mol_type = other DNA
                          organism = synthetic construct
SEQUENCE: 397
agagctatgc agcacctgta tcggccttct ccgagggttc cctcgtcgtt ttgtcgtttt    60
gtcgtt                                                                66

SEQ ID NO: 398            moltype = DNA   length = 66
FEATURE                   Location/Qualifiers
source                    1..66
                          mol_type = other DNA
                          organism = synthetic construct
SEQUENCE: 398
aaaagaggac tatgcagtaa cctcaggatc ctactttaaa agtcgtcgtt ttgtcgtttt    60
gtcgtt                                                                66

SEQ ID NO: 399            moltype = DNA   length = 65
FEATURE                   Location/Qualifiers
source                    1..65
                          mol_type = other DNA
                          organism = synthetic construct
SEQUENCE: 399
ccctaaagtt gcgttgcgct cctgcagcac actaaatcgg aacccgatac tgccatagac    60
ggcaa                                                                 65

SEQ ID NO: 400            moltype = DNA   length = 65
FEATURE                   Location/Qualifiers
source                    1..65
                          mol_type = other DNA
                          organism = synthetic construct
SEQUENCE: 400
```

-continued

```
caagatataa gatgagaagt ggctatgcgg cttaaacgca agcccgatac tgccatagac    60
ggcaa                                                                65

SEQ ID NO: 401          moltype = DNA   length = 65
FEATURE                 Location/Qualifiers
source                  1..65
                        mol_type = other DNA
                        organism = synthetic construct
SEQUENCE: 401
ttagaaattg gttactaggt acatctgcgt cacggttaga agcccgatac tgccatagac    60
ggcaa                                                                65

SEQ ID NO: 402          moltype = DNA   length = 65
FEATURE                 Location/Qualifiers
source                  1..65
                        mol_type = other DNA
                        organism = synthetic construct
SEQUENCE: 402
tctattatac agtctggcaa tactcgctag cgggagtcac agcccgatac tgccatagac    60
ggcaa                                                                65

SEQ ID NO: 403          moltype = DNA   length = 65
FEATURE                 Location/Qualifiers
source                  1..65
                        mol_type = other DNA
                        organism = synthetic construct
SEQUENCE: 403
cgagaaagga cggggaaagc cggctcaggg tctagaacgt ggcccgatac tgccatagac    60
ggcaa                                                                65

SEQ ID NO: 404          moltype = DNA   length = 65
FEATURE                 Location/Qualifiers
source                  1..65
                        mol_type = other DNA
                        organism = synthetic construct
SEQUENCE: 404
tcatttttca tcaccctaat caagtttttt tgttaaatca gccccgatac tgccatagac    60
ggcaa                                                                65

SEQ ID NO: 405          moltype = DNA   length = 65
FEATURE                 Location/Qualifiers
source                  1..65
                        mol_type = other DNA
                        organism = synthetic construct
SEQUENCE: 405
gaaggattaa gtaaatatct tcacactccc gtgggacgta gccccgatac tgccatagac    60
ggcaa                                                                65

SEQ ID NO: 406          moltype = DNA   length = 65
FEATURE                 Location/Qualifiers
source                  1..65
                        mol_type = other DNA
                        organism = synthetic construct
SEQUENCE: 406
tcaacagcga gtgggttaca tcgatggaac agttactgga tccccgatac tgccatagac    60
ggcaa                                                                65

SEQ ID NO: 407          moltype = DNA   length = 65
FEATURE                 Location/Qualifiers
source                  1..65
                        mol_type = other DNA
                        organism = synthetic construct
SEQUENCE: 407
atagaccgca aaatccctta taaatgagtt aacgtcaaaa gacccgatac tgccatagac    60
ggcaa                                                                65

SEQ ID NO: 408          moltype = DNA   length = 65
FEATURE                 Location/Qualifiers
source                  1..65
                        mol_type = other DNA
                        organism = synthetic construct
SEQUENCE: 408
gagataggac cccaatcata tgtaccccgt agacagatcg ctcccgatac tgccatagac    60
ggcaa                                                                65

SEQ ID NO: 409          moltype = DNA   length = 65
FEATURE                 Location/Qualifiers
source                  1..65
                        mol_type = other DNA
```

-continued

```
                                             organism = synthetic construct
SEQUENCE: 409
atgagcaccg ccccgaagaa cgttttgatc ctttttccaa tgcccgatac tgccatagac    60
ggcaa                                                                65

SEQ ID NO: 410              moltype = DNA  length = 65
FEATURE                     Location/Qualifiers
source                      1..65
                            mol_type = other DNA
                            organism = synthetic construct
SEQUENCE: 410
ggctggctac cacttatgcg ctcgtaatta ttttgccctt cccccgatac tgccatagac    60
ggcaa                                                                65

SEQ ID NO: 411              moltype = DNA  length = 65
FEATURE                     Location/Qualifiers
source                      1..65
                            mol_type = other DNA
                            organism = synthetic construct
SEQUENCE: 411
atatatacgt aactgtcaga ccaagatggg gccagtttac tccccgatac tgccatagac    60
ggcaa                                                                65

SEQ ID NO: 412              moltype = DNA  length = 65
FEATURE                     Location/Qualifiers
source                      1..65
                            mol_type = other DNA
                            organism = synthetic construct
SEQUENCE: 412
caacagagta tctacacgac ggggagtcac cgggtggctc aacccgatac tgccatagac    60
ggcaa                                                                65

SEQ ID NO: 413              moltype = DNA  length = 65
FEATURE                     Location/Qualifiers
source                      1..65
                            mol_type = other DNA
                            organism = synthetic construct
SEQUENCE: 413
cgtgacacga gccggtgagc gtgggtctca ccaaacgacg agcccgatac tgccatagac    60
ggcaa                                                                65

SEQ ID NO: 414              moltype = DNA  length = 65
FEATURE                     Location/Qualifiers
source                      1..65
                            mol_type = other DNA
                            organism = synthetic construct
SEQUENCE: 414
cgggcaagcg cggtattatc ccgttggatt agacattgac gccccgatac tgccatagac    60
ggcaa                                                                65

SEQ ID NO: 415              moltype = DNA  length = 65
FEATURE                     Location/Qualifiers
source                      1..65
                            mol_type = other DNA
                            organism = synthetic construct
SEQUENCE: 415
cagtaagaaa aagcatctta cggatactcc tacttggcat gacccgatac tgccatagac    60
ggcaa                                                                65

SEQ ID NO: 416              moltype = DNA  length = 65
FEATURE                     Location/Qualifiers
source                      1..65
                            mol_type = other DNA
                            organism = synthetic construct
SEQUENCE: 416
gcttttttat cggaggaccg aaggcgttga acaaagctaa cccccgatac tgccatagac    60
ggcaa                                                                65

SEQ ID NO: 417              moltype = DNA  length = 65
FEATURE                     Location/Qualifiers
source                      1..65
                            mol_type = other DNA
                            organism = synthetic construct
SEQUENCE: 417
cgacgacgaa ctcgccttga tcgttgggag agtttgaggg gacccgatac tgccatagac    60
ggcaa                                                                65

SEQ ID NO: 418              moltype = DNA  length = 65
FEATURE                     Location/Qualifiers
```

-continued

```
source                1..65
                      mol_type = other DNA
                      organism = synthetic construct
SEQUENCE: 418
ttatttttac catgagtgat aacactgcga acccctattt gtcccgatac tgccatagac   60
ggcaa                                                                65

SEQ ID NO: 419        moltype = DNA  length = 65
FEATURE               Location/Qualifiers
source                1..65
                      mol_type = other DNA
                      organism = synthetic construct
SEQUENCE: 419
tgacttggtt ttgccttcct gttttttgcta ctattctcag aacccgatac tgccatagac  60
ggcaa                                                                65

SEQ ID NO: 420        moltype = DNA  length = 65
FEATURE               Location/Qualifiers
source                1..65
                      mol_type = other DNA
                      organism = synthetic construct
SEQUENCE: 420
tagtgatagt ttgcacacgt ctggagatgg taaacggaca tccccgatac tgccatagac   60
ggcaa                                                                65

SEQ ID NO: 421        moltype = DNA  length = 65
FEATURE               Location/Qualifiers
source                1..65
                      mol_type = other DNA
                      organism = synthetic construct
SEQUENCE: 421
gtgtcgccag agtatgagta ttcaccacgt cggaacattt cccccgatac tgccatagac   60
ggcaa                                                                65

SEQ ID NO: 422        moltype = DNA  length = 65
FEATURE               Location/Qualifiers
source                1..65
                      mol_type = other DNA
                      organism = synthetic construct
SEQUENCE: 422
ataaatgctc cgctcatgag acaatggtaa agcataaccc tgcccgatac tgccatagac   60
ggcaa                                                                65

SEQ ID NO: 423        moltype = DNA  length = 65
FEATURE               Location/Qualifiers
source                1..65
                      mol_type = other DNA
                      organism = synthetic construct
SEQUENCE: 423
ttgatactat tcctagatta gaagggcacc aggtgcgttg ttcccgatac tgccatagac   60
ggcaa                                                                65

SEQ ID NO: 424        moltype = DNA  length = 65
FEATURE               Location/Qualifiers
source                1..65
                      mol_type = other DNA
                      organism = synthetic construct
SEQUENCE: 424
tgtcatgaga tacgcctatt tttatgtaga gtgttaggtt aacccgatac tgccatagac   60
ggcaa                                                                65

SEQ ID NO: 425        moltype = DNA  length = 65
FEATURE               Location/Qualifiers
source                1..65
                      mol_type = other DNA
                      organism = synthetic construct
SEQUENCE: 425
gcgaacgaag aaccagggaa aacccttaag tgacaggtac gacccgatac tgccatagac   60
ggcaa                                                                65

SEQ ID NO: 426        moltype = DNA  length = 65
FEATURE               Location/Qualifiers
source                1..65
                      mol_type = other DNA
                      organism = synthetic construct
SEQUENCE: 426
actgctatct atacaaacta agagacaaaa tgtgtaaaag gacccgatac tgccatagac   60
ggcaa                                                                65
```

-continued

```
SEQ ID NO: 427              moltype = DNA   length = 65
FEATURE                     Location/Qualifiers
source                      1..65
                            mol_type = other DNA
                            organism = synthetic construct
SEQUENCE: 427
agagctatgc agcacctgta tcggccttct ccgagggttc cccccgatac tgccatagac   60
ggcaa                                                               65

SEQ ID NO: 428              moltype = DNA   length = 65
FEATURE                     Location/Qualifiers
source                      1..65
                            mol_type = other DNA
                            organism = synthetic construct
SEQUENCE: 428
aaaagaggac tatgcagtaa cctcaggatc ctactttaaa agcccgatac tgccatagac   60
ggcaa                                                               65

SEQ ID NO: 429              moltype = DNA   length = 66
FEATURE                     Location/Qualifiers
source                      1..66
                            mol_type = other DNA
                            organism = synthetic construct
SEQUENCE: 429
cggaacccta aagttgcgtt gcgctcctgc agcacactaa attcgtcgtt ttgtcgtttt   60
gtcgtt                                                              66

SEQ ID NO: 430              moltype = DNA   length = 66
FEATURE                     Location/Qualifiers
source                      1..66
                            mol_type = other DNA
                            organism = synthetic construct
SEQUENCE: 430
aagtggctat gcggcttaaa cgcaagcaag atataagatg agtcgtcgtt ttgtcgtttt   60
gtcgtt                                                              66

SEQ ID NO: 431              moltype = DNA   length = 66
FEATURE                     Location/Qualifiers
source                      1..66
                            mol_type = other DNA
                            organism = synthetic construct
SEQUENCE: 431
aggtacatct gcgtcacggt tagaagttag aaattggtta cttcgtcgtt ttgtcgtttt   60
gtcgtt                                                              66

SEQ ID NO: 432              moltype = DNA   length = 66
FEATURE                     Location/Qualifiers
source                      1..66
                            mol_type = other DNA
                            organism = synthetic construct
SEQUENCE: 432
gcaatactcg ctagcgggag tcacagtcta ttatacagtc tgtcgtcgtt ttgtcgtttt   60
gtcgtt                                                              66

SEQ ID NO: 433              moltype = DNA   length = 66
FEATURE                     Location/Qualifiers
source                      1..66
                            mol_type = other DNA
                            organism = synthetic construct
SEQUENCE: 433
aagccggctc agggtctaga acgtggcgag aaaggacggg gatcgtcgtt ttgtcgtttt   60
gtcgtt                                                              66

SEQ ID NO: 434              moltype = DNA   length = 66
FEATURE                     Location/Qualifiers
source                      1..66
                            mol_type = other DNA
                            organism = synthetic construct
SEQUENCE: 434
tcagctcatt tttcatcacc ctaatcaagt tttttgtta aatcgtcgtt ttgtcgtttt   60
gtcgtt                                                              66

SEQ ID NO: 435              moltype = DNA   length = 66
FEATURE                     Location/Qualifiers
source                      1..66
                            mol_type = other DNA
                            organism = synthetic construct
SEQUENCE: 435
gtagcgaagg attaagtaaa tatcttcaca ctcccgtggg actcgtcgtt ttgtcgtttt   60
```

```
gtcgtt                                                                     66

SEQ ID NO: 436           moltype = DNA   length = 66
FEATURE                  Location/Qualifiers
source                   1..66
                         mol_type = other DNA
                         organism = synthetic construct
SEQUENCE: 436
tacatcgatg gaacagttac tggatctcaa cagcgagtgg gttcgtcgtt ttgtcgtttt         60
gtcgtt                                                                     66

SEQ ID NO: 437           moltype = DNA   length = 66
FEATURE                  Location/Qualifiers
source                   1..66
                         mol_type = other DNA
                         organism = synthetic construct
SEQUENCE: 437
cttataaatg agttaacgtc aaaagaatag accgcaaaat cctcgtcgtt ttgtcgtttt         60
gtcgtt                                                                     66

SEQ ID NO: 438           moltype = DNA   length = 66
FEATURE                  Location/Qualifiers
source                   1..66
                         mol_type = other DNA
                         organism = synthetic construct
SEQUENCE: 438
tcgctgagat aggaccccaa tcatatgtac cccgtagaca gatcgtcgtt ttgtcgtttt         60
gtcgtt                                                                     66

SEQ ID NO: 439           moltype = DNA   length = 66
FEATURE                  Location/Qualifiers
source                   1..66
                         mol_type = other DNA
                         organism = synthetic construct
SEQUENCE: 439
agaacgtttt gatccttttt ccaatgatga gcaccgcccc gatcgtcgtt ttgtcgtttt         60
gtcgtt                                                                     66

SEQ ID NO: 440           moltype = DNA   length = 66
FEATURE                  Location/Qualifiers
source                   1..66
                         mol_type = other DNA
                         organism = synthetic construct
SEQUENCE: 440
cttccggctg gctaccactt atgcgctcgt aattattttg cctcgtcgtt ttgtcgtttt         60
gtcgtt                                                                     66

SEQ ID NO: 441           moltype = DNA   length = 66
FEATURE                  Location/Qualifiers
source                   1..66
                         mol_type = other DNA
                         organism = synthetic construct
SEQUENCE: 441
cagaccaaga tggggccagt ttactcatat atacgtaact gttcgtcgtt ttgtcgtttt         60
gtcgtt                                                                     66

SEQ ID NO: 442           moltype = DNA   length = 66
FEATURE                  Location/Qualifiers
source                   1..66
                         mol_type = other DNA
                         organism = synthetic construct
SEQUENCE: 442
ctcaacaaca gagtatctac acgacgggga gtcaccgggt ggtcgtcgtt ttgtcgtttt         60
gtcgtt                                                                     66

SEQ ID NO: 443           moltype = DNA   length = 66
FEATURE                  Location/Qualifiers
source                   1..66
                         mol_type = other DNA
                         organism = synthetic construct
SEQUENCE: 443
acgagcgtga cacgagccgg tgagcgtggg tctcaccaaa cgtcgtcgtt ttgtcgtttt         60
gtcgtt                                                                     66

SEQ ID NO: 444           moltype = DNA   length = 66
FEATURE                  Location/Qualifiers
source                   1..66
                         mol_type = other DNA
                         organism = synthetic construct
```

```
SEQUENCE: 444
tatcccgttg gattagacat tgacgccggg caagcgcggt attcgtcgtt ttgtcgtttt    60
gtcgtt                                                               66

SEQ ID NO: 445          moltype = DNA   length = 66
FEATURE                 Location/Qualifiers
source                  1..66
                        mol_type = other DNA
                        organism = synthetic construct
SEQUENCE: 445
cttacggata ctcctacttg gcatgacagt aagaaaaagc attcgtcgtt ttgtcgtttt    60
gtcgtt                                                               66

SEQ ID NO: 446          moltype = DNA   length = 66
FEATURE                 Location/Qualifiers
source                  1..66
                        mol_type = other DNA
                        organism = synthetic construct
SEQUENCE: 446
accgaaggcg ttgaacaaag ctaaccgctt ttttatcgga ggtcgtcgtt ttgtcgtttt    60
gtcgtt                                                               66

SEQ ID NO: 447          moltype = DNA   length = 66
FEATURE                 Location/Qualifiers
source                  1..66
                        mol_type = other DNA
                        organism = synthetic construct
SEQUENCE: 447
ggggacgacg acgaactcgc cttgatcgtt gggagagttt gatcgtcgtt ttgtcgtttt    60
gtcgtt                                                               66

SEQ ID NO: 448          moltype = DNA   length = 66
FEATURE                 Location/Qualifiers
source                  1..66
                        mol_type = other DNA
                        organism = synthetic construct
SEQUENCE: 448
tttgtttatt tttaccatga gtgataacac tgcgaacccc tatcgtcgtt ttgtcgtttt    60
gtcgtt                                                               66

SEQ ID NO: 449          moltype = DNA   length = 66
FEATURE                 Location/Qualifiers
source                  1..66
                        mol_type = other DNA
                        organism = synthetic construct
SEQUENCE: 449
cagaatgact tggttttgcc ttcctgtttt tgctactatt cttcgtcgtt ttgtcgtttt    60
gtcgtt                                                               66

SEQ ID NO: 450          moltype = DNA   length = 66
FEATURE                 Location/Qualifiers
source                  1..66
                        mol_type = other DNA
                        organism = synthetic construct
SEQUENCE: 450
acgtctggag atggtaaacg gacatctagt gatagtttgc actcgtcgtt ttgtcgtttt    60
gtcgtt                                                               66

SEQ ID NO: 451          moltype = DNA   length = 66
FEATURE                 Location/Qualifiers
source                  1..66
                        mol_type = other DNA
                        organism = synthetic construct
SEQUENCE: 451
agtattcacc acgtcggaac atttccgtgt cgccagagta tgtcgtcgtt ttgtcgtttt    60
gtcgtt                                                               66

SEQ ID NO: 452          moltype = DNA   length = 66
FEATURE                 Location/Qualifiers
source                  1..66
                        mol_type = other DNA
                        organism = synthetic construct
SEQUENCE: 452
tgagacaatg gtaaagcata accctgataa atgctccgct catcgtcgtt ttgtcgtttt    60
gtcgtt                                                               66

SEQ ID NO: 453          moltype = DNA   length = 66
FEATURE                 Location/Qualifiers
source                  1..66
```

-continued

```
                         mol_type = other DNA
                         organism = synthetic construct
SEQUENCE: 453
attagaaggg caccaggtgc gttgtttga tactattcct agtcgtcgtt ttgtcgtttt   60
gtcgtt                                                              66

SEQ ID NO: 454          moltype = DNA  length = 66
FEATURE                 Location/Qualifiers
source                  1..66
                        mol_type = other DNA
                        organism = synthetic construct
SEQUENCE: 454
tatttttatg tagagtgtta ggttaatgtc atgagatacg cctcgtcgtt ttgtcgtttt   60
gtcgtt                                                              66

SEQ ID NO: 455          moltype = DNA  length = 66
FEATURE                 Location/Qualifiers
source                  1..66
                        mol_type = other DNA
                        organism = synthetic construct
SEQUENCE: 455
ggaaaaccct taagtgacag gtacgagcga acgaagaacc agtcgtcgtt ttgtcgtttt   60
gtcgtt                                                              66

SEQ ID NO: 456          moltype = DNA  length = 66
FEATURE                 Location/Qualifiers
source                  1..66
                        mol_type = other DNA
                        organism = synthetic construct
SEQUENCE: 456
aaggaactgc tatctataca aactaagaga caaaatgtgt aatcgtcgtt ttgtcgtttt   60
gtcgtt                                                              66

SEQ ID NO: 457          moltype = DNA  length = 66
FEATURE                 Location/Qualifiers
source                  1..66
                        mol_type = other DNA
                        organism = synthetic construct
SEQUENCE: 457
ttcccagagc tatgcagcac ctgtatcggc cttctccgag ggtcgtcgtt ttgtcgtttt   60
gtcgtt                                                              66

SEQ ID NO: 458          moltype = DNA  length = 66
FEATURE                 Location/Qualifiers
source                  1..66
                        mol_type = other DNA
                        organism = synthetic construct
SEQUENCE: 458
gtaacctcag gatcctactt taaaagaaaa gaggactatg catcgtcgtt ttgtcgtttt   60
gtcgtt                                                              66

SEQ ID NO: 459          moltype = DNA  length = 65
FEATURE                 Location/Qualifiers
source                  1..65
                        mol_type = other DNA
                        organism = synthetic construct
SEQUENCE: 459
cggaaccota aagttgcgtt gcgctcctgc agcacactaa atcccgatac tgccatagac   60
ggcaa                                                              65

SEQ ID NO: 460          moltype = DNA  length = 65
FEATURE                 Location/Qualifiers
source                  1..65
                        mol_type = other DNA
                        organism = synthetic construct
SEQUENCE: 460
aagtggctat gcggcttaaa cgcaagcaag atataagatg agcccgatac tgccatagac   60
ggcaa                                                              65

SEQ ID NO: 461          moltype = DNA  length = 65
FEATURE                 Location/Qualifiers
source                  1..65
                        mol_type = other DNA
                        organism = synthetic construct
SEQUENCE: 461
aggtacatct gcgtcacggt tagaagttag aaattggtta ctcccgatac tgccatagac   60
ggcaa                                                              65

SEQ ID NO: 462          moltype = DNA  length = 65
```

-continued

```
FEATURE            Location/Qualifiers
source             1..65
                   mol_type = other DNA
                   organism = synthetic construct
SEQUENCE: 462
gcaatactcg ctagcgggag tcacagtcta ttatacagtc tgcccgatac tgccatagac   60
ggcaa                                                               65

SEQ ID NO: 463          moltype = DNA  length = 65
FEATURE            Location/Qualifiers
source             1..65
                   mol_type = other DNA
                   organism = synthetic construct
SEQUENCE: 463
aagccggctc agggtctaga acgtggcgag aaaggacggg gacccgatac tgccatagac   60
ggcaa                                                               65

SEQ ID NO: 464          moltype = DNA  length = 65
FEATURE            Location/Qualifiers
source             1..65
                   mol_type = other DNA
                   organism = synthetic construct
SEQUENCE: 464
tcagctcatt tttcatcacc ctaatcaagt tttttgtta aacccgatac tgccatagac   60
ggcaa                                                               65

SEQ ID NO: 465          moltype = DNA  length = 65
FEATURE            Location/Qualifiers
source             1..65
                   mol_type = other DNA
                   organism = synthetic construct
SEQUENCE: 465
gtagcgaagg attaagtaaa tatcttcaca ctcccgtggg accccgatac tgccatagac   60
ggcaa                                                               65

SEQ ID NO: 466          moltype = DNA  length = 65
FEATURE            Location/Qualifiers
source             1..65
                   mol_type = other DNA
                   organism = synthetic construct
SEQUENCE: 466
tacatcgatg gaacagttac tggatctcaa cagcgagtgg gtcccgatac tgccatagac   60
ggcaa                                                               65

SEQ ID NO: 467          moltype = DNA  length = 65
FEATURE            Location/Qualifiers
source             1..65
                   mol_type = other DNA
                   organism = synthetic construct
SEQUENCE: 467
cttataaatg agttaacgtc aaaagaatag accgcaaaat cccccgatac tgccatagac   60
ggcaa                                                               65

SEQ ID NO: 468          moltype = DNA  length = 65
FEATURE            Location/Qualifiers
source             1..65
                   mol_type = other DNA
                   organism = synthetic construct
SEQUENCE: 468
tcgctgagat aggaccccaa tcatatgtac cccgtagaca gacccgatac tgccatagac   60
ggcaa                                                               65

SEQ ID NO: 469          moltype = DNA  length = 65
FEATURE            Location/Qualifiers
source             1..65
                   mol_type = other DNA
                   organism = synthetic construct
SEQUENCE: 469
agaacgtttt gatccttttt ccaatgatga gcaccgcccc gacccgatac tgccatagac   60
ggcaa                                                               65

SEQ ID NO: 470          moltype = DNA  length = 65
FEATURE            Location/Qualifiers
source             1..65
                   mol_type = other DNA
                   organism = synthetic construct
SEQUENCE: 470
cttccggctg gctaccactt atgcgctcgt aattattttg cccccgatac tgccatagac   60
ggcaa                                                               65
```

```
SEQ ID NO: 471          moltype = DNA   length = 65
FEATURE                 Location/Qualifiers
source                  1..65
                        mol_type = other DNA
                        organism = synthetic construct
SEQUENCE: 471
cagaccaaga tggggccagt ttactcatat atacgtaact gtcccgatac tgccatagac    60
ggcaa                                                                65

SEQ ID NO: 472          moltype = DNA   length = 65
FEATURE                 Location/Qualifiers
source                  1..65
                        mol_type = other DNA
                        organism = synthetic construct
SEQUENCE: 472
ctcaacaaca gagtatctac acgacgggga gtcaccgggt ggcccgatac tgccatagac    60
ggcaa                                                                65

SEQ ID NO: 473          moltype = DNA   length = 65
FEATURE                 Location/Qualifiers
source                  1..65
                        mol_type = other DNA
                        organism = synthetic construct
SEQUENCE: 473
acgagcgtga cacgagccgg tgagcgtggg tctcaccaaa cgcccgatac tgccatagac    60
ggcaa                                                                65

SEQ ID NO: 474          moltype = DNA   length = 65
FEATURE                 Location/Qualifiers
source                  1..65
                        mol_type = other DNA
                        organism = synthetic construct
SEQUENCE: 474
tatcccgttg gattagacat tgacgccggg caagcgcggt atcccgatac tgccatagac    60
ggcaa                                                                65

SEQ ID NO: 475          moltype = DNA   length = 65
FEATURE                 Location/Qualifiers
source                  1..65
                        mol_type = other DNA
                        organism = synthetic construct
SEQUENCE: 475
cttacggata ctcctacttg gcatgacagt aagaaaaagc atcccgatac tgccatagac    60
ggcaa                                                                65

SEQ ID NO: 476          moltype = DNA   length = 65
FEATURE                 Location/Qualifiers
source                  1..65
                        mol_type = other DNA
                        organism = synthetic construct
SEQUENCE: 476
accgaaggcg ttgaacaaag ctaaccgctt ttttatcgga ggcccgatac tgccatagac    60
ggcaa                                                                65

SEQ ID NO: 477          moltype = DNA   length = 65
FEATURE                 Location/Qualifiers
source                  1..65
                        mol_type = other DNA
                        organism = synthetic construct
SEQUENCE: 477
ggggacgacg acgaactcgc cttgatcgtt gggagagttt gacccgatac tgccatagac    60
ggcaa                                                                65

SEQ ID NO: 478          moltype = DNA   length = 65
FEATURE                 Location/Qualifiers
source                  1..65
                        mol_type = other DNA
                        organism = synthetic construct
SEQUENCE: 478
tttgtttatt tttaccatga gtgataacac tgcgaacccc tacccgatac tgccatagac    60
ggcaa                                                                65

SEQ ID NO: 479          moltype = DNA   length = 65
FEATURE                 Location/Qualifiers
source                  1..65
                        mol_type = other DNA
                        organism = synthetic construct
SEQUENCE: 479
```

-continued

```
cagaatgact tggttttgcc ttcctgtttt tgctactatt ctcccgatac tgccatagac   60
ggcaa                                                                65

SEQ ID NO: 480          moltype = DNA   length = 65
FEATURE                 Location/Qualifiers
source                  1..65
                        mol_type = other DNA
                        organism = synthetic construct
SEQUENCE: 480
acgtctggag atggtaaacg gacatctagt gatagtttgc accccgatac tgccatagac   60
ggcaa                                                                65

SEQ ID NO: 481          moltype = DNA   length = 65
FEATURE                 Location/Qualifiers
source                  1..65
                        mol_type = other DNA
                        organism = synthetic construct
SEQUENCE: 481
agtattcacc acgtcggaac atttccgtgt cgccagagta tgcccgatac tgccatagac   60
ggcaa                                                                65

SEQ ID NO: 482          moltype = DNA   length = 65
FEATURE                 Location/Qualifiers
source                  1..65
                        mol_type = other DNA
                        organism = synthetic construct
SEQUENCE: 482
tgagacaatg gtaaagcata accctgataa atgctccgct cacccgatac tgccatagac   60
ggcaa                                                                65

SEQ ID NO: 483          moltype = DNA   length = 65
FEATURE                 Location/Qualifiers
source                  1..65
                        mol_type = other DNA
                        organism = synthetic construct
SEQUENCE: 483
attagaaggg caccaggtgc gttgttttga tactattcct agcccgatac tgccatagac   60
ggcaa                                                                65

SEQ ID NO: 484          moltype = DNA   length = 65
FEATURE                 Location/Qualifiers
source                  1..65
                        mol_type = other DNA
                        organism = synthetic construct
SEQUENCE: 484
tatttttatg tagagtgtta ggttaatgtc atgagatacg cccccgatac tgccatagac   60
ggcaa                                                                65

SEQ ID NO: 485          moltype = DNA   length = 65
FEATURE                 Location/Qualifiers
source                  1..65
                        mol_type = other DNA
                        organism = synthetic construct
SEQUENCE: 485
ggaaaaccct taagtgacag gtacgagcga acgaagaacc agcccgatac tgccatagac   60
ggcaa                                                                65

SEQ ID NO: 486          moltype = DNA   length = 65
FEATURE                 Location/Qualifiers
source                  1..65
                        mol_type = other DNA
                        organism = synthetic construct
SEQUENCE: 486
aaggaactgc tatctataca aactaagaga caaaatgtgt aacccgatac tgccatagac   60
ggcaa                                                                65

SEQ ID NO: 487          moltype = DNA   length = 65
FEATURE                 Location/Qualifiers
source                  1..65
                        mol_type = other DNA
                        organism = synthetic construct
SEQUENCE: 487
ttcccagagc tatgcagcac ctgtatcggc cttctccgag ggcccgatac tgccatagac   60
ggcaa                                                                65

SEQ ID NO: 488          moltype = DNA   length = 65
FEATURE                 Location/Qualifiers
source                  1..65
                        mol_type = other DNA
```

-continued

```
                        organism = synthetic construct
SEQUENCE: 488
gtaacctcag gatcctactt taaaagaaaa gaggactatg cacccgatac tgccatagac    60
ggcaa                                                                65

SEQ ID NO: 489          moltype = DNA  length = 24
FEATURE                 Location/Qualifiers
source                  1..24
                        mol_type = other DNA
                        organism = synthetic construct
SEQUENCE: 489
tcgtcgtttt gtcgttttgt cgtt                                           24

SEQ ID NO: 490          moltype = DNA  length = 24
FEATURE                 Location/Qualifiers
source                  1..24
                        mol_type = other DNA
                        organism = synthetic construct
modified_base           1..24
                        mod_base = OTHER
                        note = Phosphorothioate Bond
SEQUENCE: 490
tcgtcgtttt gtcgttttgt cgtt                                           24

SEQ ID NO: 491          moltype = DNA  length = 24
FEATURE                 Location/Qualifiers
source                  1..24
                        mol_type = other DNA
                        organism = synthetic construct
SEQUENCE: 491
tttgatactg ccatagaagg caac                                           24
```